US010793873B2

(12) United States Patent
Wells

(10) Patent No.: US 10,793,873 B2
(45) Date of Patent: Oct. 6, 2020

(54) USE OF INTERFERING RNA IN THE PRODUCTION OF TRANSGENIC ANIMALS

(75) Inventor: Kevin Wells, Christiansburg, VA (US)

(73) Assignee: Revivicor, Inc., Blacksburg, VA (US)

(*) Notice: Subject to any disclaimer, the term of this patent is extended or adjusted under 35 U.S.C. 154(b) by 1260 days.

(21) Appl. No.: 10/996,217

(22) Filed: Nov. 22, 2004

(65) Prior Publication Data

US 2005/0266561 A1 Dec. 1, 2005

Related U.S. Application Data

(60) Provisional application No. 60/523,938, filed on Nov. 21, 2003.

(51) Int. Cl.

| | |
|---|---|
| ***C12N 15/113*** | (2010.01) |
| ***C12N 15/11*** | (2006.01) |
| ***C12N 15/85*** | (2006.01) |
| ***C12N 15/63*** | (2006.01) |
| ***A01K 67/027*** | (2006.01) |

(52) U.S. Cl.

CPC .......... *C12N 15/85* (2013.01); *A01K 67/0275* (2013.01); *C12N 15/111* (2013.01); *C12N 15/113* (2013.01); *C12N 15/1131* (2013.01); *C12N 15/63* (2013.01); *A01K 2217/058* (2013.01); *A01K 2227/108* (2013.01); *A01K 2267/02* (2013.01); *A01K 2267/025* (2013.01); *A01K 2267/03* (2013.01); *C12N 2310/14* (2013.01); *C12N 2320/10* (2013.01); *C12N 2320/12* (2013.01); *C12N 2510/00* (2013.01); *C12N 2800/60* (2013.01); *C12N 2840/44* (2013.01)

(58) Field of Classification Search

None

See application file for complete search history.

(56) References Cited

U.S. PATENT DOCUMENTS

| | | | |
|---|---|---|---|
| 5,627,059 A | 5/1997 | Capecchi | |
| 6,261,806 B1 | 7/2001 | Banerjee et al. | |
| 6,506,559 B1 | 1/2003 | Fire et al. | |
| 6,573,099 B2 | 6/2003 | Graham | |
| 2003/0108923 A1 | 6/2003 | Tuschl et al. | |
| 2003/0143597 A1 | 7/2003 | Finney et al. | |
| 2003/0143732 A1 | 7/2003 | Fosnaugh et al. | |
| 2003/0148519 A1 | 8/2003 | Engelke et al. | |
| 2003/0166282 A1 | 9/2003 | Brown et al. | |
| 2003/0203868 A1* | 10/2003 | Bushman | C12N 15/1131 514/44 R |
| 2004/0045043 A1 | 3/2004 | Finney et al. | |
| 2004/0072769 A1* | 4/2004 | Yin | 514/44 |

FOREIGN PATENT DOCUMENTS

| | | |
|---|---|---|
| EP | 1063296 A1 | 12/2000 |
| EP | 1582591 A2 | 10/2005 |
| FR | A-2646438 | 11/1990 |
| WO | WO 99/49029 A1 | 9/1999 |
| WO | WO 02/092821 A1 | 11/2002 |
| WO | WO 03/006477 A1 | 1/2003 |
| WO | WO 03/012052 A2 | 2/2003 |
| WO | WO 03/022052 | 3/2003 |
| WO | WO 03/023015 A2 | 3/2003 |
| WO | WO 03/056012 A1 | 7/2003 |
| WO | WO 03/056022 A2 | 7/2003 |
| WO | WO 03/059923 A2 | 7/2003 |
| WO | WO 04/028243 A2 | 4/2004 |

OTHER PUBLICATIONS

Wilson et al. (Journal of Virology (2003) vol. 77, No. 1, pp. 142-149).*

Wall et al., 1991 (Proc.Natl. Acad. Sci. USA. 88:1696-1700). (Year: 1991).*

Akiyoshi (J. Virol. (1998), vol. 72(5): 4503-4507). (Year: 1998).*

Akiyoshi, D.E., et al., "Identification of a full-length cDNA for an endogenous retrovirus of miniature swine," *J. Virol.*, 72(5):4503-4507 (May 1998).

Anderson, J., et al., "Bispecific short hairpin siRNA constructs targeted to CD4, CXCR4, and CCR5 confer HIV-1 resistance," *Oligonucleotides*, 13(5):303-312 (2003).

Blusch, J.H., et al., "Pig endogenous retroviruses and xenotransplantation," *Xenotransplantation*, 9(4):242-251 (Jul. 2002).

Brummelkamp, T.R., et al., "A system for stable expression of short interfering RNAs in mammalian cells.," *Science*, 296(5567):550-553 (Apr. 19, 2002) (published electronically Mar. 21, 2002).

Caplen, N.J., et al., "Specific inhibition of gene expression by small double-stranded RNAs in invertebrate and vertebrate systems," *Proc. Natl. Acad. Sci. U.S.A.*, 98(17):9742-9747 (Aug. 14, 2001) (published electronically Jul. 31, 2001).

Carmell, M.A., et al., "Germline transmission of RNAi in mice," *Nature Structural Biology*, 10(2):91-92 (Feb. 2003).

Dai, Y., et al., "Targeted disruption of the □1,3-galactosyltransferase gene in cloned pigs," *Nature Biotechnology*, 20:251-255 (Mar. 2002).

Der, S.D., et al., "A double-stranded RNA-activated protein kinase-dependent pathway mediating stress-induced apoptosis," *Proc. Natl. Acad. Sci. U.S.A.*, 94(7):3279-3283 (Apr. 1, 1997).

Elbashir, S.M., et al., "Duplexes of 21-nucleotide RNAs mediate RNA interference in cultured mammalian cells," *Nature*, 411(6386):494-498 (May 24, 2001).

Fire, A., et al., "Potent and specific genetic interference by double-stranded RNA in Caenorhabditis elegans.," *Nature*, 391(6669):806-811 (Feb. 19, 1998).

(Continued)

*Primary Examiner* — J. E Angell

(74) *Attorney, Agent, or Firm* — Foley & Lardner LLP

(57) ABSTRACT

The invention provides cells and animals, as well as methods of producing cells and animals, that express at least one interfering RNA molecule to regulate the expression of a specific gene or family of genes. The invention further provides novel iRNA molecules, as well as DNA templates for producing iRNA molecules.

15 Claims, 22 Drawing Sheets

Specification includes a Sequence Listing.

(56) References Cited

OTHER PUBLICATIONS

Galli-Taliadoros, L.A., et al., "Gene knock-out technology: a methodological overview for the interested novice.," *J. Immunol. Methods*, 181(1):1-15 (Apr. 12, 1995).
Hasuwa, H., et al., "Small interfering RNA and gene silencing in transgenic mice and rats.," *FEBS Letters*, 532(1-2):227-230 (Dec. 4, 2002).
Heneine, W., et al., "No evidence of infection with porcine endogenous retrovirus in recipients of porcine islet-cell xenografts," *Lancet*, 352(9129):695-699 (Aug. 29, 1998); Erratum in: *Lancet*, (9138):1478 (Oct. 31, 1998).
Herring, C., et al., "Monitoring xenotransplant recipients for infection by PERV," *Clin. Biochem.*, 34(1):23-27 (Feb. 2001).
Holding, C., "Modeling miRNA mechanisms," *The Scientist*, (Sep. 25, 2003), accessed at www.the-scientist.com/news/20030925/02.
Karlas, A., et al., "Inhibition of porcine endogenous retroviruses by RNA interference: increasing the safety of xenotransplantation," *Virology*, 325(1):18-23 (Jul. 20, 2004).
Kunath, T., et al., "Transgenic RNA interference in ES cell-derived embryos recapitulates a genetic null phenotype," *Nature Biotechnology*, 21(5):559-561 (May 2003) (Epublication Apr. 7, 2003).
Lai, L., et al., "Production of □-1,3-galactosyltransferase knockout pigs by nuclear transfer cloning," *Science* 295:1089-1092 (Feb. 8, 2002) and supplementary data, *Science Express*, Jan. 3, 2002.
Le Tissier, P., et al., "Two sets of human-tropic pig retrovirus," *Nature*, 389(6652):681-682 (Oct. 16, 1997).
Lee, Y., et al., "The nuclear RNase III Drosha initiates microRNA processing," *Nature*, 425(6956):415-419 (Sep. 25, 2003).
Martin, U., et al., "Expression of pig endogenous retrovirus by primary porcine endothelial cells and infection of human cells," *Lancet*, 352(9129):692-694 (Aug. 29, 1998).
Onishi, A., et al., "Pig cloning by microinjection of fetal fibroblast nuclei," *Science*, 289(5482):1188-1190 (Aug. 18, 2000).
Paradis, K., et al., "Search for cross-species transmission of porcine endogenous retrovirus in patients treated with living pig tissue. The XEN 111 Study Group," *Science*, 285(5431):1236-1241 (Aug. 20, 1999).
Patience, C., et al., "Infection of human cells by an endogenous retrovirus of pigs," *Nat Med.*, Mar. 1997;3(3):282-286 (Mar. 1997).
Patience, C., et al., "No evidence of pig DNA or retroviral infection in patients with short-term extra-corporeal connection to pig kidneys," *Lancet*, 352(9129):699-701 (Aug. 29, 1998).
Phelps, C.J., et al., "Production of □1,3-galactosyltransferase-deficient pigs," *Science*, 299:411-414 (Jan. 17, 2003).
Polejaeva, I.A., et al., "Cloned pigs produced by nuclear transfer from adult somatic cells," *Nature*, 407:86-90 (Sep. 7, 2000).
Shastry, B.S., et al., "More to learn from gene knockouts," *Mol. Cell. Biochem.*, 136(2):171-182 (Jul. 27, 1994).
Takeuchi, Y., et al., "Host range and interference studies of three classes of pig endogenous retrovirus,"*J. Virol.*, 72(12):9986-91 (Dec. 1998).
Vickers, T.A., et al., "Efficient reduction of target RNAs by small interfering RNA and RNase H-dependent antisense agents. A comparative analysis," *J. Biol. Chem.*, 278(9):7108-7118 (Feb. 28, 2003; electronic publication Dec. 23, 2002).
Wilson, C.A., et al., "Type C retrovirus released from porcine primary peripheral blood mononuclear cells infects human cells," *J. Virol.*, 72(4):3082-3087 (Apr. 1998).
Yu, J.Y., et al., "Simultaneous inhibition of GSK3alpha and GSK3beta using hairpin siRNA expression vectors," *Molecular Therapy*, 7(2):228-236 (Feb. 2003).
Vickers, et al., "Efficient reduction of target RNAs by small interfering RNA and Rnase H-dependent antisense agents", J of Biological Chemistry, vol. 278, No. 9, Feb. 28, 2003, pp. 7108-7118.
Dieckhoff, A. Karlas et al., "Inhibition of Porcine Endogenous Retroviruses (PERVs) in Primary Porcine Cells by RNA Interference Using Lentiviral Vectors.", Archives of Virology, 152: 629-634. (2007).
Dieckhoff, B. et al., "Knockdown of Porcine Endogenous Retrovirus (PERV) Expression by PERV-Specific shRNA in Transgenic Pigs.", Xenotransplantation, 15: 36-45, (2008).
Elbashir, Sayda M. et al., "Analysis of Gene Function in Somatic Mammalian Cells Using Small Interfering RNAs.", Methods, 26: 199-213, (2002).
Miyagawa, Shuji et al., "Prevention of PERV Infections in Pig to Human Xenotransplantation by the RNA Interference Siilences Gene.", J. Biochem, 137: 503-508, (2005).
Miyagishi, Makoto et al., "U6 Promoter-Driven siRNAs with Four Uridine 3' Overhangs Efficiently Suppress Targeted Gene Expression in Mammalian Cells.", Nature Biotechnology, vol. 19, (May 2002).
Lee, Nan Sook et al., "Expression of Small Interfacing RNAs Targeted Against HIV-1 rev Transcripts in Human Cells.", Nature Biotechnology, vol. 19, (May 2002).
Ramsoondar, Jagdeece et al., "Production of Transgenic Pigs that Express Porcine Endogenous Retrovirus Small Interfering RNAs.", Xenotransplantation, 16: 164-180, (2009).
Office Action for European Patent Application No. 12153484.6, dated Mar. 29, 2017.
Miyagawa S et al: "A study of the prevention of PERV infection by siRNA", Xenotransplantation, Munksgaard, DE, vol. 10, No. 5, Sep. 1, 2003 (Sep. 1, 2003), p. 491.

* cited by examiner

Gene X
A. Promoter trap
Endogenous Promoter
Exon
Intron
Exon
Intron
Exon
a
b
+ iRNA vector
5' targeting sequence
3' targeting sequence
c
B. Gene trap
Exon
Intron
Exon
Intron
Exon
+ iRNA vector gt
5' targeting sequence
Splice acceptor site
3' targeting sequence
Exon
Intron
Exon
Intron
Exon

```
6364  6370        6380  6385  6390        6400        6410        6420        6430
|     |           |     |     |           |           |           |           |
CCTTAAGCTTCGCCTCCATCGCGTGGTTCCTTACTCTGTCAATAACTCCTCAAGTTAATGGTAAACGCCTT (SEQ ID No. 276)
CCTTAAGCTTCGCCTCCATCGCGTGGTTCCTTACTCTGTCAATAACTCCTCAAGTTAATGGTAAACGCCTT (SEQ ID No. 277)
CCTTAAGCTTCGCCTCCATCGCGTGGTTCCTTACTCTGTCAATAACTCCTCAAGTTAATGGTAAACGCCTT (SEQ ID No. 278)
CCTTAAGCTTCGCCTCCATCGCGTGGTTCCTTACTCTGTCAATAACTCCTCAAGTTAATGGTAAACGCCTT (SEQ ID No. 279)
CCTTAAGCTTCGCCTCCATCGCGTGGTTCCTTACTCTGTCAATAACTCCTCAAGTTAATGGTAAACGCCTT (SEQ ID No. 280)
CCTTAAGCTTCGCCTCCATCGCGTGGTTCCTTACTCTGTCAATAACTCCTCAAGTTAATGGTAAACGCCTT (SEQ ID No. 281)
CCTTAAGCTTCGCCTCCATCGCGTGGTTCCTTACTCTGTCAATAACTCCTCAAGTTAATGGTAAACGCCTT (SEQ ID No. 282)
CCTTAAGCTTCGCCTCCATCGCGTGGTTCCTTACTCTGTCAATAACCTCTCAGACTAATGGTATGCGCATA (SEQ ID No. 283)
CCTTAAGCTTCGCCTCCATCGCGTGGTTCCTTACTCTGTCAATAACCTCTCAGACTAATGGTATGCGCATA (SEQ ID No. 284)
CCTTAAGCTTCGCCTCCATCGCCTGGTTCCTTACTCTAACAATAACTCCCCAGGCCAGTAGTAAACGCCTT (SEQ ID No. 285)
CCTTAAGCTTCGCCTCCATCGCCTGGTTCCTTACTCTAACAATAACTCCCCAGGCCAGTAGTAAACGCCTT (SEQ ID No. 286)
CCTTAAGCTTCGCCTCCATCGCCTGGTTCCTTACTCTAACAATAACTCCCCAGGCCAGTAGTAAACGCCTT (SEQ ID No. 287)
CCTTAAGCTTCGCCTCCATCGCCTGGTTCCTTACTCTAACAATAACTCCCCAGGCCAGTAGTAAACGCCTT (SEQ ID No. 288)
CCTTAAGCTTCGCCTCCATCGCTTGGTTCCTTACTCTGTCAATAACTCCTCAAGTTAATGGTAAACGCCTT (SEQ ID No. 289)
```

Figure 8 Analysis of a portion of PERV env gene/alleles identified for targeting by )r targeting by siRNA strategy 1. *AATTGGAAAACTAACCATCCCCCTTTCTCGGAGGATCCCCAACGCCTCACGGGGTTGGTGGAGTCCCTTATGTTCTCTCACCAGCC*
(SEQ ID 290)
2. AATTGGAAAACTAACCATC (SEQ ID 291)
3. ATTGGAAAACTAACCATCC (SEQ ID 292)
4. TTGGAAAACTAACCATCCC (SEQ ID 293)
5. TGGAAAACTAACCATCCCC (SEQ ID 294)
GGAAAACTAACCATCCCCC (SEQ ID 295)
GAAAACTAACCATCCCCCT (SEQ ID 296)
AAAACTAACCATCCCCCTT (SEQ ID 297)
AAACTAACCATCCCCCTTT (SEQ ID 298)
10. AACTAACCATCCCCCTTTC (SEQ ID 299)
ACTAACCATCCCCCTTTCT (SEQ ID 300)
CTAACCATCCCCCTTTCTC (SEQ ID 301)
TAACCATCCCCCTTTCTCG (SEQ ID 302)
AACCATCCCCCTTTCTCGG (SEQ ID 303)
15. ACCATCCCCCTTTCTCGGA (SEQ ID 304)
CCATCCCCCTTTCTCGGAG (SEQ ID 305)
CATCCCCCTTTCTCGGAGG (SEQ ID 306)
ATCCCCCTTTCTCGGAGGA (SEQ ID 307)
TCCCCCTTTCTCGGAGGAT (SEQ ID 308)
20. CCCCCTTTCTCGGAGGATC (SEQ ID 309)
CCCCTTTCTCGGAGGATCC (SEQ ID 310)
CCCTTTCTCGGAGGATCCC (SEQ ID 311)
CCTTTCTCGGAGGATCCCC (SEQ ID 312)
CTTTCTCGGAGGATCCCCA (SEQ ID 313)
25. TTTCTCGGAGGATCCCCAA (SEQ ID 314)
TTCTCGGAGGATCCCCAAC (SEQ ID 315)
TCTCGGAGGATCCCCAACG (SEQ ID 316)
CTCGGAGGATCCCCAACGC (SEQ ID 317)
TCGGAGGATCCCCAACGCC (SEQ ID 318)
30. CGGAGGATCCCCAACGCCT (SEQ ID 319)
GGAGGATCCCCAACGCCTC (SEQ ID 320)
GAGGATCCCCAACGCCTCA (SEQ ID 321)
AGGATCCCCAACGCCTCAC (SEQ ID 322)
GGATCCCCAACGCCTCACG (SEQ ID 323)
35. GATCCCCAACGCCTCACGG (SEQ ID 324)
ATCCCCAACGCCTCACGGG (SEQ ID 325)
TCCCCAACGCCTCACGGGG (SEQ ID 326)
CCCCAACGCCTCACGGGGT (SEQ ID 327)
CCCAACGCCTCACGGGGTT (SEQ ID 328)
40. CCAACGCCTCACGGGGTTG (SEQ ID 329)
CAACGCCTCACGGGGTTGG (SEQ ID 330)
AACGCCTCACGGGGTTGGT (SEQ ID 331)
ACGCCTCACGGGGTTGGTG (SEQ ID 332)
CGCCTCACGGGGTTGGTGG (SEQ ID 333)
45. GCCTCACGGGGTTGGTGGA (SEQ ID 334)
CCTCACGGGGTTGGTGGAG (SEQ ID 335)
CTCACGGGGTTGGTGGAGT (SEQ ID 336)
TCACGGGGTTGGTGGAGTC (SEQ ID 337)
CACGGGGTTGGTGGAGTCC (SEQ ID 338)
50. ACGGGGTTGGTGGAGTCCC (SEQ ID 339)
CGGGGTTGGTGGAGTCCCT (SEQ ID 340)
GGGGTTGGTGGAGTCCCTT (SEQ ID 341)
GGGTTGGTGGAGTCCCTTA (SEQ ID 342)
GGTTGGTGGAGTCCCTTAT (SEQ ID 343)
55. GTTGGTGGAGTCCCTTATG (SEQ ID 344)
TTGGTGGAGTCCCTTATGT (SEQ ID 345)
TGGTGGAGTCCCTTATGTT (SEQ ID 346)
(SEQ ID 347) GGTGGAGTCCCTTATGTTC
(SEQ ID 348) GTGGAGTCCCTTATGTTCT
60. (SEQ ID 349) TGGAGTCCCTTATGTTCTC
(SEQ ID 350) GGAGTCCCTTATGTTCTCT
(SEQ ID 351) GAGTCCCTTATGTTCTCTC
(SEQ ID 352) AGTCCCTTATGTTCTCTCA
(SEQ ID 353) GTCCCTTATGTTCTCTCAC
65. (SEQ ID 354) TCCCTTATGTTCTCTCACC
(SEQ ID 355) CCCTTATGTTCTCTCACCA
(SEQ ID 356) CCTTATGTTCTCTCACCAG
(SEQ ID 357) CTTATGTTCTCTCACCAGC
69. (SEQ ID 358) TTATGTTCTCTCACCAGCC

Figure 9. Representative sixty-eight potential 19 base inhibitory RNA targets for a semi-conserved region of PERV.

Figure 10

1. AATTGGAAAACTAACCATCCCCCTTTCTCGGAGGATCCCCAACGCCTCACGGGGTTGGTGGAGTCCCTTATGTTCTCTCACCAGCC (SEQ ID 359)
2. AATTGGAAAACTAACCATC (SEQ ID 360)
3. ATTGGAAAACTAACCATCC (SEQ ID 361)
4. TTGGAAAACTAACCATCCC (SEQ ID 362)
5. TGGAAAACTAACCATCCCC (SEQ ID 363)
GGAAAACTAACCATCCCCC (SEQ ID 364)
GAAAACTAACCATCCCCCT (SEQ ID 365)
AAAACTAACCATCCCCCTT (SEQ ID 366)
AAACTAACCATCCCCCTTT (SEQ ID 367)
10. AACTAACCATCCCCCTTTC (SEQ ID 368)
ACTAACCATCCCCCTTTCT (SEQ ID 369)
CTAACCATCCCCCTTTCTC (SEQ ID 370)
TAACCATCCCCCTTTCTCG (SEQ ID 371)
AACCATCCCCCTTTCTCGG (SEQ ID 372)
15. ACCATCCCCCTTTCTCGGA (SEQ ID 373)
CCATCCCCCTTTCTCGGAG (SEQ ID 374)
CATCCCCCTTTCTCGGAGG (SEQ ID 375)
ATCCCCCTTTCTCGGAGGA (SEQ ID 376)
TCCCCCTTTCTCGGAGGAT (SEQ ID 377)
20. CCCCCTTTCTCGGAGGATC (SEQ ID 378)
CCCCTTTCTCGGAGGATCC (SEQ ID 379)
CCCTTTCTCGGAGGATCCC (SEQ ID 380)
CCTTTCTCGGAGGATCCCC (SEQ ID 381)
CTTTCTCGGAGGATCCCCA (SEQ ID 382)
25. TTTCTCGGAGGATCCCCAA (SEQ ID 383)
TTCTCGGAGGATCCCCAAC (SEQ ID 384)
TCTCGGAGGATCCCCAACG (SEQ ID 385)
CTCGGAGGATCCCCAACGC (SEQ ID 386)
TCGGAGGATCCCCAACGCC (SEQ ID 387)
30. CGGAGGATCCCCAACGCCT (SEQ ID 388)
GGAGGATCCCCAACGCCTC (SEQ ID 389)
GAGGATCCCCAACGCCTCA (SEQ ID 390)
AGGATCCCCAACGCCTCAC (SEQ ID 391)
GGATCCCCAACGCCTCACG (SEQ ID 392)
35. GATCCCCAACGCCTCACGG (SEQ ID 393)
ATCCCCAACGCCTCACGGG (SEQ ID 394)
TCCCCAACGCCTCACGGGG (SEQ ID 395)
CCCCAACGCCTCACGGGGT (SEQ ID 396)
CCCAACGCCTCACGGGGTT (SEQ ID 397)
40. CCAACGCCTCACGGGGTTG (SEQ ID 398)
CAACGCCTCACGGGGTTGG (SEQ ID 399)
AACGCCTCACGGGGTTGGT (SEQ ID 400)
ACGCCTCACGGGGTTGGTG (SEQ ID 401)
CGCCTCACGGGGTTGGTGG (SEQ ID 402)
45. GCCTCACGGGGTTGGTGGA (SEQ ID 403)
CCTCACGGGGTTGGTGGAG (SEQ ID 404)
CTCACGGGGTTGGTGGAGT (SEQ ID 405)
TCACGGGGTTGGTGGAGTC (SEQ ID 406)
CACGGGGTTGGTGGAGTCC (SEQ ID 407)
50. ACGGGGTTGGTGGAGTCCC (SEQ ID 408)
CGGGGTTGGTGGAGTCCCT (SEQ ID 409)
GGGGTTGGTGGAGTCCCTT (SEQ ID 410)
GGGTTGGTGGAGTCCCTTA (SEQ ID 411)
GGTTGGTGGAGTCCCTTAT (SEQ ID 412)
55. GTTGGTGGAGTCCCTTATG (SEQ ID 413)
TTGGTGGAGTCCCTTATGT (SEQ ID 414)
TGGTGGAGTCCCTTATGTT (SEQ ID 415)
GGTGGAGTCCCTTATGTTC (SEQ ID 416)
(SEQ ID 417) GTGGAGTCCCTTATGTTCT
60. (SEQ ID 418) TGGAGTCCCTTATGTTCTC
(SEQ ID 419) GGAGTCCCTTATGTTCTCT
(SEQ ID 420) GAGTCCCTTATGTTCTCTC
(SEQ ID 421) AGTCCCTTATGTTCTCTCA
(SEQ ID 422) GTCCCTTATGTTCTCTCAC
65. (SEQ ID 423) TCCCTTATGTTCTCTCACC
(SEQ ID 424) CCCTTATGTTCTCTCACCA
(SEQ ID 425) CCTTATGTTCTCTCACCAG
(SEQ ID 426) CTTATGTTCTCTCACCAGC
(SEQ ID 427) TTATGTTCTCTCACCAGCC
70. CCTTGGTGTTATCTGTCGAATAAGGGTCATAAAAATACACACAACCTCACAGGGTTGGTGGAGGATGAAGTGAGACAATGCATTCA (SEQ ID 428)

Target: 5'AATTGGAAAACTAACCATC 3' (SEQ ID NO. 429)

iRNA: 5'($N_Y$)AAUUGGAAAACUAACCAUC($N_Y$)GAUGGUUAGUUUUCCAAUU($N_Y$) 3'
(SEQ ID NO. 430)

Figure 11

***gag* consensus sequence sequence** (target sites are shown in bold):

CTTGTGCGTCCTTGTCTACAGTTTTAATATGGGACAGACGGTGACNACCCCCCTTAGTTTGACTCTCGACCATTGGACTGAAGTTAAATCCAGGGCT
CATAATTTGTCAGTTCAGGTTAAGAAGGGACCTTGGCAGACTTTCTGTGCCTCTGAATGGCCNACATTCGATGTTGGATGGCCATCAGAGGGGACCT
TTAATTCTGAGATTATCCTGGCTGTTAAAGCAATTATTTTTCAGACTGGACCCGGCTCTCATCCTGATCAGGAGCCCTATATCCTTACGTGGCAAGA
TTTGGCAGANGATCCTCCGCCATGGGTTAAACCATGGCTNAATAANCCAAGAAAGCCAGGTCCCCGAATNCTGGCTCTTGGAGAGAAAAACAAACAC
TCGGCCGAAAAAGTCAAGCCCTCTCCTCNTATCTACCCCGAGATTGAGGAGCCGCCGGCTTGGCCGGAACCCCAATCTGTTCCCCCACCCCCTTATC
CGGCACAGGGTGCTGCGAGGGGACCCTCTGCCCCTCCTGGAGCTCCGGCGGTGGAGGGACCTGCTGCAGGGACTCGGAGCCGGAGGGGCGCCACCCC
GGAGCGGACAGACGAGATCGCGACATTACCGCTGCGCACCTATGGCCCTCCCATGCCGGGGGGCCAATTGCAGCCCCTCCAGTATTGGCCCTTTTCT
TCTGCAGATCTCTATAATTGGAAAACTAACCATCCCCCTTTCTCGGAGGATCCCCAACGCCTCACGGGGTTGGTGGAGTCCCTTATGTTCTCTCACC
AGCCTACTTGGGATGATTGTCAACAGCTGCTGCAGACACTCTTCACAACCGAGGAGCGAGAGAGAATTCTGTTAGAGGCTAGAAAAAATGTTCCTGG
GGCCGACGGGCGACCCACGCAGTTGCAAAATGAGATTGACATGGGATTTCCCTTGACTCGCCCCGGTTGGGACTACAACACGGCTGAAGGTAGGGAG
AGCTTGAAAATCTATCGCCAGGCTCTGGTGGCGGGTCTCCGGGGCGCCTCAAGACGGCCCACTAATTTGGCTAAGGTAAGAGAGGTGATGCAGGGAC
CGAATGAACCTCCCTCNGTTTTTCTTGAGAGGCTCATGGAAGCCTTCAGGCGGTTCACCCCTTTTGATCCTACCTCAGAGGCCCAGAAAGCCTCAGT
GGCTCTGGCCTTCATAGGACAGTCAGCCCTGGATATCAGAAAGAAACTTCAGAGACTGGAAGGGTTACAGGAGGCTGAGTTACGTGATCTAGTGAGA
GAGGCAGAGAAGGTGTATTACAGAAGGGAGACAGAAGAGGAGAAGGAACAGAGAAAAGAAAAGGAGAGAGAAGAAAGGGAGGAAAGACGTGATAGAC
GGCAAGAGAAGAATTTGACTAAGATCTTGGCCGCAGTGGTTGAAGGGAAGAGCAGCAGGGAGAGAGAGAGAGAGATTTTAGGAAAATTAGGTCAGGCCC
TAGACAGTCAGGGAACCTGGGCAATAGGACCCCACTCGACAAGGACCAGTGTGCGTATTGTAAAGAAAAAGGACACTGGGCAAGGAACTGCCCCAAG
AAGGGAAACAAAGGACCGAAGGTCCTAGCTCTAGAAGAAGATAAAGATTAG (SEQ ID NO. 431)

Sequence for a radial cluster of inhibitory RNA (coding strands shown in bold, antisense strands shown in italics, loops are underlined, tethers and tail shown in lowercase):

GTTAAATCCAGGGCTCATAATTTCAAGAGA*ATTATGAGCCCTGGATTTAAC*ttcaaaTTGGAAAACTAACCATCCCCCTTCAAGAG
A*GGGGGATGGTTAGTTTTCCAA*ttataaCAACCGAGGAGCGAGAGAGAATTCAAGAGA*TTCTCTCTCGCTCCTCGGTTG*tgaaaGC
CTTCAGGCGGTTCACCCCTTTCAAGAGA*AGGGGTGAACCGCCTGAAGGC* ggcaaGAGAAGAATTTGACTAAGATCTTCAAGAGA*GA*
*TCTTAGTCAAATTCTTCTC*ttttt (SEQ ID NO. 432)

Sequence for an asymmetric bubble cluster of inhibitory RNA (coding strands shown in bold, antisense strands shown in italics, bubbles are underlined, tail shown in lowercase):

GTTAAATCCAGGGCTCATAATTTCAAGAGATTGGAAAACTAACCATCCCCCTTCAAGAGACAACCGAGGAGCGAGAGAGAATTCAA
GAGAGCCTTCAGGCGGTTCACCCCTTTCAAGAGAGAGAAGAATTTGACTAAGATCTTCAAGAGA*GATCTTAGTCAAATTCTTCTCA*
*GGGGTGAACCGCCTGAAGGCTTCTCTCTCGCTCCTCGGTTGGGGGGATGGTTAGTTTTCCAAATTATGAGCCCTGGATTTAAC*ttt
tt (SEQ ID NO. 433)

Sequence for a linear cluster of inhibitory RNA (coding strands shown in bold, antisense strands shown in italics, bubbles are underlined, loop shown in uppercase, tail shown in lowercase):

GTTAAATCCAGGGCTCATAATTTCCTTGGAAAACTAACCATCCCCCTTCCCAACCGAGGAGCGAGAGAGAATTCCGCCTTCAGGCG
GTTCACCCCTTTCCGAGAAGAATTTGACTAAGATCTTCAAGAGA*GATCTTAGTCAAATTCTTCTC*AACC*AGGGGTGAACCGCCTGA*
*AGGC*AACC*TTCTCTCTCGCTCCTCGGTTG*AACC*GGGGGATGGTTAGTTTTCCAAAACCATTATGAGCCCTGGATTTAAC*ttttt
(SEQ ID NO. 434)

Sequence for two complex cluster of inhibitory RNAs (coding strands shown in bold; antisense strands shown in italics; tethers, bubbles and loops are underlined; tail shown in lowercase):

GTTAAATCCAGGGCTCATAATTTGGAAAACTAACCATCCCCCTTCAAGAGA*GGGGGATGGTTAGTTTTCCAA*CAACCGAGGAGCGA
GAGAGAAGCCTTCAGGCGGTTCACCCCTTTCAAGAGA*AGGGGTGAACCGCCTGAAGGC*GAGAAGAATTTGACTAAGATCTTCAAGA
GA*GATCTTAGTCAAATTCTTCTCTTCTCTCTCGCTCCTCGGTTGATTATGAGCCCTGGATTTAAC*ttttt (SEQ ID NO. 435)

GTTAAATCCAGGGCTCATAATTTCCTTGGAAAACTAACCATCCCCCTCAACCGAGGAGCGAGAGAGAATTCAAGAGA*TTCTCTCTC*
*GCTCCTCGGTTG*TGCCTTCAGGCGGTTCACCCCTTTCCGAGAAGAATTTGACTAAGATCTTCAAGAGA*GATCTTAGTCAAATTCTT*
*CTC*TTCC*AGGGGTGAACCGCCTGAAGGC*T*GGGGGATGGTTAGTTTTCCAA*T*ATTATGAGCCCTGGATTTAAC*ttttt (SEQ ID
NO. 436)

Figure 12

USE OF INTERFERING RNA IN THE PRODUCTION OF TRANSGENIC ANIMALS

This patent application claims priority to U.S. Ser. No. 60/523,938, filed Nov. 21, 2003, the contents of which are herein incorporated by reference.

FIELD OF THE INVENTION

The invention provides cells and animals, as well as methods of producing cells and animals, that express at least one interfering RNA molecule to regulate the expression of a specific gene or family of genes. The invention further provides novel iRNA molecules, as well as DNA templates for producing iRNA molecules.

BACKGROUND OF THE INVENTION

To exploit the potential of transgenic cells and animals in both research and therapeutic use, practical techniques must exist to control the expression of exogenous and endogenous gene transcription, and that can be adapted to produce animals in which either endogenous or exogenous gene function is heritably eliminated. Current techniques are limited in their ability to meet these requirements.

Targeted disruption of gene function is presently accomplished via techniques including microinjection or transfection of exogenous inhibitory nucleic acids, mutagenesis, and homologous recombination. Traditionally, a selected gene has been disrupted in cells by recombination with a targeting vector or by random disruption with an integration vector. Cells in which the genes of interest are disrupted can be confirmed using, for example, a selection marker inserted into the genome, or by functionally testing for the gene of interest. Once the disruption has been confirmed in the cell, a heterozygous animal can be produced by cloning via somatic cell nuclear transfer or production of offspring from embryonic stem cells. The heterozygous animal can then sometimes be bred to produce homozygous animals in which the desired gene disruption is present in each allele so that the full gene complement is rendered non-functional. The heterozygous animal can also be subject to further genetic targeting or mutagenesis. (Shastry et al. *Mol. Cellul. Biochem.* 136:171-182 (1994) and Galli-Taliadoros et al. (1995) *J. Immunol. Meth.* 181:1-15 (1995)).

Although potentially valuable, traditional techniques require time consuming and laborious production and screening programs, and demonstrate a very low success rate. Furthermore, the commonly used techniques are limited to organisms which are known to be receptive to genetic manipulation (where, for example, selectable marker genes, the ability to control genetic segregation, or sexual reproduction have been proven). Because of their low success rate, these techniques are also limited to applications in which a large number of cells or organisms can be sacrificed to isolate the desired phenotype. In addition, the known techniques are not readily applied to the modulation of exogenous genes, such as those introduced to a cell by viral infection, or to genes with redundant functions which do not lead to different assessable phenotypes. Similarly, because the gene disruption must be maintained in a homozygous state to obtain the desired phenotype, this technique cannot be widely adopted due to the required inbreeding. Any application that benefits from genetic diversity is not amenable to current methodologies.

An alternative technology for disrupting the expression of a gene has recently emerged. RNA interference (iRNA) was' originally described in the model organism *C. elegans* (Fire et al., Nature 391:806-811 (1998); U.S. Pat. No. 6,506,559 to Fire et al.). Genetic and biochemical data, primarily arising from studies in lower eukaryotes, indicate possible mechanisms for RNA interference. Small, noncoding RNA molecules mediate a posttranscriptional gene-silencing mechanism that regulates the expression of developmental genes by inhibiting the translation of target mRNAs. This mechanism is common to plants, fungi, and animals, and the generation of these microRNAs (miRNAs, also known as small inhibitory RNAs or siRNAs) involves a series of sequential steps, where primary RNA transcripts (pri-miRNAs) are cleaved in the nucleus to smaller pre-miRNAs. RNase III, such as Drosha, is a nuclease that executes the initiation step of miRNA processing in the nucleus (Lee et al (25 Sep. 2003) Nature 425, 415-419). Drosha cleaves pri-miRNA to release pre-miRNA. These are transported to the cytosol where Dicer, a member of the RNAse III nuclease family, further processes them to yield mature miRNAs from the pre-miRNAs. MiRNAs associate with multicomponent ribonucleoprotein complexes. or RISCs, which effect the silencing of the target mRNA molecules (Holding, C. "Modeling miRNA mechanisms", The Scientist, Sep. 25, 2003). RISC binds to only one strand of the double stranded miRNA molecule. The other strand is degraded by the cell.

In plants, insects, and nematodes, RNA interference is the only practical method of generating targeted knockout (KO) genotypes. However, until recently. RNA interference technology did not appear to be applicable to mammalian systems. In mammals, dsRNA activates dsRNA-activated protein kinase (PKR), resulting in an apoptotic cascade and cell death (Der et al (1997) Proc Nati Acad Sci USA. April 1; 94(7):3279-83.). Thus, RNA interference appeared to be limited to genetic modulation of lower eukaryotes. However, Elbashir and colleagues in 2001 discovered that PKR activation requires dsRNA longer than about 30 base pairs. Therefore, short RNA sequences can be introduced into a mammalian cell without initiating an apoptotic cascade. Based on data developed in *C. elegans*, siRNA sequences of 21-23 base pairs were known to be effective in limiting gene expression. Therefore, by providing these sequences in isolation, it became possible to target reduced gene expression while circumventing the cell's natural defense mechanism (Elbashir et al., (2001) Nature 411:494-498). Within 3 months of the Elbashir et al. publication, a range of siRNA molecules, all less than 30 base pairs long, had been demonstrated to effectively reduce gene expression in mammalian cells (Caplen et al. (2001) Proc Natl Acad Sci 98(17): 9742-9747). These double stranded siRNA molecules contained a sense strand and an antisense strand. Subsequent to these discoveries, several groups have identified some additional strategies to stabilize double stranded interfering RNA molecules, as well as create different types of iRNA molecules, to introduce them into cells.

U.S. Pat. No. 6,506,559 to Fire et al claims methods to inhibit expression of a target gene in a cell in vitro by introduction of a RNA into the cell in an amount sufficient to inhibit expression of a target gene, wherein the RNA is a double-stranded molecule with a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide strands are separate complementary strands that hybridize to each other to form said double-stranded molecule, and the double-stranded molecule inhibits expression of the target gene.

PCT Publication No. WO 03/012052 by Caplen et al. discloses small synthetic double stranded RNA molecules, fifteen to forty nucleotides in length, with a 3' or 5' overhang of about 0-5 nucleotides on each strand, wherein the sequence of the double stranded RNA is substantially identical to a portion of mRNA or transcript of the target gene. This publication also discloses arrays of siRNA that can be used to test the effects of gene 'silencing' on cell function.

U.S. Publication No. 2003/0166282 by Brown et al. discloses high potency siRNA molecules. This publication describes methods of synthesis, such as enzymatic, of siRNA molecules, as well as the use of modified nucleotide analogs in the siRNA molecule.

The delivery of small, double stranded RNA molecules into cells is not amenable to in vivo use, in part due to inefficiency and uncertainty of the delivery of the molecules and also because it results in only transient expression of the iRNA. The next advance in iRNA technology was the production of iRNA molecules inside the cell from DNA templates to obtain stable expression of the iRNA molecule in a cell.

U.S. Pat. No. 6,573,099 and PCT Publication No. WO 99/49029 by Benitec Australia Ltd. claim isolated genetic constructs which are capable of delaying, repressing or otherwise reducing the expression of a target gene in an animal cell which is transfected with the genetic construct, wherein the genetic construct contains at least two copies of a structural gene sequence. The structural gene sequence is described as a nucleotide sequence which is substantially identical to at least a region of the target gene, and wherein at least two copies of the structural gene sequence are placed operably under the control of a single promoter sequence such that at least one copy of the structural gene sequence is placed operably in the sense orientation under the control of the promoter sequence.

In 2002, Brummelkamp et al. (Science (2002) 296: 550-553) reported a stable vector system for expressing siRNA in mammalian cells. The vector contained an RNA polymerase III H1 promoter, followed by a siRNA sequence and a poly-T tail (pSUPER). The siRNA contained a sense strand, a loop sequence of five, seven or nine nucleotides and an antisense sequence. Also in 2002, Brummerlkamp et al (Cancer Cell (published online Aug. 22, 2002) reported the use of a retroviral to express siRNA (pRETRO-SUPER).

PCT Publication WO 03/006477 by the University of Massachusetts discloses RNA hairpins structures that provide increased stability to the dsRNA. The hairpins, made of a stem complementary to a target and a second stem complementary to it and a loop portion connecting the two, are putatively cleaved inside the cell to provide a duplexed mRNA. Such dsRNA molecules are substrates for the Dicer enzyme, as described above. The publication also discloses expression constructs containing DNA encoding such siRNA molecules under the control of exogenous promoters, such as Pol II or PolIII.

U.S. Publication No. 2003/0108923 by Tuschl et al describes isolated RNA from about 21 to about 23 nucleotides in length that mediates RNA interference of an mRNA to which it corresponds, as well as isolated DNA encoding the same.

PCT Publication No. WO 03/023015 by the California Institute of Technology discloses a method of expressing an siRNA in a cell using a retroviral vector system. Further, this publication indicates that siRNA expression may be useful for the treatment or prevention of infection by inhibiting aspects of the life cycle of a pathogen through interference with a target nucleic acid in a viral genome or a host cell gene that is necessary for viral replication. This publication is drawn specifically to the treatment of human viral infections. The constructs disclosed include at least one RNA Pol III promoter, a RNA sense region, a RNA antisense region and a loop region separating the sense and antisense regions in different orientations.

U.S. Patent Application No. 2003/0148519 by Engelke, et al. describes hairpin RNA structures for expression in a cell. This application describes expression cassettes for expressing siRNA and RNA hairpins in a cells, driven off of exogenous promoter elements, such as the U6 RNA polymerase promoter.

PCT Publication No. WO 03/056012 by Cancer Research Technology, Ltd. describes a system for stable expression of siRNA in a cell. The system comprises a RNA polymerase III (Pol III) promoter, a region encoding a siRNA, and a transcriptional termination element comprising five consecutive thymine residues. This publication discloses that multiple siRNA sequences may be used, however it is suggested that if these are used, they should be expressed as separate transcripts.

The next advance in the development of iRNA technology was to create transgenic animals that are capable of producing iRNA molecules from DNA templates and passing them on to their progeny. Providing heritable expression of iRNA molecules has become a principal research goal. The production of cells and animals in which a gene function is effectively eliminated provides both valuable research tools and is invaluable to realize the potential of xenotransplantation, therapeutic cloning, and genetically enhanced agriculture.

In 2002, Hasuwa et al (FEBS Letters 532: 227-230) reported a transgene-based RNAi system using an enhanced green fluorescent protein (eGFP) siRNA driven by a PolII promoter in mice and rats. Specifically, the promoter used was the H1 promoter and the siRNA region contained sense sequence, a connecting sequence and an antisense sequence to eGFP. This construct allowed for the random integration of the DNA into the animals genome, which was expressed ubiquitously.

In 2003, Carmell et al (Nature Structural Biology 10(2) 91-92) reported the germline transmission of RNAi in mice via the random insertion of a transgene containing an exogenous promoter and siRNA sequence. Also in 2003, Kunath et al (Nature Biotechnology May 2003 21: 559-561) reported the generation of knockdown murine embryonic stem (ES) cell lines with transgenic short-hairpin RNA (shRNA) via random integration. A linearized transgene containing the H1 RNA polymerase promoter, followed by shRNA sequence (sense and antisense sequence separated by a seven base pair spacer), followed by five thymidines to terminate transcription was introduced via electroporation into the ES cells to achieve random integration of the construct, resulting in a genetic null phenotype for the target gene. Kunath et al. discuss the benefit of assaying gene function in vivo without gene targeting through siRNA technology.

PCT Publication No. WO 03/059923 by Tranzyme, Inc. and Ozgene Pty., Ltd. describes the production of genetically modified animals using lentiviral vectors. In particular, the vectors described include selectable markers driven off of an exogenous promoter sequence for random integration. The publication describes the nucleotide sequence of interest contained in the gene transfer vector that includes a poly-nucleotide sequence, which expresses an RNA molecule capable of mediating RNA interference.

WO 03/056022 by Oxford Biomedica, Ltd. describes methods of producing transgenic cells using lentiviral vectors for random insertion into the genome. The nucleotides that can be used include an siRNA and an exogenous promoter, such as a RNA polymerase promoter.

In 2003, it was reported that iRNA targeting strategies were developed to target two genes simultaneously with expression vectors under the control of exogenous promoters for random integration (Yu et al (2003) Molecular Therapy 7: 228-236, Anderson et al (2003) Oligonucleotides, 13: 303-312). Karlas et al (2004 Virology 325: 18-23) discloses inhibition of porcine endogenous retrovruses by iRNA using iRNA molecules corresponding to different parts of the PERV gene. The iRNA molecules were expressed as short hairpin RNAs under the control of an exogenous polymerase III promoter in vitro for random integration.

U.S. Patent Publicaton No. 2004/0045043 by Finney and Lofquist, entitled, "Compositions and Methods for Generating Conditional Knockouts" discloses methods to identify disease-associated genes, produce animal models of disease and identify drug candidates through conditional knockout strategies. The publication discloses the use of homologous recombination to engineer siRNA targets (not siRNA molecules) into endogenous genes.

While these initial strategies for providing animals with heritable transgenes have been developed, additional improvements are desired to further control protein expression and minimize adverse effects on the host cell or organism.

It is therefore an object of the present invention to provide improved methods to repress the expression of proteins in cells and animals.

It is also an object of the present invention to provide cells and animals with improved ability to repress the expression of a target protein in cells and animals and optimally with minimal disruption of other normal processes.

It is yet another object of the present invention to provide new tools to accomplish the effective repression of proteins.

It is another object of the invention to apply new techniques to repress protein to specific areas of long felt need.

SUMMARY OF THE INVENTION

Improved techniques for the repression of expression of protein in cells and animals are provided. In one embodiment, the invention provides new methods and materials for the repression of expression of a protein that include the use of targeted insertion vectors which have a minimal effect on the homeostasis of the cell or animal. In particular, DNA templates that encode an iRNA to repress a target protein are provided that (i) use the endogenous regulatory elements of the cell, such as the endogenous promoter, (ii) are targeted into an intronic sequence of a gene, and/or (iii) do not disrupt the homeostasis of the cell. In a second embodiment, new iRNA molecules and DNA sequences encoding them are provided, as well as methods to produce the same. In one example, an iRNA molecule is provided in which both strands are complementary to a target mRNA (referred to herein as "cTarget") of a protein to be repressed, which can be in the form of a hairpin. In a third embodiment, iRNA molecules that regulate the expression of specific genes or family of genes that share a common, homologous sequence, such that the expression of the genes can be functionally eliminated, are provided.

In one aspect of the present invention, methods are provided to produce transgenic cells and animals that express iRNA molecules at a predetermined location, as well as the cells and animals produced thereby. In one embodiment, DNA templates or constructs, which produce iRNA molecules, that contain sequence that targets a particular location in the genome can be introduced into cells, such that the DNA templates are under the control of endogenous regulatory elements of the cell, such as the promoter and/or other regulatory elements of the gene. In another embodiment, the DNA templates can be targeted such that expression of the iRNA molecule can be achieved without disrupting the endogenous gene function. In one embodiment, the DNA templates can be in the form of vectors. The vectors can be introduced into the cells directly, or linearized prior to introduction into the cell. In another embodiment, the DNA templates can be synthesized as oligonucleotides and introduced into cells. In one embodiment, the DNA templates can integrate into the genome of the cell via targeted integration. The targeted integration can be via homologous recombination. The DNA templates can contain 5' and 3' targeting sequences that are homologous to the target gene to allow for targeted insertion. The DNA templates can be inserted via homologous recombination into, for example, a housekeeping gene such that the expression of the iRNA molecule is under the control of the associated promoter of the housekeeping gene. Alternatively, the DNA templates can be inserted via homologous recombination into a gene that is only expressed in particular cells or organs such that the expression of the iRNA molecule is under the control of the associated promoter of the cell or organ specific gene. Such templates can be introduced into mammalian cells, such as human, porcine, ovine or bovine cells, bacterial cells, such as *E. Coli*, and/or yeast cells.

In other embodiments, the DNA templates/constructs used to produce the iRNA molecules can be designed to integrate into exons of the target gene. In another embodiment, the DNA templates used to produce the iRNA molecules can be designed to integrate into introns of the target gene, such as, for example, into a non-essential location of an endogenous intron. The DNA templates can be targeted such that the endogenous promoter of the target gene directs transcription of the exogenous DNA template. In still further embodiments, the DNA templates used to produce the iRNA molecules can be embedded in engineered introns for integration into introns or exons of target genes. These engineered introns can be derived from any endogenous intron. In one embodiment, the endogenous intron can be reduced to its minimal functional components. In another embodiment, restriction sites can be added into the engineered intron. In one embodiment, the restriction enzyme sites allow for placement of the DNA template into the engineered intron. In further embodiments, the synthetic introns can be inserted into endogenous exons or introns without disrupting the function of the endogenous gene.

In another embodiment, methods are provided to produce cells and animals in which interfering RNA molecules are expressed to regulate the expression of target genes. Methods according to this aspect of the invention can include: (i) identifying at least one iRNA sequence that is complementary to the target mRNA; (ii) manufacturing a DNA construct encoding the iRNA sequence; (iii) identifying a target endogenous nucleic acid sequences in a cell; (iv) introducing the DNA construct into the cell wherein the DNA construct further contains flanking sequence homologous to the endogenous target gene; and/or (v) expressing the DNA construct in the cell under conditions such that the iRNA molecule binds to the target mRNA sequence, thereby regulating expression of one or more target mRNAs. In one embodiment, the present invention provides methods of producing non-human transgenic animals that heritably express iRNA molecules that regulate the expression of one or more target genes. In one embodiment, the animals can be produced via somatic cell nuclear transfer. The somatic cell can be engineered to express the iRNA molecule by any of the techniques described herein.

In another aspect of the present invention, ds iRNA molecules are provided in which both strands are complementary to the mRNA target sequence (referred to herein as "cTarget"). Due to the intracellular processing of double stranded iRNA (ds iRNA) molecules, only one of the two strands of the molecule actually functions to inhibit the target mRNA. The present invention provides novel ds iRNA molecules in which both strands can be functional, i.e. can bind to the target RNA sequence. Prior to this discovery, the design of iRNA molecules was such that only one strand of the iRNA molecule was functional (i.e. typically one strand was substantially identical to the target sequence, or the "sense" sequence, and the other strand was the functional strand that was complementary to the target sequence, or the "antisense" sequence), and thus if the nonfunctional strand was processed in vivo, no inhibitory effect was generated.

In one embodiment, the ds iRNA molecules can contain a first cTarget strand of nucleotides, which hybridizes to a second cTarget strand sequence. In one embodiment, the cTarget strands can contain at least fifteen, sixteen, seventeen, eighteen, nineteen, twenty, twenty-one, twenty-two, twenty-three, twenty-four or twenty-five nucleotides. To obtain such iRNA molecules, segments of cTarget sequence must be evaluated to determine the portions which will hybridize to form a ds iRNA molecule. In one embodiment, segments of cTarget sequence at least 100, 200 or 300 nucleotides in length can be analyzed to determine areas of self-hybridization. In one embodiment, these sequences can be entered into a computer program which detects areas of self-hybridization, such as, in one specific embodiment, the MFold software, as described in M. Zuker Mfold web server for nucleic acid folding and hybridization prediction. Nucleic Acids Res. 31 (13) 3406-15, (2003), [http://www-.bioinfo.rpi.edu/applications/mfold/old/rna/form1.cgi]. In one embodiment, the cTarget sequences can be complementary to the same target sequence. In another embodiment, the cTarget sequences can be complementary to different target sequences. In a further embodiment, the ds iRNA molecule can be palindromic cTarget sequences, in which both strands are identical or functionally identical. In one embodiment, a cTarget sequence can be analyzed to identify palindromic sequences, for example, through the use of a computer program, such as DNA Strider.

In other embodiments, DNA templates are provided, which produce ds iRNA molecules that are two strands of cTarget sequence. In one embodiment, DNA templates are provided that produce iRNA precursors. In one embodiment, a spacer nucleotide sequence can separate the two cTarget sequences. In another embodiment, a nucleotide sequence is provided that contains a first strand complementary to a target and a second strand complementary to a target, which substantially hybridizes to the first strand and a spacer sequence connecting the two strands. In one embodiment, the spacer can form a loop or hairpin structure. Such hairpins can be cleaved inside the cell to provide a duplexed mRNA containing the two stems. In one embodiment, the spacer nucleotide sequence can be at least 2, 3, 4, 5, 6, 7, 8, 9, 10 or 15 nucleotides in length. In another embodiment, the spacer sequence can contain nucleotides that form a loop structure, such as a mir30 loop structure, such as disclosed in Seq ID No 4 or any of the sequences described herein. In one embodiment the loop structure can contain a first nucleotide sequence, such as at least two, three, four or five nucleotides, followed by a second nucleotide sequence, such as at least two, three, four or five nucleotides, followed by a third nucleotide sequence that substantially hybridizes to the first sequence of nucleotides, followed by a fourth string of nucleotides, such as two, three, four or five nucleotides, thereby forming a two loop structure. In one embodiment, this two loop structure can serve as a substrate for a nuclease, such as Drosha.

In a further embodiment, an additional nucleotide sequence can flank the two cTarget strand sequences. In one embodiment, the additional nucleotide sequence can be at least three, four, five, ten or fifteen nucleotides 5' and 3' to the cTarget strands. In one embodiment, a stem sequence can be 5' and 3' to the cTarget strand sequences. In one embodiment, the stem sequence can contain at least four, five, six or seven nucleotides. The 5' stem sequence can contain a first, second and third nucleotide sequence upstream of the first cTarget strand. The 3' stem sequence can contain a fourth, fifth and sixth nucleotide sequence, wherein the fifth nucleotide sequence substantially hybridizes to the second nucleotide sequence of the 5' stem and the fourth and sixth nucleotide sequences do not hybridize to the first and third sequence of the 5' stem. The stem sequence can be a mir30 stem sequence, such disclosed any of the sequences described herein.

In another embodiment, the additional nucleotide sequence can be a cloning site 5' and/or 3' to the cTarget sequence. In one embodiment, the cloning site can be 5' and/or 3' of the stem sequence. The cloning site can contain engineered restriction enzyme sites to allow for cloning and splicing of nucleotide sequences within larger sequences.

In one specific embodiment, the DNA template can produce an RNA molecule with at least two of the following components wherein the Target complement A and Target complement B will be processed by the cell to form a ds iRNA molecule. One nonlimiting illustrative embodiment is depicted in FIG. 14 (SEQ ID NO: 30): In an additional embodiment, inhibitory RNAs can be constructed by addition of individual inhibitory RNAs into an array or cluster. In one embodiment, a cluster of individual hairpin iRNAs joined in tandem with or without linker sequence is provided. In one embodiment, this structure can have radial symmetry (see, for example, FIG. 2). These radial iRNA molecules can exhibit radial symmetry in structure without having radial symmetry in sequence. In an alternative embodiment, duplex RNAs can be joined with a variety of spacer sequences to produce a structure that is nearly linear or curved (see, for example, FIG. 3). These structures can be produced by linking a series of oligonucleotides with or without spacer sequence and then adding the complement sequence of these oligonucleotides in the reverse order, again with or without linker sequence. In additional embodiments, these structural strategies can be combined to produce complex structures. In other embodiments, radial iRNAs and linear clustered iRNAs can mediate targeted inhibition of mRNA via small interfering RNAs.

In other embodiments, methods are provided to optimize the hybridization of the two cTarget strands, or any sequences in which hybridization is desirable. Cytosine resides in putative sequences can be replaced with uracil residues, since non-Watson-Crick base pairing is possible in RNA molecules. These uracil residues can bind to either guanine or adenosine, thereby potentially increasing the degree of hybridization between the strands.

In a further aspect of the present invention, iRNA molecules that regulate the expression of specific genes or family of genes are provided, such that the expression of the genes can be functionally eliminated. In one embodiment, at least two iRNA molecules are provided that target the same region of a gene. In another embodiment, at least two iRNA molecules are provided that target at least two different regions of the same gene. In a further embodiment, at least two iRNA molecules are provided that target at least two different genes. Additional embodiments of the invention provide combinations of the above strategies for gene targeting.

In one embodiment, the iRNA molecules can be the same sequence. In an alternate embodiment, the iRNA molecules can be different sequences. In another embodiment, the iRNA molecules can be integrated into either the same or different vectors or DNA templates. In one embodiment, the iRNA molecules within the vector or DNA template are operably linked to a promoter sequence, such as, for example, a ubiquitously expressed promoter or cell-type specific promoter. In another embodiment, the iRNA molecules within the vector or DNA template are not under the control of a promoter sequence. In a further embodiment, these vectors or DNA templates can be introduced into a cell. In one embodiment, the vector or DNA template can integrate into the genome of the cell. The integration into the cell can either be via random integration or targeted integration. The targeted integration can be via homologous recombination.

In other embodiments, at least two iRNA molecules are provided wherein the families of one or more genes can be regulated by expression of the iRNA molecules. In another embodiment, at least three, four or five iRNA molecules are provided wherein the families of one or more genes can be regulated by expression of the iRNA molecules. The iRNA molecule can be homologous to a conserved sequence within one or more genes. The family of genes regulated using such methods of the invention can be endogenous to a cell, a family of related viral genes, a family of genes that are conserved within a viral genus, a family of related eukaryotic parasite genes, or more particularly a family of genes from a porcine endogenous retrovirus. In one specific embodiment, at least two iRNA molecules can target the at least two different genes, which are members of the same family of genes. The iRNA molecules can target homologous regions within a family of genes and thus one iRNA molecule can target the same region of multiple genes.

The iRNA molecule, for example, can be selected from, but are not limited to the following types of iRNA: antisense oligonucleotides, ribozymes, small interfering RNAs (siRNAs), double stranded RNAs (dsRNAs), inverted repeats, short hairpin RNAs (shRNAs), small temporally regulated RNAs, and clustered inhibitory RNAs (ciRNAs), including radial clustered inhibitory RNA, asymmetric clustered inhibitory RNA, linear clustered inhibitory RNA, and complex or compound clustered inhibitory RNA.

In another embodiment, expression of iRNA molecules for regulating target genes in mammalian cell lines or transgenic animals is provided such that expression of the target gene is functionally eliminated or below detectable levels, i.e. the expression of the target gene is decreased by at least about 70%, 75%, 80%, 85%, 90%, 95%, 97% or 99%.

In another embodiment of this aspect of the present invention, methods are provided to produce cells and animals in which interfering RNA molecules are expressed to regulate the expression of target genes. Methods according to this aspect of the invention can comprise, for example: identifying one or more target nucleic acid sequences in a cell; obtaining at least two iRNA molecules that bind to the target nucleic acid sequence(s); introducing the iRNA molecules, optionally packaged in an expression vector, into the cell; and expressing the iRNAs in the cell under conditions such that the iRNAs bind to the target nucleic acid sequences, thereby regulating expression of one or more target genes. In one embodiment, the present invention provides methods of producing non-human transgenic animals that heritably express at least two iRNA molecules that regulate the expression of one or more target genes. In one embodiment, the animals can be produced via somatic cell nuclear transfer. The somatic cell can be engineered to express the iRNA molecule by any of the techniques described herein.

In other embodiments, the present invention also provides methods for the expression of at least two iRNA molecules in a cell or a transgenic animal, where the iRNA targets a common location within a family of genes. Such methods can include, for example: identifying one or more target nucleic acid sequences in the cell that are homologous regions within a family of genes; preparing at least two iRNA molecules that bind to the target nucleic acid sequence(s); introducing the iRNA molecules, optionally packaged in an expression vector, into the cell; and expressing iRNAs in the cell or animal under conditions such that the iRNA molecules bind to the homologous region within the gene family.

The present invention also provides transgenic non-human animals produced by the methods of the invention. The methods of the invention are useful for example for the production of transgenic non-human mammals (e.g. mice, rats, ungulates, sheep, goats, cows, porcine animals, rabbits, dogs, horses, mules, deer, cats, monkeys and other non-human primates), birds (particularly chickens, ducks, and geese), fish, reptiles, amphibians, worms (e. g. *C. elegans*), and insects (including but not limited to, Mosquitos, *Drosophila, Trichoplusa*, and *Spodoptera*). While any species of non-human animal can be produced, in one embodiment the non-human animals are transgenic ungulates, including pigs. The present invention also provides cells, tissues and organs isolated from such non-human transgenic animals.

In embodiments of the present invention, endogenous genes that can be regulated by the expression of at least two iRNA molecules include, but are not limited to, genes required for cell survival or cell replication, genes required for viral replication, genes that encode an immunoglobulin locus, for example, Kappa light chain, and genes that encode a cell surface protein, for example, Vascular Cell Adhesion Molecule (VCAM) and other genes important to the structure and/or function of cells, tissues, organs and animals. The methods of the invention can also be used to regulate the expression of one or more non-coding RNA sequences in a transgenic cell or a transgenic animal by heritable transgene expression of interfering RNA. These non-coding RNA sequences can be sequences of an RNA virus genome, an endogenous gene, a eukaryotic parasite gene, or other non-coding RNA sequences that are known in the art and that will be familiar to the ordinarily skilled artisan.

In an exemplary embodiment of the present invention, porcine endogenous retrovirus (PERV) genes can be regulated by the expression of at least two iRNA molecules such that the expression of the PERV virus is functionally eliminated or below detection levels. PERV refers to a family of retrovirus of which three main classes have been identified to date: PERV-A (Genbank Accession No. AF038601), PERV-B (EMBL Accession No. PERY17013) and PERV-C (Genbank Accession No. AF038600) (Patience et al 1997, Akiyoshi et al 1998). The gag and pol genes of PERV-A, B, and C are highly homologous, it is the env gene that differs significantly between the different types of PERV (eg., PERV-A, PERV-B, PERV-C). PERV-D has also recently been identified (see, for example, U.S. Pat. No. 6,261,806).

In one embodiment, iRNA directed to the PERV virus can decrease the expression of PERV by at least about 70%, 75%, 80%, 85%, 90%, 95%, 97% or 99%, or alternatively, below detectable levels. To achieve this goal, the present invention provides at least two iRNA molecules that target the same sequence within the gag, pol or env region of the PERV genome. Further, at least two iRNA molecules are provided that target different sequences within the gag, pol or env regions of the PERV genome. Still further, at least two iRNA molecules are provided that each target different regions (i.e. either gag, pol or env) of the PERV genome. Additionally, multiple iRNA molecules are provided that combine these different targeting strategies, for example: at least two RNA interference molecules directed to the gag region of PERV; at least two RNA interference molecules directed to the pol region of PERV; and at least two RNA interference molecules directed to the env region of PERV are provided to target the PERV gene.

The present invention also provides ungulate, and particularly, porcine animals, as well as cells, tissues and organs isolated from non-human transgenic animals in which the expression of PERV is functionally eliminated via the expression of at least two iRNA molecules. In certain such embodiments, they are obtained from transgenic pigs that express one or more interfering RNAs that interfere with the porcine endogenous retrovirus gene, a family member of the porcine endogenous retrovirus gene or a member of a subset of the porcine endogenous retrovirus gene family.

BRIEF DESCRIPTION OF THE DRAWINGS

FIG. 8 shows an analysis of a portion of PERV env genes. The region spanning bases 6364 to 6384 is homologous between all family members shown. Two polymorphisms are shown for the dinucleotide at bases 6400 and 6401. Two transgenes are required to effectively repress the shown genes when targeting regions that include this dinucleotide. The region spanning bases 6408 to 6431 represent three polymorphisms. Likewise regions that include base 6385 represent three polymorphisms. Single transgenes that target one of the three polymorphism in tripolymorphic regions differentiate a subset of the shown sequences. A set of three transgenes, each targeting a different polymorphism in the tripolymorphic regions is required to target all shown sequences.

FIG. 9 illustrates representative inhibitory RNA targets. An 86 base consensus for a semi-conserved region of PERV is shown on the first line. Sixty-eight potential 19 base targets for inhibitory RNA within this sequence are shown on subsequent lines. Targets can be between 17 and 35 bases in length. This process can be reiterated for targets of 17-35 bases and can be applied to any region, protein coding or non-coding, included within any complete or partial PERV genome. All PERV sequences are potential targets. Line 1, PERV sequence; Lines 2-69, potential targets.

FIG. 10 illustrates the identification of potential targets that share significant homology with non-targeted genes. RNA sequence of target genes are screened for homology to non-targeted RNAs. A 19 base region of an unknown porcine expressed sequence (Genbank entry BI305054) is significantly homologous to a region of semi-conserved PERV sequence (shown in black face bold type). Though potential target regions with significant homology to non-targeted RNAs can prove useful, such target regions are excluded in initial target screens to reduce the risk of severely down-regulating unintended gene products. Line 1, PERV sequence; Lines 2-69, potential targets; Line 70, unknown expressed porcine sequence; Lines 36-56, excluded targets.

FIG. 11 represents the configuration of an inhibitory RNA designed for the potential target sequence of FIG. 9 that is listed first (Line 2, FIG. 3). Wherein "N" refers to any nucleotide and "Y" refers to any integer greater than or equal to zero. Each portion of non-specified sequence, $(N_Y)$, can be homopolymeric or can be composed of non-identical bases. In addition, any continuous stretch of non-specified sequence, $(N_Y)$, can provide additional functions such as but not limited to encoding protein, providing signals for stability or increased half-life, increasing the length of palindromic sequence, providing signals and functions for splicing, or folding into particular structures.

FIG. 12 represents the illustrative sequence for radial clustered inhibitory RNA, asymmetric bubble ciRNA, linear ciRNA, and complex ciRNA to a targeted PERV gag consensus sequence;

DETAILED DESCRIPTION OF THE INVENTION

Figure 1:
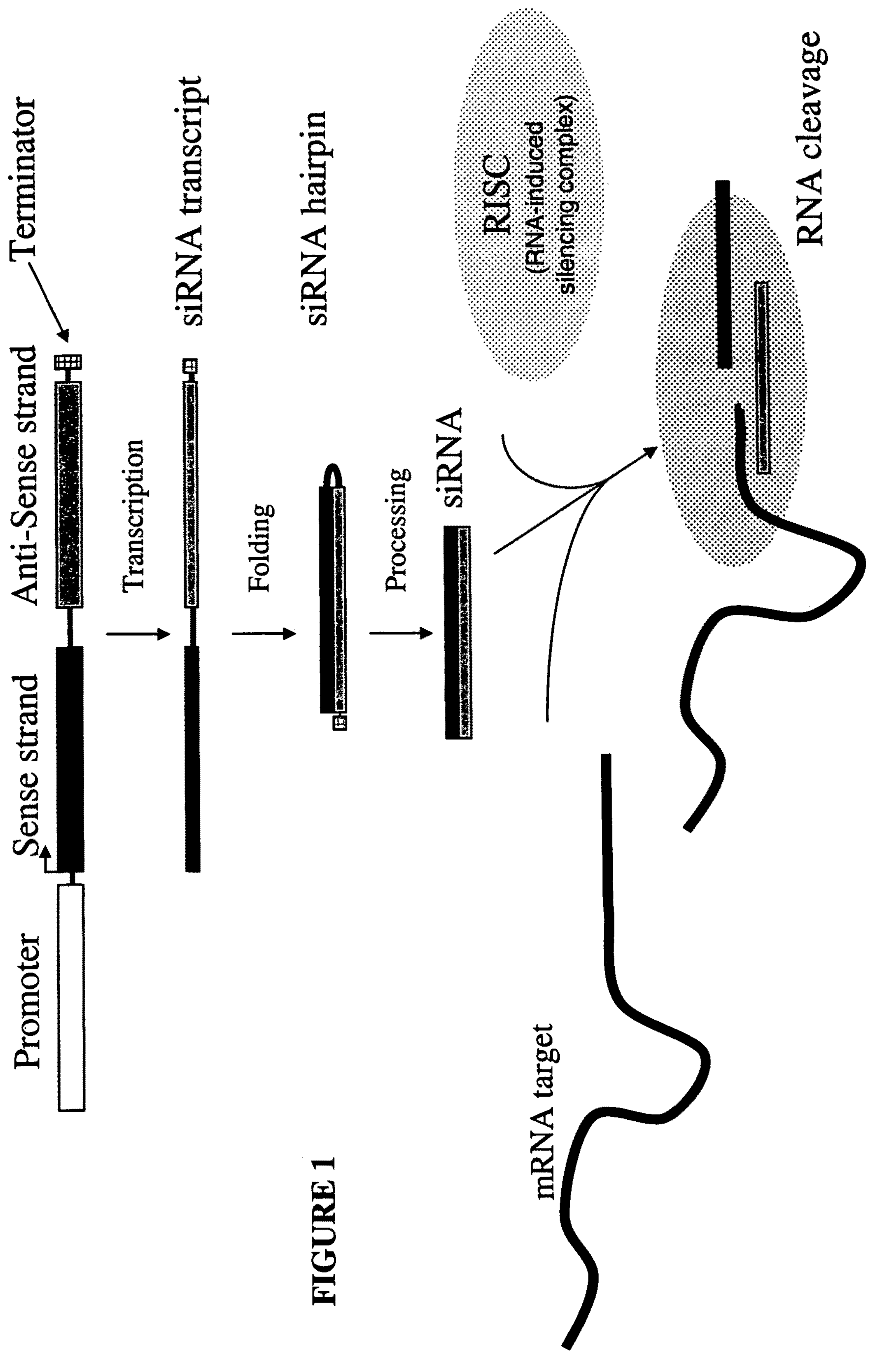
FIG. 1 illustrates an example of a mechanisms by which an interfering RNA can mediate targeted destruction of cellular RNA. In this model, an expression vector includes nucleic acid sequence encoding an RNA sense strand (black box) and antisense strand (gray box) in an inverted sequence are operably linked to a single promoter (white box). Following transcription of the construct, the sense strand binds to its complimentary antisense strand, resulting in a double stranded, 'hairpin' RNA molecule (dsRNA). The dsRNA is subsequently processed by an enzyme (Dicer, also known as RNAse III) to produce a small interfering RNA (siRNA). One siRNA then associates with an RNA-induced silencing complex (RISC) and with the target cellular mRNA. The binding of the cellular mRNA to the RISC induces cleavage of the mRNA, thereby limiting the functional expression of a specified gene product.

Improved techniques for the repression of expression of protein in cells are provided. In one embodiment, the invention provides new methods and materials for the repression of expression of a protein that include the use of targeted insertion vectors which have a minimal effect on the homeostasis of the cell. In particular, DNA templates that encode an iRNA to repress a target protein are provided that (i) use the endogenous regulatory elements of the cell, such as the endogenous promoter, (ii) are targeted into an intronic sequence of a gene, and/or (iii) do not disrupt the homeostasis of the cell. In a second embodiment, new iRNA molecules and DNA sequences encoding them are provided, as well as methods to produce the same. In one example, a iRNA molecule is provided in which both strands are complementary to a target mRNA (cTarget) of a protein to be repressed, which can be is in the form of a hairpin. In a third embodiment, iRNA molecules that regulate the expression of specific genes or family of genes that share a common, homologous sequence, such that the expression of the genes can be functionally eliminated are provided.

Unlike gene knockout technology, RNA interference (RNAi) is a genetically dominant phenomenon, i.e., the transgene does not need to be rendered homozygous. In addition, RNA interference can be directed against genes that may or may not reside in the genome.

In one aspect of the present invention, methods are provided to produce transgenic cells and animals that express iRNA molecules at a predetermined location, as well as the cells and animals produced thereby. In one embodiment, DNA templates, which produce iRNA molecules, that contain sequence that targets a particular location in the genome can be introduced into cells, such that the DNA templates are under control of the endogenous regulatory elements of the cell, such as the promoter and/or other regulatory elements of the gene. In another embodiment, the DNA templates can be targeted such that expression of the iRNA molecule can be achieved without disrupting the endogenous gene function. In one embodiment, the DNA templates can be in the form of vectors. The vectors can be introduced into the cells directly, or linearized prior to introduction into the cell. In another embodiment, the DNA templates can be synthesized as oligonucleotides and introduced into cells. In one embodiment, the DNA templates can integrate into the genome of the cell via targeted integration. The targeted integration can be via homologous recombination. The DNA templates can contain 5' and 3' targeting sequence that is homologous to the target gene to allow for targeted insertion. The DNA templates can be inserted via homologous recombination into, for example, a housekeeping gene such that the expression of the iRNA molecule is under the control of the associated promoter of the housekeeping gene. Alternatively, the DNA templates can be inserted via homologous recombination into a gene that is only expressed in particular cells or organs such that the expression of the iRNA molecule is under the control of the associated promoter of the cell or organ specific gene. Such templates can be introduced into mammalian cells, such as human, porcine, ovine or bovine cells, bacterial cells, such as *E. Coli*, and/or yeast cells.

In another aspect of the present invention, ds iRNA molecules are provided in which both strands are complementary to the mRNA target sequence (cTarget). Due to the intracellular processing of double stranded iRNA (ds iRNA) molecules, only one of the two strands of the molecule actually functions to inhibit the target mRNA. The present invention provides novel ds iRNA molecules in which both strands can be functional, i.e. can bind to the target RNA sequence. Prior to this discovery, the design of iRNA molecules was such that only one strand of the iRNA molecule was functional (i.e. typically one strand was substantially identical to the target sequence, or the "sense" sequence, and the other strand was the functional strand that was complementary to the target sequence. or the "anti-sense" sequence), and thus if the nonfunctional strand was processed in vivo, no inhibitory effect was generated.

In a further aspect of the present invention, iRNA molecules that regulate the expression of specific genes or family of genes are provided, such that the expression of the genes can be functionally eliminated. In one embodiment, at least two iRNA molecules are provided that target the same region of a gene. In another embodiment, at least two iRNA molecules are provided that target at least two different regions of the same gene. In a further embodiment, at least two iRNA molecules are provided that target at least two different genes. Additional embodiments of the invention provide combinations of the above strategies for gene targeting.

In an exemplary embodiment of the present invention, porcine endogenous retrovirus (PERV) genes can be regulated by the expression of at least two iRNA molecules such that the expression of the PERV virus is functionally eliminated or below detection levels. PERV refers to a family of retrovirus of which three main classes have been identified to date: PERV-A (Genbank Accession No. AF038601), PERV-B (EMBL Accession No. PERY17013) and PERV-C (Genbank Accession No. AF038600) (Patience et al 1997, Akiyoshi et al 1998). The gag and pol genes of PERV-A, B, and C are highly homologous, it is the env gene that differs between the different types of PERV (eg., PERV-A, PERV-B, PERV-C). PERV-D has also recently been identified (see, for example, U.S. Pat. No. 6,261,806).

I. Definitions

Unless defined otherwise, all technical and scientific terms used herein have the same meanings as commonly understood by one of ordinary skill in the art.

As used herein, the term "animal" is meant to include any animal, including but not limited to non-human mammals (including, but not limited to, pigs, sheep, goats, cows (bovine), deer, mules, horses, monkeys and other non-human primates, dogs, cats, rats, mice, rabbits), birds (including, but not limited to chickens, turkeys, ducks, geese) reptiles, fish, amphibians, worms (e.g. *C. elegans*), insects (including but not limited to, *Drosophila, Trichoplusa*, and *Spodoptera*). A "transgenic animal" is any animal containing one or more cells bearing genetic information received, directly or indirectly, by deliberate genetic manipulation at the subcellular level. A "transgenic cell" is any cell bearing genetic information received, directly or indirectly, by deliberate genetic manipulation at the subcellular level.

The term "ungulate" refers to hoofed mammals. Artiodactyls are even-toed (cloven-hooved) ungulates, including antelopes, camels, cows, deer, goats, pigs, and sheep. Perissodactyls are odd toes ungulates, which include horses, zebras, rhinoceroses, and tapirs.

As used herein, the terms "porcine", "porcine animal", "pig" and "swine" are generic terms referring to the same type of animal without regard to gender, size, or breed.

As used herein, the term "heritable," particularly when used in the context of "heritable gene," "heritable trait," "heritable characteristic," "heritable iRNA", means that the unit, e.g. the gene, trait, characteristic, iRNA, etc., are capable of being inherited or of passing by inheritance.

As used herein, the term "regulation of gene expression" refers to the act of controlling the ability, timing, level, manner or cell-type of transcription of a gene. Regulation can result in increased expression of a gene, decreased expression of a gene or maintenance of expression of a gene, as described herein.

II. iRNA Molecules

A. iRNA Design

In one aspect of the present invention, ds iRNA molecules are provided in which both strands are complementary to the target sequence (cTarget). Due to the intracellular processing of double stranded iRNA (ds iRNA) molecules, only one of the two strands of the molecule actually functions to inhibit the target mRNA. The present invention provides novel ds iRNA molecules in which both strands can be functional, i.e. can bind to the target RNA sequence. Prior to this discovery, the design of iRNA molecules was such that only one strand of the iRNA molecule was functional (i.e. typically one strand was substantially identical to the target sequence, or the "sense" sequence, and the other strand was the functional strand that was complementary to the target sequence, or the "antisense" sequence), and thus if the nonfunctional strand was processed in vivo, no inhibitory effect was generated.

Endogenous iRNA Processing.

Figure 15:
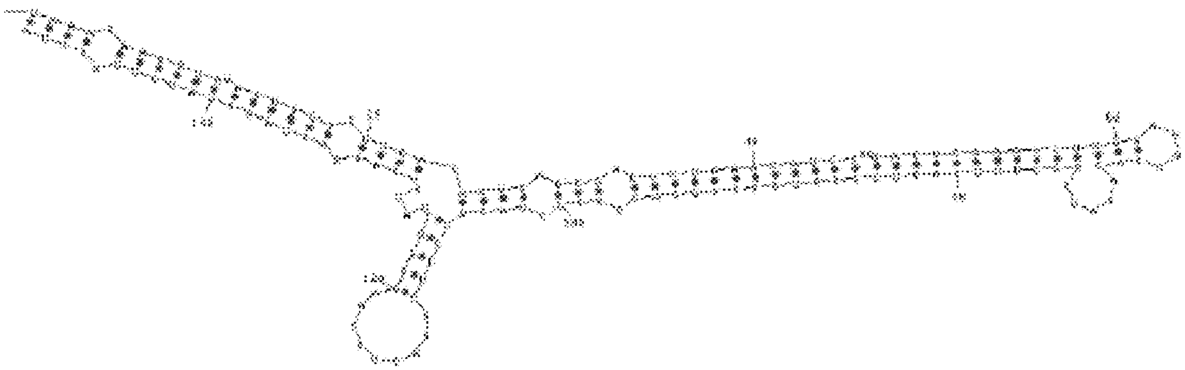
FIG. 15 depicts the putative predicted structure of a portion of pri-mir30.

Micro-RNAs (miRNAs) are small endogenous RNAs involved in post-transcriptional regulation of genes. One such miRNA (mir30) is transcribed as a large transcript (primir30) that processed via Drosha into a smaller hairpin structure (pre-mir30) that is exported from the nucleus. In the cytoplasm, pre-mir30 is further processed by Dicer to yield mature mir30. This process is known in the art (see for example, Zeng Y, Cullen B R. Structural requirements for pre-microRNA binding and nuclear export by Exportin 5. Nucleic Acids Res. 2004 Sep. 8; 32(16):4776-85; Zeng Y, Cullen B R. Sequence requirements for micro RNA processing and function in human cells. RNA. 2003 Jan.; 9(1):112-23). The MFold (M. Zuker. Mfold web server for nucleic acid folding and hybridization prediction. Nucleic Acids Res. 31 (13), 3406-15, (2003) [http://www.bioinfo.rpi.edu/applications/mfold/old/rna/form.cgi]) putative predicted structure of a portion of pri-mir30 is shown shown in FIG. 15.

Figure 16:
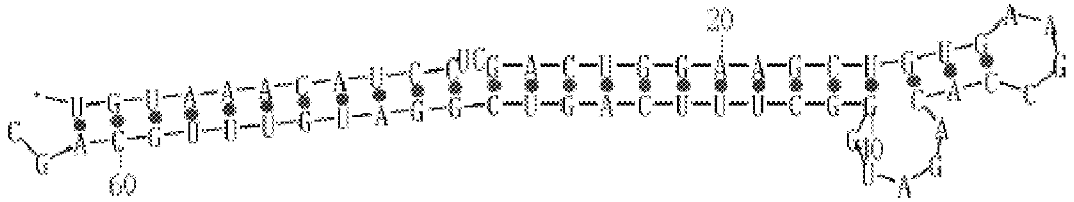
FIG. 16 depicts the MFold putative predicted structure of pre-mir30 Drosha cleavage product comprising the nucleotide sequence of SEQ ID NO: 1.

The MFold putative predicted structure of the pre-mir30 Drosha cleavage product is depicted in FIG. 16.

The nucleotide sequence of the sequence depicted in FIG. 16 is UGUAAACAUCCUCGACUGGAA GCUGUGAAGCC ACAGAUGGGCUUUCAGUCGGAUGUUUGCAGC (Seq ID No 1).

A minimal pri-mir30 Drosha substrate has been described for in vitro cleavage (Lee Y, Ahn C, Han J, Choi H, Kim J, Yim J, Lee J, Provost P, Radmark O, Kim S, Kim V N. The nuclear RNase III Drosha initiates microRNA processing. Nature. 2003 Sep. 25; 425(6956):415-9) The putative predicted structure of this substrate is depicted in FIG. 17.

Figure 17:
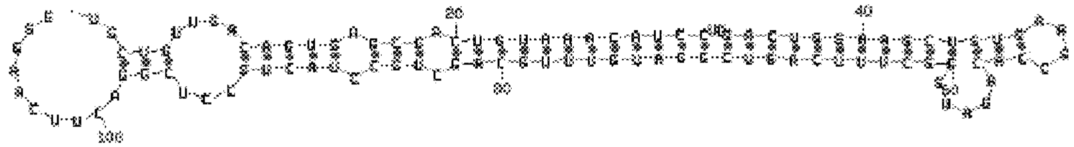
FIG. 17 depicts the putative predicted structure of the minimal pri-mir30 Drosha substrate comprising the nucleotide sequence of SEQ ID NO: 2.

The nucleotide sequence of the sequence depicted in FIG. 17 is UGCUGUUGACAGUGAGCGACUGUAAACAUCCUCGACUGGAAGCUGUGAAGCCA CAGAUGGGCUUUCAGUCGGAUGUUUGCAGCUGCCUACUGCCUCGGACUUCAAG GG (Seq ID No 2).

A minimal pri-mir30 Drosha substrate has also been described for in vivo cleavage in the context of an irrelevant mRNA (Zeng Y, Wagner E J, Cullen B R. Both natural and designed micro RNAs can inhibit the expression of cognate mRNAs when expressed in human cells. Mol Cell. 2002 June; 9(6):1327-33; Zeng Y, Cullen B R. Sequence requirements for micro RNA processing and function in human cells. RNA. 2003 January; 9(1):112-23). The putative predicted structure of this substrate is depicted in FIG. 18.

Figure 18:
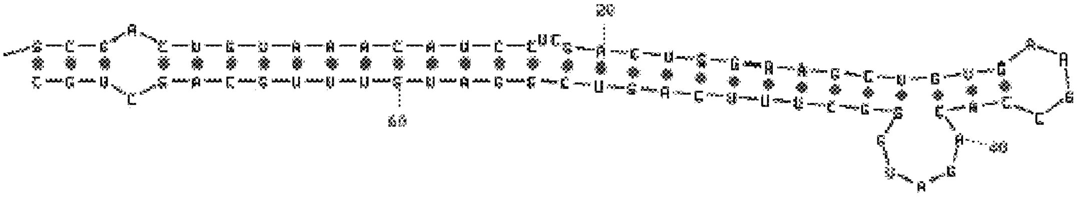
FIG. 18 depicts the putative predicted structure of the minimal pri-mir30 Drosha substrate comprising the nucleotide sequence of SEQ ID NO: 3.

The nucleotide sequence of the sequence depicted in FIG. 18 is GCGACUGUAAACAUCCUCGACUGGAAGCUGUGAAGCCACAGAUGGGCUUUCAG UCGGAUGUUUGCAGCUGC (Seq ID No 3).

Additionally, it has been shown that the active portions of miRNAs can be replaced to generate novel hairpins with siRNA activity (Zeng Y, Wagner E J, Cullen B R. Both natural and designed micro RNAs can inhibit the expression of cognate mRNAs when expressed in human cells. Mol Cell. 2002 June; 9(6):1327-33; Boden D, Pusch O, Silbermann R, Lee F, Tucker L, Ramratnam B. Enhanced gene silencing of HIV-1 specific siRNA using microRNA designed hairpins. Nucleic Acids Res. 2004 Feb. 13; 32(3):1154-8).

iRNA Molecules

In one embodiment, the ds iRNA molecules can contain a first cTarget strand of nucleotides, which hybridizes to a second cTarget strand sequence. The cTarget strands can contain at least fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty nucleotides, in particular, nineteen to thirty-two nucleotides, or twenty-one to twenty-three nucleotides in length.

Methods are also provided to obtain iRNA molecules that are a first cTarget strand of nucleotides, which hybridizes to a second cTarget strand sequence. A complementary sequence to the target sequence (cTarget) is first determined and then segments of cTarget sequence can be evaluated to determine the portions of which will hybridize together to form a ds iRNA molecule. In one embodiment, segments of cTarget sequence at least 25, 50, 100, 200 300, 400 or 500 nucleotides in length can be analyzed to determine areas of self-hybridization. In one embodiment, these sequences can be entered into a computer program which detects areas of self-hybridization, such as, in one specific embodiment, the MFold software, as described in M. Zuker Mfold web server for nucleic acid folding and hybridization prediction. Nucleic Acids Res. 31 (13) 3406-15, (2003), [http://www.bioinfo.rpi.edu/applications/mfold/old/rna/form.cgi].

In other embodiments, DNA templates are provided, which produce ds iRNA molecules that are two strands of cTarget sequence. In one embodiment, DNA templates are provided that produce iRNA precursors. In one embodiment, a spacer nucleotide sequence can separate the two cTarget sequences. In another embodiment, a nucleotide sequence is provided that contains a first strand complementary to a target and a second strand complementary to a target, which substantially hybridizes to the first strand and a spacer sequence connecting the two strands. In one embodiment, the spacer can form a loop or hairpin structure. Such hairpins can be cleaved inside the cell to provide a duplexed mRNA containing the two stems. In one embodiment, the spacer nucleotide sequence can be at least 2, 3, 4, 5, 6, 7, 8, 9, 10, 11, 12, 13, 14, 15, 16, 17, 18, 19, 20, 25, 30, 40 or 50 nucleotides in length. In another embodiment, the spacer sequence can contain nucleotides that form a loop structure, such as a mir30 loop structure. The mir30 loop structure can contain at least the following sequence: GUGAAGCCACA-GAUG (Seq ID No 4), or as indicated in any of the sequences listed herein. In one embodiment the loop structure can contain a first nucleotide sequence, such as at least two, three, four or five nucleotides, followed by a second nucleotide sequence, such as at least two, three, four or five nucleotides, followed by a third nucleotide sequence that substantially hybridizes to the first sequence of nucleotides, followed by a fourth string of nucleotides, such as two, three, four or five nucleotides, thereby forming a two loop structure. In one embodiment, this two loop structure can serve as a substrate for a nuclease, such as Drosha.

In a further embodiment, additional nucleotide sequence can flank the two cTarget strand sequences. The additional nucleotide sequence can be at least three, four, five, ten or fifteen nucleotides 5' and 3' to the cTarget strands. In one embodiment, a stem sequence can be 5' and 3' to the cTarget strand sequences. The stem sequence can contain at least four, five, six or seven nucleotides. The 5' stem sequence can contain a first, second and third nucleotide sequence upstream of the first cTarget strand. The 3' stem sequence can contain a fourth, fifth and sixth nucleotide sequence, wherein the fifth nucleotide sequence substantially hybridizes to the second nucleotide sequence of the 5' stem and the fourth and sixth nucleotide sequences do not hybridize to the first and third sequence of the 5' stem. The stem sequence can be a mir30 stem sequence, such as illustrated in any of the sequences listed herein, such as Seq ID No 5.

In another embodiment, the additional nucleotide sequence can be a cloning site 5' and/or 3' to the cTarget sequence. In one embodiment, the cloning site can be 5' and/or 3' of the stem sequence. The cloning site can contain engineered restriction enzyme sites to allow for cloning and splicing of nucleotide sequences within larger sequences.

Figure 19:
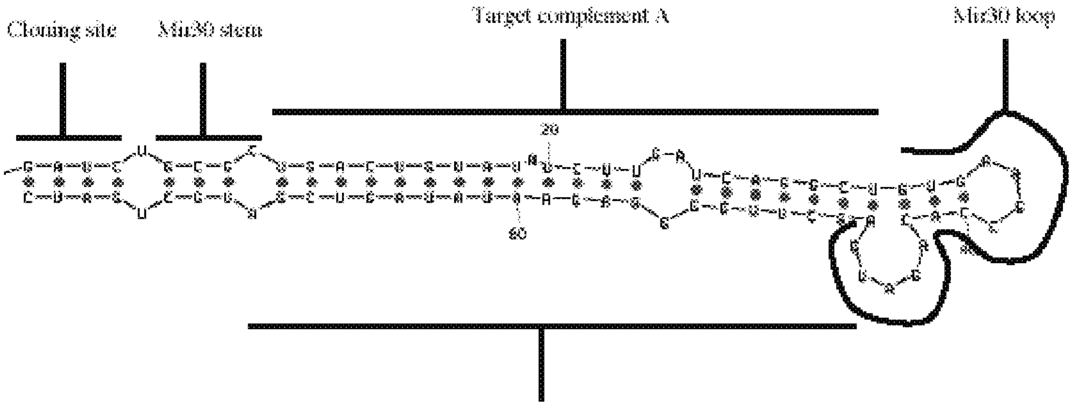
FIG. 19 illustrates an exemplary ds iRNA molecule comprising the nucleotide sequence of SEQ ID NO: 5.

In one specific embodiment, the DNA template can produce an RNA molecule with at least two of the following components, as illustrated below, wherein the Target complement A and Target complement B will be processed by the cell to form a ds iRNA molecule as depicted in FIG. 19.

The nucleotide sequence for the sequence depicted in FIG. 19 is GAUCUGCGCUGACUGUAUAUC-UUGAUCAGGCUGUGAAGCCACAGAUGAGCUU GGGGAGAAUAUAGUCGAUGCUGAUC (Seq ID No 5).

In one embodiment, the DNA template can produce a Drosha substrate that is processed into a functional iRNA molecule.

In one embodiment, the cTarget sequences can be complementary to the same target sequence. In another embodiment, the cTarget sequences can be complementary to different target sequences. In a further embodiment, the ds iRNA molecule can be palindromic cTarget sequences, in which both strands are identical or functionally identical. In one embodiment, a cTarget sequence can be analyzed to identify palindromic sequences, for example, through the use of a computer program, such as DNA Strider.

In other embodiments, methods are provided to optimize the hybridization of the two cTarget strands, or any sequences in which hybridization is desirable. Cytosine resides in putative sequences can be replaced with uracil residues, since non-Watson-Crick base pairing is possible in RNA molecules. These uracil residues can bind to either guanine or adenosine, thereby potentially increasing the degree of hybridization between the strands.

Targeting Two Sites of an mRNA Simultaneously

In one embodiment, the cTarget sequences can be complementary to the same target sequence. By using the sequence that is complementary to an mRNA, one can design iRNA molecules, such as hairpins, in which both strands of the stem are complementary to the target mRNA. In one embodiment, such hairpins can serve as a Drosha substrate and the resulting structure can be cleaved to produce two strands, each of which is capable of exerting an inhibitory effect on the target mRNA.

The complementary sequence to the target sequence (cTarget) is first determined and then segments of cTarget sequence can be evaluated to determine the portions of which will hybridize together to form a ds iRNA molecule. In one embodiment, segments of cTarget sequence at least 25, 50, 100, 200 300, 400 or 500 nucleotides in length can be analyzed to determine areas of self-hybridization. In one embodiment, these sequences can be entered into a computer program which detects areas of self-hybridization, such as, in one specific embodiment, the MFold software, as described in M. Zuker Mfold web server for nucleic acid folding and hybridization prediction. Nucleic Acids Res. 31 (13) 3406-15, (2003), [http://www.bioinfo.rpi.edu/applications/mfold/old/rna/form1.cgi]. Areas of self-hybridization can then be identified and tested for its effect in the cell.

Targeting Two mRNAs Simultaneously

In addition to the strategies describe above, one can combine the antisense strands of portions of two mRNAs to create a single iRNA molecule, such as a hairpin iRNA molecule, that potentially targets two mRNAs. Complementary sequence to each of the target sequences (cTarget) can first be determined and then segments of each cTarget sequence can be spliced together. For example, at least 25, 50, 100, 200 300, 400 or 500 nucleotides of cTarget to a first target (cTarget 1) can be joined with at least 25, 50, 100, 200 300, 400 or 500 nucleotides of cTarget to a second target (cTarget 2). This sequence of nucleotides can be evaluated to determine the portions of which will hybridize together to form a ds iRNA molecule. In one embodiment, these sequences can be entered into a computer program which detects areas of self-hybridization, such as, in one specific embodiment, the MFold software, as described in M. Zuker Mfold web server for nucleic acid folding and hybridization prediction. Nucleic Acids Res. 31 (13) 3406-15, (2003), [http://www.bioinfo.rpi.edu/applications/mfold/old/rna/form1.cgi]. Areas of hybridization between cTarget 1 and cTarget 2 can then be identified and tested for its effect on repression of the target mRNAs in a cell.

Palindromic Sequences

In a further embodiment, the ds iRNA molecule can be palindromic cTarget sequences, in which both strands are identical or functionally identical. In one embodiment, a cTarget sequence can be analyzed to identify palindromic sequences, for example, through the use of a computer program, such as DNA Strider. In one embodiment, a method to identify palindromic sequences is provided in which complementary sequence to a target mRNA is first determined. This sequence can then be analyzed for the presense of a palindromic sequence that is at least fifteen, sixteen, seventeen, eighteen, nineteen, twenty, twenty-one, twenty-two, twenty-three, twenty-four, twenty-five, twenty-sic, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty nucleotides, in particular, nineteen to thirty-two nucleotides, or twenty-one to twenty-three nucleotides in length. In an alternate embodiment, such sequences can be evaluated using a computer program, such as the DNA Strider software. Such palindromic iRNA molecules essentially eliminates the effects of endogenous strand selection in iRNA processing.

Hairpin Formation can be Optimized

In other embodiments, methods are provided to optimize the hybridization of the two cTarget strands, or any sequences in which hybridization is desirable. Cytosine resides in putative sequences can be replaced with uracil residues, since non-Watson-Crick base pairing is possible in RNA molecules. These uracil residues can bind to either guanine or adenosine, thereby potentially increasing the degree of hybridization between the strands. In one embodiment, Drosha substrates can be modified without significant alteration in RNAi targeting by using this strategy.

Clustered Inhibitory RNAs (ciRNA): Radial and Linear

Figure 2:
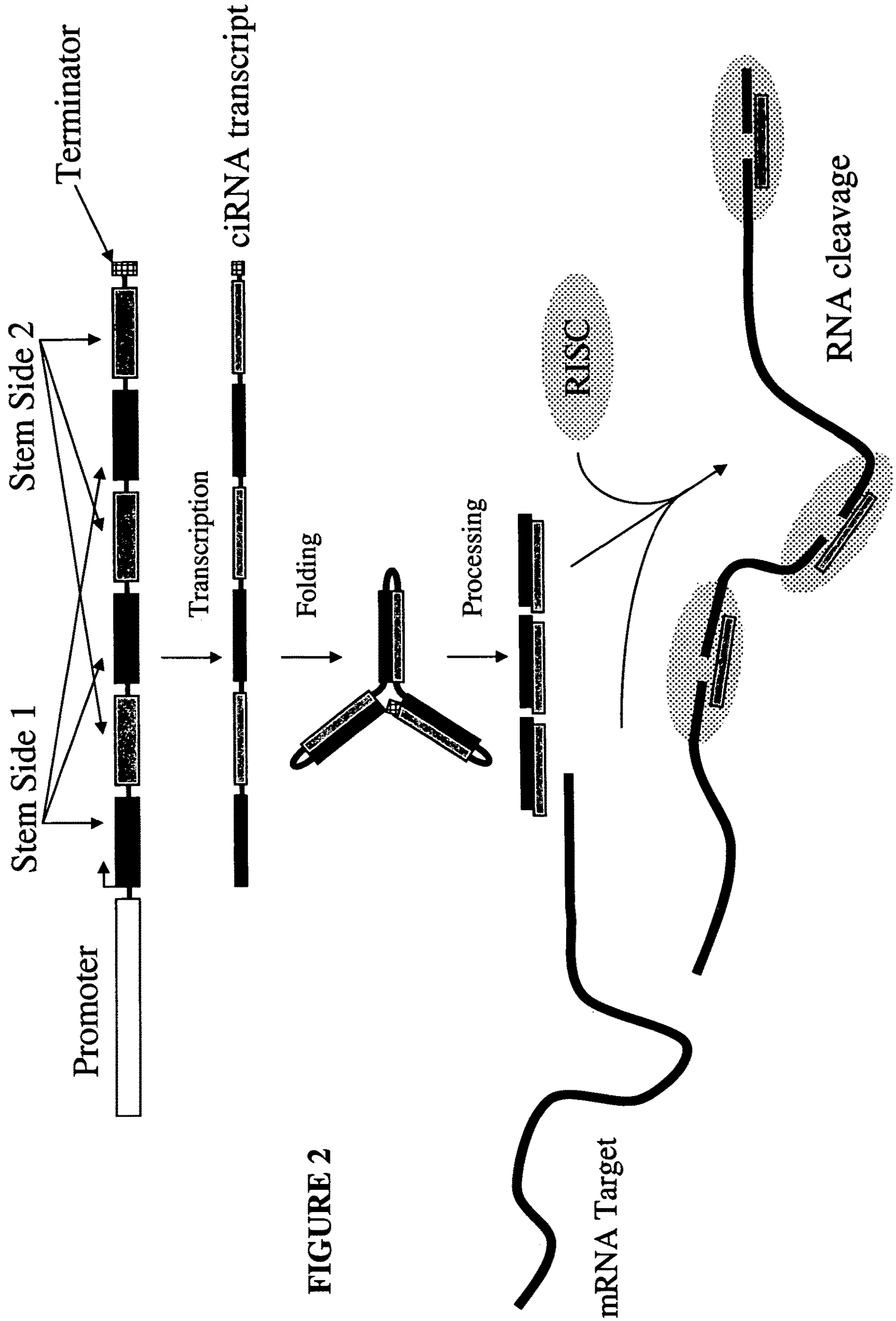
FIG. 2 illustrates an example of a mechanism by which clustered inhibitory RNA (ciRNA) can mediate the destruction of cellular RNA. In this model, an expression vector includes a pattern of nucleic acid sequences encoding multiple complimentary RNA sense strands (black boxes) and inverted antisense strands (gray boxes). This pattern can be operably linked to a single promoter (white box). Following transcription, the ciRNA transcript can autonomously fold so that each sense strand can bind to a complimentary antisense strand. This folding can result in a radially arrayed, double stranded RNA complex with a hairpin structure at each outer axis. This complex can be processed by an enzyme (Dicer, also known as RNAse III), producing multiple small interfering RNA (siRNA) molecules. The resultant siRNA molecules can associate with an RNA-induced silencing complex (RISC) and with multiple target mRNA sequences. The binding of the cellular mRNA to the RISC induces cleavage of the mRNA sequence(s), thereby eliminating the functional expression of one or more specified gene product(s).
Figure 3:
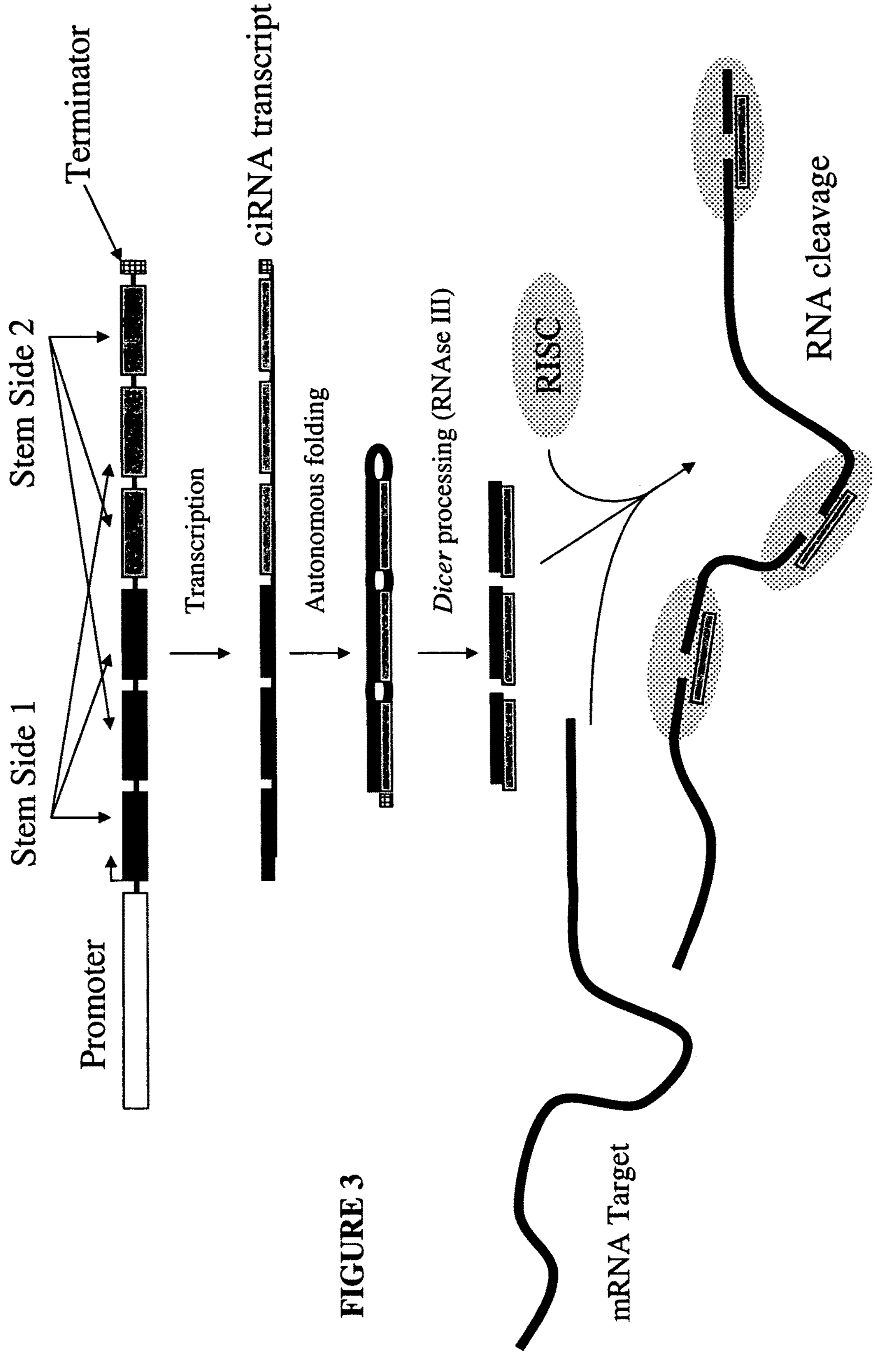
FIG. 3 illustrates another potential mechanism by which clustered inhibitory RNA (ciRNA) could mediate the targeted destruction of cellular RNA. In this model, an expression vector includes nucleic acid sequences encoding multiple complimentary RNA sense strands (black box) and inverted antisense strands (gray box), operably linked to a single promoter (white box). Following transcription, the ciRNA transcript autonomously folds so that each sense strand can bind to a complimentary antisense strand. The resulting structure can be a linear, double stranded RNA complex, containing at least one hairpin turn. The linear, double stranded ciRNA complex can then be processed by an enzyme (Dicer, also known as RNAse III), producing multiple small interfering RNA (siRNA) molecules. The resultant siRNA molecules can associate with an RNA-induced silencing complex (RISC) and with multiple target mRNA sequences. The binding of the cellular mRNA to the RISC induces cleavage of the mRNA sequence(s), thereby eliminating the functional expression of one or more specified gene product(s).

Additionally, inhibitory RNAs can be constructed by addition of individual inhibitory RNAs into an array or cluster. A variety of structural motifs can be used. One such motif is a cluster of individual hairpin RNAs joined in tandem with or without linker sequence. Such structures can have radial symmetry in structure (see, for example, FIG. 2), without having radial symmetry in sequence, i.e. radial iRNA molecules. Alternatively, duplex RNAs can be joined with a variety of spacer sequences to produce a structure that is nearly linear or curved (see, for example, FIG. 3). These structures can be produced by linking a series of oligonucleotides with or without spacer sequence and then adding the complement sequence of these oligonucleotides in the reverse order, again with or without linker sequence. In addition, the various structural strategies can be combined to produce complex structures. Both radially and clustered inhibitory RNA and linear clustered inhibitory RNA structures can mediate targeted destruction of cellular RNA via small interfering RNAs.

Figure 4:
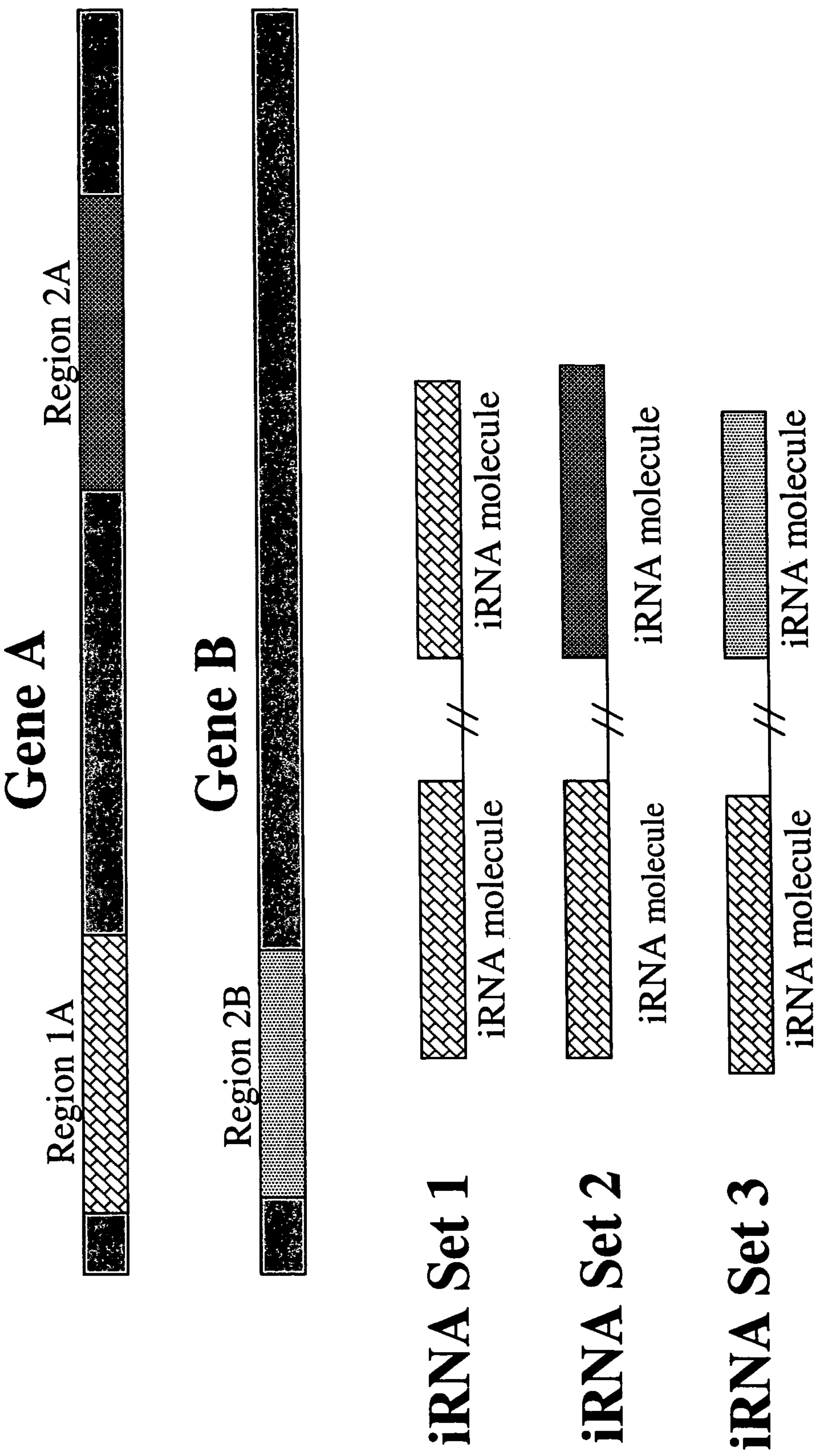
FIG. 4 is a representation of molecules of the present invention. The molecules of the invention contain one or more "sets" of iRNA sequences. These sets can comprise at least one iRNA sequence targeted to a single region of a target gene (Set 1), multiple regions of a target gene (Set 2), or regions on multiple genes (Set 3). The embodiments are further described and exemplified in the text.

Clustered inhibitory RNA can be manufactured so that a single expression vector or DNA template contains from at least 2, 3, 4, 5, 6, 7, 8, 9, 10, 11, 12, 13, 14, 15, 20, 25, 50, 75, or 100 siRNA molecules capable of targeting a single region on an mRNA sequence (see, for example, FIG. 4(*a*)). Additionally, clustered inhibitory RNA can be manufactured so that a single expression vector or DNA template contains at least 2, 3, 4, 5, 6, 7, 8, 9, 10, 11, 12, 13, 14, 15, 20, 25, 50, 75, or 100 siRNAs capable of targeting multiple regions on a single mRNA target sequence (see for example, FIG. 4(*b*)). Alternatively, clustered inhibitory RNA can be manufactured so that a single expression vector contains more than one siRNA molecule capable of targeting multiple regions on multiple mRNA targets (see, for example, FIG. 4(*c*)). In another embodiment, clustered inhibitory RNA can be manufactured so that a single expression vector contains from at least 2, 3, 4, 5, 6, 7, 8, 9, 10, 11, 12, 13, 14, 15, 20, 25, 50, 75, or 100 siRNA molecules capable of targeting a homologous region on multiple mRNA target sequences.

B. Additional iRNA Molecules

Antisense Oligonucleotides

In general, antisense oligonucleotides comprise one or more nucleotide sequences sufficient in identity, number and size to effect specific hybridization with a pre-selected nucleic acid sequence. Antisense oligonucleotides used in accordance with the present invention typically have sequences that are selected to be sufficiently complementary to the target nucleic acid sequences (suitably mRNA in a target cell or organism) so that the antisense oligonucleotide forms a stable hybrid with the mRNA and inhibits the translation of the mRNA sequence, preferably under physiological conditions. The antisense oligonucleotide can be 100% complementary to a portion of the target gene sequence. The antisense oligonucleotides can also be at least 50%, 55%, 60%, 65%, 70%, 75%, 80%, 85%, 90%, 91%, 92%, 93%, 94%, 95%, 96%, 97%, 98%, or 99% complementary to the target nucleic acid sequence.

Antisense oligonucleotides that can be used in accordance with the present invention can be synthesized and used according to procedures that are well known in the art and that will be familiar to the ordinarily skilled artisan. Representative teachings regarding the synthesis, design, selection and use of antisense oligonucleotides include without limitation, for example, U.S. Pat. Nos. 5,789,573, 6,197,584, and Ellington, "Current Protocols in Molecular Biology," 2nd Ed., Ausubel et al., eds., Wiley Interscience, New York (1992).

Ribozymes

Nucleic acid molecules that can be used in the present invention also include ribozymes. In general, ribozymes are RNA molecules having enzymatic activities usually associated with cleavage, splicing or ligation of nucleic acid sequences to which the ribozyme binds. Typical substrates for ribozymes include RNA molecules, although ribozymes can also catalyze reactions in which DNA molecules serve as substrates. Two distinct regions can be identified in a ribozyme: the binding region which gives the ribozyme its specificity through hybridization to a specific nucleic acid sequence, and a catalytic region which gives the ribozyme the activity of cleavage, ligation or splicing. Ribozymes which are active intracellularly work in cis, catalyzing only a single turnover reaction, and are usually self-modified during the reaction. However, ribozymes can be engineered to act in trans, in a truly catalytic manner, with a turnover greater than one and without being self-modified. Owing to the catalytic nature of the ribozyme, a single ribozyme molecule cleaves many molecules of target nucleic acids and therefore therapeutic activity is achieved in relatively lower concentrations than those required in an antisense treatment (See, for example, WO 96/23569).

Ribozymes that can be used in accordance with the present invention can be synthesized and used according to procedures that are well known in the art and that will be familiar to the ordinarily skilled artisan. Representative teachings regarding the synthesis, design, selection and use of ribozymes include without limitation, for example, U.S. Pat. Nos. 4,987,071, and 5,877,021.

Small Interfering RNAs (siRNA)

RNA interference is mediated by double stranded RNA (dsRNA) molecules that have sequence-specific homology to their "target" nucleic acid sequences (Caplen, N.J., et al., Proc. Natl. Acad. Sci. USA 98:9742-9747 (2001)). Biochemical studies in *Drosophila* cell-free lysates indicate that, in certain embodiments of the present invention, the mediators of RNA-dependent gene silencing are 21-25 nucleotide "small interfering" RNA duplexes (siRNAs). Accordingly, siRNA molecules are suitably used in methods of the present invention. The siRNAs are derived from the processing of dsRNA by an RNase enzyme known as Dicer (Bernstein, E., et al., Nature 409:363-366 (2001)). siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al., Nature 409:363-366 (2001); Boutla, A., et al., Curr. Biol. 11:1776-1780 (2001)).

Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 0 to about 50 nucleotides (nt). In examples of nonlimiting embodiments, siRNAs can comprise about 5 to about 40 nt, about 5 to about 30 nt, about 10 to about 30 nt, about 15 to about 25 nt, or about 20-25 nucleotides.

Inverted Repeats

Inverted repeats comprise single stranded nucleic acid molecules that contain two regions that are at least partially complementary to each other, oriented such that one region is inverted relative to the other. This orientation allows the two complementary sequences to base pair with each other, thereby forming a hairpin structure. The two copies of the inverted repeat need not be contiguous. There can be “n” additional nucleotides between the hairpin forming sequences, wherein “n” is any number of nucleotides. For example, n can be at least 1, 5, 10, 25, 50, or 100 nucleotide, or more, and can be any number of nucleotides falling within these discrete values.

Inverted repeats that can be used in accordance with the present invention can be synthesized and used according to procedures that are well known in the art and that will be familiar to the ordinarily skilled artisan. The production and use of inverted repeats for RNA interference can be found in, without limitation, for example, Kirby, K. et al. Proc. Natl. Acad. Sci. USA 99:16162-16167 (2002), Adelman, Z. N. et al. J. Virol. 76:12925-12933 (2002), Yi, C. E. et al. J. Biol. Chem. 278:934-939 (2003), Yang, S. et al. Mol. Cell Biol. 21:7807-7816 (2001), Svoboda, P. et al. Biochem. Biophys. Res. Commun. 287:1099-1104 (2001), and Martinek, S. and Young, M. W. Genetics 156:171-1725 (2000).

Short Hairpin RNA (shRNA)

Paddison, P. J., et al., Genes & Dev. 16:948-958 (2002) have used small RNA molecules folded into hairpins as a means to effect RNA interference. Such short hairpin RNA (shRNA) molecules are also advantageously used in the methods of the present invention. Functionally identical to the inverted repeats described herein, the length of the stem and loop of functional shRNAs distinguishes them from inverted repeats. In one embodiment, stem lengths can be at least fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, or fifty nucleotides and loop size can be at least 2, 3, 4, 5, 6, 7, 8, 9, 10, 11, 12, 13, 14, 15, 16, 17, 18, 19, 20, 25, 30, 40 or 50 nucleotides. While not wishing to be bound by any particular theory, it is believed that these shRNAs resemble the dsRNA products of the Dicer RNase and, in any event, have the same capacity for inhibiting expression of a specific gene. Hairpin RNA structures can mediate targeted destruction of cellular RNA via small interfering RNAs (see, for example, FIG. 1).

Transcription of shRNAs can be initiated at a polymerase III (pol III) promoter and is believed to be terminated at position 2 of a 4-5-thymine transcription termination site. Upon expression, shRNAs are thought to fold into a stem-loop structure with 3' UU-overhangs. Subsequently, the ends of these shRNAs are processed, converting the shRNAs into ~21 nt siRNA-like molecules.

Short hairpin RNAs that can be used in accordance with the present invention can be synthesized and used according to procedures that are well known in the art and that will be familiar to the ordinarily skilled artisan. The production and use of inverted repeats for RNA interference can be found in, without limitation, Paddison, P. J., et al., Genes & Dev. 16:948-958 (2002), Yu, J-Y., et al. Proc. Natl. Acad. Sci. USA 99:6047-6052 (2002), and Paul, C. P. et al. Nature Biotechnol. 20:505-508 (2002).

Small Temporallv Regulated RNAs (stRNAs)

Another group of small RNAs that can be used are the small temporally regulated RNAs (stRNAs). In general, stRNAs comprise from about 20 to about 30 nt (Banerjee and Slack, Bioessays 24:119-129 (2002)), although stRNAs of any size can also be used in accordance with the invention. Unlike siRNAs, stRNAs downregulate expression of a target mRNA after the initiation of translation without degrading the mRNA.

III. Expression of the iRNA Molecules

A. Construct Design

The present invention provides novel constructs and DNA templates to express iRNA molecules, as well as methods to make such constructs.

In one aspect of the present invention, methods are provided to produce transgenic cells and animals that express iRNA molecules at a predetermined location, as well as the cells and animals produced thereby. DNA templates, which produce iRNA molecules, that contain sequence that targets a particular location in the genome can be introduced into cells. In one embodiment, the DNA templates can be targeted such that expression of the iRNA molecule can be achieved without disrupting the endogenous gene function. In one embodiment, the DNA templates can be in the form of vectors. The vectors can be introduced into the cells directly, or linearized prior to introduction into the cell. In another embodiment, the DNA templates can be synthesized as oligonucleotides and introduced into cells. In one embodiment, the DNA templates can integrate into the genome of the cell via targeted integration. The targeted integration can be via homologous recombination. The DNA templates can be inserted via homologous recombination into, for example, a housekeeping gene such that the expression of the iRNA molecule is under the control of the associated promoter of the housekeeping gene. Alternatively, the DNA templates can be inserted via homolgous recombination into a gene that is only expressed in particular cells or organs such that the expression of the iRNA molecule is under the control of the associated promoter of the cell or organ specific gene.

In other embodiments, the DNA templates used to produce the iRNA molecules can integrate into exons of the target gene. In another embodiment, the DNA templates used to produce the iRNA molecules can integrate into introns of the target gene, such as into a non-essential location of an endogenous intron. The DNA templates can be targeted such that the endogenous promoter of the target gene directs transcription of the exogenous DNA template. In still further embodiments, the DNA templates used to produce the iRNA molecules can be embedded in engineered (or synthetic) introns for integration into introns or exons of target genes. The engineered introns can be derived from any endogenous intron. In one embodiment, the endogenous intron can be reduced to its minimal functional components. In another embodiment, restriction sites can be engineered into the synthetic intron. In one embodiment, the restriction enzyme sites allow for placement of the DNA template into the synthetic intron. In further embodiments, the synthetic introns can be inserted into endogenous exons or introns without disrupting the function of the endogenous gene.

In another embodiment, methods are provided to produce cells and animals in which interfering RNA molecules are expressed to regulate the expression of target genes. Methods according to this aspect of the invention can include, for example: identifying one or more target nucleic acid sequences in a cell; introducing DNA templates that produce iRNA molecules that bind to the target sequence and also contain flanking sequence for homologous recombination into the cell; and expressing the DNA templates in the cell under conditions such that the iRNAs bind to the target nucleic acid sequences, thereby regulating expression of one or more target genes. In one embodiment, the present invention provides methods of producing non-human transgenic animals that heritably express iRNA molecules that regulate the expression of one or more target genes. In one embodiment, the animals can be produced via somatic cell nuclear transfer. The somatic cell can be engineered to express the iRNA molecule by any of the techniques described herein.

Engineered (Synthetic) Introns

In further embodiments, the DNA templates used to produce the iRNA molecules can be embedded in engineered (or synthetic) introns for integration into introns or exons of target genes. The engineered introns can be derived from any endogenous intron. In one embodiment, the endogenous intron can be reduced to its minimal functional components. In another embodiment, restriction sites can be engineered into the synthetic intron. In one embodiment, the restriction enzyme sites allow for placement of the DNA template into the synthetic intron. In further embodiments, the synthetic introns can be inserted into endogenous exons or introns without disrupting the function of the endogenous gene.

To obtain the expression pattern, level, and timing of an endogenous gene, one can use homologous recombination to trap all regulatory elements of the endogenous gene. However for many applications, disruption of an endogenous gene would not be acceptable. To utilize this strategy within a gene that has been characterized, one can insert the siRNA(s) into a non-essential location within an endogenous intron of the target gene. Alternatively, one can assemble an exogenous intron to be inserted into an exon of the target gene. The exogenous intron can be naturally occurring or designed (Kriegler M. Assembly of enhancers, promoters, and splice signals to control expression of transferred genes. Methods Enzymol. 1990; 185:512-27; Choi T, Huang M, Gorman C, Jaenisch R. A generic intron increases gene expression in transgenic mice. Mol Cell Biol. 1991 June; 11(6):3070-4; Palmiter R D, Sandgren E P, Avarbock M R, Allen D D, Brinster R L. Heterologous introns can enhance expression of transgenes in mice. Proc Natl Acad Sci USA. 1991 Jan. 15; 88(2):478-82; Petitclerc D, Attal J, Theron M C, Bearzotti M, Bolifraud P, Kann G, Stinnakre M G, Pointu H, Puissant C, Houdebine L M. The effect of various introns and transcription terminators on the efficiency of expression vectors in various cultured cell lines and in the mammary gland of transgenic mice. J Biotechnol. 1995 Jun. 21; 40(3):169-78.

Insertion of an engineered (pr synthetic) intron within an exon of an endogenous gene will allow transcription to be controlled by that gene. Additionally, once splicing has occurred, the resulting mRNA of the endogenous gene can be returned to its normal state. The spliced intron can then be available for further processing by cellular components to produce effective inhibitory RNA.

Synthetic Intron Assembly

Figure 20:
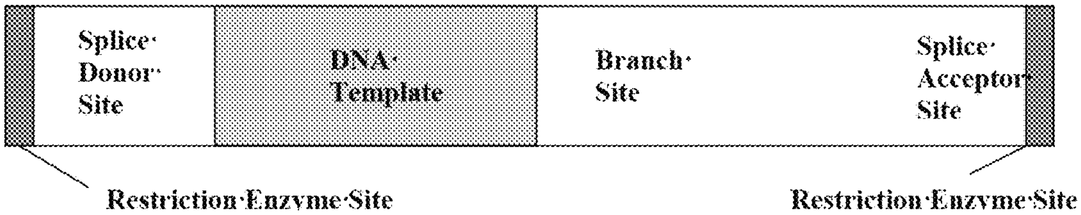
FIG. 20 depicts an exemplary synthetic intron comprising a restriction enzyme site at the 5' end, an intronic splice donor site, a DNA template that can produce at least one iRNA molecule, an intronic branch site, an intronic splice acceptor site and a restriction enzyme site at the 3' end.

A synthetic intron can be designed, based on any known intron. In one embodiment, the known intron has been well characterized in the art and thus the DNA template that produces the iRNA molecule can be inserted into a site within the intron that is known to not effect the function of the intron. Briefly, restriction enzyme sites can be engineered into the intron and the DNA template can then be inserted into the intron at a location, which is non-essential for intron function. Additionally, restriction enzyme sites can be added to the sequence 5' and 3' of the intron to allow for targeted insertion of the synthetic intron into a target exon or intron. In one particular embodiment, the synthetic intron can contain at least a restriction enzyme site at the 5' end, an intronic splice donor site, a DNA template that can produce at least one iRNA molecule, an intronic branch site, an intronic splice acceptor site and a restriction enzyme site at the 3' end, see, for example, the schematic depicted in FIG. 20.

In other embodiments, an engineered intron can be created from any known gene, for example, a cell or tissue-specific gene. In one embodiment, if the intron is uncharacterized, the following non-limiting methodology can identify an appropriate insertion point for the DNA template, which will not effect intron function. First, sequence the intron. Then, set up a reporter assay, for example, by linking the gene to a reporter gene to test for functioning of the intron. Next, engineer restriction enzyme sites into a location of the intron and then clone into the intron the DNA template sequence. Finally, test the synthetic construct in the reporter assay to determine whether insertion of the DNA template interfered with the functioning of the gene. This process can be completed until a non-essential location of the intron is identified for insertion of the DNA template. Further, this process can also include sequential deletion of intronic sequence until a minimal functional intron is identified.

B. Cloning Strategies

In embodiments of the present invention, DNA can be spliced together to form specific nucleotide sequences. In one embodiment, DNA templates are provided that contain at least a 5' targeting arm for homologous recombination, a first nucleotide sequence, optionally, a linker sequence, a second nucleotide sequence that substantially hybridizes to the first nucleotide sequence and a 3' targeting arm for homologous recombination. Optionally, these DNA template can also be cloned into a synthetic intron. In one embodiment, oligonucleotide sequences can be synthesized for each component of the DNA template and/or synthetic intron and cloned together using restriction enzymes. In another embodiment, each component can be engineered in an expression vector. In one embodiment, the vector can be introduced into the cell to achieve genetic modification of ther cell. In another embodiment, the vector can be linearized and then inserted into the cell.

In other embodiments of the present invention, at least two iRNA molecules can be expressed in a cell. In one embodiment, clustered iRNA molecules are expressed in a cell. In one embodiment, to clone a series of iRNA oligonucleotides into an expression vector the following strategy can be employed. First, a vector can be obtained with two non-compatible, unique restriction sites and then the first oligonucleotide can be directionally clone into those sites. The first oligonucleotide can be designed to destroy the one of the restriction sites upon cloning and supply a functional restriction site on the opposite end. With this strategy, cleavage sites for the two original restriction enzymes are present in the new construct and the next oligonucleotide can be cloned into those sites. The cycle can be repeated until the desired number of oligonucleotides are cloned and the transgene is assemble. As an example utilizing restriction sites for BclI (tgatca) and MluI (acgcgt) the following composition can be used:

| Prefix | stem side 1 - loop - stem side 2 | suffix |
|---|---|---|
| GATCtgcga<br>BclI<br>compatible<br>end | nnnnnnnnnnnnnnnnnnnnnnnnnnn . . . n | tgcTGATCActagtA (SEQ ID NO: 273)<br>supplied<br>Bcl I<br>site |

In another embodiment, to assemble oligonucleotides, for example, for clustered interference RNA, the following strategy can be followed. Linker sequences can be used to prevent unintentional structures from forming. Non-compatible restriction sites can be used, for example, Bcl I or Mlu I sites. These sites can be cloned directionally and upstream sites can be destroyed and also re-supplied to the new vector in the downstream region in preparation for the next hairpin oligonucleotide.

The DNA constructs, templates and/or vectors disclosed herein can be inserted in either an exon or an intron of an endogenous gene. In a particular embodiment, the insertion does not alter the function of the target intron or exon. The targeting strategy serves to maintain the functional integrity of the targeted gene while exploiting its endogenous regulatory capabilities to express the iRNA molecules in the cell. Gene, including intronic and exonic, function can be assayed using functional assays to determine whether gene function has been compromised by the insertion.

Vectors

In one embodiment, from about at least 2, 3, 4, 5, 6, 7, 8, 9, 10, 11, 12, 13, 14, 15, 20, 25, 50, or 100 iRNA molecules can be cloned into a vector. The vector containing the iRNA molecules can further be introduced or inserted into a prokaryotic or eukaryotic cell, preferably resulting in expression of the iRNA molecules. In one embodiment, the iRNA molecules can be operably linked to a promoter in the vector. The promoter can be an exogenous or endogenous promoter. In an alternative embodiment, the iRNA molecules are cloned into a promoterless vector, and inserted into the genome of a eukaryotic cell, wherein the promoterless vector is under the control of a promoter and/or other regulatory elements associated with an endogenous gene. In a particular embodiment, such promoterless vectors do not disrupt cell homeostasis or the functioning of the endogenous gene.

The term "vector," as used herein, refers to a nucleic acid molecule (preferably DNA) that provides a useful biological or biochemical property to an inserted nucleic acid. "Expression vectors" according to the invention include vectors that are capable of enhancing the expression of one or more iRNA molecules that have been inserted or cloned into the vector, upon transformation of the vector into a cell. The terms "vector" and "plasmid" are used interchangeably herein. Examples of vectors include, phages, autonomously replicating sequences (ARS), centromeres, and other sequences which are able to replicate or be replicated in vitro or in a cell, or to convey a desired nucleic acid segment to a desired location within a cell of an animal. Expression vectors useful in the present invention include chromosomal-, episomal- and virus-derived vectors, e.g., vectors derived from bacterial plasmids or bacteriophages, and vectors derived from combinations thereof, such as cosmids and phagemids. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575), TA Cloning® brand PCR cloning (Invitrogen Corp., Carlsbad, Calif.)) can also be applied to clone a nucleic acid into a vector to be used according to the present invention. The vector can further contain one or more selectable markers to identify cells transformed with the vector, such as the selectable markers and reporter genes described herein. In addition, the iRNA containing expression vector is assembled to include a cloning region and a poly(U)-dependent PolIII transcription terminator.

In accordance with the invention, any vector can be used to construct the iRNA containing expression vectors of the invention. In addition, vectors known in the art and those commercially available (and variants or derivatives thereof) can, in accordance with the invention, be engineered to include one or more recombination sites for use in the methods of the invention. Such vectors can be obtained from, for example, Vector Laboratories Inc., Invitrogen, Promega, Novagen, NEB, Clontech, Boehringer Mannheim, Pharmacia, EpiCenter, OriGenes Technologies Inc., Stratagene, PerkinElmer, Pharmingen, and Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts.

Other vectors of interest include viral origin vectors (M13 vectors, bacterial phage λ vectors, adenovirus vectors, and retrovirus vectors), high, low and adjustable copy number vectors, vectors which have compatible replicons for use in combination in a single host (pACYC184 and pBR322) and eukaryotic episomal replication vectors (pCDM8).

Vectors of interest include prokaryotic expression vectors such as pcDNA II, pSL301, pSE280, pSE380, pSE420, pTrcHisA, B, and C, pRSET A, B, and C (Invitrogen, Corp.), pGEMEX-1, and pGEMEX-2 (Promega, Inc.), the pET vectors (Novagen, Inc.), pTrc99A, pKK223-3, the pGEX vectors, pEZZ18, pRIT2T, and pMC1871 (Pharmacia, Inc.), pKK233-2 and pKK388-1 (Clontech, Inc.), and pProEx-HT (Invitrogen, Corp.) and variants and derivatives thereof. Other vectors of interest include eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHis A, B, and C, pVL1392, pBlueBacIII, pCDM8, pcDNA1, pZeoSV, pcDNA3 pREP4, pCEP4, and pEBVHis (Invitrogen, Corp.) and variants or derivatives thereof.

Other vectors that can be used include pUC18, pUC19, pBlueScript, pSPORT, cosmids, phagemids, YAC's (yeast artificial chromosomes), BAC's (bacterial artificial chromosomes), P1 (*Escherichia coli* phage), pQE70, pQE60, pQE9 (quagan), pBS vectors, PhageScript vectors, BlueScript vectors, pNH8A, pNH16A, pNH18A, pNH46A (Stratagene), pcDNA3 (Invitrogen), pGEX, pTrsfus, pTrc99A, pET-5, pET-9, pKK223-3, pKK233-3, pDR540, pRITS (Pharmacia), pSPORT1, pSPORT2, pCMVSPORT2.0 and pSV-SPORT1 (Invitrogen) and variants or derivatives thereof. Viral vectors can also be used, such as lentiviral vectors (see, for example, WO 03/059923; Tiscornia et al. PNAS 100: 1844-1848 (2003)).

Additional vectors of interest include pTrxFus, pThioHis, pLEX, pTrcHis, pTrcHis2, pRSET, pBlueBacHis2, pcDNA3.1/His, pcDNA3.1(−)/Myc-His, pSecTag, pEB-VHis, pPIC9K, pPIC3.5K, pAO815, pPICZ, pPICZα, pGAPZ, pGAPZα, pBlueBac4.5, pBlueBacHis2, pMelBac, pSinRep5, pSinHis, pIND, pIND(SP1), pVgRXR, pcDNA2.1, pYES2, pZErO1.1, pZErO-2.1, pCR-Blunt, pSE280, pSE380, pSE420, pVL1392, pVL1393, pCDM8, pcDNA1.1, pcDNA1.1/Amp, pcDNA3.1, pcDNA3.1/Zeo, pSe, SV2, pRc/CMV2, pRc/RSV, pREP4, pREP7, pREP8, pREP9, pREP 10, pCEP4, pEBVHis, pCR3.1, pCR2.1, pCR3.1-Uni, and pCRBac from Invitrogen; λ ExCell, λ gt11, pTrc99A, pKK223-3, pGEX-1λT, pGEX-2T, pGEX-2TK, pGEX-4T-1, pGEX-4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE-4abc(+), pOCUS-2, pTAg, pET-32LIC, pET-30LIC, pBAC-2cp LIC, pBACgus-2cp LIC, pT7Blue-2 LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21 abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBAC-gus-1, pBAC4x-1, pBACgus4x-1, pBAC-3cp, pBACgus-2cp, pBACsurf-1, pig, Signal pig, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6×His-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMV, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX4T-1/2/3, pYEX-S1, pBacPAK-His, pBacPAK8/9, pAcUW31, BacPAK6, pTriplEx, λgt10, λgt11, pWE15, and TriplEx from Clontech; Lambda ZAP II, pBK-CMV, pBK-RSV, pBluescript II KS+/−, 1 pBluescript II SK+/−, pAD-GAL4, pBD-GAL4 Cam, pSurfscript, Lambda FIX II, Lambda DASH, Lambda EMBL3, Lambda EMBL4, Super-Cos, pCR-Scrigt Amp, pCR-Script Cam, pCR-Script Direct, pBS+/−, pBC KS+/−, pBC SK+/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Two-hybrid and reverse two-hybrid vectors of interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

(1) Vectors Under the Control of a Promoter

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter" denotes a segment of DNA which contains sequences capable of providing promoter functions (i.e., the functions provided by a promoter element). For example, the long terminal repeats of retroviruses contain promoter functions. The promoter may be "endogenous" or "exogenous" or "heterologous." An "endogenous" promoter is one which is associated with a given gene in the genome. An "exogenous" or "heterologous" promoter is one which is placed in juxtaposition to a gene by means of genetic manipulation (i.e., molecular biological techniques such as cloning and recombination) such that transcription of that gene is directed by the linked promoter. Promoters can also contain enhancer activities.

a. Endogenous Promoters

In one embodiment, the operably linked promoter of the iRNA molecule containing vector is an endogenous promoter. In one aspect of this embodiment, the endogenous promoter can be any unregulated promoter that allows for the continual transcription of its associated gene.

In another aspect, the promoter can be a constitutively active promoter. More preferably, the endogenous promoter is associated with a housekeeping gene. Non limiting examples of housekeeping genes whose promoter can be operably linked to the iRNA include the conserved cross species analogs of the following human housekeeping genes; mitochondrial 16S rRNA, ribosomal protein L29 (RPL29), H3 histone, family 3B (H3.3B) (H3F3B), poly (A)-binding protein, cytoplasmic 1 (PABPC1), HLA-B associated transcript-1 (D6S81E), surfeit 1(SURF1), ribosomal protein L8 (RPL8), ribosomal protein L38 (RPL38), catechol-O-methyltransferase (COMT), ribosomal protein S7 (RPS7), heat shock 27 kD protein 1 (HSPB1), eukaryotic translation elongation factor 1 delta (guanine nucleotide exchange protein) (EEFID), vimentin (VIM), ribosomal protein L41 (RPL41), carboxylesterase 2 (intestine, liver) (CES2), exportin 1 (CRM1, yeast, homolog) (XPO1), ubiquinol-cytochrome c reductase hinge protein (UQCRH), Glutathione peroxidase 1 (GPX1), ribophorin II (RPN2), Pleckstrin and Sec7 domain protein (PSD), human cardiac troponin T, proteasome (prosome, macropain) subunit, beta type, 5 (PSMB5), cofilin 1 (non-muscle) (CFL1), seryl-tRNA synthetase (SARS), catenin (cadherin-associated protein), beta 1 (88 kD) (CTNNB1), Duffy blood group (FY), erythrocyte membrane protein band 7.2 (stomatin) (EPB72), Fas/Apo-1, LIM and SH3 protein 1 (LASP1), accessory proteins BAP31/BAP29 (DXS357E), nascent-polypeptide-associated complex alpha polypeptide (NACA), ribosomal protein L18a (RPL18A), TNF receptor-associated factor 4 (TRAF4), MLN51 protein (MLN51), ribosomal protein L11 (RPL11), Poly(rC)-binding protein 2 (PCBP2), thioredoxin (TXN), glutaminyl-tRNA synthetase (QARS), testis enhanced gene transcript (TEGT), prostatic binding protein (PBP), signal sequence receptor, beta (translocon-associated protein beta) (SSR2), ribosomal protein L3 (RPL3), centrin, EF-hand protein, 2 (CETN2), heterogeneous nuclear ribonucleoprotein K (HNRPK), glutathione peroxidase 4 (phospholipid hydroperoxidase) (GPX4), fusion, derived from t(12; 16) malignant liposarcoma (FUS), ATP synthase, H+ transporting, mitochondrial F0 complex, subunit c (subunit 9), isoform 2 (ATP5G2), ribosomal protein S26 (RPS26), ribosomal protein L6 (RPL6), ribosomal protein S18 (RPS18), serine (or cysteine) proteinase inhibitor, clade A (alpha-1 antiproteinase, antitrypsin), member 3 (SERPINA3), dual specificity phosphatase 1 (DUSP1), peroxiredoxin 1 (PRDX1), epididymal secretory protein (19.5 kD) (HE1), ribosomal protein S8 (RPS8), translocated promoter region (to activated MET oncogene) (TPR), ribosomal protein L13 (RPL13), SON DNA binding protein (SON), ribosomal prot L19 (RPL19), ribosomal prot (homolog to yeast S24), CD63 antigen (melanoma 1 antigen) (CD63), protein tyrosine phosphatase, non-receptor type 6 (PTPN6), eukaryotic translation elongation factor 1 beta 2 (EEFIB2), ATP synthase, H+ transporting, mitochondrial F0 complex, subunit b, isoform 1 (ATP5F1), solute carrier family 25 (mitochondrial carrier; phosphate carrier), member 3 (SLC25A3), tryptophanyl-tRNA synthetase (WARS), glutamate-ammonia ligase (glutamine synthase) (GLUL), ribosomal protein L7 (RPL7), interferon induced transmembrane protein 2 (1-8D) (IFITM2), tyrosine 3-monooxygenase/tryptophan 5-monooxygenase activation protein, beta polypeptide (YWHAB), Casein kinase 2, beta polypeptide (CSNK2B), ubiquitin A-52 residue ribosomal protein fusion product 1 (UBA52), ribosomal protein L13a (RPL13A), major histocompatibility complex, class I, E (HLA-E), jun D proto-oncogene (JUND), tyrosine 3-monooxygenase/tryptophan 5-monooxygenase activation protein, theta polypeptide (YWHAQ), ribosomal protein L23 (RPL23), Ribosomal protein S3 (RPS3), ribosomal protein L17 (RPL17), filamin A, alpha (actin-binding protein-280) (FLNA), matrix Gla protein (MGP), ribosomal protein L35a (RPL35A), peptidylprolyl isomerase A (cyclophilin A) (PPIA), villin 2 (ezrin) (VIL2), eukaryotic translation elongation factor 2 (EEF2), jun B proto-oncogene (JUNB), ribosomal protein S2 (RPS2), cytochrome c oxidase subunit VIIc (COX7C), heterogeneous nuclear ribonucleoprotein L (HNRPL), tumor protein, translationally-controlled 1 (TPT1), ribosomal protein L31 (RPL31), cytochrome c oxidase subunit VIIa polypeptide 2 (liver) (COX7A2), DEAD/H (Asp-Glu-Ala-Asp/His) box polypeptide 5 (RNA helicase, 68 kD) (DDX5), cytochrome c oxidase subunit VIa polypeptide 1 (COX6A1), heat shock 90 kD protein 1, alpha (HSPCA), Sjogren syndrome antigen B (autoantigen La) (SSB), lactate dehydrogenase B (LDHB), high-mobility group (nonhistone chromosomal) protein 17 (HMG17), cytochrome c oxidase subunit VIc (COX6C), heterogeneous nuclear ribonucleoprotein A1 (HNRPA1), aldolase A, fructose-bisphosphate (ALDOA), integrin, beta 1 (fibronectin receptor, beta polypeptide, antigen CD29 includes MDF2, MSK12) (ITGB1), ribosomal protein S11 (RPS11), small nuclear ribonucleoprotein 70 kD polypeptide (RN antigen) (SNRP20), guanine nucleotide binding protein (G protein), beta polypeptide 1 (GNB1), heterogeneous nuclear ribonucleoprotein A1 (HNRPA1), calpain 4, small subunit (30K) (CAPN4), elongation factor TU (N-terminus)/X03689, ribosomal protein L32 (RPL32), major histocompatibility complex, class II, DP alpha 1 (HLA-DPA1), superoxide dismutase 1, soluble (amyotrophic lateral sclerosis 1 (adult)) (SOD1), lactate dehydrogenase A (LDHA), glyceraldehyde-3-phosphate dehydrogenase (GAPD), Actin, beta (ACTB), major histocompatibility complex, class II, DP alpha (HLA-DRA), tubulin, beta polypeptide (TUBB), metallothionein 2A (MT2A), phosphoglycerate kinase 1 (PGK1), KRAB-associated protein 1 (TIF1B), eukaryotic translation initiation factor 3, subunit 5 (epsilon, 47 kD) (EIF3S5), NADH dehydrogenase (ubiquinone) 1 alpha subcomplex, 4 (9 kD, MLRQ) (NDUFA4), chloride intracellular channel 1 (CLIC1), adaptor-related protein complex 3, sigma 1 subunit (AP3S1), cytochrome c oxidase subunit IV (COX4), PDZ and LIM domain 1 (elfin) (PDLIM1), glutathione-S-transferase like; glutathione transferase omega (GSTTLp28), interferon stimulated gene (20 kD) (ISG20), nuclear factor I/B (NFIB), COX10 (yeast) homolog, cytochrome c oxidase assembly protein (heme A: farnesyltransferase), conserved gene amplified in osteosarcoma (OS4), deoxyhypusine synthase (DHPS), galactosidase, alpha (GLA), microsomal glutathione S-transferase 2 (MGST2), eukaryotic translation initiation factor 4 gamma, 2 (EIF4G2), ubiquitin carrier protein E2-C(UBCH10), BTG family, member 2 (BTG2), B-cell associated protein (REA), COP9 subunit 6 (MOV34 homolog, 34 kD) (MOV34-34KD), ATX1 (antioxidant protein 1, yeast) homolog 1 (ATOX1), acidic protein rich in leucines (SSP29), poly(A)-binding prot (PABP) promoter region, selenoprotein W, 1 (SEPW1), eukaryotic translation initiation factor 3, subunit 6 (48 kD) (EIF3S6), carnitine palmitoyltransferase I, muscle (CPT1B), transmembrane trafficking protein (TMP21), four and a half LIM domains 1 (FHL1), ribosomal protein S28 (RPS28), myeloid leukemia factor 2 (MLF2), neurofilament triplet L prot/U57341, capping protein (actin filament) muscle Z-line, alpha 1 (CAPZA1), 1-acylglycerol-3-phosphate O-acyltransferase 1

(lysophosphatidic acid acyltransferase, alpha) (AGPAT1), inositol 1,3,4-triphosphate 5/6 kinase (ITPK1), histidine triad nucleotide-binding protein (HINT), dynamitin (dynactin complex 50 kD subunit) (DCTN-50), actin related protein 2/3 complex, subunit 2 (34 kD) (ARPC2), histone deacetylase 1 (HDAC1), ubiquitin B, chitinase 3-like 2 (CHI3L2), D-dopachrome tautomerase (DDT), zinc finger protein 220 (ZNF220), sequestosome 1 (SQSTM1), cystatin B (stefin B) (CSTB), eukaryotic translation initiation factor 3, subunit 8 (110 kD) (EIF3S8), chemokine (C-C motif) receptor 9 (CCR9), ubiquitin specific protease 11 (USP11), laminin receptor 1 (67 kD, ribosomal protein SA) (LAMR1), amplified in osteosarcoma (OS-9), splicing factor 3b, subunit 2, 145 kD (SF3B2), integrin-linked kinase (ILK), ubiquitin-conjugating enzyme E2D 3 (homologous to yeast UBC4/5) (UBE2D3), chaperonin containing TCP1, subunit 4 (delta) (CCT4), polymerase (RNA) II (DNA directed) polypeptide L (7.6 kD) (POLR2L), nuclear receptor co-repressor 2 (NCOR2), accessory proteins BAP31/BAP29 (DXS1357E, SLC6A8), 13 kD differentiation-associated protein (LOC55967), Taxi (human T-cell leukemia virus type 1) binding protein 1 (TAX1BP1), damage-specific DNA binding protein 1 (127 kD) (DDB1), dynein, cytoplasmic, light polypeptide (PIN), methionine aminopeptidase; eIF-2-associated p67 (MNPEP), G protein pathway suppressor 2 (GPS2), ribosomal protein L21 (RPL21), coatomer protein complex, subunit alpha (COPA), G protein pathway suppressor 1(GPS1), small nuclear ribonucleoprotein D2 polypeptide (16.5 kD) (SNRPD2), ribosomal protein S29 (RPS29), ribosomal protein S10 (RPS10), ribosomal proteinS9 (RPS9), ribosomal protein S5 (RPS5), ribosomal protein L28 (RPL28), ribosomal protein L27a (RPL27A), protein tyrosine phosphatase type IVA, member 2 (PTP4A2), ribosomal prot L36 (RPL35), ribosomal protein L10a (RPL10A), Fc fragment of IgG, receptor, transporter, alpha (FCGRT), maternal G10 transcript (G10), ribosomal protein L9 (RPL9), ATP synthase, H+ transporting, mitochondrial F0 complex, subunit c (subunit 9) isoform 3 (ATP5G3), signal recognition particle 14 kD (homologous Alu RNA-binding protein) (SRP14), mutL (*E. coli*) homolog 1 (colon cancer, nonpolyposis type 2) (MLH1), chromosome 1q subtelomeric sequence DIS553/U06155, fibromodulin (FMOD), amino-terminal enhancer of split (AES), Rho GTPase activating protein 1 (ARHGAP1), non-POU-domain-containing, octamer-binding (NONO), v-raf murine sarcoma 3611 viral oncogene homolog 1 (ARAF1), heterogeneous nuclear ribonucleoprotein A1 (HNRPA1), beta 2-microglobulin (B2M), ribosomal protein S27a (RPS27A), bromodomain-containing 2 (BRD2), azoospermia factor 1 (AZF1), upregulated by 1,25 dihydroxyvitamin D-3 (VDUP1), serine (or cysteine) proteinase inhibitor, clade B (ovalbumin), member 6 (SERPINB6), destrin (actin depolymerizing factor) (ADF), thymosin beta-10 (TMSB10), CD34 antigen (CD34), spectrin, beta, non-erythrocytic 1 (SPTBN1), angio-associated, migratory cell protein (AAMP), major histocompatibility complex, class I, A (HLA-A), MYC-associated zinc finger protein (purine-binding transcription factor) (MAZ), SET translocation (myeloid leukemia-associated) (SET), paired box gene(aniridia, keratitis) (PAX6), zinc finger protein homologous to Zfp-36 in mouse (ZFP36), FK506-binding protein 4 (59 kD) (FKBP4), nucleosome assembly protein 1-like 1 (NAP1L1), tyrosine 3-monooxygenase/tryptophan 5-monooxygenase activation protein, zeta polypeptide (YWHAZ), ribosomal protein S3A (RPS3A), ADP-ribosylation factor 1, ribosomal protein S19 (RPS19), transcription elongation factor A (SII), 1 (TCEA1), ribosomal protein S6 (RPS6), ADP-ribosylation factor 3 (ARF3), moesin (MSN), nuclear factor of kappa light polypeptide gene enhancer in B-cells inhibitor, alpha (NFKBIA), complement component 1, q subcomponent binding protein (C1QBP), ribosomal protein S25 (RPS25), clusterin (complement lysis inhibitor, SP-40,40, sulfated glycoprotein 2, testosterone-repressed prostate message 2, apolipoprotein J) (CLU), nucleolin (NCL), ribosomal protein S16 (RPS16), ubiquitin-activating enzyme E1 (A1S9T and BN75 temperature sensitivity complementing) (UBE1), lectin, galactoside-binding, soluble, 3 (galectin 3) (LGALS3), eukaryotic translation elongation factor 1 gamma (EEF1G), pim-1 oncogene (PIM1), S100 calcium-binding protein A10 (annexin II ligand, calpactin I, light polypeptide (p11)) (S100A10), H2A histone family, member Z (H2AFZ), ADP-ribosylation factor 4 (ARF4) (ARF4), ribosomal protein L7a (RPL7A), major histocompatibility complex, class II, DQ alpha 1 (HLA-DQA1), FK506-binding protein 1A (12 kD) (FKBP1A), CD81 antigen (target of antiproliferative antibody 1) (CD81), ribosomal protein S15 (RPS15), X-box binding protein 1 (XBP1), major histocompatibility complex, class II, DN alpha (HLA-DNA), ribosomal protein S24 (RPS24), leukemia-associated phosphoprotein p18 (stathmin) (LAP18), myosin, heavy polypeptide 9, non-muscle (MYH9), casein kinase 2, beta polypeptide (CSNK2B), fucosidase, alpha-L-1, tissue (FUCA1), diaphorase (NADH) (cytochrome b-5 reductase) (DIA1), cystatin C (amyloid angiopathy and cerebral hemorrhage) (CST3), ubiquitin C (UBC), ubiquinol-cytochrome c reductase binding protein (UQCRB), prothymosin, alpha (gene sequence 28) (PTMA), glutathione S-transferase pi (GSTP1), guanine nucleotide binding protein (G protein), beta polypeptide 2-like 1 (GNB2L1), nucleophosmin (nucleolar phosphoprotein B23, numatrin) (NPM1), CD3E antigen, epsilon polypeptide (TiT3 complex) (CD3E), calpain 2, (m/II) large subunit (CAPN2), NADH dehydrogenase (ubiquinone) flavoprotein 2 (24 kD) (NDUFV2), heat shock 60 kD protein 1 (chaperonin) (HSPD1), guanine nucleotide binding protein (G protein), alpha stimulating activity polypeptide 1 (GNAS1), clathrin, light polypeptide (Lca) (CLTA), ATP synthase, H+ transporting, mitochondrial F1 complex, beta polypeptide, calmodulin 2 (phosphorylase kinase, delta) (CALM2), actin, gamma 1 (ACTG1), ribosomal protein S17 (RPS17), ribosomal protein, large, P1 (RPLP1), ribosomal protein, large, P0 (RPLP0), thymosin, beta 4, X chromosome (TMSB4X), heterogeneous nuclear ribonucleoprotein C (C1/C2) (HNRPC), ribosomal protein L36a (RPL36A), glucuronidase, beta (GUSB), FYN oncogene related to SRC, FGR, YES (FYN), prothymosin, alpha (gene sequence 28) (PTMA), enolase 1, (alpha) (ENO1), laminin receptor 1 (67 kD, ribosomal protein SA) (LAMR1), ribosomal protein S14 (RPS14), CD74 antigen (invariant polypeptide of major histocompatibility complex, class II antigen-associated), esterase D/formylglutathione hydrolase (ESD), H3 histone, family 3A (H3F3A), ferritin, light polypeptide (FTL), Sec23 (*S. cerevisiae*) homolog A (SEZ23A), actin, beta (ACTB), presenilin 1 (Alzheimer disease 3) (PSEN1), interleukin-1 receptor-associated kinase 1 (IRAK1), zinc finger protein 162 (ZNF162), ribosomal protein L34 (RPL34), beclin 1 (coiled-coil, myosin-like BCL2-interacting protein) (BECN1), phosphatidylinositol 4-kinase, catalytic, alpha polypeptide (PIK4CA), IQ motif containing GTPase activating protein 1 (IQGAP1), signal transducer and activator of transcription 3 (acute-phase response factor) (STAT3), heterogeneous nuclear ribonucleoprotein F (HNRPF), putative translation initiation factor (SUI1), protein translocation complex beta (SEC61B), ras homolog gene family, member A (ARHA), ferritin, heavy polypeptide 1 (FTH1), Rho GDP dissociation inhibitor (GDI) beta (ARHGDIB), H2A histone family, member O (H2AFO), annexin A11 (ANXA11), ribosomal protein L27 (RPL27), adenylyl cyclase-associated protein (CAP), zinc finger protein 91 (HPF7, HTF10) (ZNF91), ribosomal protein L18 (RPL18), farnesyltransferase, CAAX box, alpha (FNTA), sodium channel, voltage-gated, type 1, beta polypeptide (SCNIB), calnexin (CANX), proteolipid protein 2 (colonic epithelium-enriched) (PLP2), amyloid beta (A4) precursor-like protein 2 (APLP2), Voltage-dependent anion channel 2, proteasome (prosome, macropain) activator subunit 1 (PA28 alpha) (PSME1), ribosomal prot L12 (RPL12), ribosomal protein L37a (RPL37A), ribosomal protein S21 (RPS21), proteasome (prosome, macropain) 26S subunit, ATPase, 1 (PSMC1), major histocompatibility complex, class II, DQ beta 1 (HLA-DQB1), replication protein A2 (32 kD) (RPA2), heat shock 90 kD protein 1, beta (HSPCB), cytochrome c oxydase subunit VIII (COX8), eukaryotic translation elongation factor 1 alpha 1 (EEF1A1), SNRPN upstream reading frame (SNURF), lectin, galactoside-binding, soluble, 1 (galectin 1) (LGALS1), lysosomal-associated membrane protein 1 (LAMP1), phosphoglycerate mutase 1 (brain) (PGAM1), interferon-induced transmembrane protein 1 (9-27) (IFITM1), nuclease sensitive element binding protein 1 (NSEP1), solute carrier family 25 (mitochondrial carrier; adenine nucleotide translocator), member 6 (SLC25A6), ADP-ribosyltransferase (NAD+; poly (ADP-ribose) polymerase) (ADPRT), leukotriene A4 hydrolase (LTA4H), profilin 1 (PFN1), prosaposin (variant Gaucher disease and variant metachromatic leukodystrophy) (PSAP), solute carrier family 25 (mitochondrial carrier; adenine nucleotide translocator), member 5 (SLC25A5), beta-2 microglobulin, insulin-like growth factor binding protein 7, Ribosomal prot S13, Epstein-Barr Virus Small Rna-Associated prot, Major Histocompatibility Complex, Class I, C X58536), Ribosomal prot S12, Ribosomal prot L10, Transformation-Related prot, Ribosomal prot L5, Transcriptional Coactivator Pc4, Cathepsin B, Ribosomal prot L26, "Major Histocompatibility Complex, Class I X12432", Wilm S Tumor-Related prot, Tropomyosin Tm30 nm Cytoskeletal, Liposomal Protein S4, X-Linked, Ribosomal prot L37, Metallopanstimulin 1, Ribosomal prot L30, Heterogeneous Nuclear Ribonucleoprot K, Major Histocompatibility Complex, Class I, E M21533, Major Histocompatibility Complex, Class I, E M20022, Ribosomal protein L30 Homolog, Heat Shock prot 70 Kda, "Myosin, Light Chain/U02629", "Myosin, Light Chain/U02629", Calcyclin, Single-Stranded Dna-Binding prot Mssp-1, Triosephosphate Isomerase, Nuclear Mitotic Apparatus prot 1, prot Kinase Ht31 Camp-Dependent, Tubulin, Beta 2, Calmodulin Type I, Ribosomal prot S20, Transcription Factor Btf3b, Globin, Beta, Small Nuclear RibonucleoproteinPolypeptide CAlt. Splice 2, Nucleoside Diphosphate Kinase Nm23-H2s, Ras-Related C3 Botulinum Toxin Substrate, activating transcription factor 4 (tax-responsive enhancer element B67) (ATF4), prefoldin (PFDN5), N-myc downstream regulated (NDRG1), ribosomal protein L14 (RPL14), nicastrin (KIAA0253), protease, serine, 11 (IGF binding) (PRSS11), KIAA0220 protein (KIAA0220), dishevelled 3 (homologous to *Drosophila* dsh) (DVL3), enhancer of rudimentary *Drosophila* homolog (ERH), RNA-binding protein gene with multiple splicing (RBPM5), 5-aminoimidazole-4-carboxamide ribonucleotide formyltransferase/IMP cyclohydrolase (ATIC), KIAA0164 gene product (KIAA0164), ribosomal protein L39 (RPL39), tyrosine 3 monooxygenase/tryptophan 5-monooxygenase activation protein, eta polypeptide (YWHAH), Ornithine decarboxylase antizyme 1 (OAZ1), proteasome (prosome, macropain) 26S subunit, non-ATPase, 2 (PSMD2), cold inducible RNA-binding protein (CIRBP), neural precursor cell expressed, developmentally down-regulated 5 (NEDD5), high-mobility group nonhistone chromosomal protein 1 (HMG1), malate dehydrogenase 1, NAD (soluble) (MDH1), cyclin I (CCNI), proteasome (prosome, macropain) 26S subunit, non-ATPase, 7 (Mov34 homolog) (PSMD7), major histocompatibility complex, class I, B (HLA-B), ATPase, vacuolar, 14 kD (ATP6S14), transcription factor-like 1 (TCFL1), KIAA0084 protein (KIAA0084), proteasome (prosome, macropain) 26S subunit, non-ATPase, 8 (PSMD8), major histocompatibility complex, class I, A (HIA-A), alanyl-tRNA synthetase (AARS), lysyl-tRNA synthetase (KARS), ADP-ribosylation factor-like 6 interacting protein (ARL6IP), KIAA0063 gene product (KIAA0063), actin binding LIM protein 1 (ABLIM), DAZ associated protein 2 (DAZAP2), eukaryotic translation initiation factor 4A, isoform 2 (EIF4A2), CD151 antigen (CD151), proteasome (prosome, macropain) subunit, beta type, 6 (PSMB6), proteasome (prosome, macropain) subunit, beta type, 4 (PSMB4), proteasome (prosome, macropain) subunit, beta type, 2 (PSMB2), proteasome (prosome, macropain) subunit, beta type, 3 (PSMB3), Williams-Beuren syndrome chromosome region 1 (WBSCR1), ancient ubiquitous protein 1 (AUP1), KIAA0864 protein (KIAA0864), neural precursor cell expressed, developmentally down-regulated 8 (NEDD8), ribosomal protein L4 (RPL4), KIAA0111 gene product (KIAA0111), transgelin 2 (TAGLN2), Clathrin, heavy polypeptide (Hc) (CLTC, CLTCL2), ATP synthase, H+ transporting, mitochondrial F1complex, gamma polypeptide 1 (ATP5C1), calpastatin (CAST), MORF-related gene X (KIA0026), ATP synthase, H+ transporting, mitochondrial F1 complex, alpha subunit, isoform 1, cardiac muscle (ATP5A1), phosphatidylserine synthase 1 (PTDSS1), anti-oxidant protein 2 (non-selenium glutathione peroxidase, acidic calcium-independent phospholipase A2) (KIAA0106), KIAA0102 gene product (KIAA0102), ribosomal protein S23 (RPS23), CD164 antigen, sialomucin (CD164), GDP dissociation inhibitor 2 (GDI2), enoyl Coenzyme A hydratase, short chain, 1, mitochondrial (ECHS1), eukaryotic translation initiation factor 4A, isoform 1 (EIF4A1), cyclin D2 (CCND2), heterogeneous nuclear ribonucleoprotein U (scaffold attachment factor A) (HNRPU), APEX nuclease (multifunctional DNA repair enzyme) (APEX), ATP synthase, H+ transporting, mitochondrial F0 complex, subunit c (subunit 9), isoform 1 (ATP5G1), myristoylated alanine-rich protein kinase C substrate (MARCKS, 80K-L) (MACS), annexin A2 (ANXA2), similar to *S. cerevisiae* RER1 (RER1), hyaluronoglucosaminidase 2 (HYAL2), uroplakin 1A (UPK1A), nuclear pore complex interacting protein (NPIP), karyopherin alpha 4 (importin alpha 3) (KPNA4), ant the gene with multiple splice variants near HD locus on 4p16.3 (RES4-22).

In addition, the endogenous promoter can be a promoter associated with the expression of tissue specific or physiologically specific genes, such as heat shock genes. In this way, expression of the iRNA molecules can be tightly regulated.

b. Exogenous Promoters

In another embodiment, the promoter can be an exogenous promoter, such as a ubiquitiously expressed promoeter, such a RNa polymerase promoeters, such as H1 or U6; or constitutively active viral promoter. Non-limiting examples of promoters include the RSV LTR, the SV40 early promoter, the CMV IE promoter, the adenovirus major late promoter, Srα-promoter (a very strong hybrid promoter composed of the SV40 early promoter fused to the R/U5 sequences from the HTLV-I LTR), and the Hepatitis B promoter.

B. Confirmation of Target Susceptibility

Based on sequence conservation, primers are designed and used to amplify coding regions of the target genes. Initially, the most highly expressed coding region from each gene is used to build a model control gene, although any coding or non coding region can be used. Each control gene is assembled by inserting each coding region between a reporter coding region and its poly(A) signal. These plasmids produce an mRNA with a reporter gene in the upstream portion of the gene and a potential iRNA target in the 3' non-coding region. The effectiveness of individual iRNAs is assayed by suppression of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine suppression of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

Although biogenomic information and model genes are invaluable for high-throughput screening of potential iRNAs, interference activity against target nucleic acids ultimately must be established experimentally in cells which express the target nucleic acid.

To determine the interference capability of the iRNA sequence, the iRNA containing vector is transfected into appropriate cell lines which express that target nucleic acid. Each selected iRNA construct is tested for its ability to reduce steady-state mRNA of the target nucleic acid. In addition, any target mRNAs that "survive" the first round of testing are amplified by reverse transcriptase-PCR and sequenced (see, for example, Sambrook, J. et al. "Molecular Cloning: A Laboratory Manual", 2nd addition, Cold Spring Harbor Laboratory Press, Plainview, N.Y. (1989)). These sequences are analyzed to determine individual polymorphisms that allow mRNA to escape the current library of iRNAs. This information is used to further modify iRNA constructs to also target rarer polymorphisms.

Methods by which to transfect cells with iRNA vectors are well known in the art and include, but are not limited to, electroporation, particle bombardment, microinjection, transfection with viral vectors, transfection with retrovirus-based vectors, and liposome-mediated transfection.

C. Expression Patterns

Transient Expression of iRNA

In one embodiment of the present invention, expression of the iRNA in a cell is transient. Transient expression can be from an expression vector that does not insert into the genome of the cell. Alternatively, transient expression can be from the direct insertion of iRNA molecules into the cell.

Any of the types of nucleic acids that mediate RNA interference can be synthesized in vitro using a variety of methods well known in the art and inserted directly into a cell. In addition, dsRNA and other molecules that mediate RNA interference are available from commercial vendors, such as Ribopharma AG (Kulmach, Germany), Eurogentec (Seraing, Belgium), Sequitur (Natick, Mass.) and Invitrogen (Carlsbad, Calif.). Eurogentec offers dsRNA that has been labeled with fluorophores (e.g., HEX/TET; 5'-Fluorescein, 6-FAM; 3'-Fluorescein, 6-FAM; Fluorescein dT internal; 5' TAMRA, Rhodamine; 3' TAMRA, Rhodamine), which can also be used in the invention. iRNA molecules can be made through the well-known technique of solid-phase synthesis. Equipment for such synthesis is sold by several vendors including, for example, Applied Biosystems (Foster City, Calif.). Other methods for such synthesis that are known in the art can additionally or alternatively be employed. It is well-known to use similar techniques to prepare oligonucleotides such as the phosphorothioates and alkylated derivatives. By way of non-limiting example, see, for example, U.S. Pat. Nos. 4,517,338, and 4,458,066; Lyer R P, et al., Curr. Opin. Mol Ther. 1:344-358 (1999); and Verma S, and Eckstein F., Annual Rev. Biochem. 67:99-134 (1998).

iRNA directly inserted into a cell can include modifications to either the phosphate-sugar backbone or the nucleoside. For example, the phosphodiester linkages of natural RNA can be modified to include at least one of a nitrogen or sulfur heteroatom. The interfering RNA can be produced enzymatically or by partial/total organic synthesis. The constructs can be synthesized by a cellular RNA polymerase or a bacteriophage RNA polymerase (e.g., T3, T7, SP6). If synthesized chemically or by in vitro enzymatic synthesis, the RNA can be purified prior to introduction into a cell or animal. For example, RNA can be purified from a mixture by extraction with a solvent or resin, precipitation, electrophoresis, chromatography or a combination thereof as known in the art. Alternatively, the interfering RNA construct can be used without, or with a minimum of purification to avoid losses due to sample processing. The iRNA construct can be dried for storage or dissolved in an aqueous solution. The solution can contain buffers or salts to promote annealing, and/or stabilization of the duplex strands. Examples of buffers or salts that can be used in the present invention include, but are not limited to, saline, PBS, N-(2-Hydroxyethyl)piperazine-N'-(2-ethanesulfonic acid) (HEPES®), 3-(N-Morpholino)propanesulfonic acid (MOPS), 2-bis(2-Hydroxyethylene)amino-2-(hydroxymethyl)-1,3-propanediol (bis-TRIS®), potassium phosphate (KP), sodium phosphate (NaP), dibasic sodium phosphate (Na2HPO4), monobasic sodium phosphate (NaH2PO4), monobasic sodium potassium phosphate (NaKHPO4), magnesium phosphate (Mg3(PO4)2.4H2O), potassium acetate (CH3COOH), D(+)-α-sodium glycerophosphate (HOCH2CH(OH)CH2OPO3Na2) and other physiologic buffers known to those skilled in the art. Additional buffers for use in the invention include, a salt M-X dissolved in aqueous solution, association, or dissociation products thereof, where M is an alkali metal (e.g., Li+, Na+, K+, Rb+), suitably sodium or potassium, and where X is an anion selected from the group consisting of phosphate, acetate, bicarbonate, sulfate, pyruvate, and an organic monophosphate ester, glucose 6-phosphate or DL-α-glycerol phosphate.

Stable Expression of iRNA

1. Random Insertion

Genomic Insertion of the iRNA containing vector can be accomplished using any known methods of the art. In one embodiment, the vector is inserted into a genome randomly using a viral based vector. Insertion of the virally based vector occurs at random sites consistent with viral behavior (see, for example, Daley et al. (1990) Science 247:824-830;

Guild et al. (1988) J Virol 62:3795-3801; Miller (1992) Curr Topics MicroBiol Immunol 158:1-24; Samarut et al. (1995) Methods Enzymol 254:206-228). Non limiting examples of viral based vectors include Moloney murine leukemia retrovirus, the murine stem cell virus, vaccinia viral vectors, Sindbis virus, Semliki Forest alphavirus, EBV, ONYX-15, adenovirus, or lentivirus based vectors (see, for example, Hemann M T et al. (2003) Nature Genet. 33:396-400; Paddison & Hannon (2002) Cancer Cell 2:17-23; Brummelkamp T R et al. (2002) Cancer Cell 2:243-247; Stewart S A et al. (2003) RNA 9:493-501; Rubinson D A et al. (2003) Nature Genen. 33:401-406; Qin X et al. (2003) PNAS USA 100:183-188; Lois C et al. (2002) Science 295:868-872).

In another embodiment, the transgene is either cleaved from the vector or is maintained without a vector. Vector removal can be important for certain transgene configurations previously described in the art (Kjer-Nielsen L, Holmberg K, Perera J D, McCluskey J. Impaired expression of chimaeric major histocompatibility complex transgenes associated with plasmid sequences. Transgenic Res. 1992 July; 1(4):182-7.) The "vectorless" transgene is inserted into a genome randomly using any known method of the art.

2. Targeted Insertion

In another embodiment, the insertion is targeted to a specific gene locus through homologous recombination. Homologous recombination provides a precise mechanism for targeting defined modifications to genomes in living cells (see, for example, Vasquez K M et al. (2001) PNAS USA 98(15):8403-8410). A primary step in homologous recombination is DNA strand exchange, which involves a pairing of a DNA duplex with at least one DNA strand containing a complementary sequence to form an intermediate recombination structure containing heteroduplex DNA (see, for example, Radding, C. M. (1982) Ann. Rev. Genet. 16: 405; U.S. Pat. No. 4,888,274). The heteroduplex DNA can take several forms, including a three DNA strand containing triplex form wherein a single complementary strand invades the DNA duplex (see, for example, Hsieh et al. (1990) Genes and Development 4: 1951; Rao et al., (1991) PNAS 88:2984)) and, when two complementary DNA strands pair with a DNA duplex, a classical Holliday recombination joint or chi structure (Holliday, R. (1964) Genet. Res. 5: 282) can form, or a double-D loop ("Diagnostic Applications of Double-D Loop Formation" U.S. Pat. No. 5,273,881). Once formed, a heteroduplex structure can be resolved by strand breakage and exchange, so that all or a portion of an invading DNA strand is spliced into a recipient DNA duplex, adding or replacing a segment of the recipient DNA duplex. Alternatively, a heteroduplex structure can result in gene conversion, wherein a sequence of an invading strand is transferred to a recipient DNA duplex by repair of mismatched bases using the invading strand as a template (see, for example, Genes, 3rd Ed. (1987) Lewin, B., John Wiley, New York, N.Y.; Lopez et al. (1987) Nucleic Acids Res. 15: 5643). Whether by the mechanism of breakage and rejoining or by the mechanism(s) of gene conversion, formation of heteroduplex DNA at homologously paired joints can serve to transfer genetic sequence information from one DNA molecule to another.

A number of papers describe the use of homologous recombination in mammalian cells. Illustrative of these papers are Kucherlapati et al. (1984) Proc. Natl. Acad. Sci. USA 81:3153-3157; Kucherlapati et al. (1985) Mol. Cell. Bio. 5:714-720; Smithies et al. (1985) Nature 317:230-234; Wake et al. (1985) Mol. Cell. Bio. 8:2080-2089; Ayares et al. (1985) Genetics 111:375-388; Ayares et al. (1986) Mol. Cell. Bio. 7:1656-1662; Song et al. (1987) Proc. Natl. Acad. Sci. USA 84:6820-6824; Thomas et al. (1986) Cell 44:419-428; Thomas and Capecchi, (1987) Cell 51: 503-512; Nandi et al. (1988) Proc. Natl. Acad. Sci. USA 85:3845-3849; and Mansour et al. (1988) Nature 336:348-352; Evans and Kaufman, (1981) Nature 294:146-154; Doetschman et al. (1987) Nature 330:576-578; Thoma and Capecchi, (1987) Cell 51:503-512; Thompson et al. (1989) Cell 56:316-321.

Cells useful for homologous recombination include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc.

The vector construct containing the iRNA template may comprise a full or partial sequence of one or more exons and/or introns of the gene targeted for insertion, a full or partial promoter sequence of the gene targeted for insertion, or combinations thereof. In one embodiment of the invention, the nucleic acid sequence of the iRNA containing construct comprises a first nucleic acid sequence region homologous to a first nucleic acid sequence region of the gene targeted for insertion, and a second nucleic acid sequence region homologous to a second nucleic acid sequence region of the gene targeted for insertion. The orientation of the vector construct should be such that the first nucleic acid sequence is upstream of the second nucleic acid sequence and the iRNA template should be therebetween.

A nucleic acid sequence region(s) can be selected so that there is homology between the iRNA template containing vector construct sequence(s) and the gene of interest. Preferably, the construct sequences are isogenic sequences with respect to the target sequences. The nucleic acid sequence region of the construct may correlate to any region of the gene provided that it is homologous to the gene. A nucleic acid sequence is considered to be "homologous" if it is at least about 90% identical, preferably at least about 95% identical, or most preferably, about 98% identical to the nucleic acid sequence. Furthermore, the 5' and 3' nucleic acid sequences flanking the selectable marker should be sufficiently large to provide complementary sequence for hybridization when the construct is introduced into the genomic DNA of the target cell. For example, homologous nucleic acid sequences flanking the selectable marker gene should be at least about 500 bp, preferably, at least about 1 kilobase (kb), more preferably about 2-4 kb, and most preferably about 3-4 kb in length. In one embodiment, both of the homologous nucleic acid sequences flanking the selectable marker gene of the construct should be should be at least about 500 bp, preferably, at least about 1 kb, more preferably about 2-4 kb, and most preferably about 3-4 kb in length.

Another type of DNA sequence can be a cDNA sequence provided the cDNA is sufficiently large. Each of the flanking nucleic acid sequences used to make the construct is preferably homologous to one or more exon and/or intron regions, and/or a promoter region.

Each of these sequences is different from the other, but may be homologous to regions within the same exon and/or intron. Alternatively, these sequences may be homologous to regions within different exons and/or introns of the gene. Preferably, the two flanking nucleic acid sequences of the construct are homologous to two sequence regions of the same or different introns of the gene of interest. In addition, isogenic DNA can be used to make the construct of the present invention. Thus, the nucleic acid sequences obtained to make the construct are preferably obtained from the same cell line as that being used as the target cell.

Alternatively, a targeting construct can be used in which a single region of homology is present. In such constructs, a single homologous cross-over event produces an insertion within the homolgous regions. This construct can either be supplied circular or is linear and spontaineously circularized within the cell via natural processes (Hasty P, Rivera-Perez J, Chang C, Bradley A. Target frequency and integration pattern for insertion and replacement vectors in embryonic stem cells. Mol Cell Biol. 1991 September; 11(9):4509-17).

In one embodiment of the present invention, homologous recombination is used to insert an iRNA containing expression vector operably linked to a promoter into the genome of a cell, such as a fibroblast. The DNA can comprise at least a portion of the gene at the particular locus with introduction of the expression vector into preferably at least one, optionally both copies, of the targeted gene.

Alternatively, an iRNA containing expression vector lacking a promoter can be inserted into an endogenous gene. The insertion allows expression of the promoterless vector to be driven by the endogenous gene's associated promoter. In one embodiment, the vector is inserted into the 3' non-coding region of a gene. In a particular aspect of the invention, the vector is inserted into a tissue specific or physiologically specific gene. For example, hepatocyte specific expression is provided by targeting an endogenous gene that is expressed in every hepatocyte at the desired level and temporal pattern.

In another embodiment, a targeting vector is assembled such that the iRNA vector is inserted into a single allele of a housekeeping gene. Non limiting examples of targeted housekeeping genes include the conserved cross species analogs of the following human housekeeping genes; mitochondrial 16S rRNA, ribosomal protein L29 (RPL29), H3 histone, family 3B (H3.3B) (H3F3B), poly(A)-binding protein, cytoplasmic 1 (PABPC1), HLA-B associated transcript-1 (D6S81E), surfeit 1 (SURF1), ribosomal protein L8 (RPL8), ribosomal protein L38 (RPL38), catechol-O-methyltransferase (COMT), ribosomal protein S7 (RPS7), heat shock 27 kD protein 1 (HSPB1), eukaryotic translation elongation factor 1 delta (guanine nucleotide exchange protein) (EEFID), vimentin (VIM), ribosomal protein L41 (RPL41), carboxylesterase 2 (intestine, liver) (CES2), exportin 1 (CRM1, yeast, homolog) (XPO1), ubiquinol-cytochrome c reductase hinge protein (UQCRH), Glutathione peroxidase 1 (GPX1), ribophorin II (RPN2), Pleckstrin and Sec7 domain protein (PSD), human cardiac troponin T, proteasome (prosome, macropain) subunit, beta type, 5 (PSMB5), cofilin 1 (non-muscle) (CFL1), seryl-tRNA synthetase (SARS), catenin (cadherin-associated protein), beta 1 (88 kD) (CTNNB1), Duffy blood group (FY), erythrocyte membrane protein band 7.2 (stomatin) (EPB72), Fas/Apo-1, LIM and SH3 protein 1 (LASP1), accessory proteins BAP31/BAP29 (DXS1357E), nascent-polypeptide-associated complex alpha polypeptide (NACA), ribosomal protein L8a (RPL18A), TNF receptor-associated factor 4 (TRAF4), MLN51 protein (MLN51), ribosomal protein L11 (RPL11), Poly(rC)-binding protein 2 (PCBP2), thioredoxin (TXN), glutaminyl-tRNA synthetase (QARS), testis enhanced gene transcript (TEGT), prostatic binding protein (PBP), signal sequence receptor, beta (translocon-associated protein beta) (SSR2), ribosomal protein L3 (RPL3), centrin, EF-hand protein, 2 (CETN2), heterogeneous nuclear ribonucleoprotein K (HNRPK), glutathione peroxidase 4 (phospholipid hydroperoxidase) (GPX4), fusion, derived from t(12; 16) malignant liposarcoma (FUS), ATP synthase, H+ transporting, mitochondrial F0 complex, subunit c (subunit 9), isoform 2 (ATP5G2), ribosomal protein S26 (RPS26), ribosomal protein L6 (RPL6), ribosomal protein S18 (RPS18), serine (or cysteine) proteinase inhibitor, clade A (alpha-1 antiproteinase, antitrypsin), member 3 (SERPINA3), dual specificity phosphatase 1 (DUSP1), peroxiredoxin 1 (PRDX1), epididymal secretory protein (19.5 kD) (HE1), ribosomal protein S8 (RPS8), translocated promoter region (to activated MET oncogene) (TPR), ribosomal protein L13 (RPL13), SON DNA binding protein (SON), ribosomal prot L19 (RPL19), ribosomal prot (homolog to yeast S24), CD63 antigen (melanoma 1 antigen) (CD63), protein tyrosine phosphatase, non-receptor type 6 (PTPN6), eukaryotic translation elongation factor 1 beta 2 (EEFIB2), ATP synthase, H+ transporting, mitochondrial F0 complex, subunit b, isoform 1 (ATP5F1), solute carrier family 25 (mitochondrial carrier; phosphate carrier), member 3 (SLC25A3), tryptophanyl-tRNA synthetase (WARS), glutamate-ammonia ligase (glutamine synthase) (GLUL), ribosomal protein L7 (RPL7), interferon induced transmembrane protein 2 (1-8D) (IFITM2), tyrosine 3-monooxygenase/tryptophan 5-monooxygenase activation protein, beta polypeptide (YWHAB), Casein kinase 2, beta polypeptide (CSNK2B), ubiquitin A-52 residue ribosomal protein fusion product 1 (UBA52), ribosomal protein L13a (RPL13A), major histocompatibility complex, class I, E (HLA-E), jun D proto-oncogene (JUND), tyrosine 3-monooxygenase/tryptophan 5-monooxygenase activation protein, theta polypeptide (YWHAQ), ribosomal protein L23 (RPL23), Ribosomal protein S3 (RPS3), ribosomal protein L17 (RPL17), filamin A, alpha (actin-binding protein-280) (FLNA), matrix Gla protein (MGP), ribosomal protein L35a (RPL35A), peptidylprolyl isomerase A (cyclophilin A) (PPIA), villin 2 (ezrin) (VIL2), eukaryotic translation elongation factor 2 (EEF2), jun B proto-oncogene (JUNB), ribosomal protein S2 (RPS2), cytochrome c oxidase subunit VIIc (COX7C), heterogeneous nuclear ribonucleoprotein L (HNRPL), tumor protein, translationally-controlled 1 (TPT1), ribosomal protein L31 (RPL31), cytochrome c oxidase subunit VIIa polypeptide 2 (liver) (COX7A2), DEAD/H (Asp-Glu-Ala-Asp/His) box polypeptide 5 (RNA helicase, 68 kD) (DDX5), cytochrome c oxidase subunit VIa polypeptide 1 (COX6A1), heat shock 90 kD protein 1, alpha (HSPCA), Sjogren syndrome antigen B (autoantigen La) (SSB), lactate dehydrogenase B (LDHB), high-mobility group (nonhistone chromosomal) protein 17 (HMG17), cytochrome c oxidase subunit VIc (COX6C), heterogeneous nuclear ribonucleoprotein A1 (HNRPA1), aldolase A, fructose-bisphosphate (ALDOA), integrin, beta 1 (fibronectin receptor, beta polypeptide, antigen CD29 includes MDF2, MSK12) (ITGB1), ribosomal protein S11(RPS11), small nuclear ribonucleoprotein 70 kD polypeptide (RN antigen) (SNRP20), guanine nucleotide binding protein (G protein), beta polypeptide 1 (GNB1), heterogeneous nuclear ribonucleoprotein A1 (HNRPA1), calpain 4, small subunit (30K) (CAPN4), elongation factor TU (N-terminus)/X03689, ribosomal protein L32 (RPL32), major histocompatibility complex, class II, DP alpha 1 (HLA-DPA1), superoxide dismutase 1, soluble (amyotrophic lateral sclerosis 1 (adult)) (SOD1), lactate dehydrogenase A (LDHA), glyceraldehyde-3-phosphate dehydrogenase (GAPD), Actin, beta (ACTB), major histocompatibility complex, class II, DP alpha (HLA-DRA), tubulin, beta polypeptide (TUBB), metallothionein 2A (MT2A), phosphoglycerate kinase 1 (PGK1), KRAB-associated protein 1 (TIF1B), eukaryotic translation initiation factor 3, subunit 5 (epsilon, 47 kD) (EIF3S5), NADH dehydrogenase (ubiquinone) 1 alpha subcomplex, 4 (9 kD, MLRQ) (NDUFA4), chloride intracellular channel 1 (CLIC1), adaptor-related protein complex 3, sigma 1 subunit (AP3S1), cytochrome c oxidase subunit IV (COX4), PDZ and LIM domain 1 (elfin) (PDLIM1), glutathione-S-transferase like; glutathione transferase omega (GSTTLp28), interferon stimulated gene (20 kD) (ISG20), nuclear factor I/B (NFIB), COX10 (yeast) homolog, cytochrome c oxidase assembly protein (heme A: farnesyltransferase), conserved gene amplified in osteosarcoma (OS4), deoxyhypusine synthase (DHPS), galactosidase, alpha (GLA), microsomal glutathione S-transferase 2 (MGST2), eukaryotic translation initiation factor 4 gamma, 2 (EIF4G2), ubiquitin carrier protein E2-C(UBCH10), BTG family, member 2 (BTG2), B-cell associated protein (REA), COP9 subunit 6 (MOV34 homolog, 34 kD) (MOV34-34 KD), ATX1 (antioxidant protein 1, yeast) homolog 1 (ATOX1), acidic protein rich in leucines (SSP29), poly(A)-binding prot (PABP) promoter region, selenoprotein W, 1 (SEPW1), eukaryotic translation initiation factor 3, subunit 6 (48 kD) (EIF3S6), carnitine palmitoyltransferase I, muscle (CPT1B), transmembrane trafficking protein (TMP21), four and a half LIM domains 1 (FHL1), ribosomal protein S28 (RPS28), myeloid leukemia factor 2 (MLF2), neurofilament triplet L prot/U57341, capping protein (actin filament) muscle Z-line, alpha 1 (CAPZA1), 1-acylglycerol-3-phosphate O-acyltransferase 1 (lysophosphatidic acid acyltransferase, alpha) (AGPAT1), inositol 1,3,4-triphosphate 5/6 kinase (ITPK1), histidine triad nucleotide-binding protein (HINT), dynamitin (dynactin complex 50 kD subunit) (DCTN-50), actin related protein 2/3 complex, subunit 2 (34 kD) (ARPC2), histone deacetylase 1 (HDAC1), ubiquitin B, chitinase 3-like 2 (CHI3L2), D-dopachrome tautomerase (DDT), zinc finger protein 220 (ZNF220), sequestosome 1 (SQSTM1), cystatin B (stefin B) (CSTB), eukaryotic translation initiation factor 3, subunit 8 (110 kD) (EIF3S8), chemokine (C-C motif) receptor 9 (CCR9), ubiquitin specific protease 11 (USP11), laminin receptor 1 (67 kD, ribosomal protein SA) (LAMR1), amplified in osteosarcoma (OS-9), splicing factor 3b, subunit 2, 145 kD (SF3B2), integrin-linked kinase (ILK), ubiquitin-conjugating enzyme E2D 3 (homologous to yeast UBC4/5) (UBE2D3), chaperonin containing TCP1, subunit 4 (delta) (CCT4), polymerase (RNA) II (DNA directed) polypeptide L (7.6 kD) (POLR2L), nuclear receptor co-repressor 2 (NCOR2), accessory proteins BAP31/BAP29 (DXS1357E, SLC6A8), 13 kD differentiation-associated protein (LOC55967), Taxi (human T-cell leukemia virus type I) binding protein 1 (TAX1BP1), damage-specific DNA binding protein 1 (127 kD) (DDB1), dynein, cytoplasmic, light polypeptide (PIN), methionine aminopeptidase; eIF-2-associated p67 (MNPEP), G protein pathway suppressor 2 (GPS2), ribosomal protein L21 (RPL21), coatomer protein complex, subunit alpha (COPA), G protein pathway suppressor 1 (GPS1), small nuclear ribonucleoprotein D2 polypeptide (16.5 kD) (SNRPD2), ribosomal protein S29 (RPS29), ribosomal protein S10 (RPS10), ribosomal proteinS9 (RPS9), ribosomal protein S5 (RPS5), ribosomal protein L28 (RPL28), ribosomal protein L27a (RPL27A), protein tyrosine phosphatase type IVA, member 2 (PTP4A2), ribosomal prot L36 (RPL35), ribosomal protein L10a (RPL10A), Fc fragment of IgG, receptor, transporter, alpha (FCGRT), maternal G10 transcript (G10), ribosomal protein L9 (RPL9), ATP synthase, H+ transporting, mitochondrial F0 complex, subunit c (subunit 9) isoform 3 (ATP5G3), signal recognition particle 14 kD (homologous Alu RNA-binding protein) (SRP14), mutL (*E. coli*) homolog 1 (colon cancer, nonpolyposis type 2) (MLH1), chromosome 1q subtelomeric sequence D1S553./U06155, fibromodulin (FMOD), amino-terminal enhancer of split (AES), Rho GTPase activating protein 1 (ARHGAP1), non-POU-domain-containing, octamer-binding (NONO), v-raf murine sarcoma 3611 viral oncogene homolog 1 (ARAF1), heterogeneous nuclear ribonucleoprotein A1 (HNRPA1), beta 2-microglobulin (B2M), ribosomal protein S27a (RPS27A), bromodomain-containing 2 (BRD2), azoospermia factor 1 (AZF1), upregulated by 1,25 dihydroxyvitamin D-3 (VDUP1), serine (or cysteine) proteinase inhibitor, clade B (ovalbumin), member 6 (SERPINB6), destrin (actin depolymerizing factor) (ADF), thymosin beta-10 (TMSB10), CD34 antigen (CD34), spectrin, beta, non-erythrocytic 1 (SPTBN1), angio-associated, migratory cell protein (AAMP), major histocompatibility complex, class I, A (HLA-A), MYC-associated zinc finger protein (purine-binding transcription factor) (MAZ), SET translocation (myeloid leukemia-associated) (SET), paired box gene(aniridia, keratitis) (PAX6), zinc finger protein homologous to Zfp-36 in mouse (ZFP36), FK506-binding protein 4 (59 kD) (FKBP4), nucleosome assembly protein 1-like 1 (NAP1L1), tyrosine 3-monooxygenase/tryptophan 5-monooxygenase activation protein, zeta polypeptide (YWHAZ), ribosomal protein S3A (RPS3A), ADP-ribosylation factor 1, ribosomal protein S19 (RPS19), transcription elongation factor A (SII), 1 (TCEA1), ribosomal protein S6 (RPS6), ADP-ribosylation factor 3 (ARF3), moesin (MSN), nuclear factor of kappa light polypeptide gene enhancer in B-cells inhibitor, alpha (NFKBIA), complement component 1, q subcomponent binding protein (C1QBP), ribosomal protein S25 (RPS25), clusterin (complement lysis inhibitor, SP-40,40, sulfated glycoprotein 2, testosterone-repressed prostate message 2, apolipoprotein J) (CLU), nucleolin (NCL), ribosomal protein S16 (RPS16), ubiquitin-activating enzyme E1 (A1S9T and BN75 temperature sensitivity complementing) (UBE1), lectin, galactoside-binding, soluble, 3 (galectin 3) (LGALS3), eukaryotic translation elongation factor 1 gamma (EEF1G), pim-1 oncogene (PIM1), S100 calcium-binding protein A10 (annexin II ligand, calpactin I, light polypeptide (p11)) (S100A10), H2A histone family, member Z (H2AFZ), ADP-ribosylation factor 4 (ARF4) (ARF4), ribosomal protein L7a (RPL7A), major histocompatibility complex, class II, DQ alpha 1 (HLA-DQA1), FK506-binding protein 1A (12 kD) (FKBP1A), CD81 antigen (target of antiproliferative antibody 1) (CD81), ribosomal protein S15 (RPS15), X-box binding protein 1 (XBP1), major histocompatibility complex, class II, DN alpha (HLA-DNA), ribosomal protein S24 (RPS24), leukemia-associated phosphoprotein p18 (stathmin) (LAP18), myosin, heavy polypeptide 9, non-muscle (MYH9), casein kinase 2, beta polypeptide (CSNK2B), fucosidase, alpha-L-1, tissue (FUCA1), diaphorase (NADH) (cytochrome b-5 reductase) (DIA1), cystatin C (amyloid angiopathy and cerebral hemorrhage) (CST3), ubiquitin C (UBC), ubiquinol-cytochrome c reductase binding protein (UQCRB), prothymosin, alpha (gene sequence 28) (PTMA), glutathione S-transferase pi (GSTP1), guanine nucleotide binding protein (G protein), beta polypeptide 2-like 1 (GNB2L1), nucleophosmin (nucleolar phosphoprotein B23, numatrin) (NPM1), CD3E antigen, epsilon polypeptide (TiT3 complex) (CD3E), calpain 2, (m/II) large subunit (CAPN2), NADH dehydrogenase (ubiquinone) flavoprotein 2 (24 kD) (NDUFV2), heat shock 60 kD protein 1 (chaperonin) (HSPD1), guanine nucleotide binding protein (G protein), alpha stimulating activity polypeptide 1 (GNAS1), clathrin, light polypeptide (Lca) (CLTA), ATP synthase, H+ transporting, mitochondrial F1 complex, beta polypeptide, calmodulin 2 (phosphorylase kinase, delta) (CALM2), actin, gamma 1 (ACTG1), ribosomal protein S17 (RPS17), ribosomal protein, large, P1 (RPLP1), ribosomal protein, large, P0 (RPLP0), thymosin, beta 4, X chromosome (TMSB4X), heterogeneous nuclear ribonucleoprotein C (C1/C2) (HNRPC), ribosomal protein L36a (RPL36A), glucuronidase, beta (GUSB), FYN oncogene related to SRC, FGR, YES (FYN), prothymosin, alpha (gene sequence 28) (PTMA), enolase 1, (alpha) (ENO1), laminin receptor 1 (67 kD, ribosomal protein SA) (LAMR1), ribosomal protein S14 (RPS14), CD74 antigen (invariant polypeptide of major histocompatibility complex, class II antigen-associated), esterase D/formylglutathione hydrolase (ESD), H3 histone, family 3A (H3F3A), ferritin, light polypeptide (FTL), Sec23 (*S. cerevisiae*) homolog A (SEZ23A), actin, beta (ACTB), presenilin 1 (Alzheimer disease 3) (PSEN1), interleukin-1 receptor-associated kinase 1 (IRAK1), zinc finger protein 162 (ZNF162), ribosomal protein L34 (RPL34), beclin 1 (coiled-coil, myosin-like BCL2-interacting protein) (BECN1), phosphatidylinositol 4-kinase, catalytic, alpha polypeptide (PIK4CA), IQ motif containing GTPase activating protein 1 (IQGAP1), signal transducer and activator of transcription 3 (acute-phase response factor) (STAT3), heterogeneous nuclear ribonucleoprotein F (HNRPF), putative translation initiation factor (SUI1), protein translocation complex beta (SEC61B), ras homolog gene family, member A (ARHA), ferritin, heavy polypeptide 1 (FTH1), Rho GDP dissociation inhibitor (GDI) beta (ARHGDIB), H2A histone family, member O (H2AFO), annexin A11 (ANXA11), ribosomal protein L27 (RPL27), adenylyl cyclase-associated protein (CAP), zinc finger protein 91 (HPF7, HTF10) (ZNF91), ribosomal protein L18 (RPL8), farnesyltransferase, CAAX box, alpha (FNTA), sodium channel, voltage-gated, type I, beta polypeptide (SCNIB), calnexin (CANX), proteolipid protein 2 (colonic epithelium-enriched) (PLP2), amyloid beta (A4) precursor-like protein 2 (APLP2), Voltage-dependent anion channel 2, proteasome (prosome, macropain) activator subunit 1 (PA28 alpha) (PSME1), ribosomal prot L12 (RPL12), ribosomal protein L37a (RPL37A), ribosomal protein S21 (RPS21), proteasome (prosome, macropain) 26S subunit, ATPase, 1 (PSMC1), major histocompatibility complex, class II, DQ beta 1 (HLA-DQB1), replication protein A2 (32 kD) (RPA2), heat shock 90 kD protein 1, beta (HSPCB), cytochrome c oxydase subunit VIII (COX8), eukaryotic translation elongation factor 1 alpha 1 (EEF1A1), SNRPN upstream reading frame (SNURF), lectin, galactoside-binding, soluble, 1 (galectin 1) (LGALS1), lysosomal-associated membrane protein 1 (LAMP1), phosphoglycerate mutase 1 (brain) (PGAM1), interferon-induced transmembrane protein 1 (9-27) (IFITM1), nuclease sensitive element binding protein 1 (NSEP1), solute carrier family 25 (mitochondrial carrier, adenine nucleotide translocator), member 6 (SLC25A6), ADP-ribosyltransferase (NAD+; poly (ADP-ribose) polymerase) (ADPRT), leukotriene A4 hydrolase (LTA4H), profilin 1 (PFN1), prosaposin (variant Gaucher disease and variant metachromatic leukodystrophy) (PSAP), solute carrier family 25 (mitochondrial carrier; adenine nucleotide translocator), member 5 (SLC25A5), beta-2 microglobulin, insulin-like growth factor binding protein 7, Ribosomal prot S13, Epstein-Barr Virus Small Rna-Associated prot, Major Histocompatibility Complex, Class I, C X58536), Ribosomal prot S12, Ribosomal prot L10, Transformation-Related prot, Ribosomal prot L5, Transcriptional Coactivator Pc4, Cathepsin B, Ribosomal prot L26, “Major Histocompatibility Complex, Class I X12432”, Wilm S Tumor-Related prot, Tropomyosin Tm30 nm Cytoskeletal, Liposomal Protein S4, X-Linked, Ribosomal prot L37, Metallopanstimulin 1, Ribosomal prot L30, Heterogeneous Nuclear Ribonucleoprot K, Major Histocompatibility Complex, Class I, E M21533, Major Histocompatibility Complex, Class I, E M20022, Ribosomal protein L30 Homolog, Heat Shock prot 70 Kda, “Myosin, Light Chain/U02629”, “Myosin, Light Chain/U02629”, Calcyclin, Single-Stranded Dna-Binding prot Mssp-1, Triosephosphate Isomerase, Nuclear Mitotic Apparatus prot 1, prot Kinase Ht31 Camp-Dependent, Tubulin, Beta 2, Calmodulin Type I, Ribosomal prot S20, Transcription Factor Btf3b, Globin, Beta, Small Nuclear RibonucleoproteinPolypeptide CAlt. Splice 2, Nucleoside Diphosphate Kinase Nm23-H2s, Ras-Related C3 Botulinum Toxin Substrate, activating transcription factor 4 (tax-responsive enhancer element B67) (ATF4), prefoldin (PFDN5), N-myc downstream regulated (NDRG1), ribosomal protein L14 (RPL4), nicastrin (KIAA0253), protease, serine, 11 (IGF binding) (PRSS11), KIAA0220 protein (KIAA0220), dishevelled 3 (homologous to *Drosophila* dsh) (DVL3), enhancer of rudimentary *Drosophila* homolog (ERH), RNA-binding protein gene with multiple splicing (RBPM5), 5-aminoimidazole-4-carboxamide ribonucleotide formyltransferase/IMP cyclohydrolase (ATIC), KIAA0164 gene product (KIAA0164), ribosomal protein L39 (RPL39), tyrosine 3 monooxygenase/tryptophan 5-monooxygenase activation protein, eta polypeptide (YWHAH), Ornithine decarboxylase antizyme 1 (OAZ1), proteasome (prosome, macropain) 26S subunit, non-ATPase, 2 (PSMD2), cold inducible RNA-binding protein (CIRBP), neural precursor cell expressed, developmentally down-regulated 5 (NEDD5), high-mobility group nonhistone chromosomal protein 1 (HMG1), malate dehydrogenase 1, NAD (soluble) (MDH1), cyclin 1 (CCNI), proteasome (prosome, macropain) 26S subunit, non-ATPase, 7 (Mov34 homolog) (PSMD7), major histocompatibility complex, class I, B (HLA-B), ATPase, vacuolar, 14 kD (ATP6S14), transcription factor-like 1 (TCFL1), KIAA0084 protein (KIAA0084), proteasome (prosome, macropain) 26S subunit, non-ATPase, 8 (PSMD8), major histocompatibility complex, class I, A (HIA-A), alanyl-tRNA synthetase (AARS), lysyl-tRNA synthetase (KARS), ADP-ribosylation factor-like 6 interacting protein (ARL6IP), KIAA0063 gene product (KIAA0063), actin binding LIM protein 1 (ABLIM), DAZ associated protein 2 (DAZAP2), eukaryotic translation initiation factor 4A, isoform 2 (EIF4A2), CD151 antigen (CD151), proteasome (prosome, macropain) subunit, beta type, 6 (PSMB6), proteasome (prosome, macropain) subunit, beta type, 4 (PSMB4), proteasome (prosome, macropain) subunit, beta type, 2 (PSMB2), proteasome (prosome, macropain) subunit, beta type, 3 (PSMB3), Williams-Beuren syndrome chromosome region 1 (WBSCR1), ancient ubiquitous protein 1 (AUP1), KIAA0864 protein (KIAA0864), neural precursor cell expressed, developmentally down-regulated 8 (NEDD8), ribosomal protein L4 (RPL4), KIAA0111 gene product (KIAA0111), transgelin 2 (TAGLN2), Clathrin, heavy polypeptide (Hc) (CLTC, CLTCL2), ATP synthase, H+ transporting, mitochondrial F1complex, gamma polypeptide 1 (ATP5C1), calpastatin (CAST), MORF-related gene X (KIA0026), ATP synthase, H+ transporting, mitochondrial F1 complex, alpha subunit, isoform 1, cardiac muscle (ATP5A1), phosphatidylserine synthase 1 (PTDSS1), anti-oxidant protein 2 (non-selenium glutathione peroxidase, acidic calcium-independent phospholipase A2) (KIAA0106), KIAA0102 gene product (KIAA0102), ribosomal protein S23 (RPS23), CD164 antigen, sialomucin (CD164), GDP dissociation inhibitor 2 (GDI2), enoyl Coenzyme A hydratase, short chain, 1, mitochondrial (ECHS1), eukaryotic translation initiation factor 4A, isoform 1 (EIF4A1), cyclin D2 (CCND2), heterogeneous nuclear ribonucleoprotein U (scaffold attachment factor A) (HNRPU), APEX nuclease (multifunctional DNA repair enzyme) (APEX), ATP synthase, H+ transporting, mitochondrial F0 complex, subunit c (subunit 9), isoform 1 (ATP5G1), myristoylated alanine-rich protein kinase C substrate (MARCKS, 80K-L) (MACS), annexin A2 (ANXA2), similar to *S. cerevisiae* RER1 (RER1), hyaluronoglucosaminidase 2 (HYAL2), uroplakin 1A (UPK1A), nuclear pore complex interacting protein (NPIP), karyopherin alpha 4 (importin alpha 3) (KPNA4), ant the gene with multiple splice variants near HD locus on 4p16.3 (RES4-22).

In one embodiment an iRNA template containing vector is inserted into a targeted housekeeping gene within an intron of the target housekeeping gene. In one sub-embodiment, the target housekeeping gene is prevented from being translated by insertion of a promoterless engineered iRNA template that contains multiple stop codons in the 3' end of the construct within an intron of the target gene. Using this 'promoter-trap' strategy, the iRNA construct is spliced into the chromosome, potentially in frame with the upstream of the exon comprising the target gene. This results in the expression of the iRNA template prior to the targeted housekeeping gene. In some embodiments, the iRNA template expression concomitantly inhibits expression of the housekeeping gene due to the presence of multiple stop codons downstream of the iRNA template. Furthermore, expression of the iRNA template is under control of the endogenous housekeeping gene promoter. For such a "promoter-trap" strategy, a housekeeping gene targeting construct is designed which contains a sequence with homology to an intron sequence of the target housekeeping gene, a downstream intron splice acceptor signal sequence comprising the AG dinucleotide splice acceptor site, a promoterless iRNA template engineered to contain multiple stop codons 3' of the iRNA template, the intron splice donor signal sequence comprising the GT dinucleotide splice donor site for splicing the engineered iRNA template to the immediate downstream exon, and additional sequence with homology to the intron sequence of the target gene to aid with annealing to the target gene.

In another embodiment, the 'promoter trap' strategy is used to insert the iRNA template containing vector in the target housekeeping gene by replacing an endogenous housekeeping exon with an in-frame, promoterless iRNA template containing vector. The iRNA template containing vector is spliced into the chromosome and results in the expression of the iRNA template and concomitant inhibited expression of the full-length target housekeeping gene. Further, the iRNA template is under the control of the housekeeping gene's associated promoter.

This 'promoter trap' gene targeting construct may be designed to contain a sequence with homology to the target housekeeping gene 3' intron sequence upstream of the start codon, the upstream intron splice acceptor sequence comprising the AG dinucleotide splice acceptor site, a Kozak consensus sequence, a promoterless iRNA template containing vector containing e.g., a polyA termination sequence, a splice donor sequence comprising the GT dinucleotide splice donor site from a intron region downstream of the start codon, and a sequence with 5' sequence homology to the downstream intron. It will be appreciated that the method may be used to target any exon within the targeted housekeeping gene.

In one embodiment, the DNA is randomly inserted into the chromosome and is designed to signal its presence via the activation of a reporter gene, which both mimics the expression of the endogenous gene and potentially mutates the locus. By selecting in cell culture those cells in which the reporter gene has been activated, animals can be generated far more quickly than by conventional gene mutation because there is no need to target each gene separately.

In another embodiment, the iRNA involves the transgene expression of a vector containing iRNA operably linked to a promoter through the use of an Epstein-Barr Virus (EBV) mini-chromosome vector. A number of papers discuss the use of EBV mini-chromosomes for transgene expression of vectors (see, for example, Saeki Y et al. (1998) Human Gene Therapy 10:2787-2794; Saeki Y et al. (1998) Gene Therapy 5:1031-1037).

In embodiments of the present invention, linearized vectors or synthetic oligonucleotides that contain 5' and 3' recombination arms and a DNA template encoding iRNA are provided. In one embodiment, these targeting constructs can be inserted into an exon or intron of an endogenous gene without disrupting the expression of the endogenous gene. In another embodiment, the siRNA template is embedded within a self-contained, sequence that is capable of functional as an intron. The siRNA-containing intron is then inserted into an exon of an endogenous gene such that the resulting recombination allows siRNA expression under the control of the endogenous gene regulatory elements and does not prevent expression and translation of the same endogenous gene.

In another embodiment, the targeting construct can be inserted into a gene and render the gene inactivated, "knock-out" the gene. In particular embodiments of the present invention, the targeting constructs produced according to the methods described herein can knockout xenoantigenic genes, such as alpha-1,3-galactosyltransferase (such as described in Phelps, et al., *Science,* 299: pp. 411-414 (2003) or WO 2004/028243). Additional genes that are considered potential barriers to xenotransplanataion and thus can be targeted include: the porcine iGb3 synthase gene (see, for example, U.S. Ser. No. 60/517,524), the CMP-Neu5Ac hydroxylase gene (see, for example, U.S. Ser. No. 10/863, 116), and/or the Forssman synthase gene (see, for example, U.S. Patent Application 60/568,922). In particular embodiments, the targeting constructs described herein can contain 5' and 3' targeting arms that are homologous to gene sequence encoding one or more of these xenoantigens. In other embodiment, heterozygous and/or homozygous knockouts can be produced. In a particular embodiment, the targeting constructs produced according to the methods described herein can produce iRNA molecules that repress the expression of PERV 1 porcine cells and knockout at least one xenoantigen.

In other embodiments, the vectors or synthetic oligoncleotide constructs encoding the iRNA molecules can also include a selectable marker gene. The selectable marker gene can fused in reading frame with the upstream sequence of the target gene. In other embodiments, the cells can be assayed functionally to determine whether successful targeting has occurred. In further embodiments, the cells can be analyzed bu restriction analysis, electrophoresis, Southern analysis, polymerase chain reaction, sequencing or another technique known in the art to determine whether appropriate integration of the DNA encoding the iRNA molecules has occurred.

Suitable selectable marker genes include, but are not limited to: genes conferring the ability to grow on certain media substrates, such as the tk gene (thymidine kinase) or the hprt gene (hypoxanthine phosphoribosyltransferase) which confer the ability to grow on HAT medium (hypoxanthine, aminopterin and thymidine); the bacterial gpt gene (guanine/xanthine phosphoribosyltransferase) which allows growth on MAX medium (mycophenolic acid, adenine, and xanthine). See Song et al., Proc. Nat'l Acad. Sci. U.S.A. 84:6820-6824 (1987). See also Sambrook et al., Molecular Cloning—A Laboratory Manual, Cold Spring Harbor Laboratory, Cold Spring Harbor, N.Y. (1989), see chapter 16. Other examples of selectable markers include: genes conferring resistance to compounds such as antibiotics, genes conferring the ability to grow on selected substrates, genes encoding proteins that produce detectable signals such as luminescence, such as green fluorescent protein, enhanced green fluorescent protein (eGFP). A wide variety of such markers are known and available, including, for example, antibiotic resistance genes such as the neomycin resistance gene (neo), Southern, P., and P. Berg, J. Mol. Appl. Genet. 1:327-341 (1982); and the hygromycin resistance gene (hyg), Nucleic Acids Research 11:6895-6911 (1983), and Te Riele et al., Nature 348:649-651 (1990). Other selectable marker genes include: acetohydroxy acid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline.

Methods for the incorporation of antibiotic resistance genes and negative selection factors will be familiar to those of ordinary skill in the art (see, e.g., WO 99/15650; U.S. Pat. Nos. 6,080,576; 6,136,566; Niwa, et al., *J. Biochem.* 113: 343-349 (1993); and Yoshida, et al., Transgenic Research, 4:277-287 (1995)).

Additional selectable marker genes useful in this invention, for example, are described in U.S. Pat. Nos. 6,319,669; 6,316,181; 6,303,373; 6,291,177; 6,284,519; 6,284,496; 6,280,934; 6,274,354; 6,270,958; 6,268,201; 6,265,548; 6,261,760; 6,255,558; 6,255,071; 6,251,677; 6,251,602; 6,251,582; 6,251,384; 6,248,558; 6,248,550; 6,248,543; 6,232,107; 6,228,639; 6,225,082; 6,221,612; 6,218,185; 6,214,567; 6,214,563; 6,210,922; 6,210,910; 6,203,986; 6,197,928; 6,180,343; 6,172,188; 6,153,409; 6,150,176; 6,146,826; 6,140,132; 6,136,539; 6,136,538; 6,133,429; 6,130,313; 6,124,128; 6,110,711; 6,096,865; 6,096,717; 6,093,808; 6,090,919; 6,083,690; 6,077,707; 6,066,476; 6,060,247; 6,054,321; 6,037,133; 6,027,881; 6,025,192; 6,020,192; 6,013,447; 6,001,557; 5,994,077; 5,994,071; 5,993,778; 5,989,808; 5,985,577; 5,968,773; 5,968,738; 5,958,713; 5,952,236; 5,948,889; 5,948,681; 5,942,387; 5,932,435; 5,922,576; 5,919,445; and 5,914,233. Combinations of selectable markers can also be used.

Cells that have been homologously recombined to introduce DNA encoding iRNA molecules into the genome can then be grown in appropriately-selected medium to identify cells providing the appropriate integration. Those cells which show the desired phenotype can then be further analyzed by restriction analysis, electrophoresis, Southern analysis, polymerase chain reaction, or another technique known in the art. By identifying fragments which show the appropriate insertion at the target gene site, cells can be identified in which homologous recombination has occurred.

Cells which show the desired phenotype based on expression of iRNA molecules can then be further analyzed by restriction analysis, electrophoresis, Southern analysis, polymerase chain reaction, etc to analyze the DNA in order to establish whether homologous or non-homologous recombination occurred. This can be determined by employing probes for the insert and then sequencing the 5' and 3' regions flanking the insert for the presence of the DNA template encoding the iRNA molecule extending beyond the flanking regions of the construct. Primers can also be used which are complementary to a sequence within the construct and complementary to a sequence outside the construct and at the target locus. In this way, one can only obtain DNA duplexes having both of the primers present in the complementary chains if homologous recombination has occurred. By demonstrating the presence of the primer sequences or the expected size sequence, the occurrence of homologous recombination is supported.

The polymerase chain reaction used for screening homologous recombination events is described in Kim and Smithies, Nucleic Acids Res. 16:8887-8903, 1988; and Joyner et al., Nature 338:153-156, 1989. The combination of a mutant polyoma enhancer and a thymidine kinase promoter to drive the neomycin gene has been shown to be active in both embryonic stem cells and EC cells by Thomas and Capecchi, supra, 1987; Nicholas and Berg (1983) in Teratocarcinoma Stem Cell, eds. Siver, Martin and Strikland (Cold Spring Harbor Lab., Cold Spring Harbor, N.Y. (pp. 469-497); and Linney and Donerly, Cell 35:693-699, (1983).

The cell lines obtained from the first round of targeting are likely to be heterozygous for the targeted allele. Homozygosity, in which both alleles are modified, can be achieved in a number of ways. One approach is to grow up a number of cells in which one copy has been modified and then to subject these cells to another round of targeting using a different selectable marker. Alternatively, homozygotes can be obtained by breeding animals heterozygous for the modified allele, according to traditional Mendelian genetics. In some situations, it can be desirable to have two different modified alleles. This can be achieved by successive rounds of gene targeting or by breeding heterozygotes, each of which carries one of the desired modified alleles.

IV. Genes Regulated/Targeted by iRNA Molecules

In a further aspect of the present invention, iRNA molecules that regulate the expression of specific genes or family of genes are provided, such that the expression of the genes can be functionally eliminated. In one embodiment, at least two iRNA molecules are provided that target the same region of a gene. In another embodiment, at least two iRNA molecules are provided that target at least two different regions of the same gene. In a further embodiment, at least two iRNA molecules are provided that target at least two different genes. Additional embodiments of the invention provide combinations of the above strategies for gene targeting.

In one embodiment, the iRNA molecules can be the same sequence. In an alternate embodiment, the iRNA molecules can be different sequences. In another embodiment, the iRNA molecules can be integrated into either the same or different vectors or DNA templates. In one embodiment, the iRNA molecules within the vector or DNA template are operably linked to a promoter sequence, such as, for example, a ubiquitously expressed promoter or cell-type specific promoter. In another embodiment, the iRNA molecules within the vector or DNA template are not under the control of a promoter sequence. In a further embodiment, these vectors or DNA templates can be introduced into a cell. In one embodiment, the vector or DNA template can integrate into the genome of the cell. The integration into the cell can either be via random integration or targeted integration. The targeted integration can be via homologous recombination.

In other embodiments, at least two iRNA molecules are provided wherein the families of one or more genes can be regulated by expression of the iRNA molecules. In another embodiment, at least three, four or five iRNA molecules are provided wherein the families of one or more genes can be regulated by expression of the iRNA molecules. The iRNA molecule can be homologous to a conserved sequence within one or more genes. The family of genes regulated using such methods of the invention can be endogenous to a cell, a family of related viral genes, a family of genes that are conserved within a viral genus, a family of related eukaryotic parasite genes, or more particularly a family of genes from a porcine endogenous retrovirus. In one specific embodiment, at least two iRNA molecules can target the at least two different genes, which are members of the same family of genes. The iRNA molecules can target homologous regions within a family of genes and thus one iRNA molecule can target the same region of multiple genes.

The iRNA molecule can be selected from, but not limited to the following types of iRNA: antisense oligonucleotides, ribozymes, small interfering RNAs (siRNAs), double stranded RNAs (dsRNAs), inverted repeats, short hairpin RNAs (shRNAs), small temporally regulated RNAs, and clustered inhibitory RNAs (ciRNAs), including radial clustered inhibitory RNA, asymmetric clustered inhibitory RNA, linear clustered inhibitory RNA, and complex or compound clustered inhibitory RNA.

In another embodiment, expression of iRNA molecules for regulating target genes in mammalian cell lines or transgenic animals is provided such that expression of the target gene is functionally eliminated or below detectable levels, i.e. the expression of the target gene is decreased by at least about 70%, 75%, 80%, 85%, 90%, 95%, 97% or 99%.

In another embodiment of this aspect of the present invention, methods are provided to produce cells and animals in which interfering RNA molecules are expressed to regulate the expression of target genes. Methods according to this aspect of the invention can comprise, for example: identifying one or more target nucleic acid sequences in a cell; obtaining at least two iRNA molecules that bind to the target nucleic acid sequence(s); introducing the iRNA molecules, optionally packaged in an expression vector, into the cell; and expressing the iRNAs in the cell under conditions such that the iRNAs bind to the target nucleic acid sequences, thereby regulating expression of one or more target genes. In one embodiment, the present invention provides methods of producing non-human transgenic animals that heritably express at least two iRNA molecules that regulate the expression of one or more target genes. In one embodiment, the animals can be produced via somatic cell nuclear transfer. The somatic cell can be engineered to express the iRNA molecule by any of the techniques described herein.

In other embodiments, the present invention also provides methods for the expression of at least two iRNA molecules in a cell or a transgenic animal, where the iRNA targets a common location within a family of genes. Such methods can include, for example: identifying one or more target nucleic acid sequences in the cell that are homologous regions within a family of genes; preparing at least two iRNA molecules that bind to the target nucleic acid sequence(s); introducing the iRNA molecules, optionally packaged in an expression vector, into the cell; and expressing iRNAs in the cell or animal under conditions such that the iRNA molecules bind to the homologous region within the gene family.

The present invention also provides transgenic non-human animals produced by the methods of the invention. The methods of the invention are useful for the production of transgenic non-human mammals (e.g. mice, rats, sheep, goats, cows, pigs, rabbits, dogs, horses, mules, deer, cats, monkeys and other non-human primates), birds (particularly chickens, ducks, and geese), fish, reptiles, amphibians, worms (e. g. *C. elegans*), and insects (including but not limited to, Mosquitos, *Drosophila, Trichoplusa*, and *Spodoptera*). While any species of non-human animal can be produced, in one embodiment the non-human animals are transgenic pigs. The present invention also provides cells, tissues and organs isolated from such non-human transgenic animals.

In embodiments of the present invention, endogenous genes that can be regulated by the expression of at least two iRNA molecules include, but are not limited to, genes required for cell survival or cell replication, genes required for viral replication, genes that encode an immunoglobulin locus, for example, Kappa light chain, and genes that encode a cell surface protein, for example, Vascular Cell Adhesion Molecule (VCAM) and other genes important to the structure and/or function of cells, tissues, organs and animals. The methods of the invention can also be used to regulate the expression of one or more non-coding RNA sequences in a transgenic cell or a transgenic animal by heritable transgene expression of interfering RNA. These non-coding RNA sequences can be sequences of an RNA virus genome, an endogenous gene, a eukaryotic parasite gene, or other non-coding RNA sequences that are known in the art and that will be familiar to the ordinarily skilled artisan.

iRNA molecules that are expressed in cells or animals according to the aspects of the present invention can decrease, increase or maintain expression of one or more target genes. In order to identify specific target nucleic acid regions in which the expression of one or more genes, family of genes, desired subset of genes, or alleles of a gene is to be regulated, a representative sample of sequences for each target gene can be obtained. Sequences can be compared to find similar and dissimilar regions. This analysis can determine regions of identity between all family members and within subsets (i.e. groups within the gene family) of family members. In addition, this analysis can determines region of identity between alleles of each family member. By considering regions of identity between alleles of family members, between subsets of family members, and across the entire family, target regions can be identified that specify the entire family, subsets of family members, individual family members, subsets of alleles of individual family members, or individual alleles of family members.

Regulation of expression can decrease expression of one or more target genes. Decreased expression results in post-transcriptional down-regulation of the target gene and ultimately the final product protein of the target gene. For down-regulation, the target nucleic acid sequences are identified such that binding of the iRNA to the sequence will decrease expression of the target gene. Decreased expression of a gene refers to the absence of, or observable or detectable decrease in, the level of protein and/or mRNA product from a target gene relative to that without the introduction of the iRNA. Complete suppression/inhibition as well as partial suppressed expression of the target gene are possible with the methods of the present invention. By "partial suppressed expression," it is meant that the target gene is suppressed (i.e. the expression of the target gene is reduced) from about 10% to about 99%, with 100% being complete suppression/inhibition of the target gene. For example, about 10%, about 20%, about 30%, about 40%, about 50%, about 60%, about 70%, about 80%, about 90%, about 95%, or about 99% of gene expression of the one or more genes can be suppressed. Alternatively, expression is suppressed or inhibited below detectable threshold limits.

In other embodiments of the invention, regulation of expression can increase expression of one or more genes. Increased expression can result when the interfering RNA targets a nucleic acid sequence that acts as a suppressor of one or more genes of interest. In this embodiment of the invention, the target nucleic acid and the gene of interest can be separate sequences. Increased expression of a gene refers to the presence, or observable increase, in the level of protein and/or mRNA product from one or more target genes relative to that without the introduction of the iRNA. By increased expression of a gene, it is meant that the measurable amount of the target gene that is expressed is increased any amount relative to that without the introduction of the iRNA. For example, the level of expression of the gene can be increased about two-fold, about five-fold, about 10-fold, about 50-fold, about 100-fold, about 500-fold, about 1000-fold, or about 2000-fold, above that which occurs in the absence of the interfering RNA.

In still other aspects of the invention, regulation of expression can maintain expression of one or more genes, when the one or more genes are placed under environmental conditions that generally lead to increased or decreased expression of the one or more genes. Expression of one or more genes can be maintained under environmental conditions that would normally increase or decrease gene expression results in a steady-state level (i.e. no increase or decrease in expression with time) of gene expression relative to expression prior to the presence of environmental conditions that would otherwise increase or decrease expression. Examples of environmental conditions that can increase gene expression include, but are not limited to, the presence of growth factors, increased glucose production, hyperthermia and cell cycle changes. Examples of environmental conditions that can decrease gene expression include, but are not limited to, hypoxia, hypothermia, lack of growth factors and glucose depletion.

Quantitation of gene expression can allow one to determine the degree of inhibition (or enhancement) of gene expression in a cell or animal that contain one or more iRNA molecules. Lower doses of injected material and longer times after administration or integration of the iRNA can result in inhibition or enhancement in a smaller fraction of cells or animals (e.g., at least 10%, 20%, 50%, 75%, 90%, or 95% of targeted cells or animals). Quantitation of gene expression in a cell or animal can show similar amounts of inhibition or enhancement at the level of accumulation of target mRNA or translation of target protein. The efficiency of inhibition or enhancement can be determined by assessing the amount of gene product in the cell or animal using any method known in the art. For example, mRNA can be detected with a hybridization probe having a nucleotide sequence outside the region used for the interfering RNA, or translated polypeptide can be detected with an antibody raised against the polypeptide sequence of that region. Methods by which to quantitate mRNA and polypeptides are well-known in the art see, for example, Sambrook, J. et al. "Molecular Cloning: A Laboratory Manual," 2nd addition, Cold Spring Harbor Laboratory Press, Plainview, N.Y. (1989).

The present invention also relates to the regulation of expression of a family of genes. The term "family of genes" refers to one or more genes that have a similar function, sequence, or phenotype. A family of genes can contain a conserved sequence, i.e. a nucleotide sequence that is the same or highly homologous among all members of the gene family. In certain embodiments, the iRNA sequence can hybridize to this conserved region of a gene family, and thus one iRNA sequence can target more than one member of a gene family.

In one embodiment, the target gene or family of genes are genes of an endogenous virus, for example, porcine endogenous retrovirus. In another embodiment of the invention, the target genes or gene family are genes of an exogenous virus. Examples of exogenous viruses include, but are not limited to, zoonotic viruses (such as West Nile Virus, Hantavirus, Herpesvirus, Parvovirus, Enterovirus, Rabies, Filoviruses, Human Immunodeficiency Virus, Influenza, and Napah Virus), livestock viruses (such as Rinderpest virus, foot and mouth disease virus, and Marek's disease virus), synthetic viruses and endemic viruses. Any viral gene that is not heritable as an integral element of the genome (chromosomal or extrachromsomal) of the species can be considered an exogenous virus and can be regulated by the methods of the invention. In one such embodiment, the family of one or more genes of an exogenous virus that are regulated can be a family of related viral genes. Examples of related viral genes include, but are not limited to, gag genes, env genes and pol genes, which are related as a family of retroviral genes.

The methods of the present invention can also be used to regulate expression of genes within an evolutionarily related family of genes. Evolutionarily related genes are genes that have diverged from a common progenitor genetic sequence, which can or can not have itself been a sequence encoding for one or more mRNAs. Within this evolutionarily related family can exist a subset of genes, and within this subset, a conserved nucleotide sequence can exist. The present invention also provides methods by which to regulate expression of this subset of genes by targeting the iRNA molecules to this conserved nucleotide sequence. Evolutionarily related genes that can be regulated by the methods of the present invention can be endogenous or exogenous to a cell or an animal and can be members of a viral family of genes. In addition, the family of viral genes that can be regulated by the methods of the present invention can have family members that are endogenous to the cell or animal.

In another embodiment of the invention, the methods of the invention can be used to regulate the life-cycle of a virus. In one such aspect of the invention, this regulation can result in the truncation, or shortening, of the life-cycle of a virus. By truncation or shortening of the life-cycle, it is meant that the virus survives for a shorter period of time than an identical virus that has not been regulated. A shorter period of time encompasses any amount of time that is less than the life-cycle of an identical virus that has not been regulated. For example, the virus can survive for an amount of time that is about 1%, about 5%, about 10%, about 33%, about 50%, about 67%, about 75%, about 80%, about 85%, about 90%, about 95%, about 96%, about 97%, about 98%, about 99% or about 100% shorter than an identical virus that has not been regulated. A virus that is said to have its life-cycle truncated 100% represents a virus that does not survive for any amount of time after treatment of the virus, or a host cell harboring the virus, with an iRNA.

In an alternative aspect, the iRNA induced regulation can result in the expansion, or lengthening of the life cycle of a virus. By expansion or lengthening of the life-cycle, it is meant that the virus survives for a longer period of time than an identical virus that has not been regulated. A longer period of time encompasses any amount of time that is greater than the life-cycle of an identical virus that has not been regulated. For example, the virus can survive for an amount of time that is about two-fold, about five-fold, about 10-fold, about fold, about 50-fold, about 70-fold, about 100-fold, about 500-fold, about 1000-fold, about 2000-times, etc., longer than an identical virus that has not been regulated.

In still other aspects of the invention, regulation of expression can maintain the life cycle of a virus, when the virus is placed under environmental conditions that generally lead to expansion or truncation of its life-cycle. A life-cycle of a virus that is maintained under environmental conditions that would normally expand or truncate this life-cycle results in a steady-state (i.e. no expansion or truncation) life-cycle relative to a virus life-cycle in the presence of environmental conditions that would otherwise expand or truncate the life-cycle of the virus. Examples of environmental conditions that can expand the life-cycle of a virus include, but are not limited to, the presence of growth factors, increased glucose production, hyperthermia, cell cycle changes. Examples of environmental conditions that can truncate the life-cycle of a virus include, but are not limited to, hypoxia, hypothermia, lack of growth factors and glucose depletion.

Regulation of the life-cycle of a virus can result from regulation of an endogenous gene or family of endogenous genes that are required for the life-cycle of the virus. The interfering RNA can also target a viral gene or family of viral genes, thereby regulating the life-cycle of the virus.

In other embodiments, the methods of the present invention can be used to regulate expression of genes, or family of genes, that are endogenous to a cell or animal. An endogenous gene is any gene that is heritable as an integral element of the genome of the animal species. Regulation of endogenous genes by methods of the invention can provide a method by which to suppress or enhance a phenotype or biological state of a cell or an animal. Examples of phenotypes or biological states that can be regulated include, but are not limited to, shedding or transmission of a virus, feed efficiency, growth rate, palatability, prolificacy, secondary sex characteristics, carcass yield, carcass fat content, wool quality, wool yield, disease resistance, post-partum survival and fertility. Additional endogenous genes that can also be regulated by the methods of the invention include, but are not limited to, endogenous genes that are required for cell survival, endogenous genes that are required for cell replication, endogenous genes that are required for viral replication, endogenous genes that encode an immunoglobulin locus, and endogenous genes that encode a cell surface protein. Further examples of endogenous genes include developmental genes (e. g., adhesion molecules, cyclin kinase inhibitors, Writ family members, Pax family members, Winged helix family members, Hox family members, cytokines/lymphokines and their receptors, growth/differentiation factors and their receptors, neurotransmitters and their receptors), tumor suppressor genes (e.g., APC, BRCA1, BRCA2, MADH4, MCC, NF 1, NF2, RB 1, TP53, and WTI) and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases).

In one embodiment of the invention, the regulated genes, or family of genes, are genes of an integrated endogenous virus. Examples of integrated endogenous virus genes include, but are not limited to: porcine endogenous retrovirus (PERV) genes, oncogenes (e. g., ABLI, BCL1, BCL2, BCL6, CBFA2, CBL, CSFIR, ERBA, ERBB, EBRB2, ETSI, ETS1, ETV6, FGR, FOS, FYN, HCR, HRAS, JUN, KRAS, LCK, LYN, MDM2, MLL, MYB, MYC, MYCLI, MYCN, NRAS, PIM 1, PML, RET, SRC, TALI, TCL3, and YES), growth factor receptor genes, B virus genes, and Simian T Lymphotrophic virus genes. Any viral gene that is inherited as an element of the genome of a species can be considered an endogenous viral gene and can be regulated by the methods of the invention. In one embodiment, the family of one or more genes that is regulated can be a family of related viral genes.

The methods of the present invention can also be used to regulate the expression of a specific allele. Alleles are polymorphic variants of a gene that occupy the same chromosomal locus. The methods of the present invention allow for regulation of one or more specific alleles of a gene or a family of genes. In this embodiment, the sequence of the iRNA can be prepared such that one or more particular alleles of a gene or a family of genes are regulated, while other additional alleles of the same gene or family of genes are not regulated.

In another embodiment of the invention, the regulated gene or family of genes is a gene of a eukaryotic parasite. Examples of eukaryotic parasites include, but are not limited to, helminths, protozoa and arthropods.

In further embodiment, the methods of the present invention allow for the regulation of expression of non-coding RNA sequences. Non-coding RNA sequences are sequences that do not transcribe active proteins. These non-coding RNA sequences can be sequences of an endogenous or exogenous viral genome, they can be endogenous to the cell or animal, or they can also be sequences of a eukaryotic parasite.

In further embodiments, the methods of the present invention allow for enrichment of homologous recombination events. If the siRNA transgene is located “outside” of the homologous targeting arms, then the siRNA transgene is not retained in the genome of the cell in which recombination has occurred. However, if the the targeting vector integrates at a random location and therefore does not represent a homologous recombination event, the siRNA transgene will be present in the genome of such cells. When the siRNA transgene targets either a required gene, a gene that produces a selectable phenotype, or the selectable marker contained in the original targeting vector, then random integrations can be differentiated from targeting events. In this case, one can enrich for targeting events in relation to non-targeting integration events.

A. PERV

In one exemplary embodiment of the invention, the regulated genes, or family of genes, are genes of an integrated endogenous virus. A prototype of an endogenous virus is PERV (porcine endogenous retrovirus).

In an exemplary embodiment of the present invention, porcine endogenous retrovirus (PERV) genes can be regulated by the expression of at least two iRNA molecules such that the expression of the PERV virus is functionally eliminated or below detection levels. PERV refers to a family of retrovirus of which three main classes have been identified to date: PERV-A (Genbank Accession No. AF038601), PERV-B (EMBL Accession No. PERY17013) and PERV-C (Genbank Accession No. AF038600) (Patience et al 1997, Akiyoshi et al 1998). The gag and pol genes of PERV-A, B, and C are highly homologous, it is the env gene that differs significantly between the different types of PERV (eg., PERV-A, PERV-B, PERV-C). PERV-D has also recently been identified (see, for example, U.S. Pat. No. 6,261,806).

In one embodiment, iRNA directed to the PERV virus can decrease the expression of PERV by at least about 70%, 75%, 80%, 85%, 90%, 95%, 97% or 99%, or alternatively, below detectable levels. To achieve this goal, the present invention provides at least two iRNA molecules that target the same sequence within the gag, pol or env region of the PERV genome. Further, at least two iRNA molecules are provided that target different sequences within the gag, pol or env regions of the PERV genome. Still further, at least two iRNA molecules are provided that each target different regions (i.e. either gag, pol or env) of the PERV genome. Additionally, multiple iRNA molecules are provided that combine these different targeting strategies, for example: at least two RNA interference molecules directed to the gag region of PERV; at least two RNA interference molecules directed to the pol region of PERV; and at least two RNA interference molecules directed to the env region of PERV are provided to target the PERV gene.

The present invention also provides porcine animals, as well as cells, tissues and organs isolated from non-human transgenic animals in which the expression of PERV is decreased or functionally eliminated via the expression of at least two iRNA molecules. In certain such embodiments, they are obtained from transgenic pigs that express one or more interfering RNAs that interfere with the porcine endogenous retrovirus gene, a family member of the porcine endogenous retrovirus gene or a member of a subset of the porcine endogenous retrovirus gene family.

With the recent success in pig cloning (Polejaeva et al, 2000; Onishi et al, 2000) and the knockout of $\alpha$1,3-galactosyltransferase ($\alpha$1,3GT) gene in pigs (Dai et al, 2002; Lai et al, 2002), xenotransplantation is closer to becoming reality. The complete removal of the $\alpha$1,3 gal epitope, the major xeno antigen, from pig organs and tissues should significantly reduce hyperacute rejection of pig xenografts. One potential risk for pig to human xenotransplantation is the potential for human infection with porcine endogenous retroviruses (PERVs). PERVs are type-C family retrovirus, ubiquitously found in all pig cells, tissues or organs. PERVs are an integral part of the pig genome with as many as 50 copies of PERV proviruses per cell (Le Tissier et al, 1997). Most of the proviruses are defective, and only very few of them are replication-competent (Herring et al, 2001). At least three distinct PERV sequences have been identified (PERV-A, —B and —C), which are classed according to relative homologies within three different env gene subfamilies (Takeuchi Y et al, 1998; Blusch 2002). Perv-A and PERV-B show 92% amino-acid identity to one another and 63-66% identity to gibbon ape leukemia virus, feline leukemia virus and Friend murine leukemia virus. Replication-competent PERV-A and PERV-B have been detected from PK-15 (porcine kidney-derived) cells, activated peripheral blood mononuclear cells (PBMCs), pig pancreatic islets and porcine aortic endothelial cells (Martin et al, 1998; Takeuchi et al, 1998; Wilson et al, 1998). Both PERV-A and PERV-B are able to infect human and porcine cells, while PERV-C, an ecotropic retrovirus, has not been shown to be able to infect normal human cells. Infection and pseudotyping experiments have demonstrated that PERV-A, —B and -C use different cell receptors. Studies of humans treated with living pig organs, tissues or cells have not found any evidence of PERV infection so far (Heneine 1998; Paradis 1999; Patience 1998). However, in these studies, only human PBMC cells were screened and most of the patients were not under immunosuppression. In the xenograft setting, organs or cells from pigs may be exposed directly to the bloodstream of the patient, and because these patients are usually immunosuppressed, the risk of PERV infection may be enhanced. In addition, with the development of $\alpha$1,3Gal negative pigs, another natural defense against viruses, such as PERV, may be suppressed. Normally, pre-formed high-titer antibodies against alpha gal, present in all humans, would act as a first line of defense against viruses whose envelope is decorated with $\alpha$-gal epitopes. However, if endogenous proviruses arise from $\alpha$1,3Gal negative pigs, they will also lack $\alpha$-gal, and thus could avoid this primary immune defense. As such, the potential exists that PERVs from $\alpha$1,3Gal negative pigs may have a greater chance to infect the patient.

Current strategies to reduce transmission of porcine endogenous retrovirus (PERV) involve reduction of PERV copy number by traditional breeding. Since PERV copy number and integration sites vary between pigs it is possible that one could use selective breeding to reduce the number of PERVs in the pig genome. This strategy is not only impractical from the point of view of required time, but also assumes that PERVs are transmitted exclusively by Mendelian inheritance. Since type-C retroviruses can integrate to form new proviruses, this assumption is false (Mang, et al, 2001). A similar strategy is to screen large numbers of individual pigs and breeds of pigs in the hope of finding a genetic background that has a low number of PERVs and/or primarily defective PERVs. Again, assumptions are made that PERV numbers and integration sites are stable. In addition, an artificial comfort is created because such pigs would have been selected for few functional or human-tropic PERVs. However, most human-transmissible PERVs that have been characterized result from novel mRNA recombinations to generate new PERVs that were not in the original genome (Oldmixon et al, 2002).

In one aspect of the invention, a family of PERV genes can be regulated. Related PERV viruses include, for example PERV A, PERV B, PERV C, and PERV D. Examples of related PERV genes include, but are not limited to, gag genes, env genes and pol genes.

Representative gag sequences can be found with the following Genbank accession numbers: AF038599, AF038600, AF147808, AF163266, AF417210, AF417211, AF417212, AF417213, AF417214, AF417215, AF417216, AF417217, AF417218, AF417219, AF417220, AF417221, AF435967, AW231947, AW308385, AW358862, AY056035, AY099323, AY099324, AY265811, BF441465, BF441466, BF441468, BF441469, BF443400, B1181099, BI183356, BI1186129, B1398794, B1399234, CB468878, CB468924, CB479915 or EMBL; AJ133816, AJ133817, AJ133818, AJ279056, AJ279057, AJ293656, AJ293657, Y17013. Representative pol sequences can be found with the following Genbank accession numbers: AF000572, AF033259, AF033260, AF038599, AF038600, AF147808, AF163265, AF163268, AF274705, AF402661, AF402662, AF402663, AF435966, AF435967, AF511088, AF511089, AF511090, AF511091, AF511092, AF511093, AF511094, AF511095, AF511096, AF511097, AF511098, AF511099, AW416859, AW435835, AW447645, AY056035, AY099323, AY099324, BE013835, BF709087, BF709087, BI119493, BI183551, BI183551, BI304652, BI336152, CB287225, CF178916, CF178929, CF180285, CF180296, CF181622, CF181673, CF360188, CF360268, U77599, U77600 or EMBL; AJ005399, AJ005400, AJ005401, AJ005402, AJ005403, AJ005404, AJ005405, AJ005406, AJ005407, AJ005408, AJ005409, AJ005410, AJ005411, AJ005412, AJ133816, AJ133817, AJ133818, AJ279056, AJ279057, AJ293656, AJ293657, Y12238, Y12239, Y17013, Y18744, Y18745, Y18746, Y18747, Y18748, Y18749, X99933.

Representative env-A sequences can be found with the following Genbank accession numbers: AF130444, AF163264, AF163267, AF163269, AF296168, AF318386, AF318387, AF318389, AF417222, AF417223, AF417224, AF417225, AF417226, AF417230, AF417231, AF417232, AF426917, AF426918, AF426919, AF426920, AF426921, AF426922, AF426923, AF426924, AF426925, AF426926, AF426927, AF426928, AF426929, AF426930, AF426931, AF426934, AF426941, AF426942, AF426943, AF426944, AF426945, AF507940, BI19493, BI185465, BI185535, BI304699, B1336152, CB287431, CF178929 or EMBL; AJ288584, AJ288585, Y12238.

Representative env-B sequences can be found with the following Genbank accession numbers: AF014162, AF426916, AF426932, AF426933, AF426935, AF426936, AF426937, AF426938, AF426939, AF426940, AF426946, AW657531, AY056024, AY056025, AY056026, AY056027, AY056028, AY056029, AY056030, AY056031, AY056032, AY056033, AY056034, BI118348, BI244560, CF180296, CF181717 or EMBL; AJ288586, AJ288587, AJ288588, AJ288589, AJ288590, AJ288591, AJ288592, Y12239.

Representative env-C sequences can be found with the following Genbank accession numbers: AF318383, AF318384, AF318385, AF318388, AF402660, AF417227, AF417228, AF417229, BI336316, BM190587.

Representative env-D sequences can be found with the following Genbank accession numbers: AF402661, AF402662, AF402663 or in U.S. Pat. No. 6,261,806.

In one embodiment, the PERV-A, PERV-B, and PERV-C family of genes can be targeted simultaneously by at least two iRNA molecules. In another embodiment, the virus is a subset of a porcine endogenous retrovirus family.

In another, the cells, tissues and organs of pigs that contain iRNA molecules that regulate PERV can be used for xenotransplantation.

Cell Types

The constructs, templates and vectors described herein can be introduced into host cells via any technique known in the art, including but not limited to microinjection, transfection, transformation, and/or electroporation. The host cell can be any mammalian, plant, yeast or bacterial cell. In one embodiment, the host cell is a prokaryote, such as a bacterial cell including, but not limited to an *Escherichia* or a *Pseudomonas* species. In another embodiment the host cell is a eukaryotic cell, for example an insect cell, including but not limited to a cell from a *Spodoptera, Trichoplusia, Drosophila* or an *Estigmene* species, or a mammalian cell, including but not limited to a human cell, murine cell, a porcine cell, a bovine cell, an ovine cell, a rodent cell, a hamster cell, a monkey, a primate or a human cell. The mammalian cell can be a cell obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus or adult animal; or epithelial cells, fibroblast cells, neural cells, keratinocytes, hematopoietic cells, melanocytes, chondrocytes, lymphocytes (B and T), macrophages, monocytes, mononuclear cells, cadiac muscle cells, other muscle cells, granulose cells, cumulus cells, epidermal cells or endothelial cells. The host cells can be HEK cells, COS cells, or other cell commonly used in cell culture. In another embodiment, the host cell is a plant cell, including, but not limited to, a tobacco cell, corn, a cell from an *Arabidopsis* species, potato or rice cell.

V. Production of Genetically Modified Animals

The present invention also includes methods of producing non-human transgenic animals which heritably express one or more interfering RNAs. Any non-human transgenic animal can be produced by any one of the methods of the present invention including, but not limited to, non-human mammals (including, but not limited to, pigs, sheep, goats, cows (bovine), deer, mules, horses, monkeys and other non-human primates, dogs, cats, rats, mice, rabbits), birds (including, but not limited to chickens, turkeys, ducks, geese and the like) reptiles, fish, amphibians, worms (e.g. *C. elegans*), insects (including but not limited to, *Drosophila, Trichoplusa*, and *Spodoptera*).

The present invention also provides a non-human transgenic animal that has at least two iRNA sequences inserted in its genome. In one embodiment, the animal is capable of expressing the iRNA molecule within the majority of its cells. In another embodiment, the animal is capable of expressing the iRNA molecule in virtually all of its cells. Since the sequence is incorporated into the genome of the animal, the iRNA molecules will be inherited by subsequent generations, thus allowing these generations to also produce the iRNA within their cells.

In one aspect of the present invention, non-human transgenic animals are produced via the process of nuclear transfer. In an alternate aspect, the present invention provides methods of producing a non-human transgenic animal through the genetic modification of totipotent embryonic cells.

Nuclear Transfer/Cloning

In one embodiment of the present invention, non-human transgenic animals are produced via the process of nuclear transfer. In one embodiment, the nuclear donor cells can be genetically modified by the targeting constructs described herein to produce iRNA molecules. Production of non-human transgenic animals which express one or more interfering RNAs via nuclear transfer comprises: (a) identifying one or more target nucleic acid sequences in an animal; (b) preparing one or more interfering RNAs, wherein the interfering RNAs bind to the target nucleic acid sequences; (c) preparing one or more expression vectors containing the one or more interfering RNAs; (d) inserting the one or more interfering RNA expression vectors into the genome of a nuclear donor cell; (e) transferring the genetic material of the nuclear donor cell to an acceptor cell; (f) transferring the acceptor cell to a recipient female animal; and (g) allowing the transferred acceptor cell to develop to term in the female animal. Any animal can be produced by nuclear transfer, including, but not limited to: porcine, bovine, ovine, equine, and rodents, including mice and rats, rabbits.

Nuclear transfer techniques or nuclear transplantation techniques are known in the art (Campbell et al, *Theriogenology,* 43:181 (1995); Collas, et al, *Mol. Report Dev.,* 38:264-267 (1994); Keefer et al, *Biol. Reprod.,* 50:935-939 (1994); Sims, et al, *Proc. Natl. Acad. Sci., USA,* 90:6143-6147 (1993); WO 94/26884; WO 94/24274, and WO 90/03432, U.S. Pat. Nos. 4,944,384 and 5,057,420). In one nonlimiting example, methods are provided such as those described in U.S. Patent Publication No. 2003/0046722 to Collas, et al., which describes methods for cloning mammals that allow the donor chromosomes or donor cells to be reprogrammed prior to insertion into an enucleated oocyte. The invention also describes methods of inserting or fusing chromosomes, nuclei or cells with oocytes.

A donor cell nucleus, can be transferred to a recipient porcine oocyte. The use of this method is not restricted to a particular donor cell type. The donor cell can be as described in Wilmut, et al., *Nature* 385 810 (1997); Campbell, et al., *Nature* 380 64-66 (1996); or Cibelli, et al., *Science* 280 1256-1258 (1998). All cells of normal karyotype, including embryonic, fetal and adult somatic cells which can be used successfully in nuclear transfer can in principle be employed. Fetal fibroblasts are a particularly useful class of donor cells. Generally suitable methods of nuclear transfer are described in Campbell, et al., *Theriogenology* 43 181 (1995), Collas, et al., *Mol. Reprod. Dev.* 38 264-267 (1994), Keefer, et al., *Biol. Reprod.* 50 935-939 (1994), Sims, et al., *Proc. Nat T. Acad. Sci. USA* 90 6143-6147 (1993), WO-A-9426884, WO-A-9424274, WO-A-9807841, WO-A-9003432, U.S. Pat. Nos. 4,994,384 and 5,057,420. Differentiated or at least partially differentiated donor cells can also be used. Donor cells can also be, but do not have to be, in culture and can be quiescent. Nuclear donor cells which are quiescent are cells which can be induced to enter quiescence or exist in a quiescent state in vivo. Prior art methods have also used embryonic cell types in cloning procedures (Campbell, et al. (*Nature,* 380:64-68, 1996) and Stice, et al (*Biol. Reprod.,* 20 54:100-110, 1996).

Somatic nuclear donor cells may be obtained from a variety of different organs and tissues such as, but not limited to, skin, mesenchyme, lung, pancreas, heart, intestine, stomach, bladder, blood vessels, kidney, urethra, reproductive organs, and a disaggregated preparation of a whole or part of an embryo, fetus or adult animal. In a suitable embodiment of the invention, nuclear donor cells are selected from the group consisting of epithelial cells, fibroblast cells, neural cells, keratinocytes, hematopoietic cells, melanocytes, chondrocytes, lymphocytes (B and T), macrophages, monocytes, mononuclear cells, cadiac muscle cells, other muscle cells, granulose cells, cumulus cells, epidermal cells or endothelial cells. In another embodiment, the nuclear cell is an embryonic stem cell. In a preferred embodiment, fibroblast cells can be used as donor cells.

In another embodiment of the invention, the nuclear donor cells of the invention are germ cells of an animal. Any germ cell of an animal species in the embryonic, fetal, or adult stage may be used as a nuclear donor cell. In a suitable embodiment, the nuclear donor cell is an embryonic germ cell.

Nuclear donor cells may be arrested in any phase of the cell cycle (GO, GI, G2, S, M). Any method known in the art may be used to manipulate the cell cycle phase. Methods to control the cell cycle phase include, but are not limited to, GO quiescence induced by contact inhibition of cultured cells, GO quiescence induced by removal of serum or other essential nutrient, GO quiescence induced by senescence, GO quiescence induced by addition of a specific growth factor, GO or GI quiescence induced by physical or chemical means such as heat shock, hyperbaric pressure or other treatment with a chemical, hormone, growth factor or other substance; S-phase control via treatment with a chemical agent which interferes with any. Point of the replication procedure; M-phase control via selection using fluorescence activated cell sorting, mitotic shake off, treatment with microtubule disrupting agents or any chemical which disrupts progression in mitosis (see also Freshney, R. I., "Culture of Animal Cells: A Manual of Basic Technique," Alan R. Liss, Inc, New York (1983)).

Methods for isolation of oocytes are well known in the art. For example, oocytes can be isolated from the ovaries or reproductive tract of an animal. A readily available source of animal oocytes is slaughterhouse materials. For the combination of techniques such as genetic engineering, nuclear transfer and cloning, oocytes must generally be matured in vitro before these cells can be used as recipient cells for nuclear transfer, and before they can be fertilized by the sperm cell to develop into an embryo. This process generally requires collecting immature (prophase I) oocytes from mammalian ovaries, e.g., bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. This period of time is known as the "maturation period".

A metaphase II stage oocyte can be the recipient oocyte, at this stage it is believed that the oocyte can be or is sufficiently "activated" to treat the introduced nucleus as it does a fertilizing sperm. Metaphase II stage oocytes, which have been matured in vivo have been successfully used in nuclear transfer techniques. Essentially, mature metaphase II oocytes can be collected surgically from either non-superovulated or superovulated porcine 35 to 48, or 39-41, hours past the onset of estrus or past the injection of human chorionic gonadotropin (hCG) or similar hormone.

After a fixed time maturation period, which ranges from about 10 to 40 hours, and preferably about 16-18 hours, the oocytes can be enucleated. Prior to enucleation the oocytes can be removed and placed in appropriate medium, such as HECM containing 1 milligram per milliliter of hyaluronidase prior to removal of cumulus cells. The stripped oocytes can then be screened for polar bodies, and the selected metaphase II oocytes, as determined by the presence of polar bodies, are then used for nuclear transfer. Enucleation follows.

Enucleation can be performed by known methods, such as described in U.S. Pat. No. 4,994,384. For example, metaphase II oocytes can be placed in either HECM, optionally containing 7.5 micrograms per milliliter cytochalasin B, for immediate enucleation, or can be placed in a suitable medium, for example an embryo culture medium such as CR1aa, plus 10% estrus cow serum, and then enucleated later, preferably not more than 24 hours later, and more preferably 16-18 hours later. Enucleation can be accomplished microsurgically using a micropipette to remove the polar body and the adjacent cytoplasm. The oocytes can then be screened to identify those of which have been successfully enucleated. One way to screen the oocytes is to stain the oocytes with 1 microgram per milliliter 33342 Hoechst dye in HECM, and then view the oocytes under ultraviolet irradiation for less than 10 seconds. The oocytes that have been successfully enucleated can then be placed in a suitable culture medium, for example, CR1aa plus 10% serum.

A single mammalian cell of the same species as the enucleated oocyte can then be transferred into the perivitelline space of the enucleated oocyte used to produce the NT unit. The mammalian cell and the enucleated oocyte can be used to produce NT units according to methods known in the art. For example, the cells can be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels can open between the two cells. Due to the thermodynamic instability of such a small opening, it enlarges until the two cells become one. See, for example, U.S. Pat. No. 4,997,384 by Prather et al. A variety of electrofusion media can be used including, for example, sucrose, mannitol, sorbitol and phosphate buffered solution. Fusion can also be accomplished using Sendai virus as a fusogenic agent (Graham, *Wister Inot. Symp. Monogr.,* 9, 19, 1969). Also, the nucleus can be injected directly into the oocyte rather than using electroporation fusion. See, for example, Collas and Barnes, *Mol. Reprod. Dev.,* 38:264-267 (1994). After fusion, the resultant fused NT units are then placed in a suitable medium until activation, for example, CR1aa medium. Typically activation can be effected shortly thereafter, for example less than 24 hours later, or about 4-9 hours later.

The NT unit can be activated by any method that accomplishes the desired result. Such methods include, for example, culturing the NT unit at sub-physiological temperature, in essence by applying a cold, or actually cool temperature shock to the NT unit. This can be most conveniently done by culturing the NT unit at room temperature, which is cold relative to the physiological temperature conditions to which embryos are normally exposed. Alternatively, activation can be achieved by application of known activation agents. For example, penetration of oocytes by sperm during fertilization has been shown to activate prefusion oocytes to yield greater numbers of viable pregnancies and multiple genetically identical animals, such as pigs, after nuclear transfer. Also, treatments such as electrical and chemical shock can be used to activate NT embryos after fusion. See, for example, U.S. Pat. No. 5,496,720, to Susko-Parrish, et al. Additionally, activation can be effected by simultaneously or sequentially by increasing levels of divalent cations in the oocyte, and reducing phosphorylation of cellular proteins in the oocyte. This can generally be effected by introducing divalent cations into the oocyte cytoplasm, e.g., magnesium, strontium, barium or calcium, e.g., in the form of an ionophore. Other methods of increasing divalent cation levels include the use of electric shock, treatment with ethanol and treatment with caged chelators. Phosphorylation can be reduced by known methods, for example, by the addition of kinase inhibitors, e.g., serine-threonine kinase inhibitors, such as 6-dimethyl-aminopurine, staurosporine, 2-aminopurine, and sphingosine. Alternatively, phosphorylation of cellular proteins can be inhibited by introduction of a phosphatase into the oocyte, e.g., phosphatase 2A and phosphatase 2B.

The activated NT units can then be cultured in a suitable in vitro culture medium until the generation of cell colonies. Culture media suitable for culturing and maturation of embryos are well known in the art. Examples of known media, which can be used for embryo culture and maintenance, include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media.

Afterward, the cultured NT unit or units can be washed and then placed in a suitable media contained in well plates which preferably contain a suitable confluent feeder layer. Suitable feeder layers include, by way of example, fibroblasts and epithelial cells. The NT units are cultured on the feeder layer until the NT units reach a size suitable for transferring to a recipient female, or for obtaining cells which can be used to produce cell colonies. Preferably, these NT units can be cultured until at least about 2 to 400 cells, more preferably about 4 to 128 cells, and most preferably at least about 50 cells.

Activated NT units can then be transferred (embryo transfers) to the oviduct of an female animals. In one embodiment, the female animals can be an estrus-synchronized recipient gilt. Crossbred gilts (large white/Duroc/Landrace) (280-400 lbs) can be used. The gilts can be synchronized as recipient animals by oral administration of 18-20 mg ReguMate (Altrenogest, Hoechst, Warren, N.J.) mixed into the feed. Regu-Mate can be fed for 14 consecutive days. One thousand units of Human Chorionic Gonadotropin (hCG, Intervet America, Millsboro, Del.) can then be administered i.m. about 105 h after the last Regu-Mate treatment. Embryo transfers of the can then be performed about 22-26 h after the hCG injection. In one embodiment, the pregnancy can be brought to term and result in the birth of live offspring. In another embodiment, the pregnancy can be 5 terminated early and embryonic cells can be harvested.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. See, for example, Siedel, G. E., Jr. "Critical review of embryo transfer procedures with cattle" in *Fertilization and Embryonic Development in Vitro* (1981) L. Mastroianni, Jr. and J. D. Biggers, ed., Plenum Press, New York, N.Y., page 323.

Other Methods to Produce Genetically Modified Animals

In additional embodiments of the present invention, transgenic animals can be produced by any means known in the art, including, but not limited to the following: microinjection of DNA into oocytes, zygotes or pre-implantation blastomers (such as 2 cell, 4 cell or 8 cell blastomers), transfection of embryonic stem cells, sperm-mediated deliver of DNA and transfecting embryos in vivo via the blood steam.

In one embodiment, the present invention provides methods of producing a non-human transgenic animal that express at least two interfering RNAs through the genetic modification of totipotent embryonic cells. In one embodiment, the animals can be produced by: (a) identifying one or more target nucleic acid sequences in an animal; (b) preparing one or more interfering RNAs, wherein the interfering RNAs bind to the target nucleic acid sequences; (c) preparing one or more expression vectors containing the one or more interfering RNAs; (d) inserting the one or more interfering RNA expression vectors into the genomes of a plurality of totipotent cells of the animal species, thereby producing a plurality of transgenic totipotent cells; (e) obtaining a tetraploid blastocyst of the animal species; (f) inserting the plurality of totipotent cells into the tetraploid blastocyst, thereby producing a transgenic embryo; (g)

transferring the embryo to a recipient female animal; and (h) allowing the embryo to develop to term in the female animal. The method of transgenic animal production described here by which to generate a transgenic animal, such as a mouse, is further described in U.S. Pat. No. 6,492,575.

In another embodiment, the totipotent cells can be embryonic stem (ES) cells. The isolation of ES cells from blastocysts, the establishing of ES cell lines and their subsequent cultivation are carried out by conventional methods as described, for example, by Doetchmann et al., J. Embryol. Exp. Morph. 87:27-45 (1985); Li et al., Cell 69:915-926 (1992); Robertson, E. J. "Tetracarcinomas and Embryonic Stem Cells: A Practical Approach," ed. E. J. Robertson, IRL Press, Oxford, England (1987); Wurst and Joyner, "Gene Targeting: A Practical Approach," ed. A. L. Joyner, IRL Press, Oxford, England (1993); Hogen et al., "Manipulating the Mouse Embryo: A Laboratory Manual," eds. Hogan, Beddington, Costantini and Lacy, Cold Spring Harbor Laboratory Press, New York (1994); and Wang et al., Nature 336:741-744 (1992).

In a further embodiment of the invention, the totipotent cells can be embryonic germ (EG) cells. Embryonic Germ cells are undifferentiated cells functionally equivalent to ES cells, that is they can be cultured and transfected in vitro, then contribute to somatic and germ cell lineages of a chimera (Stewart et al., Dev. Biol. 161:626-628 (1994)). EG cells are derived by culture of primordial germ cells, the progenitors of the gametes, with a combination of growth factors: leukemia inhibitory factor, steel factor and basic fibroblast growth factor (Matsui et al., Cell 70:841-847 (1992); Resnick et al., Nature 359:550-551 (1992)). The cultivation of EG cells can be carried out using methods known to one skilled in the art, such as described in Donovan et al., "Transgenic Animals, Generation and Use," Ed. L. M. Houdebine, Harwood Academic Publishers (1997).

Tetraploid blastocysts for use in the invention can be obtained by natural zygote production and development, or by known methods by electrofusion of two-cell embryos and subsequently cultured as described, for example, by James et al., Genet. Res. Camb. 60:185-194 (1992); Nagy and Rossant, "Gene Targeting: A Practical Approach," ed. A. L. Joyner, IRL Press, Oxford, England (1993); or by Kubiak and Tarkowski, Exp. Cell Res. 157:561-566 (1985).

The introduction of the ES cells or EG cells into the blastocysts can be carried out by any method known in the art, for example, as described by Wang et al., EMBO J. 10:2437-2450(1991).

A "plurality" of totipotent cells can encompass any number of cells greater than one. For example, the number of totipotent cells for use in the present invention can be about 2 to about 30 cells, about 5 to about 20 cells, or about 5 to about 10 cells. In one embodiment, about 5-10 ES cells taken from a single cell suspension are injected into a blastocyst immobilized by a holding pipette in a micromanipulation apparatus. Then the embryos are incubated for at least 3 hours, possibly overnight, prior to introduction into a female recipient animal via methods known in the art (see for example Robertson, E. J. "Teratocarcinomas and Embryonic Stem Cells: A Practical Approach" IRL Press, Oxford, England (1987)). The embryo can then be allowed to develop to term in the female animal.

In one embodiment of the invention, the methods of producing transgenic animals, whether utilizing nuclear transfer, embryo generation, or other methods known in the art, result in a transgenic animal comprising a genome that does not contain significant fragments of the expression vector used to transfer the iRNA molecules. The term "significant fragment" of the expression vector as used herein denotes an amount of the expression vector that comprises about 10% to about 100% of the total original nucleic acid sequence of the expression vector. This excludes the iRNA insert portion that was transferred to the genome of the transgenic animal. Therefore, for example, the genome of a transgenic animal that does NOT contain significant fragments of the expression vector used to transfer the iRNA, can contain no fragment of the expression vector, outside of the sequence that contains the iRNA. Similarly, the genome of a transgenic animal that does not contain significant fragments of the expression vector used to transfer the iRNA can contain about 1%, about 2%, about 3%, about 4%, about 5%, about 6%, about 7%, about 8%, about 9%, or about 10% of the expression vector, outside of the sequence that contains the iRNA. Any method which allows transfer of the iRNA sequence to the genome while also limiting the amount of the expression vector that is also transferred to a fragment that is not significant can be used in the methods of the present invention.

One embodiment of the invention which allows transfer of the iRNA sequence to the genome while also limiting the amount of the expression vector that is also transferred to a fragment that is not significant, is the method of recombinational cloning, see, for example, U.S. Pat. Nos. 5,888,732 and 6,277,608.

Recombinational cloning (see, for example, U.S. Pat. Nos. 5,888,732 and 6,277,608) describes methods for moving or exchanging nucleic acid segments using at least one recombination site and at least one recombination protein to provide chimeric DNA molecules. One method of producing these chimeric molecules which is useful in the methods of the present invention to produce the iRNA expression vectors comprises: combining in vitro or in vivo, (a) one or more nucleic acid molecules comprising the one or more iRNA sequences of the invention flanked by a first recombination site and a second recombination site, wherein the first and second recombination sites do not substantially recombine with each other, (b) one or more expression vector molecules comprising a third recombination site and a fourth recombination site, wherein the third and fourth recombination sites do not substantially recombine with each other; and (c) one or more site specific recombination proteins capable of recombining the first and third recombinational sites and/or the second and fourth recombinational sites, thereby allowing recombination to occur, so as to produce at least one cointegrate nucleic acid molecule which comprises the one or more iRNA sequences.

Recombination sites and recombination proteins for use in the methods of the present invention, include, but are not limited to those described in U.S. Pat. Nos. 5,888,732 and 6,277,608, such as, Cre/loxP, Integrase (λInt, Xis, IHF and FIS)/att sites (attB, attP, attL and attR), and FLP/FRT. Members of a second family of site-specific recombinases, the resolvase family (e.g., gd, Tn3 resolvase, Hin, Gin, and Cin) are also known and can be used in the methods of the present invention. Members of this highly related family of recombinases are typically constrained to intramolecular reactions (e.g., inversions and excisions) and can require host-encoded factors. Mutants have been isolated that relieve some of the requirements for host factors (Maeser and Kahnmann Mol. Gen. Genet. 230:170-176 (1991)), as well as some of the constraints of intramolecular recombination.

Other site-specific recombinases similar to λInt and similar to P1 Cre that are known in the art and that will be familiar to one of ordinary skill can be substituted for Int and Cre. In many cases the purification of such other recombinases has been described in the art. In cases when they are not known, cell extracts can be used or the enzymes can be partially purified using procedures described for Cre and Int.

The family of enzymes, the transposases, have also been used to transfer genetic information between replicons and can be used in the methods of the present invention to transfer iRNAs. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., J. Virol. 67:4566-4579 (1993)). For example, Devine and Boeke (Nucl. Acids Res. 22:3765-3772 (1994)) disclose the construction of artificial transposons for the insertion of DNA segments, in vitro, into recipient DNA molecules. The system makes use of the integrase of yeast TYI virus-like particles. The nucleic segment of interest is cloned, using standard methods, between the ends of the transposon-like element TYI. In the presence of the TYI integrase, the resulting element integrates randomly into a second target DNA molecule.

Additional recombination sites and recombination proteins, as well as mutants, variants and derivatives thereof, for example, as described in U.S. Pat. Nos. 5,888,732, 6,277,608 and 6,143,557 can also be used in the methods of the present invention.

Following the production of an expression vector containing one or more iRNAs flanked by recombination proteins, the iRNA nucleic acid sequences can be transferred to the genome of a target cell via recombinational cloning. In this embodiment, the recombination proteins flanking the iRNA are capable of recombining with one or more recombination proteins in the genome of the target cell. In combination with one or more site specific recombination proteins capable of recombining the recombination sites, the iRNA sequence is transferred to the genome of the target cell without transferring a significant amount of the remaining expression vector to the genome of the target cell. The recombination sites in the genome of the target cell can occur naturally or the recombination sites can be introduced into the genome by any method known in the art. In either case, the recombination sites flanking the one or more iRNA sequences in the expression vector must be complementary to the recombination sites in the genome of the target cell to allow for recombinational cloning.

Another embodiment of the invention relates to methods to produce a non-human transgenic or chimeric animal comprising crossing a male and female non-human transgenic animal produced by any one of the methods of the invention to produce additional transgenic or chimeric animal offspring. By crossing transgenic male and female animals that both contain the one or more iRNAs in their genome, the progeny produced by this cross also contain the iRNA sequences in their genome. This crossing pattern can be repeated as many times as desired.

In another embodiment, a male or female non-human transgenic animal produced by the methods of the invention can be crossed with a female or male animal respectively, wherein the second female or male animal involved in the cross is not a non-human transgenic animal produced by the methods of the invention. Since iRNA is dominant in nature, the progeny from these crosses can also express the iRNA sequences in this genomes. Crosses where at least one animal is a non-human transgenic animal of the present invention can result in progeny that possess the iRNA sequences in their genomes. In another embodiment, semen from a male non-human transgenic animal produced by the methods of the invention can be used to impregnate female animals and produce progeny that contain the iRNA sequences in their genome.

VI. Therapeutic Uses and Pharmaceutical Compositions

A. Therapeutic Uses

The non-human transgenic animals of the present invention can also be used as sources for therapeutic proteins expressed from transgenes.

In one embodiment, the methods of the present invention can be used to reduce the amount of one or more endogenous proteins expressed by an animal. The transgene expression can be targeted to specific tissues or cells types to provide compartmentalized isolation of such proteins. For example, a protein can be concentrated in milk of a transgenic animal by driving expression of the protein from a mammary specific promoter. In addition, a transgene can be selectively expressed in a specific cell type to allow for specific processing. For example, a human immunoglobulin locus can be used to direct recombination, expression, and processing of human polyclonal antibodies in livestock B-cells. One of the current problems with utilizing transgenic animals as sources of therapeutic proteins is that proteins endogenous to the animal can contaminate the material collected (i.e. peptides, proteins and nucleic acids) for purification and ultimate use in a therapeutic setting. While contaminating proteins can be evolutionarily unrelated, they can co-purify with the desired product. Alternatively, the contaminating protein can be the endogenous counterpart of the transgene product. In either case, a reduction in expression of the endogenous gene or genes is beneficial from both an economic and therapeutic standpoint. One embodiment of the methods of the invention is the reduction of endogenous immunoglobulin genes to allow production of non-chimeric, non-contaminated human polyclonal antibodies in transgenic animals.

In another aspect, the present invention provides iRNA-mediated gene regulation in non-human transgenic animals via knockout/inhibition of the entire repertoire of endogenous immunoglobulin (Ig) gene loci, and replacement of the animal Ig genes with their human equivalents. The genetically modified animals produced using this strategy are thus be able to produce fully human antibodies, in both their blood and in milk, when challenged with a specific pathogen or immunogen. There are numerous applications for this technology in the general healthcare arena including: infectious disease prophylaxis, treatment of antibiotic-resistant infections, passive immunization in immunocompromised patients, for immune globulin in post-transplant viral prophylaxis against hepatitis and CMV, HIV therapy, immunization against Hepatitis C, anti-venoms, as a polyclonal anti-cancer agent, cancer diagnostics, treatment of autoimmune diseases (Multiple Sclerosis, Kawasaki's), and production of anti-D for Rh negative mothers.

In addition, non-human transgenic animals producing human polyclonal antibodies have important applications in biowarfare countermeasures, whereby the animals are immunized with any of the known infectious disease pathogens, or their products, and produce specific human antibodies (preferably IgG), for use as a therapeutic, or for passive immunization of Armed Forces personnel. The use of human polyclonal antibodies derived from animals is broad-spectrum, and not limited to one or a few pathogenic organisms. Any immunogen could be used to immunize these animals, to induce the production of antibodies for prophylaxis from a variety of pathogenic organisms including, but not limited to, anthrax, staphylococcus, gram negative bacteria, Ebola virus, and Hanta virus. Additional immunogen include, but are not limited to, venoms, and bacterial toxins. The production of human antibodies in animals has the advantage of scale, given that depending on whether they were isolated from blood or milk, one could obtain 2-5 kilograms of specific antibody per animal (especially when considering the use of porcine, ovine or bovine) per year, such that a small number of animals could easily supply the needs of thousands of patients. Antibodies to many of these organisms are currently unavailable in any significant quantity due to their rarity in the general developed population, and because they cannot be used as immunogens in any form in humans due to their virulence/toxicity. Also, because these antibodies are fully human, they are far superior in specificity, avidity, and potency to anti-serums currently being produced in horses and goats. Precedence for this application has been achieved in mice, using mouse ES cell technology. Mendez et. al. (Nature Genet. 15:146-156, (1997)) demonstrated functional transplantation of megabase human immunoglobulin loci into Ig-deficient knockout mice, and observed human antibody production in these mice that closely resembled that seen in humans.

In one embodiment, the methods of the present invention provides for production of human polyclonal antibodies in transgenic cattle, sheep and pigs. Cattle can be produced that expressed human immunoglobulins, these bovine however have limited utility because of antibody chimerism and contamination of endogenous antibodies. A method to render the bovine genes inactive is highly desirable from the point of view of both production and purification. The application of RNA interference via the methods of the present invention allows one to inactivate/suppress the highly repetitive livestock Ig genes with relatively few inhibitory RNAs, and without the requirement of having to clone out large pieces of uncharacterized genomic DNA. Cloned animals that expressed human Ig genes, in the absence of livestock Igs, produce human polyclonal antibodies that are then easily purified without the issues of contamination from the endogenous animal Igs. Methods to purify antibodies isolated from the non-human transgenic animals of the present invention are known in the art (see for example Sambrook, J. et al. "Molecular Cloning: A Laboratory Manual", 2nd addition, Cold Spring Harbor Laboratory Press, Plainview, N.Y. (1989)).

In one embodiment, the invention provides organs, tissues and/or purified or substantially pure cells or cell lines obtained from animals that express iRNA molecules.

In one embodiment, the invention provides organs, any organ can be used, including, but not limited to: brain, heart, lungs, glands, brain, eye, stomach, spleen, pancreas, kidneys, liver, intestines, uterus, bladder, skin, hair, nails, ears, nose, mouth, lips, gums, teeth, tongue, salivary glands, tonsils, pharynx, esophagus, large intestine, small intestine, rectum, anus, pylorus, thyroid gland, thymus gland, suprarenal capsule, bones, cartilage, tendons, ligaments, skeletal muscles, smooth muscles, blood vessels, blood, spinal cord, trachea, ureters, urethra, hypothalamus, pituitary, adrenal glands, ovaries, oviducts, uterus, vagina, mammary glands, testes, seminal vesicles, penis, lymph, lymph nodes and lymph vessels.

In another embodiment, the invention provides tissues. Any tissue can be used, including, but not limited to: epithelium, connective tissue, blood, bone, cartilage, muscle, nerve, adenoid, adipose, areolar, bone, brown adipose, cancellous, muscle, cartaginous, cavernous, chondroid, chromaffin, dartoic, elastic, epithelial, fatty, fibrohyaline, fibrous, Gamgee, gelatinous, granulation, gut-associated lymphoid, Haller's vascular, hard hemopoietic, indifferent, interstitial, investing, islet, lymphatic, lymphoid, mesenchymal, mesonephric, mucous connective, multilocular adipose, myeloid, nasion soft, nephrogenic, nodal, osseous, osteogenic, osteoid, periapical, reticular, retiform, rubber, skeletal muscle, smooth muscle, and subcutaneous tissue.

In a further embodiment, the invention provides cells and cell lines from animals that express iRNA molecules. In one embodiment, these cells or cell lines can be used for xenotransplantation. Cells from any tissue or organ can be used, including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, pancreatic insulin secreting cells, pancreatic alpha-2 cells, pancreatic beta cells, pancreatic alpha-1 cells, blood cells, blood precursor cells, bone cells, bone precursor cells, neuronal stem cells, primordial stem cells., hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopamiergic cells, squamous epithelial cells, osteocytes, osteoblasts, osteoclasts, dopaminergic cells, embryonic stem cells, fibroblasts and fetal fibroblasts. In a specific embodiment, pancreatic cells, including, but not limited to, Islets of Langerhans cells, insulin secreting cells, alpha-2 cells, beta cells, alpha-1 cells from pigs that lack expression of functional alpha-1,3-GT are provided.

Nonviable derivatives include tissues stripped of viable cells by enzymatic or chemical treatment these tissue derivatives can be further processed via crosslinking or other chemical treatments prior to use in transplantation. In one embodiment, the derivatives include extracellular matrix derived from a variety of tissues, including skin, urinary, bladder or organ submucosal tissues. Also, tendons, joints and bones stripped of viable tissue to include heart valves and other nonviable tissues as medical devices are provided.

The cells can be administered into a host in order in a wide variety of ways. Modes of administration are parenteral, intraperitoneal, intravenous, intradermal, epidural, intraspinal, intrasternal, intra-articular, intra-synovial, intrathecal, intra-arterial, intracardiac, intramuscular, intranasal, subcutaneous, intraorbital, intracapsular, topical, transdermal patch, via rectal, vaginal or urethral administration including via suppository, percutaneous, nasal spray, surgical implant, internal surgical paint, infusion pump, or via catheter. In one embodiment, the agent and carrier are administered in a slow release formulation such as a direct tissue injection or bolus, implant, microparticle, microsphere, nanoparticle or nanosphere.

Disorders that can be treated by infusion of the disclosed cells include, but are not limited to, diseases resulting from a failure of a dysfunction of normal blood cell production and maturation (i.e., aplastic anemia and hypoproliferative stem cell disorders); neoplastic, malignant diseases in the hematopoietic organs (e.g., leukemia and lymphomas); broad spectrum malignant solid tumors of non-hematopoietic origin; autoimmune conditions; and genetic disorders. Such disorders include, but are not limited to diseases resulting from a failure or dysfunction of normal blood cell production and maturation hyperproliferative stem cell disorders, including aplastic anemia, pancytopenia, agranulocytosis, thrombocytopenia, red cell aplasia, Blackfan-Diamond syndrome, due to drugs, radiation, or infection, idiopathic; hematopoietic malignancies including acute lymphoblastic (lymphocytic) leukemia, chronic lymphocytic leukemia, acute myelogenous leukemia, chronic myelogenous leukemia, acute malignant myelosclerosis, multiple myeloma, polycythemia vera, agnogenic myelometaplasia, Waldenstrom's macroglobulinemia, Hodgkin's lymphoma, non-Hodgkin's lymphoma; immunosuppression in patients with malignant, solid tumors including malignant melanoma, carcinoma of the stomach, ovarian carcinoma, breast carcinoma, small cell lung carcinoma, retinoblastoma, testicular carcinoma, glioblastoma, rhabdomyosarcoma, neuroblastoma, Ewing's sarcoma, lymphoma; autoimmune diseases including rheumatoid arthritis, diabetes type I, chronic hepatitis, multiple sclerosis, systemic lupus erythematosus; genetic (congenital) disorders including anemias, familial aplastic, Fanconi's syndrome, dihydrofolate reductase deficiencies, formamino transferase deficiency, Lesch-Nyhan syndrome, congenital dyserythropoietic syndrome I-IV, Chwachmann-Diamond syndrome, dihydrofolate reductase deficiencies, formamino transferase deficiency, Lesch-Nyhan syndrome, congenital spherocytosis, congenital elliptocytosis, congenital stomatocytosis, congenital Rh null disease, paroxysmal nocturnal hemoglobinuria, G6PD (glucose-6-phhosphate dehydrogenase) variants 1, 2, 3, pyruvate kinase deficiency, congenital erythropoietin sensitivity, deficiency, sickle cell disease and trait, thalassemia alpha, beta, gamma, met-hemoglobinemia, congenital disorders of immunity, severe combined immunodeficiency disease (SCID), bare lymphocyte syndrome, ionophore-responsive combined immunodeficiency, combined immunodeficiency with a capping abnormality, nucleoside phosphorylase deficiency, granulocyte actin deficiency, infantile agranulocytosis, Gaucher's disease, adenosine deaminase deficiency, Kostmann's syndrome, reticular dysgenesis, congenital Leukocyte dysfunction syndromes; and others such as osteoporosis, myelosclerosis, acquired hemolytic anemias, acquired immunodeficiencies, infectious disorders causing primary or secondary immunodeficiencies, bacterial infections (e.g., Brucellosis, Listerosis, tuberculosis, leprosy), parasitic infections (e.g., malaria, Leishmaniasis), fungal infections, disorders involving disproportionsin lymphoid cell sets and impaired immune functions due to aging, phagocyte disorders, Kostmann's agranulocytosis, chronic granulomatous disease, Chediak-Higachi syndrome, neutrophil actin deficiency, neutrophil membrane GP-180 deficiency, metabolic storage diseases, mucopolysaccharidoses, mucolipidoses, miscellaneous disorders involving immune mechanisms, Wiskott-Aldrich Syndrome, alpha 1-antirypsin deficiency, etc.

Diseases or pathologies include neurodegenerative diseases, hepatodegenerative diseases, nephrodegenerative disease, spinal cord injury, head trauma or surgery, viral infections that result in tissue, organ, or gland degeneration. Such neurodegenerative diseases include but are not limited to, AIDS dementia complex; demyeliriating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder, demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Parkinson's Disease, Wernicke-Korsakoff syndrome; chronic alcoholism; Creutzfeldt-Jakob disease; Subacute sclerosing panencephalitis hallerrorden-Spatz disease; and Dementia pugilistica. See, e.g., Berkow et. al., (eds.) (1987), The Merck Manual, ($15^{th}$) ed.), Merck and Co., Rahway, N.J.

The non-human transgenic animals of the present invention can be used to screen any type of compound, for example, antibiotics, antifungals, antivirals, chemotherapeutics, cardiovascular drugs, and hormones. Compounds that can be screened by using the animals of the present invention can be small molecules or biologics (e.g. proteins, peptides, nucleic acids). Compounds to be tested can be introduced to the animals of the invention via any delivery route known in the art, such as, but not limited to, intravenous injection, intramuscular injection, intraperitoneal injection, orally, sublingually, subcutaneously, via inhalation, intranasally, intrathecally, ocularly, rectally, and transdermally.

The activity of the one or more compounds can be determined by measuring one or more biological or physiological responses of the cells of the animal. For example, cells or animals contacted with the one or more compounds to be screened (i.e. "treated") are compared to "control" cells or animals that have been contacted with one or more inactive compounds (i.e. placebo(s) or other control treatment(s)), or in other embodiments, the control cells are not contacted with a compound. The response(s) of the cells or animals to the one or more compounds are then measured and comparisons between control and treated samples are made to determine the therapeutic effectiveness of the one or more compounds.

The activity of the one or more compounds can be assessed by measuring the amount of target mRNA or protein produced in a cell. Analyzing "treated" and "control" cell samples allows for a quantitative comparison to determine the therapeutic effectiveness of the one or more compounds screened above that of the control sample. Alternatively, the amount of compound associated with both target and non-target proteins, cells, tissues or organs can be measured and compared to determine to pharmacokinetic profile of the one or more compounds of both control and treated cells or animals. Assays for determining the amount of mRNA and protein in a cell are well known in the art (see for example Sambrook, J. et al. "Molecular Cloning: A Laboratory Manual," 2nd addition, Cold Spring Harbor Laboratory Press, Plainview, N.Y. (1989)). Methods by which to measure the amount of compound bound to a protein, cell, tissue or organ are also well known in the art (see for example Appendix II and the references therein in Gilman, et al., "Goodman and Gilman's The Pharmacological Basis of Therapeutics," Macmillan Publishing Co, Inc., New York (1980)).

Examples of biological responses of a cell or animal that can be measured to determine the therapeutic effectiveness of one or more compounds include, but are not limited to, inflammation, generation of active oxygen species, cell lysis, cell death, immunological response (i.e. antibody production), protein production.

Examples of physiological responses of a cell or animal that can be measured to determine the therapeutic effectiveness of one or more compounds include, but are not limited to, temperature changes, pH changes, oxygen concentration, glucose concentration, blood flow, electro-physiologic properties.

Biological and physiological responses are determined by methods well known in the art, including but not limited to, spectroscopic analysis, microscopic or other visualization utilizing marker dyes and probes known in the art, instrumental monitoring (i.e. temperature, pH, blood pressure, blood flow, electrical measurements).

The term "therapeutically effective" indicates that the compound or composition has an activity that impacts a cell or an animal suffering from a disease or disorder in a positive sense and/or impacts a pathogen or parasite in a negative sense. Thus, a therapeutically effective compound can cause or promote a biological or biochemical activity within an animal that is detrimental to the growth and/or maintenance of a pathogen or parasites, or [within] cells, tissues or organs of an animal that have abnormal growth or biochemical characteristics such as cancer cells. Alternatively, a therapeutically effective compound can impact a cell or an animal in a positive sense by causing or promoting a biological or biochemical activity within the cell or animal that is beneficial to the growth and/or maintenance of the cell or animal. Whether (or the extent to which) a therapeutically effective compound impacts a cell or animal in a positive way (or a pathogen or parasite in a negative way) can be determined by examining the level of a given biological or biochemical characteristic or function observed in the treated cell or animal and comparing that level to the level of the same biological or biochemical characteristic or function observed in an untreated control cell or animal, using art-known assays of a variety of biological or biochemical characteristics or functions. Any compound or composition that induces a change in the examined biological or biochemical characteristic or function in the treated cell or animal by an amount that is quantitatively discernable from that observed in a control cell or animal is said to be "therapeutically effective." A quantitatively discernable amount is any amount that is above the standard experimental error associated with the method or measurement used to determine therapeutic effectiveness. For example, a quantitatively discernable amount that can indicate that a tested compound or composition is therapeutically effective is a difference in the assayed characteristic or function in the treated cell or animal of about 1%, about 5%, about 10%, about 33%, about 50%, about 67%, about 75%, about 90%, about 95%, or about 100% relative to the level of the assayed characteristic or function in a control cell or animal.

In one such embodiment of the invention, the transgenic cell to be contacted with one or more compounds to be tested can be removed from the transgenic animal and maintained and assayed in culture. This embodiment of the invention allows for a high throughput screening approach to assess the therapeutic effectiveness of a compound, where multiple, different compounds could be tested on individual cells of the same biologic type or animal species. Similarly, a single compound could be tested on many different cell types (e.g. muscle, bone, skin, neurologic) from a single animal species, or on cells from multiple species. Methods for maintaining cells in culture are well known in the art (see for example Sambrook, J. et al. "Molecular Cloning: A Laboratory Manual", 2nd addition, Cold Spring Harbor Laboratory Press, Plainview, N.Y. (1989) and Freshney, R. I., "Culture of Animal Cells: A Manual of Basic Technique," Alan R. Liss, Inc, New York (1983)).

Another embodiment of the invention is a method of screening one or more compounds for a therapeutic effect on a human tumor that has been implanted into a non-human transgenic animal of the invention, comprising:

(a) implanting a human tumor or a human tumor cell into a transgenic animal;

(b) contacting the human tumor with one or more compounds to be tested;

(c) measuring one or more biological or physiological responses of the tumor to the one or more compounds; and (d) determining the therapeutic effectiveness of one or more compounds on the human tumor.

Any non-human animal produced by any one of the methods of the present invention can be used as a tumor recipient, including but not limited to, non-human mammals (including, but not limited to, pigs, sheep, goats, cows (bovine), deer, mules, horses, monkeys and other non-human primates, dogs, cats, rats, mice, rabbits and the like), birds (including, but not limited to chickens, turkeys, ducks, geese and the like) reptiles, fish, amphibians and the like.

Any human tumor or tumor cell line can be implanted into the animal for screening purposes. Tumors include, but are not limited to, a breast cancer tumor, a uterine cancer tumor, an ovarian cancer tumor, a prostate cancer tumor, a testicular cancer tumor, a lung cancer tumor, a leukemic tumor, a lymphatic tumor, a colon cancer tumor, a gastrointestinal cancer tumor, a pancreatic cancer tumor, a bladder cancer tumor, a kidney cancer tumor, a bone cancer tumor, a neurological cancer tumor, a head and neck cancer tumor, a skin cancer tumor, a sarcoma, an adenoma and a myeloma. The tumor implanted into the animal can be in the form of a solid tumor mass, a single tumor cell, or multiple (i.e. 2, 10, 50, 100, 1000) tumor cells. The tumor can be implanted in any tissue or organ of the animal, or can be delivered systemically. Any method known in the art by which to implant tumors and tumor cells into animals can be used in the present invention. Human tumors or tumor cells can come from any source, including but not limited to, established tumor cell lines, excised primary tumor tissue and commercial/government/academic sources including tissue banks and the like.

The non-human transgenic animal of the invention with the implanted human tumor can be used to screen small molecules or biologics (e.g. proteins, peptides, nucleic acids). Compounds to be tested can be introduced to the animals of the invention via any delivery route known in the art, such as, but not limited to, intravenous injection, intramuscular injection, intraperitoneal injection, orally, sublingually, subcutaneously, via inhalation, intranasally, intrathecally, ocularly, rectally, and transdermally.

The activity of the one or more compounds can be determined by measuring one or more biological or physiological responses of the human tumor implanted into the animal. For example, the activity of the compounds can be assessed by measuring the amount of target mRNA or protein produced in a cell. Alternatively, the amount of compound associated with both target and non-target proteins, cells, tissues or organs can be measured and compared. Assays for determining the amount of mRNA and protein in a cell are well known in the art.

Examples of biological responses of an implanted human tumor that can be measured to determine the therapeutic effectiveness of one or more compounds include, but are not limited to, inflammation, generation of active oxygen species, cell lysis, immunological response (i.e. antibody production), protein production, and the like.

Examples of physiological responses of an implanted human tumor that can be measured to determine the therapeutic effectiveness of one or more compounds include, but are not limited to, temperature changes, pH changes, oxygen concentration, tumor growth, glucose concentration, blood flow, and the like.

In this context, the term "therapeutically effective" indicates that the compound has an activity that impacts the implanted human tumor in a negative sense. Thus, a therapeutically effective compound can cause or promote a biological or biochemical activity within an animal that is detrimental to the growth and/or maintenance of the tumor.

The present invention also provides therapeutically effective compounds identified using any one of the screening methods of the present invention. These compounds can be small molecules or biologics. In such an embodiment, the compounds can contain one or more pharmaceutically acceptable carrier or excipient. The compounds provided by the screening methods of the present invention can produce any level of therapeutic effectiveness that is discernable relative to control.

EXAMPLES

Example 1: Targeting Families of Genes

For specific targeting of a family of genes, a desired subset of genes, or specific alleles of a gene or gene family, a representative sample of sequences is obtained. These sequences are compared to identify areas of similarity. The comparison determines areas of similarity and identity between given gene families, as well as within subsets of sequences within a family. In addition, this analysis determines areas of similarity and identity between alleles of family members. By considering these sequences, regions are identified that can be used to target either the entire family, subsets of family members, individual family members, subsets of alleles of individual family members, or individual alleles of family members.

The results of a typical analysis are shown in FIG. 8. In this analysis, Region 2 can target all members of the given 4-gene family. Likewise, the sequence of Region 3 differentiates Gene 1 and 2 from Gene 3 and 4, and Region 4 can be used to differentiate Gene 1 and 4 from Gene 2 and 3. Region 5 can be used to differentiate Gene 1, Allele A and B from all other family members, while Region 1 or Region 6 can specify individual alleles of any gene in the family.

Figure 5:
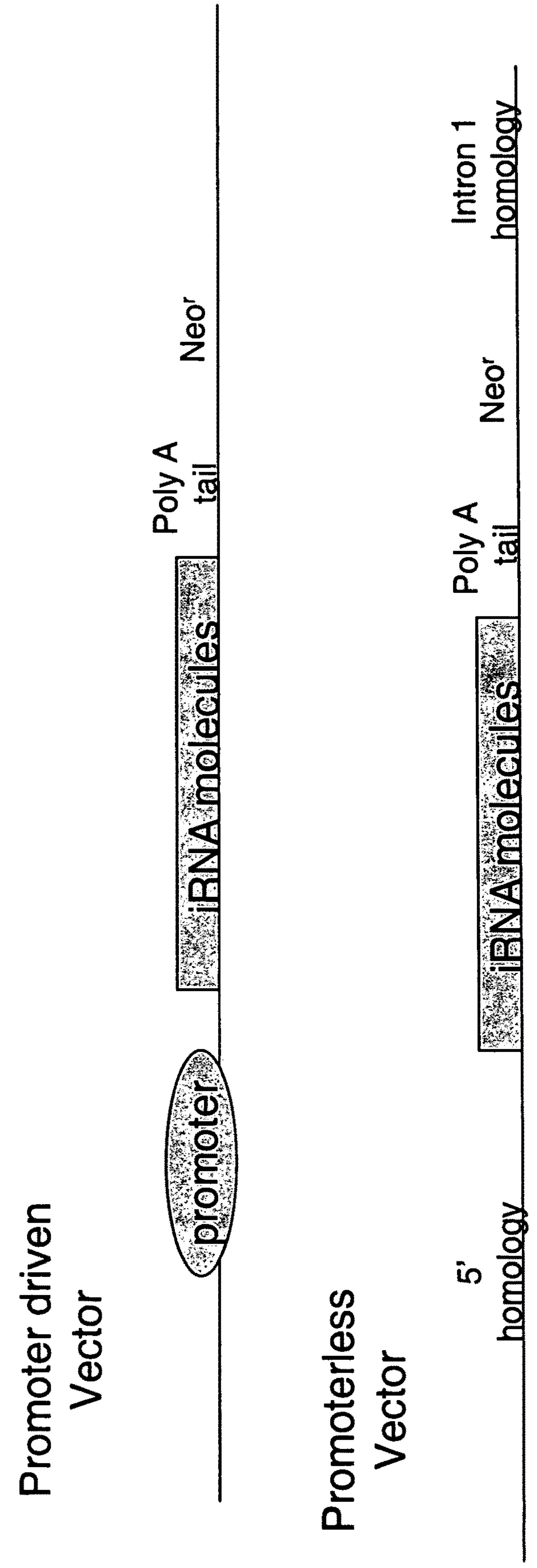
FIG. 5 is a graphical depiction of a representative vector promoter driven vector (top) and a graphical representation of a representative promoterless vector which can be used in the practice of the invention.
Figure 6:
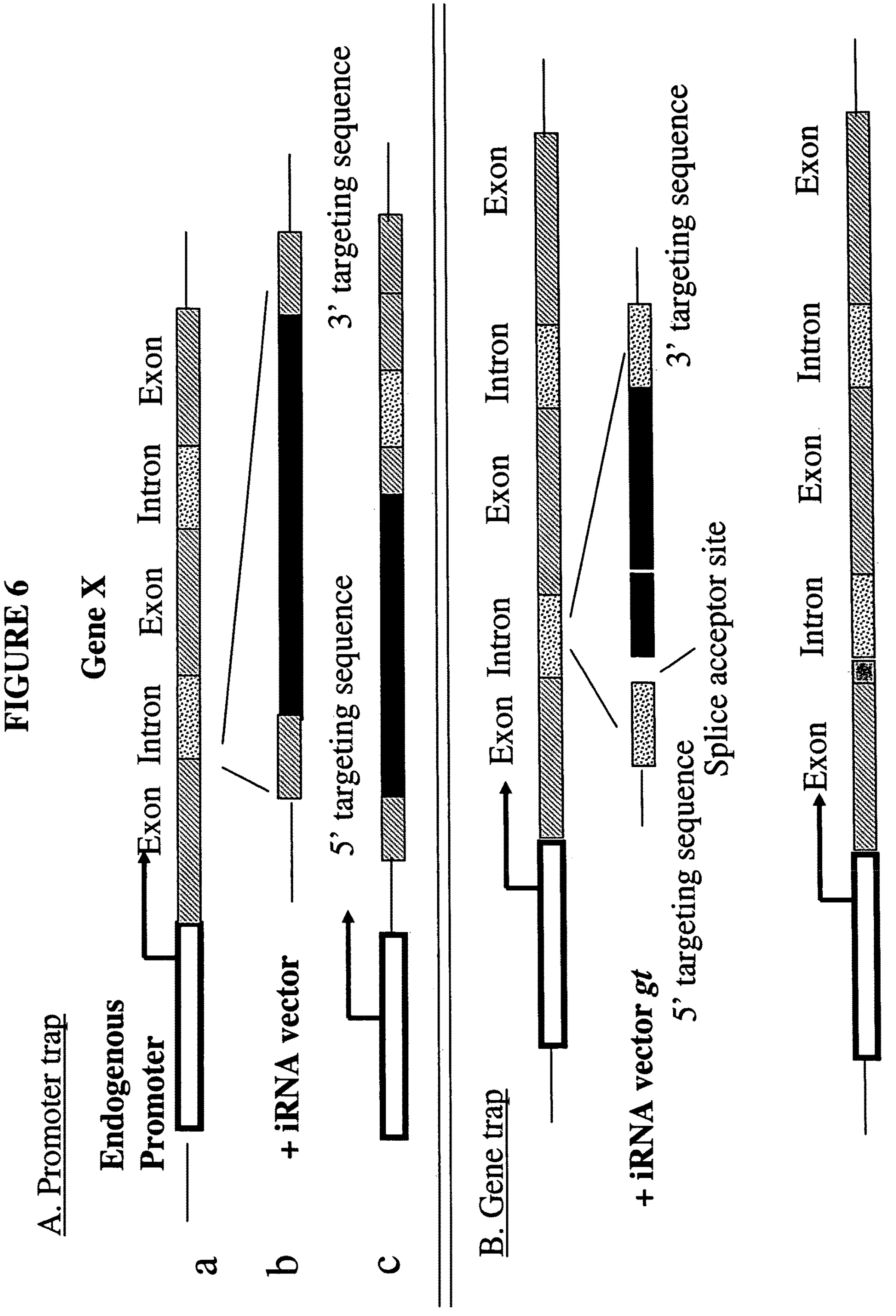
FIG. 6 is a representation of the process of "promoter trap" (top panel) and "gene trap" (bottom panel) technologies described in the text. In the top panel, the iRNA vector includes one or more iRNA sequences (black boxes) and a 5' and 3' sequence homologous to one or more exon sequences of a desired gene (diagonally striped boxes). The figure shows the homologous sequences recombining to provide a final gene with an iRNA insert. In the lower panel, the gene trap vector is shown containing one or more RNA sequences, sequences homologous to an intron region in a gene (striped boxes), and a splice acceptor (SA) site immediately upstream of the promoterless iRNA sequence insert. The integration of the iRNA insert in an intron can lead to a fusion transcript with the upstream exon of the gene upon transcription.
Figure 7:
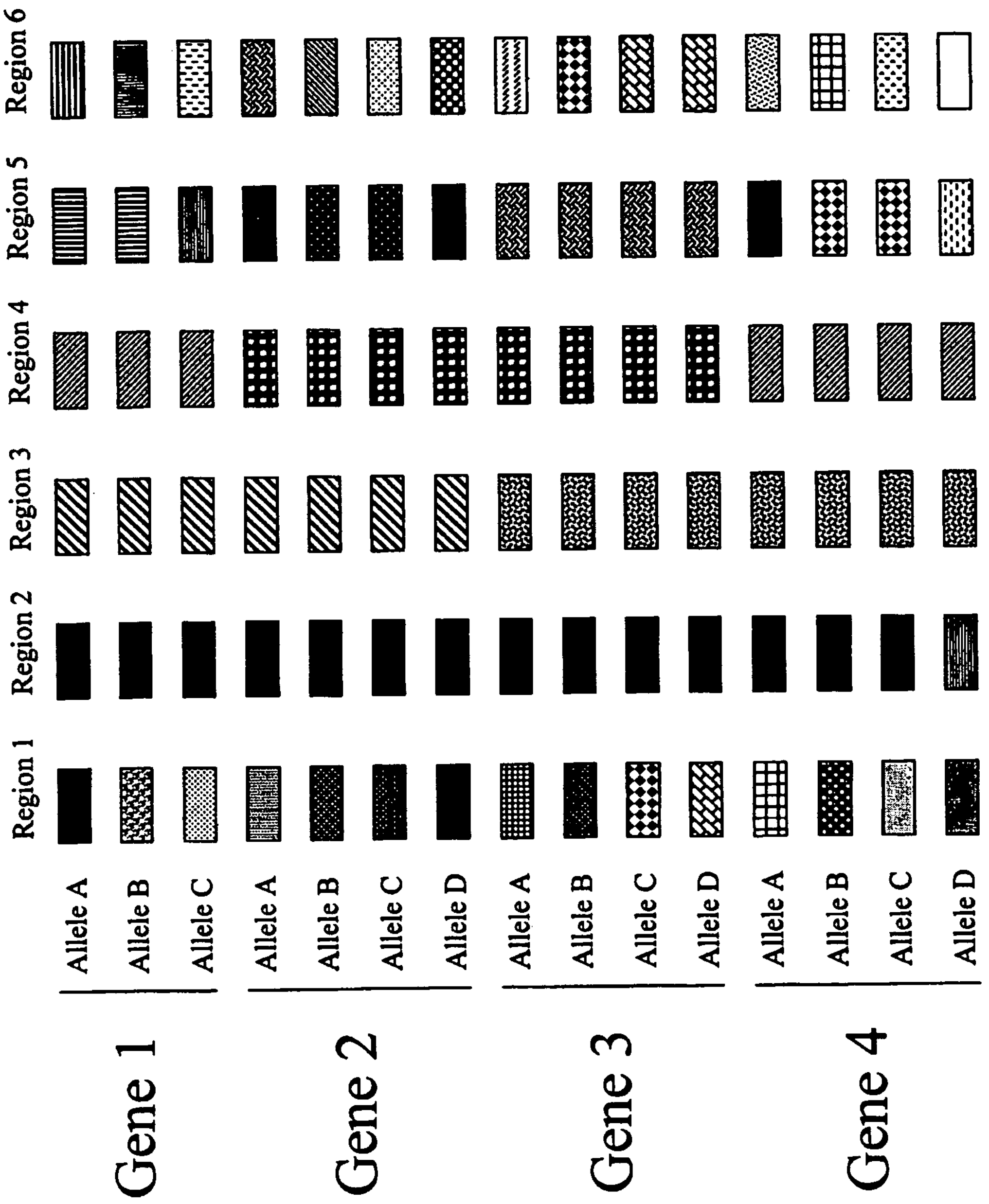
FIG. 7 is a graphical representation of an analysis of the alleles of four genes. Gene 1 is shown to have three alleles. Gene 2, 3, and 4 are shown to have four alleles each. Boxes with the same pattern, within a region, represent sequences that are identical. Boxes with different patterns within a region represent different sequences within that region. Region 1 differs in sequence between all genes and alleles except for Gene 1, allele A and B. Region 2 is conserved among all family members. Only two sequences are found in region 3. Likewise, only two sequences are found in region 4. Seven sequences are found in region 5. Region 6 is not conserved among any family members. Effective targeting of region 2 provides suppression of all family members. Effective targeting of one of the two sequences found in region three specifies a subset of genes. Sets of targeting transgenes can be assembled to repress subsets of alleles or genes.

After potential targets regions are identified, a "reporter" construct (vector) that includes, but need not be limited to, one or more potential target regions is constructed. The expression of the reporter construct is measurable, either by measuring the output of the target gene or by measuring output of an additional gene, such as a fluorescent reporter (readout). The reporter construct is introduced to a cell or a cell population. In addition to the reporter construct, iRNA constructs are assembled that encode potential iRNA molecules. The iRNA constructs can be assembled by, for example, combining DNA fragments that include sequences that serve as a promoter of transcription and sequences that represent an iRNA molecule to be tested (see FIG. 5). The test constructs are also introduced into the above cultured cells. Measurement of the reporter construct readout indicate efficacy of the iRNA molecule(s), such that if the transgene encodes an effective iRNA molecule, the readout of the reporter molecule is altered. Test constructs that successfully provide down regulation of the reporter gene provide iRNA sequences that are used alone or in combination to produce transgenic animals. Methods of introducing the iRNA molecules into cells to produce transgenic animals include homologous recombination using endogenous or exogenous promoters. The resulting animals enjoy reduced expression of a targeted gene family, subsets of genes within a given family, individual genes, subsets of alleles of individual genes, or individual alleles of a single gene.

In the exemplary analysis shown in FIG. 8, subsets of genes or alleles may not contain unique targeting regions that are present in every member of the subset. In such cases, multiple constructs are used so that each iRNA molecule specifies at least one member of the desired target gene subset but none of the members of the excluded targets. Therefore, the group of iRNA molecules specify a unique subset of targets even though no single molecule in the group of iRNA transcripts is capable of targeting all members of the desired subset.

After identifying sequences that affect a target or set of targets, additional constructs are developed to fully reduce the expression of the target(s). Constructs are developed that provide collections of iRNA molecules or sets of molecules that target specific genes, families of genes, or alleles within a family. These grouped constructs are developed by combining multiple test construct sequences, or by assembly of a new construct that encodes multiple copies of iRNA or groups of iRNA targeting molecules.

In the example analysis shown in FIG. 8, a combination of test constructs that are effective against the vertical stripped sequence, horizontal stripped sequence, and bricked sequence in Region 5 down-regulate all alleles of Gene 1 and Gene 3. On the other hand, in this set of grouped constructs, omission of a construct specifying the horizontal stripped sequence in Region 5 results in targeting Gene 1, Allele A and B, and all alleles of Gene 3.

Example 2—Use of RNA Interference to Inhibit Porcine Endogenous Retrovirus

RNA interference is used to heritably suppress expression of a family of related sequences encoding different yet homologous retroviruses found in pigs. Broadly, a transgene is constructed that results in production of an iRNA molecule with sense and inverted antisense sequences, homologous to a region of the porcine endogenous retrovirus genome that is conserved between PERV variants, at least three of which are known (PERV-A, -B and -C). The transgene is added to the genome of a pig to produce a genetic line that heritably expresses an RNA molecule that can self hybridize to form dsRNA. This RNA induces interference of expressed porcine endogenous retrovirus in each cell that expresses the transgene. Not only is total PERV production severely down regulated, but recombination between targeted variants may not produce a novel untargeted variant. Cells, tissues, or organs from such animals can be used for xenotransplantation with reduced risk of PERV transmission.

Step 1:

Assays are developed to quantify the effectiveness of individual iRNA molecules. In addition, a reporter vector is constructed to allow streamlined screening of iRNAs and an iRNA expression vector assembled to allow efficient insertion of individual potential iRNA-encoding sequences. Potential targets are identified by sequence analysis of the family of target PERVs.

Model-Gene Control Plasmids:

Based on sequence conservation, primers are designed and used to amplify gag, pol, and env coding regions from both the cell line PK-15, a cell line known to shed infective PERVs (Le Tissier et al., 1997), and in fetal fibroblasts (including $\alpha$1,3-GT knockout fibroblasts). The most highly expressed coding region from each gene is used to build a model reporter construct. Each reporter construct is assembled by inserting a PERV coding region (gag, pol, or env) between a reporter molecule coding region and its poly(A) signal. The plasmids thus produce an mRNA with a reporter gene (i.e. $\beta$-Gal, GFP) upstream of a potential iRNA target (in the 3' non-coding region). The effectiveness of individual iRNA molecules is assayed by analyzing suppression of the reporter gene expression. The protocol can also be modified to analyze non-coding PERV sequence in lieu of, or addition to, the coding sequences.

iRNA Expression Plasmids:

Several RNA polymerase III (Pol III) dependent promoters are amplified, cloned, and tested for ubiquitous expression in transgenic animals. Pol III promoters can drive expression of iRNAs without addition of terminal sequence (i.e. a poly(A) tail). The Pol III promoters may include the promoters from HIRNA, snRNAU6, 7SK, MRP RNA, or 7SL. Pol III promoters can be screened to choose a promoter with ubiquitous expression. An iRNA test vector is assembled, including a cloning region and a poly(U)-dependent Pol III transcription terminator. Protein coding regions may also be provided within the gene for the interfering RNA.

Perv Assays:

Specific probes against PERV-A, —B and —C are developed to detect corresponding proviral PERV DNA sequences. PCR assays for proviral PERV DNA utilize primers specific to gag, pol and env regions, as well as to an internal control gene such as the $\beta$-globulin gene. Real-time PCR with primers specific to porcine mitochondrial DNA (mtDNA) or centromeric sequences is used to quantify porcine cell contamination (chimerism) in transmissibility assays. PCR primers specific to gag and pol regions of PERV are also developed to detect PERV RNA in target samples.

Step 2:

An ideal target for iRNA is a region of the PERV mRNA that is conserved across most PERVs. Such sequences are identified for initial constructs. Analysis of all known PERV sequences and additional PERV sequences that arise from this effort provide information for logical design of iRNA vectors. All iRNA vectors are tested for function in cell assays before use in transgenic animal production.

Bioinformatics:

Analysis of all available PERV env mRNA sequences is shown in FIG. 8. This analysis is performed to determine both regions of conservation and consensus sequences. An effective iRNA targeted to the region between 6364 bp and 6384 bp will target all PERV env genes shown in this example. Alternatively, a pair of effective iRNA molecules targeted to the two sequences in the region between 6386 bp and 6407 bp would also target all PERV env genes shown in this example. An attempt to target sequences that include the region from 6408 bp to 6431 bp requires three effective iRNA molecules, each targeting one of the three represented sequences. Likewise, targeting a region that includes base 6385 also requires three effective iRNA molecules.

Because the sequence analysis is limited to the experimental sequence obtained, it is possible that not all PERV sequences are represented. It is possible that an unknown or undescribed variant exists. The identified iRNAs are therefore re-tested for effectiveness against the native target instead of an artificial marker gene. Any mRNA that escapes interference is cloned and added to the analysis. The entire process is repeated until all mRNA is repressed.

Another method of selecting potential targets for interfering RNA is shown in FIG. 9. An 86 base consensus for a semi-conserved region of PERV is shown on the first line (line 1, underlined and bold text). Sixty-eight potential 19 base targets for inhibitory RNA within this sequence are shown on subsequent lines (lines 2-69). Targets are between 17 and 35 bases in length and ideally between 21 and 25 bases in length. This process is reiterated for targets of 17-35 bases and can be applied to any region, protein coding or non-coding, included within any complete or partial PERV genome. All PERV sequences are potential targets. In this example, sequences of a fixed length of 19 nucleotides are selected as potential targets.

In addition to the simplified screen shown in FIG. 9, bioinformatics can be used to reduce non-specific target sequences. As shown in FIG. 10, targeted genes may share homology with non-targeted genes. In this case, potential targets that share significant homology with non-targeted genes are eliminated from the screening process. RNA sequence of target genes are screened for homology to non-targeted RNAs. A 19 base region of an unknown porcine expressed sequence (Genbank entry B1305054) is significantly homologous to a region of semi-conserved PERV sequence (shown in black face bold type and underlined). Though potential target regions with significant homology to non-targeted RNAs can prove useful, such target regions are excluded in initial target screens to reduce the risk of severely down-regulating unintended gene products. Line 1 of FIG. 11 represents PERV sequence. Lines 2-69 represent targeted PERV sequence identified by bioinformatics. Line 70 represents an unknown expressed porcine sequence. Lines 36-56 represent the result of the sequence analysis, illustrating the excluded targets.

FIG. 12 illustrates an example of a proposed three dimensional configuration of an expressed iRNA. The iRNA is designed for the target sequence 5'AAT TGG AAA ACT AAC CAT C 3 (FIG. 10, Line 2). An exemplary iRNA sequence is 5'($N_Y$) AAU UGG AAA ACU AAC CAU C($N_Y$)G AUG GUU AGU UUU CCA AUU ($N_Y$) 3' (SEQ ID NO: 275; wherein "N" refers to any nucleotide and "Y" refers to any integer greater than or equal to zero). Each portion of non-specified sequence, ($N_Y$), can be homopolymeric. The nonidentical sequence can also be composed of non-identical bases. In addition, any continuous stretch of non-specified sequence, ($N_Y$), can provide additional functions such as but not limited to encoding protein, providing signals for stability or increased half-life, increasing the length of palindromic sequence, providing signals and functions for splicing, or folding into particular structures.

Step 3.

Tissue Culture Confirmation:

Based on the sequences and plasmids identified in Steps 1 and 2, multiple individual iRNA expressing plasmids are designed, constructed and tested for function in tissue culture using the protocol described in Step 1. Each iRNA plasmid is tested for stable expression and effectiveness against the a reporter plasmid containing the appropriate target sequence. Interference activity against native PERV mRNAs is established experimentally. In addition, reduction in PERV mRNA is correlated with a decrease in viral particle production.

Each selected iRNA construct is transfected into PK-15 cells, which are known to shed human-transmissible PERVs. Each selected iRNA construct is tested for ability to reduce steady-state mRNA, reduce the number of viral particles shed, and reduce the transmissibility of PERVs to human cells. In addition, any PERV mRNAs that are found after the first round of testing, are amplified by RT-PCR and sequenced. These sequences are analyzed to determine individual polymorphisms that allow mRNA to escape iRNA. This information is used to further modify iRNA constructs to target rare polymorphisms.

After identification of individual iRNA constructs, groups of constructs are developed that will effectively eliminate expression of PERV in selected cells. The specific sequences included in the groupings are identified using the methods described in the previous steps.

Step 4:

Creation of PERV-Free Cells:

An alpha-GT knock out line or a line of pigs that express complement inhibiting proteins is used, however a PERV-free genetic background can be achieved using any line of swine. Fibroblasts are engineered with iRNA constructs to allow a degree of functional testing prior to generating animals. These cells are also screened for integration sites to analyze functional effects. The use of fibroblasts is advantageous over other methods of producing transgenic animals, where normally one can only assay integration-site-specific transgene expression after the animals are born.

Primary alpha-1,3-GT knockout fetal fibroblasts are engineered to express functionally-screened, optimized iRNA designed in Steps 1 to 3. Individual colonies of cells, each representing unique integration events, are selected. These colonies are propagated and a subset is stored (frozen) for later screening for gene expression and function. The stored cells may also serve to provide cells for somatic cell nuclear transfer.

Function is established for each cell line's unique PERVs. Each colony of fibroblasts containing genome integrated iRNA is tested for reduced steady-state PERV mRNA. Any surviving PERV mRNAs is amplified by RT-PCR and sequenced. These sequenced mRNAs are analyzed to determine individual polymorphisms that allow these mRNAs to escape current iRNAs. This information is used to further modify iRNA constructs to target rarer polymorphisms.

Step 5:

Somatic cell nuclear transfer allows for an efficient, relatively inexpensive and relatively fast production of transgenic pigs. Cells that have been developed and screened in Step 4 (alpha-1,3 GT knockout fibroblasts engineered to contain optimized, functional, PERV-suppressing iRNAs) are used as nucleus donors in somatic cell nuclear transfer. The technique of somatic cell nuclear transfer includes removing the nucleus from an oocyte of a pig, then fusing or inserting the nucleus from the fibroblast into the enucleated oocyte. The cells are then grown to the blastocyte stage and then frozen and implanted in a sow.

Though tissue culture experiments with PK-15 cells and fetal fibroblasts will prove very useful, to date no in vitro assay exists to perfectly model in vivo transgene function. In addition, some tissue specific variation may exist in both iRNA function and PERV mRNA expression. Analysis of fetal tissues of transgenic pigs allows more extensive analysis of iRNA utility.

Mid-gestation fetuses are collected. Tissues are harvested and analyzed for iRNA expression and PERV mRNA suppression. Integration sites that provide effective PERV suppression are selected. Somatic cell nuclear transfer allows for the generation of transgenic pigs that have identical integration events as the screened fetuses. Cloning allows cells that are being propagated, recovered from storage, or cells collected from the mid-gestation fetuses, to be used to make transgenic animals. Cells that have been screened and wherein PERV has been effectively eliminated are used as nucleus donors in somatic cell nuclear transfer. Reconstructed embryos are transferred to recipient females and allowed to develop to term.

The full elimination of PERV is confirmed in live animals. Piglets are sacrificed at various stages of maturity and analyzed for transgene expression and suppression of PERV mRNA. In addition, multiple tissues are tested to ensure that PERV is eliminated in therapeutically useful organs.

Specific PERV Targets

The specific gag, pol and env sequences of PERV that were used to identify potential siRNA targets are listed below. Each sequence is a subset of the full length gene. The subset represents the portion of each gene that we used to assemble the model genes. Regions that are to be excluded from consideration have been replaced with a homopolymer (ttttt . . . t, or GGGG . . . G)

```
                                         (Seq ID No 6)
                                                   gag
GGACAGACGGTGAAGACCCCCCTTAGTTTGACTCTCGAAAATTGGACTGA
AGTTAGATCCAGGGCTCATAATTTGTCAGTTCAGGTTAAGAAGGGACCTT
GGGAGATTTCCCGTGCCTCTGAATGGCAAACATTCGATGTTGGATGGCCA
TCAGAGGGGACTTTTAATTCTGAAATTATCCTGGCTGTTAAAGCAATCAT
TTTTCAGACTGGACCCGGCTCTCATCCTGATCAGGAGCCCTATATCCTTA
CGTGGCAAGATTTGGCAGAAGATCCTCCGCCATGGGTTAAACCATGGCTA
TGGGGGGGGGGAGCCAGGCCCCCGAATCCTGGCTCTTGGAGAGAAAAAC
AAACACTCGGCCGAAAAAGGGGGGGGGGTCCTCATATCTACCCCGAGAT
CGAGGAGCCGCCGACTTGGCCGGAACCCCAACCTGTTCCGGGGGGGGGGG
TTCCAGCACAGGGTGCTGCGAGGGGACCCTCTGCCCCTCCTGGAGCTCCG
GTGGTGGAGGGACCTGCTGCCGGGACTCGGAGCCGGAGAGGCGCCACCCC
GGAGCGGACAGACGAGATCGCGATATTACCGCTGTGCACCTATGGCCCTC
CCATGGCGGGGGGCCAATTGCAGCCCCTCCAGTATTGGCCCTTTTCTTCT
GCAGATCTCTATAATTGGAAAACTAACCATCCCCCTTTCTCGGAGGATCC
CAACGCCTCACGGGGTTGGTGGAGTCCCTTATGTTCTCTCACCAGCCTAC
TTGGGATGATTGTCAAGGGGGGGGGGGGGGGGGGGGGGGGGGGGGGGGGG
GGGGGGGAATTCTGTTAGAGGCTAGAAAAAATGTTCCTGGGGCCGACGGG
CGACCCACGCAGTTGCAAAATGAGATTGACATGGGATTTCCCTTGACTCG
CCCCGGTTGGGACTACAACACGGCTGAAGGTAGGGAGAGCTTGAAAATCT
ATCGCCAGGCTCTGGTGGCGGGTCTCCGGGGCGCCTCAAGACGGCCCACT
AATTTGGCTAAGGTAAGAGAGGTGATGCAGGGACCGAACGAACCTCCCTC
```

-continued

GGTATTTCTTGAGAGGCTCATGGAAGCCTTCAGGCGGTTCACCCCTTTTT
GGGGGGGGGGGGGGGGGGGGGGGGCCTCAGTGGCCCTGGCCTTCATTGGG
CAGTCGGCTCTGGATATCAGAAAGAAACTTCAGAGACTGGAAGGGTTACA
GGAGGCTGAGTTACGTGATCTAGTGAGAGAGGCAGAGAAGGTGTATTACA
GAAGGGAGGGGGGGGGGGGGGGGGGGGGGGGGGGGGGGGGGGGGGGGGGG
GGGGGGGGGGGGGGGGGGGGGGGGGGGGGGGGGGGGGGGGGGGGGGGGGG
GGGGGGGGGGGGGGGGGGGGGGGGGGGGGGGGGGGGGGGGGGGGGGGGGG
GGGGGGGGGGGGGGGGGGGGGGGGGGGGGGGGGGGGGGGGGGGGGGGGGG
GGGGGGGGGGGGGGGGGGGGGGGGGGGGGGGGGGGGAAAAAGGACACTGG
GCAAGGAACTGCCCCAAGAAGGGAAACAAAGGACCGAATTTCCTATTTCT
AGAAGAA (Seq ID No 7)

pol
GGCAACGGCAGTATCCATGGACTACCCGAAGAACCGTTGACTTGGCAGTG
GGACGGGTAACCCACTCGTTTCTGGTCATCCCTGAGTGCCCAGTACCCCT
TCTAGGTAGAGACTTACTGACCAAGATGGGAGCTCAAATTTCTTTTGAAC
AAGGAAGACCAGAAGTGTCTGTGAATAACAAACCCATCACTGTGTTGACC
CTCCAATTAGATGATGAATATCGACTATATTCTCCCCAAGTAAAGCCTGA
TCAAGATATACAGTCCTGGTTGGAGCAGTTTCCCCAAGCCTGGGCAGAAA
CCGCAGGGATGGGTTTGGCAAAGCAAGTTCCCCCACAGGTTATTCAACTG
AAGGCCAGTGCTACACCAGTATCAGTCAGACAGTACCCCTTGAGTAGAGA
GGCTCGAGAAGGAATTTGGCCGCATGTTCAAAGATTAATCCAACAGGGCA
TCCTAGTTCCTGTCCAATCCCCTTGGAATACTCCCCTGCTACCGGTTAGG
ttttttttttttttttttttttttttttttttttttttGAGAGAGGTCAA
TAAAAGGGTGcaggacatacacccaacggtcccgaaccccttataacctct
tgagcgccctcccgcctgaacggaactggtacacagtattggacttaaaa
gatgccttcttctgcctgagattacaccccactagccaaccgcttttttgc
cttcgaatggagagatccaggtacgggaaGAACCGGGCAGCttttttttt
ttttttttttttttttttttttttttttttttttttttttttACGAAGCC
CTACACAGGGACCTGGCCAACTTCAGGATCCAACACCCCCAGTGACCCTC
TCCAGTACTGGGATGACCTGCTTCTAGTGGAGCCACCAACAGGACTGCTA
GAAGGTACGAAGGCACTACTACTGAATTGTCTGACCTAGGCTACGAGCCT
CAGCTAAAAGGCCCAGATTGCAGAGAGAGGTAACATACTTGGGTACAGTC
TGCGGGACGGGCAGTGATGGCTGACGGAGGCACGGAAGAGAACTGTAGTC
CAGATACCttttttttttttttttttttCAAGTGAGAGAGTTTTGGGGAC
AGCTGGATTTTGCAGACTGTGGATCCCGGGGTTTGCGACCTTAGCAGCCC
CACTCTACCCGCTAACCAAAGAAAAAGGGGAGTTCTCCTGGGCTCCTGAG
CACCAGAAGGCATTTGATGCTATCAAAAAGGCCCTGCTGAGCACACCTGC
TCTGGCCCTCCCTGATGTAACTAAACCCTTTACTCTTTATGTGGATGAAT
GTAAGGGGGTAGCCCGGGGAGTTTTAACCCAATCCCTAGGACCATGGAGG
AGACCTGTTGCCTACCTGTCAAAGAAGCTCGATCCTGTAGCCAGTGGTTG
GCCCATATGCCTGAAGGCTATCGCAGCCGTGGCCATACTGGTCAAGGACG
CTGACAAATTGACTTTGGGACAGAATATAACTGTAATAGCCCCCCATGCG
TTGGAGAACATCGTCCGGCAGCCCCCAGACCGATGGATGACCAACGCCCG -continued CATGACCCACTATCAAAGCCTGCTTCTCACAGAGAGGATCACGTTCACTC
TACCAGCTGCTCTCAACCCTGCCACTCTTCTGCCTGAAGAGACTGATGAA
CCAGTGA (Seq ID No 8)

env
CATCCCACGTTAAGCCGGCGCCACCTCCCGATTCGGGGTGGAAAGCCGAA
AAGACTGAAAATCCCCTTAAGCTTCGCCTCCATCGCGTGGTTCCTTACTC
TGTCAATAACCTCTCAGACTAATGGTATGCGCATAGGAGACAGCCTGAAC
TCCCATAAACCCTTATCTCTCACCTGGTTAATTACTGACTCCGGCACAGG
TATTAATATCAACAACACTCAAGGGGAGGCTCCTTTAGGAACCTGGTGGC
CTGATCTATACGTTTGCCTCAGATCAGTTATTCCtttttttttttttttt
tttttttttttttttttttTCCATGCTCACGGATTTTATGTTTGCCCAGG
ACCACCAAATAATGGAAAACATTGCGGAAATCCCAGAGATTTCTTTTGTA
AACAATGGAACTGTGTAACCTCTAATGATGGATATTGGAAATGGCCAACC
TCTCAGCAGGATAGGGTAAGTTTTTCTTATGTCAAttttttttttttttt
tttttttttttttttttttttttttttttttttttttttttttttttttt
tttttttttttttttttttttttttttttttttttttttttttttttttT
AGATTACCTAAAAATAAGTTTCACTGAGAAGGGAAACCAAGAAAATATCC
TAAAATGGGTAAATGGTATGTCTTGGGGAATGGTATATTATGGAGGCTCG
GGTAAACAACCAGGCTCCATTCTAACTATTCGtttttttttttttttttt
tttttttCCTCCAATGGCTATAGGACCAAATACGGTCTTGACGGGTCAAA
GACCCCCAACCCAAGGACCAGGACCATCCTCTAACATAACCTCTtttttt
tttttttttttttttttttttttttttttttttttttttttttttttttt
tttttttttttttttttttttttttttttttCTAGCAGCACGACTAAAAT
GGGGGCAAAACTTTTTAGCCTCATCCAGGGAGCTTTTCAAGCTCTTAACT
CCACGACTCCAGAGGCTACCTCTTCTFGTTGGCTATGCTTAGCTTTGGGC
CCACCTTACTATGAAGGAATGGCTAGAAGAGGGAAATTCAATGTGACAAA
AGAACATAGAGACCAATGCACATGGGGATCCCAAAATAAGCTTACCCTTA
CTGAGGTTTCTGGAAAAGGCACCTGCATAGGAAAGGTTCCCCCATCCCAC
CAACACCTTTGttttttttttttttttttttttttttCCTCTGAGAGTCA
ATATCTGGTACCTGGTTATGACAGGTGGTGGGCATGTAATACTGGATTAA
CCCCTTGTGTTTCCACCTTGGTTTTTAACCAAACTAAAGATTTTTGCATT
ATGGTCCAAATTGTTCCCCGAGTGTATTACTATCCCGAAAAAGCAATCCT
TGATGAATATGACTACAGAAATCATCGACAAAAGAGAGGACCCATATCTC
TGACACTTGCTGTGATGCTCGGACTTGGAGTGGCAGCAGGTGTAGGAACA
GGAACAGCTGCCCTGGTCACGGGACCACAGCAGCTAGAAACAGGACTTAG
TAACCTACATCGAATTGTAACAGAAGATCTCCAAGCCCTAGAAAAATCTG
TCAGTAACCTGGAGGAATCCCTAACCTCCTTATCTGAAGTAGTCCTACAG
AATAGAAGAGGGTTAGATTTATTATTTCTAAAAGAAGGAGGATTATGTGT
AGCCTTtttttttttttttttttttttttttttttttttttttttttttt
tttGACTCCATGAACAAACTTAGAGAAAGGTTGGAGAAGCGTCGAAGGGA
AAAGGAAACTACTCAAGGGTGGTTTGAGGGATGGTTCAACAGGTCTCCTT
GGTTGGCTACCCTACTTTCTGCTTTAACAGGACCCTTAATAGTCCTCCTC
CTGTTACTCACAGTTGGGCCATGTATTATTAACAAGTTAATTGCCTTCAT
TAGAGAACGAATAAGTGttttttttttttttttttttttttttttttttt
tttttttttttttttttttttttttCTGGCCGCTAG The specific siRNA sequences that were derived from these model gene sequences are listed below.

TABLE 1

| Target Name | Target Sequence | "Top" oligonucleotide | "Bottom" oligonucleotide |
|---|---|---|---|
| env | ATAAGCTTAC CCTTACTGA (Seq ID No. 49) | tcccaATAAGCTTACCCTTACTGAttcaagagaTC AGTAAGGGTAAGCTTATtt (Seq ID No. 50) | caaaaaATAAGCTTACCCTTACTGAtctcttgaaTCAGT AAGGGTAAGCTTATt (Seq ID No. 51) |
| env | ATAAGCTTAC CCTTACTGA (Seq ID No. 52) | tcccaATAAGCTTACCCTTACTGAttcaagagaTC AGTAAGGGTAAGCTTAtt (Seq ID No. 53) | caaaaaTAAGCTTACCCTTACTGAtctcttgaaTCAGTA AGGGTAAGCTTATt (Seq ID No. 54) |
| env | TAAGCTTACC CTTACTGA (Seq ID No. 55) | tcccaTAAGCTTACCCTTACTGAttcaagagaTCA GTAAGGGTAAGCTTATtt (Seq ID No. 56) | caaaaaATAAGCTTACCCTTACTGAtctcttgaaTCAGT AAGGGTAAGCTTAt (Seq ID No. 57) |
| env | TAAGCTTACC CTTACTGA (Seq ID No. 58) | tcccaTAAGCTTACCCTTACTGAttcaagagaTCA GTAAGGGTAAGCTTAtt (Seq ID No. 59) | caaaaaTAAGCTTACCCTTACTGAtctcttgaaTCAGTA AGGGTAAGCTTAt (Seq ID No. 60) |
| env | AAGCAATCCT TGATGAATA (Seq ID No. 61) | tcccaAAGCAATCCTTGATGAATAttcaagagaT ATTCATCAAGGATTGCTTtt (Seq ID No. 62) | caaaaaAAGCAATCCTTGATGAATAtctcttgaaTATTC ATCAAGGATTGCTTt (Seq ID No. 63) |
| env | AAGCAATCCT TGATGAATA (Seq ID No. 64) | tcccaAAGCAATCCTTGATGAATAttcaagagaT ATTCATCAAGGATTGCtt (Seq ID No. 65) | caaaaaGCAATCCTTGATGAATAtctcttgaaTATTCAT CAAGGATTGCTTt (Seq ID No. 66) |

TABLE 1-continued

| Target Name | Target Sequence | "Top" oligonucleotide | "Bottom" oligonucleotide |
|---|---|---|---|
| env | AGCAATCCTT GATGAATA (Seq ID No. 67) | tcccaAGCAATCCTTGATGAATAttcaagagaTAT TCATCAAGGATTGCTTtt (Seq ID No. 68) | caaaaaAAGCAATCCTTGATGAATAtctcttgaaTATTC ATCAAGGATTGCTt (Seq ID No. 69) |
| env | AGCAATCCTT GATGAATA (Seq ID No. 70) | tcccaAGCAATCCTTGATGAATAttcaagagaTAT TCATCAAGGATTGCtt (Seq ID No. 71) | caaaaaGCAATCCTTGATGAATAtctcttgaaTATTCAT CAAGGATTGCTt (Seq ID No. 72) |
| env | TGATGAATAT GACTACAGA (Seq ID No. 73) | tcccaTGATGAATATGACTACAGAttcaagagaT CTGTAGTCATATTCATCAtt (Seq ID No. 74) | caaaaaTGATGAATATGACTACAGAtctcttgaaTCTGT AGTCATATTCATCAt (Seq ID No. 75) |
| env | GAAGGTGGGT TATGTGTAG (Seq ID No. 76) | tcccaGAAGGTGGGTTATGTGTAGttcaagagaC TACACATAACCCACCTTCtt (Seq ID No. 77) | caaaaaGAAGGTGGGTTATGTGTAGtctcttgaaCTACA CATAACCCACCTTCt (Seq ID No. 78) |
| env | GAAGGAGGAT TATGTGTAG (Seq ID No. 79) | tcccaGAAGGAGGATTATGTGTAGttcaagagaC TACACATAATCCTCCTTCtt (Seq ID No. 80) | caaaaaGAAGGAGGATTATGTGTAGtctcttgaaCTACA CATAATCCTCCTTCt (Seq ID No. 81) |
| env | TCCATCGCGT GGTTCCTTA (Seq ID No. 82) | tcccaTCCATCGCGTGGTTCCTTAttcaagagaTA AGGAACCACGCGATGGAtt (Seq ID No. 83) | caaaaaTCCATCGCGTGGTTCCTTAtctcttgaaTAAGG AACCACGCGATGGAt (Seq ID No. 84) |
| env | GTGGTTCCTTA CTCTGTCA (Seq ID No. 85) | tcccaGTGGTTCCTTACTCTGTCAttcaagagaTG ACAGAGTAAGGAACCACtt (Seq ID No. 86) | caaaaaGTGGTTCCTTACTCTGTCAtctcttgaaTGACA GAGTAAGGAACCACt (Seq ID No. 87) |
| env | CTCCTCAAGTT AATGGTaA (Seq ID No. 88) | tcccaCTCCTCAAGTTAATGGTaAttcaagagaTT ACCATTAACTTGAGGAGtt (Seq ID No. 89) | caaaaaCTCCTCAAGTTAATGGTaAtctcttgaaTTACCA TTAACTTGAGGAGt (Seq ID No. 90) |
| env | CTATAGATAT AATCGGCCA (Seq ID No. 91) | tcccaCTATAGATATAATCGGCCAttcaagagaT GGCCGATTATATCTATAGtt (Seq ID No. 92) | caaaaaCTATAGATATAATCGGCCAtctcttgaaTGGCC GATTATATCTATAGt (Seq ID No. 93) |
| env | AGAGAGGCGT CGAAGGGAA (Seq ID No. 94) | tcccaAGAGAGGCGTCGAAGGGAAttcaagagaT TCCCTTCGACGCCTCTCTtt (Seq ID No. 95) | caaaaaAGAGAGGCGTCGAAGGGAAtctcttgaaTTCC CTTCGACGCCTCTCTt (Seq ID No. 96) |
| env | CCAAGGCCTT CTGAGCCAA (Seq ID No. 97) | tcccaCCAAGGCCTTCTGAGCCAAttcaagagaTT GGCTCAGAAGGCCTTGGtt (Seq ID No. 98) | caaaaaCCAAGGCCTTCTGAGCCAAtctcttgaaTTGGC TCAGAAGGCCTTGGt (Seq ID No. 99) |
| env | GAACATAGAG ACCAATGCA (Seq ID No. 100) | tcccaGAACATAGAGACCAATGCAttcaagagaT GCATTGGTCTCTATGTTCtt (Seq ID No. 101) | caaaaaGAACATAGAGACCAATGCAtctcttgaaTGCAT TGGTCTCTATGTTCt (Seq ID No. 102) |
| env | TGACCTACAT CGAATTGTA (Seq ID No. 103) | tcccaTGACCTACATCGAATTGTAttcaagagaTA CAATTCGATGTAGGTCAtt (Seq ID No. 104) | caaaaaTGACCTACATCGAATTGTAtctcttgaaTACAA TTCGATGTAGGTCAt (Seq ID No. 105) |
| env | TCAGTAACCT AGAGGAATC (Seq ID No. 106) | tcccaTCAGTAACCTAGAGGAATCttcaagagaG ATTCCTCTAGGTTACTGAtt (Seq ID No. 107) | caaaaaTCAGTAACCTAGAGGAATCtctcttgaaGATTC CTCTAGGTTACTGAt (Seq ID No. 108) |
| env | TAACCTACAT CGAATTGTA (Seq ID No. 109) | tcccaTAACCTACATCGAATTGTAttcaagagaTA CAATTCGATGTAGGTTAtt (Seq ID No. 110) | caaaaaTAACCTACATCGAATTGTAtctcttgaaTACAA TTCGATGTAGGTTAt (Seq ID No. 111) |
| env | ACATCGAATT GTAACAGAA (Seq ID No. 112) | tcccaACATCGAATTGTAACAGAAttcaagagaT TCTGTTACAATTCGATGTtt (Seq ID No. 113) | caaaaaACATCGAATTGTAACAGAAtctcttgaaTTCTG TTACAATTCGATGTt (Seq ID No. 114) |
| env | ACATCGAATT GTAACAGAA (Seq ID No. 115) | tcccaACATCGAATTGTAACAGAAttcaagagaT TCTGTTACAATTCGATGtt (Seq ID No. 116) | caaaaaCATCGAATTGTAACAGAAtctcttgaaTTCTGT TACAATTCGATGTt (Seq ID No. 117) |
| env | CATCGAATTG TAACAGAA (Seq ID No. 118) | tcccaCATCGAATGTAACAGAAttcaagagaTT CTGTTACAATTCGATGTtt (Seq ID No. 119) | caaaaaACATCGAATTGTAACAGAAtctcttgaaTTCTG TTACAATTCGATGt (Seq ID No. 120) |

TABLE 1-continued

| Target Name | Target Sequence | "Top" oligonucleotide | "Bottom" oligonucleotide |
|---|---|---|---|
| env | CATCGAATTG TAACAGAA (Seq ID No. 121) | tcccaCATCGAATTGTAACAGAAttcaagagaTT CTGTTACAATTCGATGtt (Seq ID No. 122) | caaaaaCATCGAATTGTAACAGAAtctcttgaaTTCTGT TACAATTCGATGt (Seq ID No. 123) |
| env | TCTCTCACCTG GTTACTTA (Seq ID No. 124) | tcccaTCTCTCACCTGGTTACTTAttcaagagaTA AGTAACCAGGTGAGAGAtt (Seq ID No. 125) | caaaaaTCTCTCACCTGGTTACTTAtctcttgaaTAAGTA ACCAGGTGAGAGAt (Seq ID No. 126) |
| env | AGAAGGAGGA TTATGTGTA (Seq ID No. 127) | tcccaAGAAGGAGGATTATGTGTAttcaagagaT ACACATAATCCTCCTTCTtt (Seq ID No. 128) | caaaaaAGAAGGAGGATTATGTGTAtctcttgaaTACAC ATAATCCTCCTTCTt (Seq ID No. 129) |
| env | AGAAGGAGGA TTATGTGTA (Seq ID No. 130) | tcccaAGAAGGAGGATTATGTGTAttcaagagaT ACACATAATCCTCCTTCtt (Seq ID No. 131) | caaaaaGAAGGAGGATTATGTGTAtctcttgaaTACACA TAATCCTCCTTCTt (Seq ID No. 132) |
| env | GAAGGAGGAT TATGTGTA (Seq ID No. 133) | tcccaGAAGGAGGATTATGTGTAttcaagagaTA CACATAATCCTCCTTCTtt (Seq ID No. 134) | caaaaaAGAAGGAGGATTATGTGTAtctcttgaaTACAC ATAATCCTCCTTCt (Seq ID No. 135) |
| env | GAAGGAGGAT TATGTGTA (Seq ID No. 136) | tcccaGAAGGAGGATTATGTGTAttcaagagaTA CACATAATCCTCCTTCtt (Seq ID No. 137) | caaaaaGAAGGAGGATTATGTGTAtctcttgaaTACACA TAATCCTCCTTCt (Seq ID No. 138) |
| env | CCACCTTACTA TGAGGGAA (Seq ID No. 139) | tcccaCCACCTTACTATGAGGGAAttcaagagaTT CCCTCATAGTAAGGTGGtt (Seq ID No. 140) | caaaaaCCACCTTACTATGAGGGAAtctcttgaaTTCCC TCATAGTAAGGTGGt (Seq ID No. 141) |
| env | GTAGTCCTAC AGAATAGAA (Seq ID No. 142) | tcccaGTAGTCCTACAGAATAGAAttcaagagaT TCTATTCTGTAGGACTACtt (Seq ID No. 143) | caaaaaGTAGTCCTACAGAATAGAAtctcttgaaTTCTA TTCTGTAGGACTACt (Seq ID No. 144) |
| env | GGAACTGTGT AACCTCTAA (Seq ID No. 145) | tcccaGGAACTGTGTAACCTCTAAttcaagagaTT AGAGGTTACACAGTTCCtt (Seq ID No. 146) | caaaaaGGAACTGTGTAACCTCTAAtctcttgaaTTAGA GGTTACACAGTTCCt (Seq ID No. 147) |
| env | ACAACCAGGC TCCATTCTA (Seq ID No. 148) | tcccaACAACCAGGCTCCATTCTAttcaagagaTA GAATGGAGCCTGGTTGTtt (Seq ID No. 149) | caaaaaACAACCAGGCTCCATTCTAtctcttgaaTAGAA TGGAGCCTGGTTGTt (Seq ID No. 150) |
| env | ACAACCAGGC TCCATTCTA (Seq ID No. 151) | tcccaACAACCAGGCTCCATTCTAttcaagagaTA GAATGGAGCCTGGTTGtt (Seq ID No. 152) | caaaaaCAACCAGGCTCCATTCTAtctcttgaaTAGAAT GGAGCCTGGTTGTt (Seq ID No. 153) |
| env | CAACCAGGCT CCATTCTA (Seq ID No. 154) | tcccaCAACCAGGCTCCATTCTAttcaagagaTAG AATGGAGCCTGGTTGTtt (Seq ID No. 155) | caaaaaACAACCAGGCTCCATITCTAtctcttgaaTAGAA TGGAGCCTGGTTGt (Seq ID No. 156) |
| env | CAACCAGGCT CCATTCTA (Seq ID No. 157) | tcccaCAACCAGGCTCCATTCTAttcaagagaTAG AATGGAGCCTGGTTGtt (Seq ID No. 158) | caaaaaCAACCAGGCTCCATTCTAtctcttgaaTAGAAT GGAGCCTGGTTGt (Seq ID No. 159) |
| env | CAACCAGGCT CCATTCTAA (Seq ID No. 160) | tcccaCAACCAGGCTCCATTCTAAttcaagagaTT AGAATGGAGCCTGGTTGtt (Seq ID No. 161) | caaaaaCAACCAGGCTCCATTCTAAtctcttgaaTTAGA ATGGAGCCTGGTTGt (Seq ID No. 162) |
| env | CCAGGCTCCA TTCTAACTA (Seq ID No. 163) | tcccaCCAGGCTCCATTCTAACTAttcaagagaTA GTTAGAATGGAGCCTGGtt (Seq ID No. 164) | caaaaaCCAGGCTCCATTCTAACTAtctcttgaaTAGTT AGAATGGAGCCTGGt (Seq ID No. 165) |
| env | GGACCAGGAC CATCCTCTA (Seq ID No. 166) | tcccaGGACCAGGACCATCCTCTAttcaagagaT AGAGGATGGTCCTGGTCCtt (Seq ID No. 167) | caaaaaGGACCAGGACCATCCTCTAtctcttgaaTAGAG GATGGTCCTGGTCCt (Seq ID No. 168) |
| env | GGACCATCCT CTAACATAA (Seq ID No. 169) | tcccaGGACCATCCTCTAACATAAttcaagagaTT ATGTTAGAGGATGGTCCtt (Seq ID No. 170) | caaaaaGGACCATCCTCTAACATAAtctcttgaaTTATG TTAGAGGATGGTCCt (Seq ID No. 171) |
| gag | GCCTTCAGGC GGTTCACCCCT (Seq ID No. 172) | TCCCAGCCTTCAGGCGGTTCACCCCTTTCA AGAGAAGGGGTGAACCGCCTGAAGGCTT (Seq ID No. 173) | CAAAAAGCCTTCAGGCGGTTCACCCCTTCTCTT GAAAGGGGTGAACCGCCTGAAGGCT (Seq ID No. 174) |

TABLE 1-continued

| Target Name | Target Sequence | "Top" oligonucleotide | "Bottom" oligonucleotide |
|---|---|---|---|
| gag | GCCTTCAGGC GGTTCACCC (Seq ID No. 175) | tcccaGCCTTCAGGCGGTTCACCCttcaagagaG GGTGAACCGCCTGAAGGCtt (Seq ID No. 176) | caaaaaGCCTTCAGGCGGTTCACCCTCTCTTGAAG GGTGAACCGCCTGAAGGCt (Seq ID No. 177) |
| gag | GGGTTACAGG AGGCTGAG (Seq ID No. 178) | tcccaGGGTTACAGGAGGCTGAGttcaagagaAC TCagCCTCctGTAACCCtt (Seq ID No. 179) | caaaaaGGGTTACAGGAGGCTGAGTTCTCTTGAAA CTCagCCTCctGTAACCCt (Seq ID No. 180) |
| gag | GAGGCTGAGT TACGTGATC (Seq ID No. 181) | tcccaGAGGCTGAGTTACGTGATCttcaagagaG ATCACGTAACTCAGCCTCtt (Seq ID No. 182) | caaaaaGAGGCTGAGTTACGTGATCtctcttgaaGATCA CGTAACTCAGCCTCt (Seq ID No. 183) |
| gag | TGAGTTACGT GATCTAGTG (Seq ID No. 184) | tcccaTGAGTTACGTGATCTAGTGttcaagagaCA CTAGATCACGTAACTCAtt (Seq ID No. 185) | caaaaaTGAGTTACGTGATCTAGTGtctcttgaaCACTA GATCACGTAACTCAtt (Seq ID No. 186) |
| gag | GTTACGTGAT CTAGTGAGA (Seq ID No. 187) | tcccaGTTACGTGATCTAGTGAGAttcaagagaTC TCACTAGATCACGTAACtt (Seq ID No. 188) | caaaaaGTTACGTGATCTAGTGAGAtctcttgaaTCTCA CTAGATCACGTAACtt (Seq ID No. 189) |
| gag | GCAGAGAAGG TGTATTACA (Seq ID No. 190) | tcccaGCAGAGAAGGTGTATTACAttcaagagaT GTAATACACCTTCTCTGCtt (Seq ID No. 191) | caaaaaGCAGAGAAGGTGTATTACAtctcttgaaTGTAA TACACCTTCTCTGCtt (Seq ID No. 192) |
| gag | AAGGACACTG GGCAAGGAA (Seq ID No. 193) | tcccaAAGGACACTGGGCAAGGAAttcaagagaT TCCTTGCCCAGTGTCCTTtt (Seq ID No. 194) | caaaaaAAGGACACTGGGCAAGGAAtctcttgaaTTCCT TGCCCAGTGTCCTTt (Seq ID No. 195) |
| gag | GGAGCCCTAT ATCCTTACG (Seq ID No. 196) | tcccaGGAGCCCTATATCCTTACGttcaagagaCG TAAGGATATAGGGCTCCtt (Seq ID No. 197) | caaaaaGGAGCCCTATATCCTTACGtctcttgaaCGTAA GGATATAGGGCTCCt (Seq ID No. 198) |
| gag | GATCCTCCGC CATGGGTTA (Seq ID No. 199) | tcccaGATCCTCCGCCATGGGTTAttcaagagaTA ACCCATGGCGGAGGATCtt (Seq ID No. 200) | caaaaaGATCCTCCGCCATGGGTTAtctcttgaaTAACC CATGGCGGAGGATCt (Seq ID No. 201) |
| gag | TCCTGGCTCTT GGAGAGAA (Seq ID No. 202) | tcccaTCCTGGCTCTTGGAGAGAAttcaagagaTT CTCTCCAAGAGCCAGGAtt (Seq ID No. 203) | caaaaaTCCTGGCTCTTGGAGAGAAtctcttgaaTTCTC TCCAAGAGCCAGGAt (Seq ID No. 204) |
| gag | TCCTGGCTCTT GGAGAGAA (Seq ID No. 205) | tcccaTCCTGGCTCTTGGAGAGAAttcaagagaTT CTCTCCAAGAGCCAGGAtt (Seq ID No. 206) | caaaaaTCCTGGCTCTTGGAGAGAAtctcttgaaTTCTC TCCAAGAGCCAGGAt (Seq ID No. 207) |
| gag | TCCTGGCTCTT GGAGAGAA (Seq ID No. 208) | tcccaTCCTGGCTTGGAGAGAAttcaagagaTT CTCTCCAAGAGCCAGGAtt (Seq ID No. 209) | caaaaaTCCTGGCTCTTGGAGAGAATCTCTTGAAT TCTCTCCAAGAGCCAGGAt (Seq ID No. 210) |
| gag | GTTAGATCCA GGGCTCATAAT (Seq ID No. 211) | TCCCAGTTAGATCCAGGGCTCATAATTTC AAGAGAATTATGAGCCCTGGATCTAACTT (Seq ID No. 212) | CAAAAAGTTAGATCCAGGGCTCATAATTCTCTT GAAATTATGAGCCCTGGATCTAACT (Seq ID No. 213) |
| gag | AGACGAGATC GCGATATTA (Seq ID No. 214) | tcccaAGACGAGATCGCGATATTAttcaagagaT AATATCGCGATCTCGTCTtt (Seq ID No. 215) | caaaaaAGACGAGATCGCGATATTAtctcttgaaTAATA TCGCGATCTCGTCTt (Seq ID No. 216) |
| gag | GCAGATCTCT ATAATTGGA (Seq ID No. 217) | tcccaGCAGATCTCTATAATTGGAttcaagagaTC CAATTATAGAGATCTGCtt (Seq ID No. 218) | caaaaaGCAGATCTCTATAATTGGAtctcttgaaTCCAA TTATAGAGATCTGCt (Seq ID No. 219) |
| gag | TTGGAAAACT AACCATCCCCC (Seq ID No. 220) | TCCCATTGGAAAACTAACCATCCCCCTTC AAGAGAGGGGGATGGTTAGTTTTCCAATT (Seq ID No. 221) | CAAAAATTGGAAAACTAACCATCCCCCTCTCTT GAAGGGGGATGGTTAGTTTTCCAAT (Seq ID No. 222) |
| gag | AGTCCCTTATG TTCTCTCA (Seq ID No. 223) | tcccaAGTCCCTTATGTTCTCTCAttcaagagaTG AGAGAACATAAGGGACTtt (Seq ID No. 224) | caaaaaAGTCCCTTATGTTCTCTCAtctcttgaaTGAGA GAACATAAGGGACTtt (Seq ID No. 225) |
| gag | CTACTTGGGA TGATTGTCA (Seq ID No. 226) | tcccaCTACTTGGGATGATTGTCAttcaagagaTG ACAATCATCCCAAGTAGtt (Seq ID No. 227) | caaaaaCTACTTGGGATGATTGTCAtctcttgaaTGACA ATCATCCCAAGTAGt (Seq ID No. 228) |

TABLE 1-continued

| Target Name | Target Sequence | "Top" oligonucleotide | "Bottom" oligonucleotide |
|---|---|---|---|
| gag | TTAAGAAGGG ACCTTGGGAGA (Seq ID No. 229) | TCCCATTAAGAAGGGACCTTGGGAGATTC AAGAGATCTCCCAAGGTCCCTTCTTAATT (Seq ID No. 230) | CAAAAATTAAGAAGGGACCTTGGGAGATCTCTT GAATCTCCCAAGGTCCCTTCTTAAT (Seq ID No. 231) |
| gag | ACACGGCTGA AGGTAGGGA (Seq ID No. 232) | tcccaACACGGCTGAAGGTAGGGAttcaagagaT CCCTACCTTCAGCCGTGTtt (Seq ID No. 233) | caaaaaACACGGCTGAAGGTAGGGAtctcttgaaTCCCT ACCTTCAGCCGTGTt (Seq ID No. 234) |
| gag | CACGGCTGAA GGTAGGGAG (Seq ID No. 235) | tcccaCACGGCTGAAGGTAGGGAGttcaagagaC TCCCtaccttCAGCCGTGtt (Seq ID No. 236) | caaaaaCACGGCTGAAGGTAGGGAGTCTCTTGAAC TCCCtaccttCAGCCGTGt (Seq ID No. 237) |
| gag | TCTATCGCCA GGCTCTG (Seq ID No. 238) | tcccaTCTATCGCCAGGCTCTGttcaagagaCAGA GCCTGGCGATAGAtt (Seq ID No. 239) | caaaaaTCTATCGCCAGGCTCTGTCTCTTGAACAG AGCCTGGCGATAGAt (Seq ID No. 240) |
| gag | GCAAGCTGAC CCTGAAGTTCA (Seq ID No. 241) | TCCCAGCAAGCTGACCCTGAAGTTCATTC AAGAGATGAACTTCAGGGTCAGCTTGCTT (Seq ID No. 242) | CAAAAAGCAAGCTGACCCTGAAGTTCATCTCTT GAATGAACTTCAGGGTCAGCTTGCT (Seq ID No. 243) |
| pol | GTAGAGACTT ACTGACCAA (Seq ID No. 244) | TCCCAGTAGAGACTTACTGACCAATTCAA GAGATTGGTCAGTAAGTCTCTACTT (Seq ID No. 245) | CAAAAAGTAGAGACTTACTGACCAATCTCTTGA ATTGGTCAGTAAGTCTCTACT (Seq ID No. 246) |
| pol | ACCTGTTGCCT ACCTGTCA (Seq ID No. 247) | TCCCAACCTGTTGCCTACCTGTCATTCAAG AGATGACAGGTAGGCAACAGGTT (Seq ID No. 248) | CAAAAAACCTGTTGCCTACCTGTCATCTCTTGA ATGACAGGTAGGCAACAGGTT (Seq ID No. 249) |
| pol | CCTGTTGCCTA CCTGTCAA (Seq ID No. 250) | tcccaCCTGTTGCCTACCTGTCAAttcaagagaTT GACAGGTAGGCAACAGGtt (Seq ID No. 251) | caaaaaCCTGTTGCCTACCTGTCAAtctcttgaaTTGAC AGGTAGGCAACAGGt (Seq ID No. 252) |
| pol | GAAGCTCGAT CCTGTAGCC (Seq ID No. 253) | TCCCAGAAGCTCGATCCTGTAGCCTTCAA GAGAGGCTACAGGATCGAGCTTCTT (Seq ID No. 254) | CAAAAAGAAGCTCGATCCTGTAGCCTCTCTTGA AGGCTACAGGATCGAGCTTCT (Seq ID No. 255) |
| pol | CCGTGGCCAT ACTGGTCAA (Seq ID No. 256) | TCCCACCGTGGCCATACTGGTCAATTCAA GAGATTGACCAGTATGGCCACGGTT (Seq ID No. 257) | CAAAAACCGTGGCCATACTGGTCAATCTCTTGA ATTGACCAGTATGGCCACGGT (Seq ID No. 258) |
| pol | GCCTGCTTCTC ACAGAGAG (Seq ID No. 259) | TCCCAGCCTGCTTCTCACAGAGAGTTCAA GAGACTCTCTGTGAGAAGCAGGCTT (Seq ID No. 260) | CAAAAAGCCTGCTTCTCACAGAGAGTCTCTTGA ACTCTCTGTGAGAAGCAGGCT (Seq ID No. 261) |
| pol | CCACTCTTCTG CCTGAAGA (Seq ID No. 262) | TCCCACCACTCTTCTGCCTGAAGATTCAA GAGATCTTCAGGCAGAAGAGTGGTT (Seq ID No. 263) | CAAAAACCACTCTTCTGCCTGAAGATCTCTTGA ATCTTCAGGCAGAAGAGTGGT (Seq ID No. 264) |
| pol | TGAAGAGACT GATGAACCA (Seq ID No. 265) | TCCCATGAAGAGACTGATGAACCATTCAA GAGATGGTTCATCAGTCTCTTCATT (Seq ID No. 266) | CAAAAATGAAGAGACTGATGAACCATCTCTCTTGA ATGGTTCATCAGTCTCTTCAT (Seq ID No. 267) |
| pol | TCACTGTGTTG ACCCTCCA (Seq ID No. 268) | TCCCATCACTGTGTTGACCCTCCATTCAAG AGATGGAGGGTCAACACAGTGATT (Seq ID No. 269) | CAAAAATCACTGTGTTGACCCTCCATCTCTTGA ATGGAGGGTCAACACAGTGAT (Seq ID No. 270) |
| pol | GTACAGGACT TGAGAGAGG (Seq ID No. 271) | tcccaGTACAGGACTTGAGAGAGGttcaagagaC CTCTCTCAAGTCCTGTACtt (Seq ID No. 272) | caaaaaGTACAGGACTTGAGAGAGGtctcttgaaCCTCT CTCAAGTCCTGTACt (Seq ID No. 273) |

Figure 13:
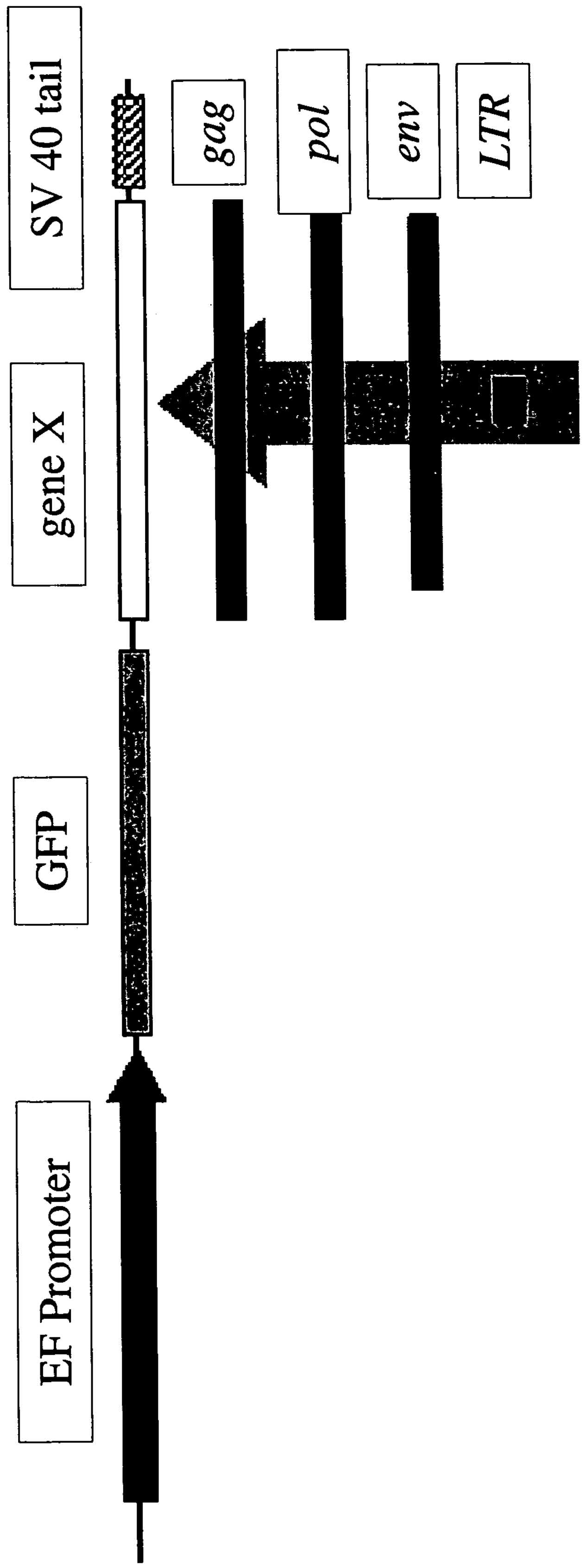
FIG. 13 represents a representation of a cloning strategy to insert portions of a gene into a vector.
Figure 14:
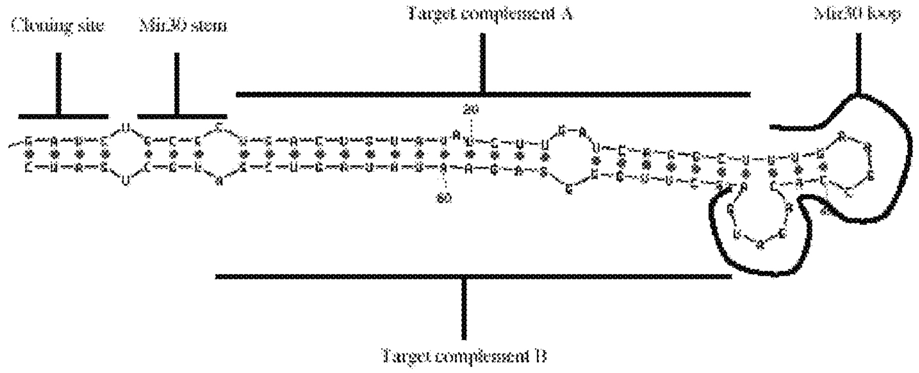
FIG. 14 illustrates an exemplary ds iRNA molecule comprising the nucleotide sequence of SEQ ID NO: 30.

Oligonucleotides were designed, built, annealed, and cloned into an siRNA expression plasmid. The siRNA expression plasmids were screened for effectiveness with the appropriate model gene (anti gag siRNA with a gag model, anti-pol siRNA with a pol model, etc.) in mammalian cells. Most of the siRNA expression plasmids displayed some level of effectiveness. The most potent anti-gag expression plasmid (g49) and the most potent anti-pol expression plasmid (p106) were confirmed effective against PERV mRNA in transfections of PK-15 cells. This effect was assayed by both detection of PERV-produced reverse transcriptase activity and direct measurement of PERV mRNA.

iRNA Expression Plasmids:

Portions of gag, pol, envA, envB, and envC were amplified and cloned into pCR-XLTOPO (Invitrogen, Carlsbad, Calif.). Each insert was independently subcloned as an XbaI/SpeI fragment into a house vector pPL732.8 at an XbaI site located between the coding region of a reporter gene and its poly(A) signal. A graphic representation of the strategy in FIG. 13.

For each iRNA, oligos were cloned into psiRNA-H neo (InvivoGen, San Diego, Calif.) according to the manufacturers recommendations. In brief, the oligos were annealed and cloned into the BbsI sites in place of the LacZ alpha peptide for blue/white screening. For each plasmid, iRNA integrity was confirmed by sequencing.

To test for robust function of each iRNA, the appropriate model gene and a single iRNA test vector were co-transfected into CHO or PK-15 cells using GenePORTER (Gene Therapy Systems, Inc. (GTS), San Diego, Calif.) according to the manufacturers suggestions. As controls, cells were also co-transfected with the reporter gene and an anti-GFP iRNA vector or with the reporter and a non-functional, negative control iRNA consruct. Suppression of the either the total level of reporter expression per transfected cell (as measured by FACS) or the proportion of cells that expressed the reporter gene (visual appraisal or FACS) was considered indicative of iRNA function. The apparently most potent iRNA for both gag and pol were independently transfected into PK-15 cells without the reporter model gene. To determine suppression of viral particle production, reverse transcriptase was measured in the medium of these cells using a commercially available kit (Cavidi Tech, Uppsala, Sweden). Additionally, stable colonies were isolated for each iRNA and the level of steady-state mRNA was measured via quantitative RTPCR. These colonies were also assessed for RT activity and their ability to suppress transiently transfected model gene.

Additional PERV Targeting Strategies: Identification of Drosha Substrates

The following sequence (Fragment A) represents a portion of PERV pol in which potentially non-unique sequence has been replaced with an equal number of lower case "t".

(Seq ID No 9)

Fragment A:

GGCAACGGCAGTATCCATGGACTACCCGAAGAACCGTTGACTTGGCAGTG

GGACGGGTAACCCACTCGTTTCTGGTCATCCCTGAGTGCCCAGTACCCCT

TCTAGGTAGAGACTTACTGACCAAGATGGGAGCTCAAATTTCTTTTGAAC

AAGGAAGACCAGAAGTGTCTGTGAATAACAAACCCATCACTGTGTTGACC

CTCCAATTAGATGATGAATATCGACTATATTCTCCCCAAGTAAAGCCTGA

TCAAGATATACAGTCCTGGTTGGAGCAGTTTCCCCAAGCCTGGGCAGAAA

CCGCAGGGATGGGTTTGGCAAAGCAAGTTCCCCCACAGGTTATTCAACTG

AAGGCCAGTGCTACACCAGTATCAGTCAGACAGTACCCCTTGAGTAGAGA

GGCTCGAGAAGGAATTTGGCCGCATGTTCAAAGATTAATCCAACAGGGCA

TCCTAGTTCCTGTCCAATCCCCTTGGAATACTCCCCTGCTACCGGTTAGG ttttttttttttttttttttttttttttttttttttt*GAGAGAGGTCAAT*

*AAAAGGGTGcaggacatacacccaacggtcccgaacccttataacctctt*

*gagcgccctcccgcctgaacggaactggtacacagtattggacttaaaag*

*atgccttcttctgcctgagattacaccccactagccaaccgcttttgcc*

*ttcgaatggagagatccaggtacgggaaGAACCGGGCAGC*tttttttttt tttttttttttttttttttttttttttttttttttttttttACGAAGCCC

TACACAGGGACCTGGCCAACTTCAGGATCCAACACCCCCAGTGACCCTCT

CCAGTACTGGGATGACCTGCTTCTAGTGGAGCCACCAACAGGACTGCTAG

AAGGTACGAAGGCACTACTACTGAATTGTCTGACCTAGGCTACGAGCCTC

AGCTAAAAGGCCCAGATTGCAGAGAGAGGTAACATACTTGGGTACAGTCT

GCGGGACGGGCAGTGATGGCTGACGGAGGCACGGAAGAGAACTGTAGTCC

-continued

AGATACCtttttttttttttttttttCAAGTGAGAGAGTTTTGGGGGACA

GCTGGATTTTGCAGACTGTGGATCCCGGGGTTTGCGACCTTAGCAGCCCC

ACTCTACCCGCTAACCAAAGAAAAAGGGGAGTTCTCCTGGGCTCCTGAGC

ACCAGAAGGCATTTGATGCTATCAAAAAGGCCCTGCTGAGCACACCTGCT

CTGGCCCTCCCTGATGTAACTAAACCCTTTACTCTTTATGTGGATGAATG

TAAGGGGGTAGCCCGGGGAGTTTTAACCCAATCCCTAGGACCATGGAGGA

GACCTGTTGCCTACCTGTCAAAGAAGCTCGATCCTGTAGCCAGTGGTTGG

CCCATATGCCTGAAGGCTATCGCAGCCGTGGCCATACTGGTCAAGGACGC

TGACAAATTGACTTTGGGACAGAATATAACTGTAATAGCCCCCCATGCGT

TGGAGAACATCGTCCGGCAGCCCCCAGACCGATGGATGACCAACGCCCGC

ATGACCCACTATCAAAGCCTGCTTCTCACAGAGAGGATCACGTTCACTCT

ACCAGCTGCTCTCAACCCTGCCACTCTTCTGCCTGAAGAGACTGATGAAC

CAGTGA

The section of pol shown underlined above has been converted to its complement below (Fragment B):

(Seq ID No 10)

Fragment B.

GGTATCTGGACTACAGTTCTCTTCCGTGCCTCCGTCAGCCATCACTGCCC

GTCCCGCAGACTGTACCCAAGTATGTTACCTCTCTCTGCAATCTGGGCCT

TTTAGCTGAGGCTCGTAGCCTAGGTCAGACAATTCAGTAGTAGTGCCTTC

GTACCTTCTAGCAGTCCTGTTGGTGGCTCCACTAGAAGCAGGTCATCCCA

GTACTGGAGAGGGTCACTGGGGGTGTTGGATCCTGAAGTTGGCCAGGTCC

CTGTGTAGGGCTTCGT

MFold (M. Zuker. Mfold web server for nucleic acid folding and hybridization prediction. Nucleic Acids Res. 31 (13) 3406-15, (2003), [http://www.bioinfo.rpi.edu/applications/mfold/old/rna/form1.cgi]) was used to produce the "folded" structure prediction of Fragment B depicted in FIG. 21.

Figure 21:
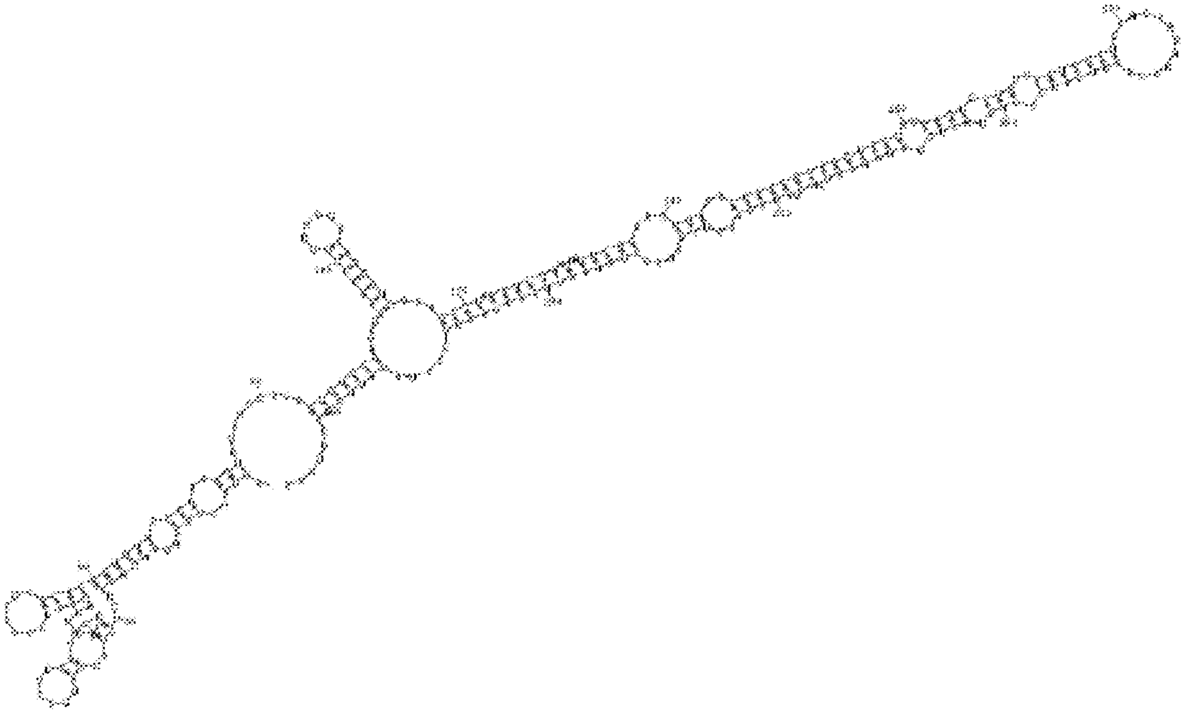
FIG. 21 depicts the predicted "folded" structure of Fragment B comprising the nucleotide sequence of SEQ ID NO: 10.

In the structure depicted in FIG. 21, bases 118-248 form a significant hairpin structure. Bases 147-166 (CTTCGTACCTTCTAGCAGTC (Seq ID No 11)) and bases 199-218 (ACTGGAGAGGGTCACTGGGG (Seq ID No 12)) were used to design a Drosha substrate with a mir-30 loop and base. The MFold predicted structure of that substrate is depicted in FIG. 22.

Figure 22:
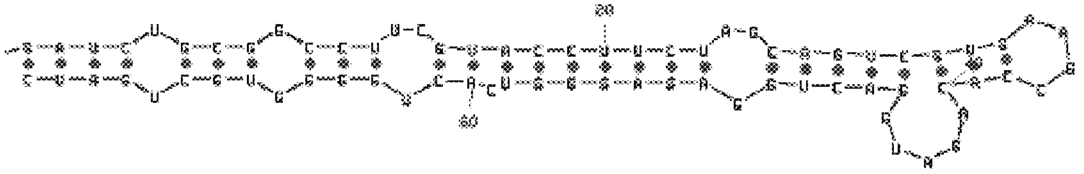
FIG. 22 depicts the predicted structure of a Drosha substrate with a mir-30 loop and base, wherein the Drosha substrate comprises the nucleotide sequence of SEQ ID NO: 13.

The nucleotide sequence of the sequence depicted in FIG. 22 is GAUCUGCGGCCUUCGUACCUUCUAGCAGUCGUGAAGCCACAGAUGGACUG GAGAGGGUCACUGGGGUGCUGAUC (Seq ID No 13).

In a similar manner, bases 192-214 (GTCATCCCAGTACTGGAGAGGGT (Seq ID No14)) and bases 155-178 (CTTCTAGCAGTCCTGTTGGTGGCT (Seq ID No15)) were used to design a Drosha substrate with a mir-30 loop and base. The MFold predicted structure of that substrate is depicted in FIG. 23.

Figure 23:
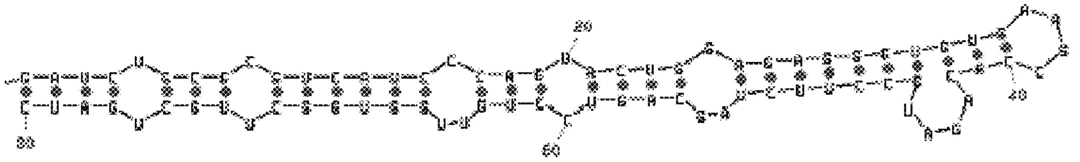
FIG. 23 depicts the predicted structure of a Drosha substrate with a mir-30 loop and base, wherein the Drosha substrate comprises the nucleotide sequence of SEQ ID NO: 16.

The nucleotide sequence of the sequence depicted in FIG. 23 is GAUCUGCGCGUCAUCCCAGUACUGGAGAGGGUGUGAAGCCACAGAUGCCU UCUAGCAGUCCUGUUGGUGGCUUGCUGAUC (Seq ID No 16).

Likewise, bases 118-139 (GCCTAGGTCAGACAATTCAGTA (Seq ID No17)) and bases 230-251 (ATcCTGAAGTTGGCCAGGTCCC(Seq ID No18)) were used to design a Drosha substrate with a mir-30 loop and base. The lowercase "c" at base three of the second oligo was changed to an "A" to optimize folding. The MFold predicted structure of that substrate is depicted in FIG. 24.

Figure 24:
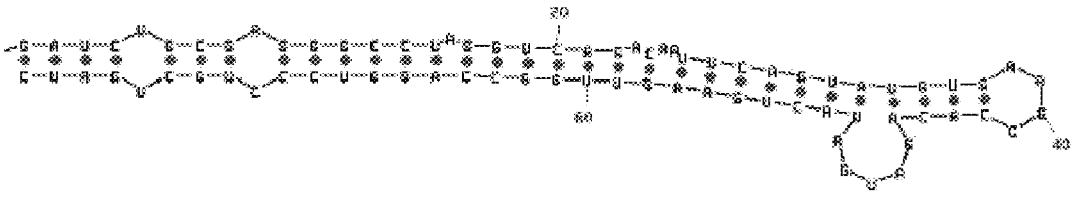
FIG. 24 depicts the predicted structure of a Drosha substrate with a mir-30 loop and base, wherein the Drosha substrate comprises the nucleotide sequence of SEQ ID NO: 19

The nucleotide sequence of the sequence depicted in FIG. 24 is GAUCUGCGAGGGCCUAGGUCAGACAAUUCAGUAUGUGAAGCCACAGAUGA UACUGAAGUUGGCCAGGUCCCUGCUGAUC (Seq ID No 19).

Fragment C is shown below and is the complement of the sequence shown in italics above in Fragment A.

(Seq ID No 20)

Figure 25:
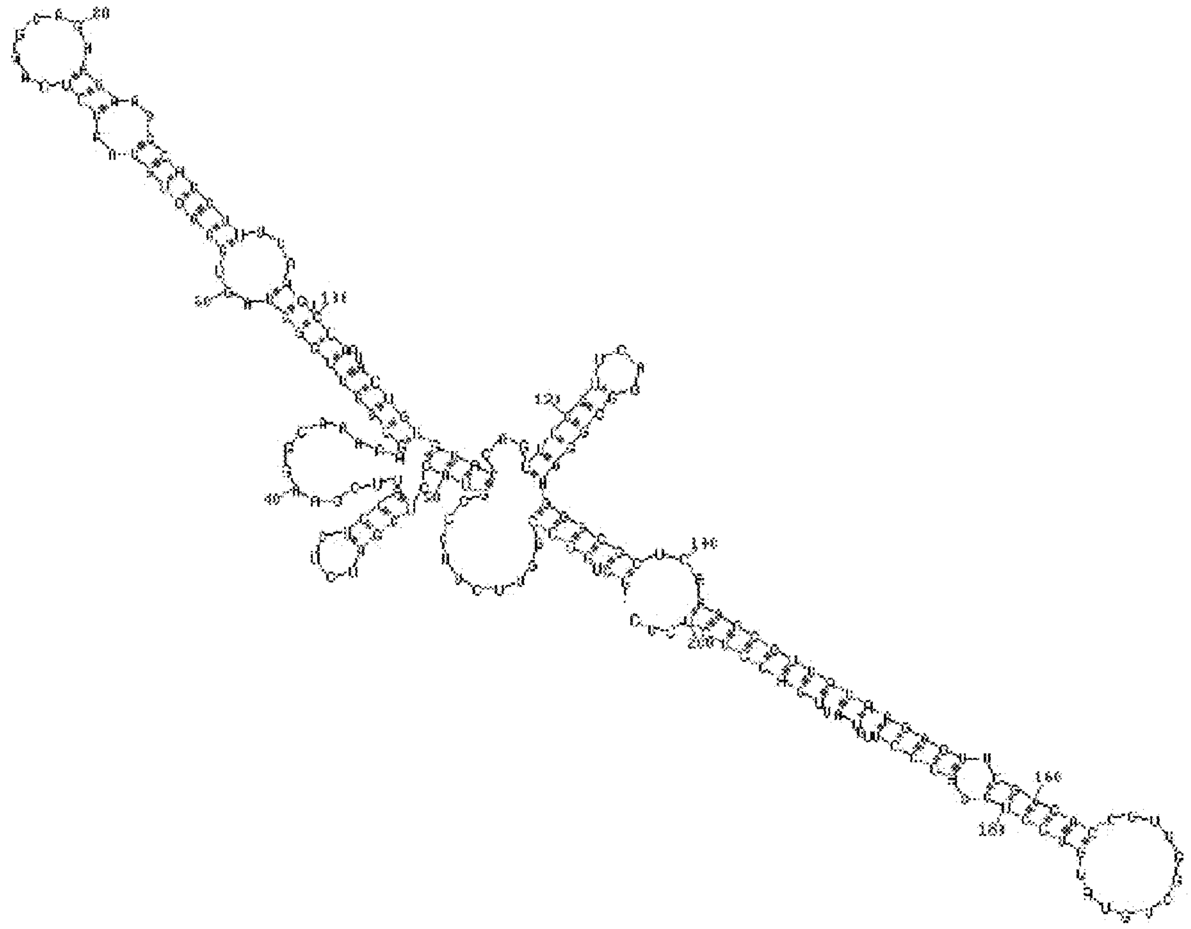
FIG. 25 depicts the predicted folded structure of Fragment C comprising the nucleotide sequence of SEQ ID NO: 20.

Fragment C:
gctgcccggttcttcccgtacctggatctctccattcgaaggcaaaaagc ggttggctagtggggtgtaatctcaggcagaagaaggcatcttttaagtc caatactgtgtaccagttccgttcaggcgggagggcgctcaagaggttat aagggttcgggaccgttgggtgtatgtcctgcaccctttttattgacctct ctc A folded Fragment C structure predicted by MFold shown in FIG. 25.

In the structure depicted in FIG. 25, bases 142-200 form a significant hairpin structure. Bases 141-163 (AAGAGGTTATAAGGGTTCGGGAC (Seq ID No 21)) and bases 176-201 (GTCCTGCACCCITTTATTGACCTCTC (Seq ID No 22)) were used to design a Drosha substrate with a mir-30 loop and base. The MFold predicted structure of that substrate is depicted in FIG. 26.

Figure 26:
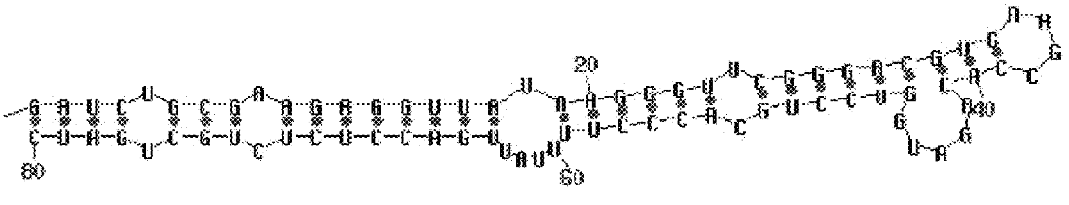
FIG. 26 depicts the predicted structure of a Drosha substrate with a mir-30 loop and base, wherein the Drosha substrate comprises the nucleotide sequence of SEQ ID NO: 23.

The nucleotide sequence of the sequence depicted in FIG. 26 is GAUCUGCGAAGAGGUUAUAAGGGUUCGGGACGUGAAGCCACAGAUGGUCC UGCACCCUUUUAUUGACCUCUCUGCUGAUC (Seq ID No 23).

Fragment D is shown below and is the complement of the sequence shown in bold in Fragment A.

(Seq ID No 24)

Fragment D:
CAGTTGAATAACCTGTGGGGGAACTTGCTTTGCCAAACCCATCCCTGCGG

TTTCTGCCCAGGCTTGGGGAAACTGCTCCAACCAGGACTGTATATCTTGA

TCAGGCTTTACTTGGGGAGAATATAGTCGATATTCATCATCTAATTGGAG

GGTCAACACAGTGATGGGTTTGTTATTCAC

Figure 27:
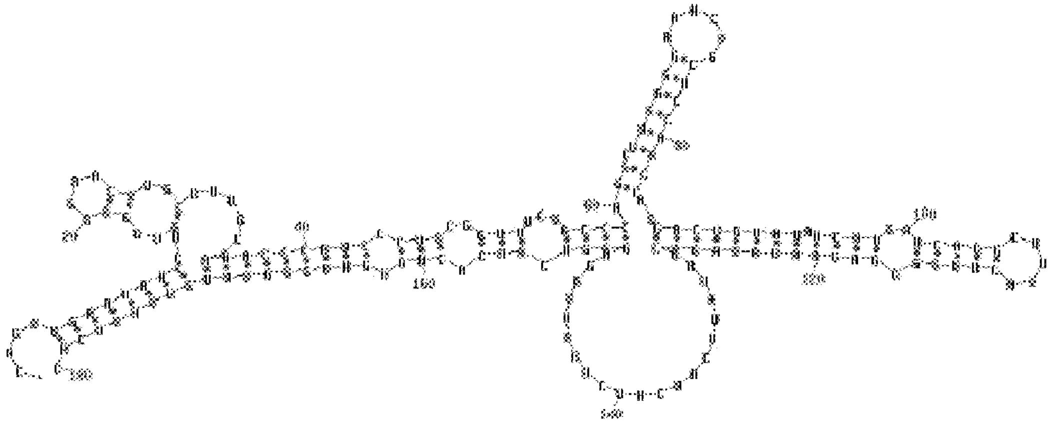
FIG. 27 depicts the predicted folded structure of Fragment D comprising the nucleotide sequence of SEQ ID NO: 24.

A folded Fragment D structure predicted by MFold is depicted in FIG. 27.

In the structure depicted in FIG. 27, bases 35-171 form a significant hairpin structure. Bases 36-61 (AACCCATCCCTGCGGTTCTGCCCAG (Seq ID No 25)) and bases 150-171 (GGGTCAACACAGTGATGGGTTT (Seq ID No 26)) were used to design a Drosha substrate with a mir-29 loop and a mir-30 base. The mir-29 loop was chosen because of complementation between the base 36-61 fragment and the mir-30 loop. The MFold predicted structure of that substrate is depicted in FIG. 28.

Figure 28:
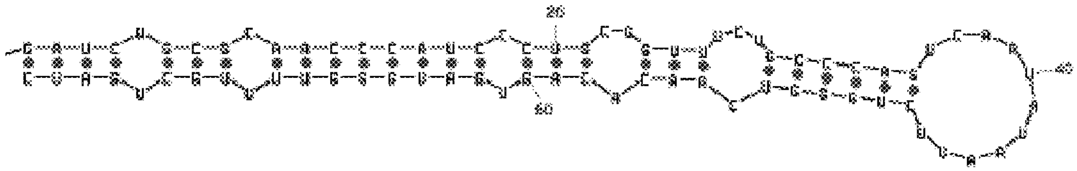
FIG. 28 depicts the predicted structure of a Drosha substrate with a mir-30 loop and mir-30 base, wherein the Drosha substrate comprises the nucleotide sequence of SEQ ID NO: 27.

The nucleotide sequence of the sequence depicted in FIG. 28 is GAUCUGCGCAACCCAUCCCUGCGGUUUCUGCCCAGUCAAUAUAAUUCUGGG UCAACACAGUGAUGGGUUUUGCUGAUC (Seq ID No 27).

In a similar manner, bases 86-107 (GACTGTATATCTTGATCAGGCT (Seq ID No 28)) and bases 111-130 (CTTGGGGAGAATATAGTCGA (Seq ID No 29) were used to design a Drosha substrate with a mir-30 loop and base. The MFold predicted structure of that substrate is depicted in FIG. 29.

Figure 29:
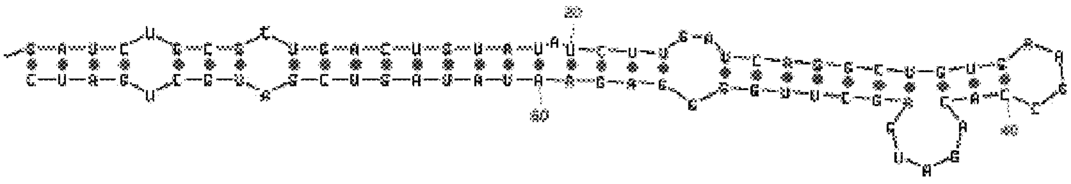
FIG. 29 depicts the predicted structure of a Drosha substrate with a mir-30 loop and base, wherein the Drosha substrate comprises the nucleotide sequence of SEQ ID NO: 30.

The nucleotide sequence of the sequence depicted in FIG. 29 is GAUCUGCGCUGACUGUAUAUCUUGAUCAGGCUGUGAAGCCACAGAUGAGC UUGGGGAGAAUAUAGUCGAUGCUGAUC (Seq ID No 30).

Additional PERV Targeting Strategies: Targeting Two mRNAs Simultaneously:

The antisense strands of portions of two mRNAs were combined to create a single hairpin that targets two mRNAs.

The sequence below is a combined region of the complement of gag (italics) and the complement of pol (underline).

(Seq ID No 31)

*GGGTTGAGAgcagctggtagagtgaacgtgatccTCTCTGTGAGAAGCAG*

*GCTTTGATAGTGGT*CCCTTCTGTAATACACCTTCTCTGCCTCTCTCACTag atcacgtaactcagcctcctgtAACCCTTCCAGTCTCTGAAGTTTCTTTC

TGATATCCAGAG

Figure 30:
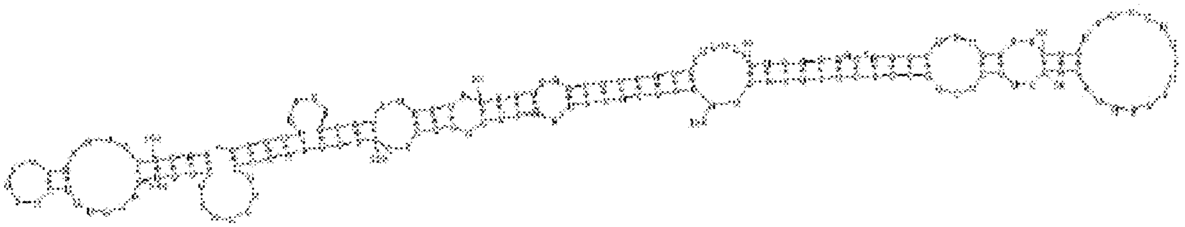
FIG. 30 depicts the potential structure of a fragment comprising the nucleotide sequence of SEQ ID NO: 31.

When the potential structure of this fragment is predicted by MFold, the structure depicted in FIG. 30 is produced.

Figure 31:
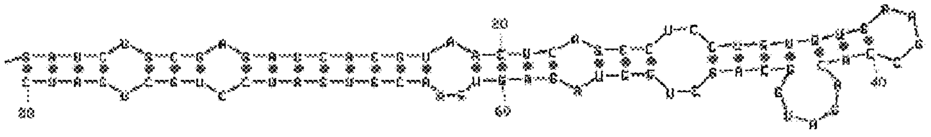
FIG. 31 depicts the predicted structure of a Drosha substrate with a mir-30 loop and base, wherein the Drosha substrate comprises the nucleotide sequence of SEQ ID NO: 32.

To create a single hairpin with the potential to target both gag and pol, bases 100-123 (agatcacgtaactcagcctcctgt (Seq ID No 33)) and bases 10-34 (gcagctggtagagtgaacgtgatcc (Seq ID No 34)) were used to design a Drosha substrate with a mir-30 base and loop and has the MFold predicted structure depicted in FIG. 31.

The nucleotide sequence of the sequence depicted in FIG. 31 is GAUCUGCGAGAUCACGUAACUCAGCCUCCUGUGUGAAGCCACAGAUGGCA GCUGGUAGAGUGAACGUGAUCCUGCUGAUC (Seq ID No 32).

Additional PERV Targeting Strategies: Use of Palindromic siRNAs

To reduce the effects of strand selection of siRNA efficacy, both strands of the hairpin can be designed to be identical or functionally identical. For example, the complement of pol (Fragment A) was analyzed using DNA Strider to identify potential palindromes. In one such analysis (parameters: stringency 11, window 23), the following sequence was identified: TGGGCCTTTTAGCTGAGGCTCG (Seq ID No 36). This sequence was used to design a Drosha substrate with mir-30 base and loop and has the MFold predicted structure depicted in FIG. 32.

Figure 32:
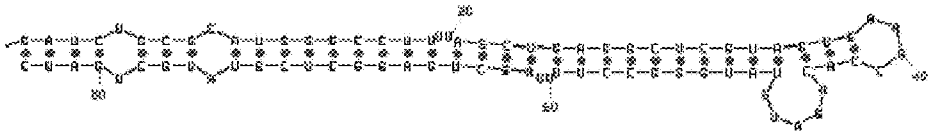
FIG. 32 depicts the predicted structure of a Drosha substrate with a mir-30 loop and base, wherein the Drosha substrate comprises the nucleotide sequence of SEQ ID NO: 37.

The nucleotide sequence of the sequence depicted in FIG. 32 is GAUCUGCGCAUGGGCCUUUUAGCUGAGGCUCGUAGUGAAGCCACAGAUGU AUGGGCCUUUUAGCUGAGGCUCGUAUGCUGAUC (Seq ID No 37).

Figure 33:
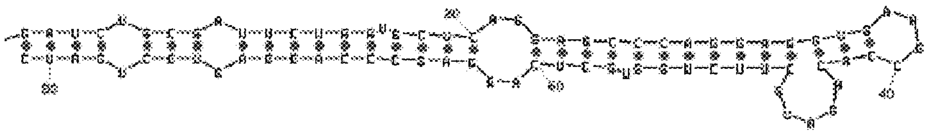
FIG. 33 depicts the predicted structure of a Drosha substrate with a mir-30 loop and base, wherein the Drosha substrate comprises the nucleotide sequence of SEQ ID NO: 39.

In a similar manner, another partial palindrome was identified, CTTCTGGTGCTCAGGAGCCCAGGAG (Seq ID No 38), used to design a Drosha substrate with mir-30 base and loop, and has the MFold predicted structure depicted in FIG. 33.

The nucleotide sequence of the sequence depicted in FIG. 33 is GAUCUGCGAUUCUGGUGCUCAGGAGCCCAGGAGGUGAAGCCACAGAUGCU UCUGGUGCUCAGGAGCCCAGGAGUGCUGAUC (Seq ID No 39).

Figure 34:
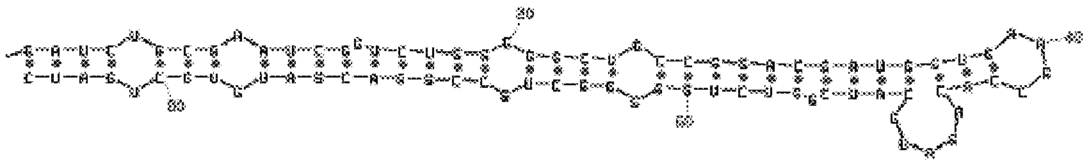
FIG. 34 depicts the predicted structure of a Drosha substrate with a mir-30 loop and base, wherein the Drosha substrate comprises the nucleotide sequence of SEQ ID NO: 41.

Likewise, another partial palindrome was identified, CATCGGTCTGGGGGCTGCCGGACGATG (Seq ID No 40), used to design a Drosha substrate with mir-30 base and loop, and has the MFold predicted structure depicted in FIG. 34.

The nucleotide sequence of the sequence depicted in FIG. 34 is GAUCUGCGAAUCGGUCUGGGGGCUGCCG-GACGAUGGUGAAGCCACAGAUG CAUCGGU-CUGGGGGCUGCCGGACGAUGUGCUGAUC (Seq ID No 41).

Additional PERV Targeting Strategies: Optimization of Hairpin Formation

Figure 35:
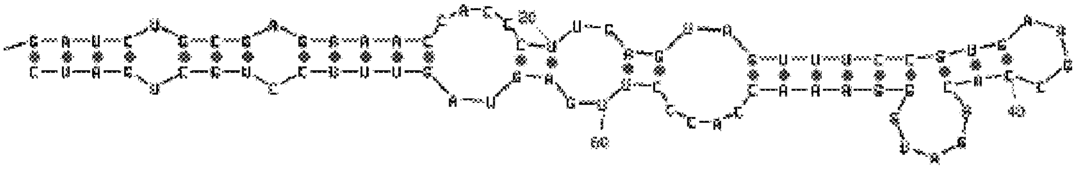
FIG. 35 depicts a Drosha substrate designed to target a portion of PERV env mRNA, wherein the Drosha substrate comprises the nucleotide sequence of SEQ ID NO: 42.

Imperfect hairpins can result from using the above strategies. However, since non Watson/Crick base pairing is possible in RNA, the Drosha substrates can be modified without significant alteration in RNAi targeting. A Drosha substrate designed to target a portion of PERV env mRNA is depicted in FIG. 35. Several "bubbles" are present in the stem portion of the hairpin.

The nucleotide sequence of the sequence depicted in FIG. 35 is GAUCUGCGAGAAACCACCCUUGA-GUAGUUUCCGUGAAGCCACAGAUGGGA AACCAC-CCUUGAGUAGUUUCCUGCUGAUC (Seq ID No 42).

The "C" at position 15 was changed to "U". The "U" can still base-pair with the "G" found in the target as the complement of "C". However, the "U" can also base-pair with the "A" a position 65 in the hairpin. Similarly, the "C" at position 18 was also changed to a "U" to base-pair with the "A" at position 62. The resulting predicted structure has an improved stem and is shown in FIG. 36.

Figure 36:
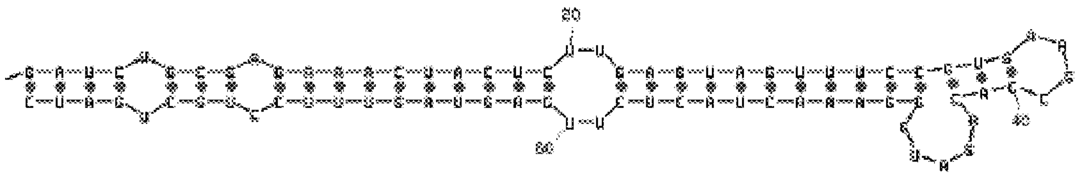
FIG. 36 depicts a Drosha substrate designed to target a portion of PERV env mRNA, wherein the Drosha substrate comprises the nucleotide sequence of SEQ ID NO: 43.

The nucleotide sequence of the sequence depicted in FIG. 36 is GAUCUGCGAGAAACUACUCUUGA-GUAGUUUCCGUGAAGCCACAGAUGGGA AACUA-CUCUUGAGUAGUUUCCUGCUGAUC (Seq ID No 43).

See also, Zeng Y, Cullen B R. Structural requirements for pre-microRNA binding and nuclear export by Exportin 5. Nucleic Acids Res. 2004 Sep. 8; 32(16):4776-85; Zeng Y, Cullen B R. Sequence requirements for micro RNA processing and function in human cells. RNA. 2003 January; 9(1):112-23; Zeng Y, Wagner E J, Cullen B R. Both natural and designed micro RNAs can inhibit the expression of cognate mRNAs when expressed in human cells. Mol Cell. 2002 June; 9(6):1327-33; Boden D, Pusch O, Silbermann R, Lee F, Tucker L, Ramratnam B. Enhanced gene silencing of HIV-1 specific siRNA using microRNA designed hairpins. Nucleic Acids Res. 2004 Feb. 13; 32(3):1154-8; Lee Y, Ahn C, Han J, Choi H, Kim J, Yim J, Lee J, Provost P, Radmark O, Kim S, Kim V N. The nuclear RNase III Drosha initiates microRNA processing. Nature. 2003 Sep. 25; 425(6956): 415-9; M. Zuker. Mfold web server for nucleic acid folding and hybridization prediction. Nucleic Acids Res. 31 (13), 3406-15, (2003) [http://www.bioinfo.rpi.edu/applications/mfold/old/rna/form1.cgi].

Example 3: Sequential Cloning of Hairpin Oligonucleotides

To assemble oligos for clustered interference RNA, linker sequences must the considered to prevent unintentional structures from forming. If the same restriction sites are used sequentially, homologies at the base of the hairpin can cause unintentional base pairing. For example, if a vector is designed with two, non-compatible restriction sites a sequence can be cloned directionally into those two sites. In the process, the upstream site can be destroyed and also re-supplied to the new vector in the downstream region in preparation for the next hairpin.

Vector ends after being cut with BclI and MluI:

| BclI Overhang | Mlul Overhang |
| --- | --- |
| NNNT 3'<br>NNNACTAG 5' | 3'CGCGTNNN<br>5'ANNN |

Hybridized Oligonucleotides:

(Seq ID No 44)
5'GATCtgcgcTTAGATCCAGGGCTCATAATgtgaagccacagatgATTA TGAGCCCTGGATCTAATtgcTGATCActagtA 3'

(Seq ID No 45)
3'acgcgAATCTAGGTCCCGAGTATTAcacttcggtgtctacTAATACTC GGGACCTAGATTAacgACTAGTgatcaTGCGC 5'

Resulting Clone:

Destroyed Recreated Bcl I (italics) — Supplied Bcl I (underlined) — Mlu I (bold)

*NT*GATCtgcgcTTAGATCCAGGGCTCATAATgtgaagccacagatgATTATGAGCCCTGGATCTAATtgcTGATCActagtACGCGTN
*NACTAG*acgcgAATCTAGGTCCCGAGTATTAcacttcggtgtctacTAATACTCGGGACCTAGATTAacgACTAGTgatcaTGCGCAN
(Seq ID No 46)

In this strategy, the oligonucleotide-supplied Bcl I site can be used for the next cloning step and new oligonucleotides can continue to be added to each successive vector provided that none of the introduced stem sequences supply additional sites for either Bcl I or Mlu I.

Below is the resulting sequence of a series of three oligos cloned into a series of vectors using the strategy just described (vector, oligo 1, oligo 2, oligo 3):

(Seq ID No 47)
*NT*GATCtgcgcTTAGATCCAGGGCTCATAATgtgaagccacagatgATTA

TGAGCCCTGGATCTAATtgcTGATCtgcgcGGTAGAGACTTACTGACCAA gtgaagccacagatgTTGGTCAGTAAGTCTCTACCTtgcT*GATCtgcgcA*

*GAACATAGAGACCAATGCAgtgaagccacagatgTGCATTGGTCTCTATG*

*TTCTTtgcTGATCActagtA**CGCGTN*

Figure 37:
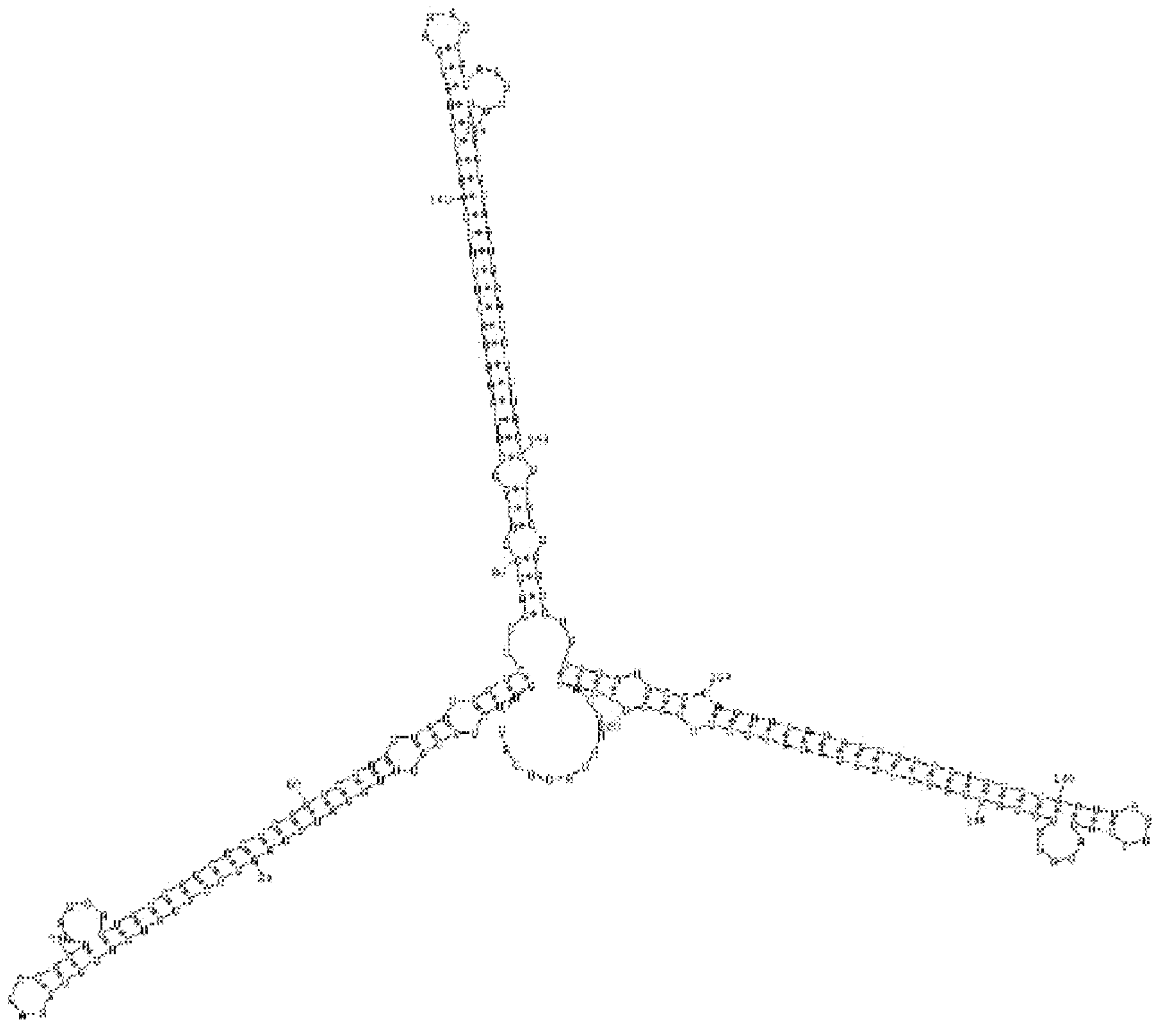
FIG. 37 depicts a predicted structure of an oligonucleotide comprising the nucleotide sequence of SEQ ID NO: 47.

The predicted structure of this sequence is depicted in FIG. 37. Each of the three hairpins are predicted to have the same general structure.

Using this strategy, any number of additional Drosha substrates can be added without alteration of their individual predicted structures.

Example 4: Synthetic Intron Assembly

An intron was designed, based loosely on the intron found in the murine eosinophil-associated, ribonuclease A family genes (EarX) and a commercially available vector pCpG (InvivoGen, San Diego, Calif.). The design of this intron included creation of restriction sites that allow of for placement of the inton into any SbfI site within exon sequence. Upon splicing of primary transcripts containing this intron, the resulting mRNA is unaltered in comparison to its non-engineered, endogenous counterpart. In addition, a small series of cloning sites were included within the intron to allow subsequent cloning of iRNA molecules/Drosha substrates. This sequence was cloned into an SbfI site found naturally within the coding region of a dsRED expression vector (a red fluorescent protein from a corallimorpharian). Upon transfection into mammalian cells, the resulting intron is appropriately spliced to yield functional dsRED protein. Since the central six nucleotides of an SbfI site comprise a PstI site, this intron can also be cloned directly into PstI sites.

Intron Sequence:

(Sbf I sites shown bold, multiple cloning sites shown italics, functional intron underlined.)

(Seq ID No 48)

cctgcagGTAAGTCACTGCTGTCTATGCCTGGGAAAGGGGGGCAGGAGAT

GGGGCAGTGCAGGAAAAGTGGCACTATGAACCCG*tgatcactagtacgcg*

*tgtaca*ATTGTACTAACCTTCTTCTCTTTCCTCTCCTGCAGg

Example 5—Use of iRNA to Reduce Expression of Contaminating Proteins

In this example, expression of an endogenous protein is reduced to prevent or reduce contamination of a product of a transgene. Transgenic animals are beginning to be used as sources for therapeutic proteins. These proteins are expressed from transgenes. The transgene expression can be targeted to specific tissues or cells types to provide compartmentalized harvesting of such proteins. For example, a protein can be concentrated in milk of transgenic animals by driving expression of said protein from a mammary specific promoter. In addition, a transgene may be selectively expressed in a specific cell type to allow for specific processing. For example, a human immunoglobulin locus can be used to direct recombination, expression, and processing of human polyclonal antibodies in livestock B-cells. In either of these cases, endogenous proteins can contaminate the material collected for purification. This protein may be evolutionarily unrelated but co-purifies with the desired product. Alternatively, the contaminating protein may be the endogenous counterpart of the transgene product.

To provide guidance for the application of interfering RNA to reduce contaminating protein production in transgenic livestock, the following example is provided using immunoglobulin genes:

Step 1.

The technique as described in Example 2, is used wherein the gag, pol and env genes described in Example 2 are replaced with genes for variable domains of porcine immunoglobulin (Ig), either variable or constant. In addition, Ig heavy-chain, Ig light chain kappa, and Ig light chain lambda are included as potential targets in the strategy.

Step 2:

The technique as described in Example 2 is used wherein the analysis of PERV targets is replaced by an analysis of Ig targets to determine the specificity of the iRNA constructs to the given target. In addition to the test of porcine Ig targets, potential targets that share homology with the human Ig transgene expressed in the animals are excluded.

Step 3:

Each selected iRNA construct is introduced into a porcine B-cell cell line. Down-regulation of Ig gene products is assayed by the methods described in Example 2. Specifically, mRNA is assessed by RT-PCR, and surface Ig is measured via labeled antibodies.

Steps 4 and 5:

Fetal fibroblasts are contacted with the iRNA constructs identified in preceding steps. However, as fetal fibroblasts do not express Ig gene products, their utility in screening in this assay is limited. In this case, late gestation fetuses are used to confirm iRNA effectiveness by RT-PCR and immunoassays. In a parallel set of experiments, fetal fibroblasts are engineered to expressed porcine Ig transgenes corresponding to the identified targets and iRNA constructs are tested for efficacy. Unintended targeting of human Ig is also assayed. Only iRNA constructs that do not target human Ig transgenes are used to produce fetuses.

Total mRNA is harvested from thymus, spleen, and blood of late gestation fetuses. This RNA is used to screen for endogenous Ig down-regulation by RT-PCR using primers specific to each Ig locus. Each assay includes additional control sequences to ensure that no errors are introduced.

Cells that contain human Ig transgenes are used to reconstruct embryos via nuclear transfer. These cells can be derived from screened fetuses, frozen and stored cell colonies, or cells used to produce the screened fetuses. Reconstructed embryos are used to produce transgenic offspring with the desired traits.

Confirmation of both down-regulation of endogenous porcine Ig gene products and expression of transgenic gene products (i.e. human Ig) is confirmed. Animals are bled at various stages of maturity and analyzed for iRNA transgene expression, Ig transgene expression, and endogenous Ig gene suppression. The procedure is also repeated under conditions eliciting various immunological states.

Example 6—Use of Interfering RNA to Produce Virus Resistant Animals

RNA interference technology is applied to produce animals that are resistant to a virus and/or have reduced capacity to shed or propagate a virus. A transgene is constructed that results in expression of interfering RNA that targets one or more essential regions of Marek's disease virus. The transgene construct is then added to the genome of chickens to produce a genetic line that heritably expresses iRNA. In this example, the genetic line heritably expresses two. RNAs that hybridize to produce a dsRNA molecule, targeted to the essential regions of Marek's disease virus. In a non-disease state the dsRNA is functionally inert, however, when a cell becomes infected with Marek's disease virus, the dsRNA interferes with a viral gene, thus disrupting the viral life-cycle. Such chickens are therefore resistant to Marek's disease.

To provide guidance in the application of interfering RNA to produce animals with enhanced resistance to a virus, the following is provided:

Method:

The technique as described in Example 1 is used wherein PERV is replaced by Marek's disease virus. In addition, a cell that sheds Marek's disease is used instead of PK-15 cells. Furthermore, methods for the production of transgenic poultry, varying slightly from those described but known in the art, can be implemented. Embryonic chicks are used to confirm effectiveness. The appropriate integration site for the iRNA is identified by screening for iRNA expression in transgenic animals after they have reproduced. To this end, transgenic offspring are available for further propagation of appropriate lines.

Example 7—Use of Interfering RNA to Reduce Rejection of Xenotransplanted Organs

Using the techniques described above, a transgene is constructed for expression of dsRNA that targets VCAM to suppress inflammation in xenotransplanted organs. To provide guidance in the application of interfering RNA to produce xenotransplantation pigs with enhanced organ survival, the following is provided:

Method:

The methods described in Examples 1 serve as a model for screening iRNA targets. In this embodiment, porcine VCAM is the target. A porcine cell line that expresses VCAM is used in place of PK-15 cells. A similar strategy as disclosed in Example 1, Step 2 and FIG. 11 is employed to remove iRNA targets that are active against VCAM family members.

Example 8—Use of Interfering RNA to Reduce Expression of an Endogenous Gene

RNA interference is used to suppress expression of an endogenous gene in a tissue specific manner. A transgene is assembled for expression of dsRNA which targets myostatin (GDF-8). In this example, the suppression of the target is intended to be incomplete. Mutations of myostatin provide increased muscle mass in livestock and mice, indicating that an economically beneficial phenotype could accompany a loss of function in myostatin. However, complete elimination of myostatin produces a phenotype that is not economically viable for meat production (Yang J. et al. (2001) *Mol. Reprod. Dev.* 60(3):351-61). Interfering RNA technology is used to produce animals suppressed expression of myostatin. Tissue specific expression of an iRNA molecule that provides less than complete suppression is provided by a tissue specific manner on a pol III promoter.

Method:

The methods described in Example 1 serve as a model for screening iRNA targets. In this example, porcine GDF-8 is the target rather than PERV. A porcine cell line that expressed GDF-8 is used instead of PK-15 cells. The iRNA molecules identified, first by virtual sequence alignment and thereafter by in vitro screening are subject to elimination if they are not effective within the parameters identified. Therefore, unlike the previous examples, complete abolition of myostatin eliminates an iRNA molecule from consideration.

Example 9—Use of Interfering RNA to Provide Resistance to Viruses

RNA interference technology is applied to produce pigs that are resistant to viruses that are dangerous to patients undergoing xenotransplantation. In xenotransplantation procedures, a risk exists that donor organs are a reservoir human, in addition to porcine, viruses. For example, one virus that poses a risk to a patient undergoing a xenotransplant is an influenza virus. Therefore, a transgene is constructed that results in the expression of interfering RNA that targets one or more essential regions of viruses that present risks to a patient receiving a xenotransplanted organ. The methods as described in Example 1 serve as a model for screening iRNA targets. In this case, the influenza virus and its homologous provide the targets, instead of PERV. Instead of PK-cells, a cell that sheds influenza virus is used for screening. The iRNA constructs are screened for their capacity to fully inhibit influenza viral mRNA as well as viral particle production. When useful iRNA sequences are identified, they are linked within a vector to provide a transgenic construct that can completely eliminate the expression of the viral gene products. Further rounds of screening ensure that the most effective combination is identified. After screening, the constructs are introduced into fibroblasts to be used in nuclear transfer procedures, thus providing a transgenic cell line resistant to influenza virus.

Example 10—Use of Interfering RNA to Provide Genetic Selection

Selectable markers are limiting in mammalian cells in that most marker genes provide antibiotic resistance and a finite number have been characterized. Therefore, siRNA transgenes that provide a selectable phenotype can serve as selectable marker genes. The methods described in Example 1 serve as a model for screening iRNA targets. In this case, a cell that provides a selectable phenotype which a particular gene is downregulated is used. The iRNA constructs are screened for their capacity to produce the selectable phenotype. When useful iRNA construct are identified, they can be linked to other genes or other DNA fragments to provide a selectable phenotype. Additionally, this strategy can be used to create combinations of genes that allow selection of homologous recombination events. As an example, a non-iRNA selectable marker gene is included between two targeting arms. Outside of these arms an anti-selectable marker iRNA transgene is placed. The iRNA transgene is identified as in above examples using the selectable marker gene as the target gene. Upon random integration, the iRNA transgene prevents function of the selectable marker and the integration event is not selected. Upon homologous recombination, the iRNA transgene is not present and the selectable marker gene functions. Similarly and alternatively, the iRNA transgene can be directed against a gene essential to cell survival.

The invention described herein can be practiced in the absence of any element or elements, limitation or limitations which is not specifically disclosed herein. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed can be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group.

I claim:

1. A heritable DNA template encoding iRNA molecules that regulate the expression of a porcine endogenous retrovirus (PERV) family of genes wherein:

(i) the heritable DNA template encodes at least two iRNA molecules that can stably integrate into the genome of a porcine cell;

(ii) at least one of the iRNA molecules is homologous to (a) the following pol sequence of PERV: GTAGAGACTTACTGACCAA (SEQ ID NO. 244) or a complement thereof: or (b) the following gag sequence of PERV: GTTAGATCCAGGGCTCATAAT (SEQ ID NO. 211) or a complement thereof; and (iii) PERV gene expression is functionally eliminated by the iRNA molecules in porcine cells and animals infected by PERV.

2. The heritable DNA template of claim 1, wherein the at least two iRNA molecules target the same region of a gene.

3. The heritable DNA template of claim 1, wherein the at least two iRNA molecules target at least two different regions of the same gene.

4. The heritable DNA template of claim 1, wherein the iRNA molecules bind to a PERV selected from the group consisting of PERV-A, PERV-B and PERV-C.

5. The heritable DNA template of claim 1, wherein the iRNA molecules bind to PERV-A and PERV-B.

6. The heritable DNA template of claim 1 wherein the iRNA molecules bind to PERV-A and PERV-C.

7. The heritable DNA template of claim 1 wherein the iRNA molecules bind to PERV-B and PERV-C.

8. The heritable DNA template of claim 1, wherein an additional iRNA molecule targets the env region of the porcine endogenous retrovirus.

9. The heritable DNA template of claim 1, wherein at least one of the iRNA molecules is homologous to the following gag sequence: GTTAGATCCAGGGCTCATAAT (SEQ ID NO. 211), or a complement thereof.

10. The heritable DNA template of claim 1, wherein at least one of the iRNA molecules is homologous to the following pol sequence: GTAGAGACTTACTGACCAA (SEQ ID NO. 244), or a complement thereof.

11. The heritable DNA template of claim 1, wherein the iRNA molecules target the pol, env and gag region of the porcine endogenous retrovirus.

12. The heritable DNA template of claim 1, wherein at least one of the iRNA molecules is homologous to the following gag sequence: GTTAGATCCAGGGCTCATAAT (SEQ ID NO. 211), or a complement thereof; and wherein at least one of the iRNA molecules is homologous to the following pol sequence GTAGAGACTTACTGACCAA (SEQ ID NO. 244), or a complement thereof.

13. A heritable DNA template encoding iRNA molecules that regulate the expression of a family of genes wherein:

(i) the heritable DNA template encodes at least two iRNA molecules that can stably integrate into the genome of a porcine cell;

(ii) the iRNA molecules are homologous to a conserved sequence of a gag region of porcine endogenous retrovirus (PERV) genes;

(iii) the iRNA molecules target the following gag sequence of PERV: GTTAGATCCAGGGCTCATAAT (SEQ ID NO. 211), or a complement thereof; and (iv) PERV gene expression is functionally eliminated by the iRNA molecules in porcine cells and animals infected by PERV.

14. A heritable DNA template encoding iRNA molecules that regulate the expression of a family of genes wherein:

(i) the heritable DNA template encodes at least two iRNA molecules that can stably integrate into the genome of a porcine cell;

(ii) the iRNA molecules are homologous to a conserved sequence of a pol region of porcine endogenous retrovirus (PERV) genes;

(iii) the iRNA molecules target the following pol sequence of PERV: GTAGAGACTTACTGACCAA (SEQ ID NO. 244) or a complement thereof; and (iv) PERV gene expression is functionally eliminated by the iRNA molecules in porcine cells and animals infected by PERV.

15. A heritable DNA template encoding iRNA molecules that regulate the expression of a family of genes wherein:

(i) the heritable DNA template encodes at least two iRNA molecules that can stably integrate into the genome of a porcine cell;

(ii) at least one iRNA molecule is homologous to the following pol sequence of PERV: GTAGAGACT-TACTGACCAA (SEQ ID NO. 244) or a complement thereof;

(iii) at least one iRNA molecule is homologous to the following gag sequence of PERV: GTTAGATCCA-GGGCTCATAAT (SEQ ID NO. 211) or a complement thereof; and (iv) PERV gene expression is functionally eliminated by the iRNA molecules in porcine cells and animals infected by PERV.

* * * * *

SEQUENCE LISTING

<160> NUMBER OF SEQ ID NOS: 272

<210> SEQ ID NO 1
<211> LENGTH: 63
<212> TYPE: RNA
<213> ORGANISM: Artificial Sequence
<220> FEATURE:
<223> OTHER INFORMATION: Synthetic Construct

<400> SEQUENCE: 1
uguaaacauc cucgacugga agcugugaag ccacagaugg gcuuucaguc ggauguuugc 60
agc 63

<210> SEQ ID NO 2
<211> LENGTH: 108
<212> TYPE: RNA
<213> ORGANISM: Artificial Sequence
<220> FEATURE:
<223> OTHER INFORMATION: Synthetic Construct

<400> SEQUENCE: 2
ugcuguugac agugagcgac uguaaacauc cucgacugga agcugugaag ccacagaugg 60
gcuuucaguc ggauguuugc agcugccuac ugccucggac uucaaggg 108

<210> SEQ ID NO 3
<211> LENGTH: 71
<212> TYPE: RNA
<213> ORGANISM: Artificial Sequence
<220> FEATURE:
<223> OTHER INFORMATION: Synthetic Construct

<400> SEQUENCE: 3
gcgacuguaa acauccucga cuggaagcug ugaagccaca gaugggcuuu cagucggaug 60
uuugcagcug c 71

<210> SEQ ID NO 4
<211> LENGTH: 15
<212> TYPE: RNA
<213> ORGANISM: Artificial Sequence
<220> FEATURE:
<223> OTHER INFORMATION: Synthetic Construct

<400> SEQUENCE: 4
gugaagccac agaug 15

<210> SEQ ID NO 5
<211> LENGTH: 77
<212> TYPE: RNA
<213> ORGANISM: Artificial Sequence
<220> FEATURE:
<223> OTHER INFORMATION: Synthetic Construct

<400> SEQUENCE: 5
gaucugcgcu gacuguauau cuugaucagg cugugaagcc acagaugagc uuggggagaa 60
uauagucgau gcugauc 77

<210> SEQ ID NO 6
<211> LENGTH: 1557
<212> TYPE: DNA
<213> ORGANISM: Artificial Sequence
<220> FEATURE:
<223> OTHER INFORMATION: Synthetic Construct

<400> SEQUENCE: 6

```
ggacagacgg tgaagacccc ccttagtttg actctcgaaa attggactga agttagatcc     60

agggctcata atttgtcagt tcaggttaag aagggacctt gggagatttc ccgtgcctct    120

gaatggcaaa cattcgatgt tggatggcca tcagagggga cttttaattc tgaaattatc    180

ctggctgtta aagcaatcat tttcagact ggacccggct ctcatcctga tcaggagccc    240

tatatcctta cgtggcaaga tttggcagaa gatcctccgc catgggttaa accatggcta    300

tggggggggg ggagccaggc ccccgaatcc tggctcttgg agagaaaaac aaacactcgg    360

ccgaaaaagg ggggggggt cctcatatct accccgagat cgaggagccg ccgacttggc    420

cggaacccca acctgttccg gggggggggg ttccagcaca gggtgctgcg aggggaccct    480

ctgcccctcc tggagctccg gtggtggagg gacctgctgc cgggactcgg agccggagag    540

gcgccacccc ggagcggaca gacgagatcg cgatattacc gctgtgcacc tatggccctc    600

ccatggcggg gggccaattg cagcccctcc agtattggcc cttttcttct gcagatctct    660

ataattggaa aactaaccat ccccctttct cggaggatcc caacgcctca cggggttggt    720

ggagtccctt atgttctctc accagcctac ttgggatgat tgtcaagggg gggggggggg    780

gggggggggg gggggggggg ggggggggaat tctgttagag gctagaaaaa atgttcctgg    840

ggccgacggg cgacccacgc agttgcaaaa tgagattgac atgggatttc ccttgactcg    900

ccccggttgg gactacaaca cggctgaagg tagggagagc ttgaaaatct atcgccaggc    960

tctggtggcg ggtctccggg gcgcctcaag acggcccact aatttggcta aggtaagaga   1020

ggtgatgcag ggaccgaacg aacctccctc ggtatttctt gagaggctca tggaagcctt   1080

caggcggttc acccctttt gggggggggg gggggggggg ggggcctcag tggccctggc   1140

cttcattggg cagtcggctc tggatatcag aaagaaactt cagagactgg aagggttaca   1200

ggaggctgag ttacgtgatc tagtgagaga ggcagagaag gtgtattaca gaagggaggg   1260

gggggggggg gggggggggg gggggggggg gggggggggg gggggggggg gggggggggg   1320

gggggggggg gggggggggg gggggggggg gggggggggg gggggggggg gggggggggg   1380

gggggggggg gggggggggg gggggggggg gggggggggg gggggggggg gggggggggg   1440

gggggggggg gggggggggg gggggggggg gggggggggg ggggggaaaa aggacactgg   1500

gcaaggaact gccccaagaa gggaaacaaa ggaccgaatt tcctatttct agaagaa      1557
```

<210> SEQ ID NO 7
<211> LENGTH: 1657
<212> TYPE: DNA
<213> ORGANISM: Artificial Sequence
<220> FEATURE:
<223> OTHER INFORMATION: Synthetic Construct

<400> SEQUENCE: 7

```
ggcaacggca gtatccatgg actacccgaa gaaccgttga cttggcagtg ggacgggtaa     60

cccactcgtt tctggtcatc cctgagtgcc cagtacccct tctaggtaga gacttactga    120

ccaagatggg agctcaaatt tcttttgaac aaggaagacc agaagtgtct gtgaataaca    180

aacccatcac tgtgttgacc ctccaattag atgatgaata tcgactatat tctccccaag    240

taaagcctga tcaagatata cagtcctggt tggagcagtt tccccaagcc tgggcagaaa    300

ccgcagggat gggtttggca aagcaagttc ccccacaggt tattcaactg aaggccagtg    360

ctacaccagt atcagtcaga cagtacccct tgagtagaga ggctcgagaa ggaatttggc    420

cgcatgttca aagattaatc caacagggca tcctagttcc tgtccaatcc ccttggaata    480
```

-continued

```
ctcccctgct accggttagg tttttttttt tttttttttt tttttttttt ttttttttga    540

gagaggtcaa taaaagggtg caggacatac acccaacggt cccgaaccct tataacctct    600

tgagcgccct cccgcctgaa cggaactggt acacagtatt ggacttaaaa gatgccttct    660

tctgcctgag attacacccc actagccaac cgctttttgc cttcgaatgg agagatccag    720

gtacgggaag aaccgggcag cttttttttt tttttttttt tttttttttt tttttttttt    780

tttttttttt ttacgaagcc ctacacaggg acctggccaa cttcaggatc caacaccccc    840

agtgaccctc tccagtactg ggatgacctg cttctagtgg agccaccaac aggactgcta    900

gaaggtacga aggcactact actgaattgt ctgacctagg ctacgagcct cagctaaaag    960

gcccagattg cagagagagg taacatactt gggtacagtc tgcgggacgg gcagtgatgg   1020

ctgacggagg cacggaagag aactgtagtc cagatacctt tttttttttt ttttttttcaa   1080

gtgagagagt tttgggggac agctggattt tgcagactgt ggatcccggg gtttgcgacc   1140

ttagcagccc cactctaccc gctaaccaaa gaaaaagggg agttctcctg ggctcctgag   1200

caccagaagg catttgatgc tatcaaaaag gccctgctga gcacacctgc tctggccctc   1260

cctgatgtaa ctaaaccctt tactctttat gtggatgaat gtaagggggt agcccgggga   1320

gttttaaccc aatccctagg accatggagg agacctgttg cctacctgtc aaagaagctc   1380

gatcctgtag ccagtggttg gcccatatgc ctgaaggcta tcgcagccgt ggccatactg   1440

gtcaaggacg ctgacaaatt gactttggga cagaatataa ctgtaatagc cccccatgcg   1500

ttggagaaca tcgtccggca gcccccagac cgatggatga ccaacgcccg catgacccac   1560

tatcaaagcc tgcttctcac agagaggatc acgttcactc taccagctgc tctcaaccct   1620

gccactcttc tgcctgaaga gactgatgaa ccagtga                              1657
```

<210> SEQ ID NO 8
<211> LENGTH: 2036
<212> TYPE: DNA
<213> ORGANISM: Artificial Sequence
<220> FEATURE:
<223> OTHER INFORMATION: Synthetic Construct

<400> SEQUENCE: 8

```
catcccacgt taagccggcg ccacctcccg attcggggtg gaaagccgaa aagactgaaa     60

atccccttaa gcttcgcctc catcgcgtgg ttccttactc tgtcaataac ctctcagact    120

aatggtatgc gcataggaga cagcctgaac tcccataaac ccttatctct cacctggtta    180

attactgact ccggcacagg tattaatatc aacaacactc aaggggaggc tcctttagga    240

acctggtggc ctgatctata cgtttgcctc agatcagtta ttcctttttt tttttttttt    300

tttttttttt tttttttttt ccatgctcac ggattttatg tttgcccagg accaccaaat    360

aatggaaaac attgcggaaa tcccagagat ttcttttgta aacaatggaa ctgtgtaacc    420

tctaatgatg gatattggaa atggccaacc tctcagcagg atagggtaag tttttcttat    480

gtcaattttt tttttttttt tttttttttt tttttttttt tttttttttt tttttttttt    540

tttttttttt tttttttttt tttttttttt tttttttttt tttttttttt tttttttttt    600

tagattacct aaaaataagt ttcactgaga agggaaacca agaaaatatc ctaaaatggg    660

taaatggtat gtcttgggga atggtatatt atggaggctc gggtaaacaa ccaggctcca    720

ttctaactat tcgttttttt tttttttttt ttttttttcc tccaatggct ataggaccaa    780

atacggtctt gacgggtcaa agacccccaa cccaaggacc aggaccatcc tctaacataa    840

cctctttttt tttttttttt tttttttttt tttttttttt tttttttttt tttttttttt    900
```

```
ttttttttt ttttttttt ttttttttt ttctagcagc acgactaaaa tgggggcaaa    960
actttttagc ctcatccagg gagcttttca agctcttaac tccacgactc cagaggctac   1020
ctcttcttgt tggctatgct tagctttggg cccaccttac tatgaaggaa tggctagaag   1080
agggaaattc aatgtgacaa aagaacatag agaccaatgc acatggggat cccaaaataa   1140
gcttaccctt actgaggttt ctggaaaagg cacctgcata ggaaaggttc ccccatccca   1200
ccaacacctt tgtttttttt ttttttttt tttttttcc tctgagagtc aatatctggt   1260
acctggttat gacaggtggt gggcatgtaa tactggatta accccttgtg tttccacctt   1320
ggtttttaac caaactaaag atttttgcat tatggtccaa attgttcccc gagtgtatta   1380
ctatcccgaa aaagcaatcc ttgatgaata tgactacaga aatcatcgac aaaagagagg   1440
acccatatct ctgacacttg ctgtgatgct cggacttgga gtggcagcag gtgtaggaac   1500
aggaacagct gccctggtca cgggaccaca gcagctagaa acaggactta gtaacctaca   1560
tcgaattgta acagaagatc tccaagccct agaaaaatct gtcagtaacc tggaggaatc   1620
cctaacctcc ttatctgaag tagtcctaca gaatagaaga gggttagatt tattatttct   1680
aaaagaagga ggattatgtg tagccttttt ttttttttt ttttttttt ttttttttt   1740
ttttttttt ttttgactcc atgaacaaac ttagagaaag gttggagaag cgtcgaaggg   1800
aaaaggaaac tactcaaggg tggtttgagg gatggttcaa caggtctcct tggttggcta   1860
ccctactttc tgctttaaca ggacccttaa tagtcctcct cctgttactc acagttgggc   1920
catgtattat taacaagtta attgccttca ttagagaacg aataagtgtt ttttttttt   1980
ttttttttt ttttttttt ttttttttt ttttttttt tttttctggc cgctag        2036
```

<210> SEQ ID NO 9
<211> LENGTH: 1657
<212> TYPE: DNA
<213> ORGANISM: Artificial Sequence
<220> FEATURE:
<223> OTHER INFORMATION: Synthetic Construct

<400> SEQUENCE: 9

```
ggcaacggca gtatccatgg actacccgaa gaaccgttga cttggcagtg ggacgggtaa     60
cccactcgtt tctggtcatc cctgagtgcc cagtacccct tctaggtaga gacttactga    120
ccaagatggg agctcaaatt tcttttgaac aaggaagacc agaagtgtct gtgaataaca    180
aacccatcac tgtgttgacc ctccaattag atgatgaata tcgactatat tctccccaag    240
taaagcctga tcaagatata cagtcctggt tggagcagtt tccccaagcc tgggcagaaa    300
ccgcagggat gggtttggca aagcaagttc ccccacaggt tattcaactg aaggccagtg    360
ctacaccagt atcagtcaga cagtacccct tgagtagaga ggctcgagaa ggaatttggc    420
cgcatgttca aagattaatc caacagggca tcctagttcc tgtccaatcc ccttggaata    480
ctcccctgct accggttagg ttttttttt ttttttttt ttttttttt tttttttga    540
gagaggtcaa taaaagggtg caggacatac acccaacggt cccgaaccct tataacctct    600
tgagcgccct cccgcctgaa cggaactggt acacagtatt ggacttaaaa gatgccttct    660
tctgcctgag attacacccc actagccaac cgctttttgc cttcgaatgg agagatccag    720
gtacgggaag aaccgggcag cttttttttt ttttttttt ttttttttt ttttttttt    780
ttttttttt ttacgaagcc ctacacaggg acctggccaa cttcaggatc caacaccccc    840
agtgaccctc tccagtactg ggatgacctg cttctagtgg agccaccaac aggactgcta    900
```

gaaggtacga aggcactact actgaattgt ctgacctagg ctacgagcct cagctaaaag 960
gcccagattg cagagagagg taacatactt gggtacagtc tgcgggacgg gcagtgatgg 1020
ctgacggagg cacggaagag aactgtagtc cagatacctt tttttttttt tttttttcaa 1080
gtgagagagt tttgggggac agctggattt tgcagactgt ggatcccggg gtttgcgacc 1140
ttagcagccc cactctaccc gctaaccaaa gaaaaagggg agttctcctg ggctcctgag 1200
caccagaagg catttgatgc tatcaaaaag gccctgctga gcacacctgc tctggccctc 1260
cctgatgtaa ctaaaccctt tactctttat gtggatgaat gtaagggggt agcccgggga 1320
gttttaaccc aatccctagg accatggagg agacctgttg cctacctgtc aaagaagctc 1380
gatcctgtag ccagtggttg gcccatatgc ctgaaggcta tcgcagccgt ggccatactg 1440
gtcaaggacg ctgacaaatt gactttggga cagaatataa ctgtaatagc cccccatgcg 1500
ttggagaaca tcgtccggca gcccccagac cgatggatga ccaacgcccg catgacccac 1560
tatcaaagcc tgcttctcac agagaggatc acgttcactc taccagctgc tctcaaccct 1620
gccactcttc tgcctgaaga gactgatgaa ccagtga 1657

<210> SEQ ID NO 10
<211> LENGTH: 266
<212> TYPE: DNA
<213> ORGANISM: Artificial Sequence
<220> FEATURE:
<223> OTHER INFORMATION: Synthetic Construct

<400> SEQUENCE: 10
ggtatctgga ctacagttct cttccgtgcc tccgtcagcc atcactgccc gtcccgcaga 60
ctgtacccaa gtatgttacc tctctctgca atctgggcct tttagctgag gctcgtagcc 120
taggtcagac aattcagtag tagtgccttc gtaccttcta gcagtcctgt tggtggctcc 180
actagaagca ggtcatccca gtactggaga gggtcactgg gggtgttgga tcctgaagtt 240
ggccaggtcc ctgtgtaggg cttcgt 266

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
cttcgtacct tctagcagtc 20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
actggagagg gtcactgggg 20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13 actgg agagg gtcactgggg 20

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct

<400> SEQUENCE: 14
gtcatcccag tactggagag ggt 23

<210> SEQ ID NO 15
<211> LENGTH: 24
<212> TYPE: DNA
<213> ORGANISM: Artificial Sequence
<220> FEATURE:
<223> OTHER INFORMATION: Synthetic Construct

<400> SEQUENCE: 15
cttctagcag tcctgttggt ggct 24

<210> SEQ ID NO 16
<211> LENGTH: 80
<212> TYPE: DNA
<213> ORGANISM: Artificial Sequence
<220> FEATURE:
<223> OTHER INFORMATION: Synthetic Construct

<400> SEQUENCE: 16
gaucugcgcg ucaucccagu acuggagagg gugugaagcc acagaugccu ucuagcaguc 60
cuguuggugg cuugcugauc 80

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
gcctaggtca gacaattcag ta 22

<210> SEQ ID NO 18
<211> LENGTH: 22
<212> TYPE: DNA
<213> ORGANISM: Artificial Sequence
<220> FEATURE:
<223> OTHER INFORMATION: Synthetic Construct

<400> SEQUENCE: 18
atcctgaagt tggccaggtc cc 22

<210> SEQ ID NO 19
<211> LENGTH: 79
<212> TYPE: DNA
<213> ORGANISM: Artificial Sequence
<220> FEATURE:
<223> OTHER INFORMATION: Synthetic Construct

<400> SEQUENCE: 19
gaucugcgag ggccuagguc agacaauuca guaugugaag ccacagauga uacugaaguu 60
ggccaggucc cugcugauc 79

-continued

<210> SEQ ID NO 20
<211> LENGTH: 203
<212> TYPE: DNA
<213> ORGANISM: Artificial Sequence
<220> FEATURE:
<223> OTHER INFORMATION: Synthetic Construct

<400> SEQUENCE: 20
gctgcccggt tcttcccgta cctggatctc tccattcgaa ggcaaaaagc ggttggctag 60
tggggtgtaa tctcaggcag aagaaggcat cttttaagtc caatactgtg taccagttcc 120
gttcaggcgg gagggcgctc aagaggttat aagggttcgg gaccgttggg tgtatgtcct 180 gcacccttttt attgacctct ctc 203

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
aagaggttat aagggttcgg gac 23

<210> SEQ ID NO 22
<211> LENGTH: 26
<212> TYPE: DNA
<213> ORGANISM: Artificial Sequence
<220> FEATURE:
<223> OTHER INFORMATION: Synthetic Construct

<400> SEQUENCE: 22
gtcctgcacc cttttattga cctctc 26

<210> SEQ ID NO 23
<211> LENGTH: 80
<212> TYPE: DNA
<213> ORGANISM: Artificial Sequence
<220> FEATURE:
<223> OTHER INFORMATION: Synthetic Construct

<400> SEQUENCE: 23
gaucugcgaa gagguuauaa ggguucggga cgugaagcca cagauggucc ugcacccuuu 60
uauugaccuc ucugcugauc 80

<210> SEQ ID NO 24
<211> LENGTH: 180
<212> TYPE: DNA
<213> ORGANISM: Artificial Sequence
<220> FEATURE:
<223> OTHER INFORMATION: Synthetic Construct

<400> SEQUENCE: 24
cagttgaata acctgtgggg gaacttgctt tgccaaaccc atccctgcgg tttctgccca 60
ggcttgggga aactgctcca accaggactg tatatcttga tcaggcttta cttggggaga 120
atatagtcga tattcatcat ctaattggag ggtcaacaca gtgatgggtt tgttattcac 180

<210> SEQ ID NO 25
<211> LENGTH: 26
<212> TYPE: DNA
<213> ORGANISM: Artificial Sequence
<220> FEATURE:
<223> OTHER INFORMATION: Synthetic Construct

<400> SEQUENCE: 25
aacccatccc tgcggtttct gcccag                                              26

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct

<400> SEQUENCE: 26
gggtcaacac agtgatgggt tt                                                  22

<210> SEQ ID NO 27
<211> LENGTH: 78
<212> TYPE: DNA
<213> ORGANISM: Artificial Sequence
<220> FEATURE:
<223> OTHER INFORMATION: Synthetic Construct

<400> SEQUENCE: 27
gaucugcgca acccaucccu gcgguuucug cccagucaau auaauucugg gucaacacag         60
ugauggguuu ugcugauc                                                       78

<210> SEQ ID NO 28
<211> LENGTH: 22
<212> TYPE: DNA
<213> ORGANISM: Artificial Sequence
<220> FEATURE:
<223> OTHER INFORMATION: Synthetic Construct

<400> SEQUENCE: 28
gactgtatat cttgatcagg ct                                                  22

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
cttggggaga atatagtcga                                                     20

<210> SEQ ID NO 30
<211> LENGTH: 77
<212> TYPE: DNA
<213> ORGANISM: Artificial Sequence
<220> FEATURE:
<223> OTHER INFORMATION: Synthetic Construct

<400> SEQUENCE: 30
gaucugcgcu gacuguauau cuugaucagg cugugaagcc acagaugagc uuggggagaa         60
uauagucgau gcugauc                                                        77

<210> SEQ ID NO 31
<211> LENGTH: 163
<212> TYPE: DNA
<213> ORGANISM: Artificial Sequence
<220> FEATURE:
<223> OTHER INFORMATION: Synthetic Construct

<400> SEQUENCE: 31
gggttgagag cagctggtag agtgaacgtg atcctctctg tgagaagcag gctttgatag 60
tggtcccttc tgtaatacac cttctctgcc tctctcacta gatcacgtaa ctcagcctcc 120
tgtaaccctt ccagtctctg aagtttcttt ctgatatcca gag 163

<210> SEQ ID NO 32
<211> LENGTH: 80
<212> TYPE: DNA
<213> ORGANISM: Artificial Sequence
<220> FEATURE:
<223> OTHER INFORMATION: Synthetic Construct

<400> SEQUENCE: 32
gaucugcgag aucacguaac ucagccuccu gugugaagcc acagauggca gcugguagag 60
ugaacgugau ccugcugauc 80

<210> SEQ ID NO 33
<211> LENGTH: 24
<212> TYPE: DNA
<213> ORGANISM: Artificial Sequence
<220> FEATURE:
<223> OTHER INFORMATION: Synthetic Construct

<400> SEQUENCE: 33
agatcacgta actcagcctc ctgt 24

<210> SEQ ID NO 34
<211> LENGTH: 25
<212> TYPE: DNA
<213> ORGANISM: Artificial Sequence
<220> FEATURE:
<223> OTHER INFORMATION: Synthetic Construct

<400> SEQUENCE: 34
gcagctggta gagtgaacgt gatcc 25

<210> SEQ ID NO 35
<211> LENGTH: 54
<212> TYPE: DNA
<213> ORGANISM: Artificial Sequence
<220> FEATURE:
<223> OTHER INFORMATION: Synthetic Construct

<400> SEQUENCE: 35
caaaaagtac aggacttgag agaggtctct tgaacctctc tcaagtcctg tact 54

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
tgggcctttt agctgaggct cg 22

<210> SEQ ID NO 37
<211> LENGTH: 83
<212> TYPE: DNA
<213> ORGANISM: Artificial Sequence
<220> FEATURE:
<223> OTHER INFORMATION: Synthetic Construct

<400> SEQUENCE: 37
gaucugcgca ugggccuuuu agcugaggcu cguagugaag ccacagaugu augggccuuu 60
uagcugaggc ucguaugcug auc 83

<210> SEQ ID NO 38
<211> LENGTH: 25
<212> TYPE: DNA
<213> ORGANISM: Artificial Sequence
<220> FEATURE:
<223> OTHER INFORMATION: Synthetic Construct

<400> SEQUENCE: 38
cttctggtgc tcaggagccc aggag 25

<210> SEQ ID NO 39
<211> LENGTH: 81
<212> TYPE: DNA
<213> ORGANISM: Artificial Sequence
<220> FEATURE:
<223> OTHER INFORMATION: Synthetic Construct

<400> SEQUENCE: 39
gaucugcgau ucuggugcuc aggagcccag gaggugaagc cacagaugcu ucuggugcuc 60
aggagcccag gagugcugau c 81

<210> SEQ ID NO 40
<211> LENGTH: 27
<212> TYPE: DNA
<213> ORGANISM: Artificial Sequence
<220> FEATURE:
<223> OTHER INFORMATION: Synthetic Construct

<400> SEQUENCE: 40
catcggtctg ggggctgccg gacgatg 27

<210> SEQ ID NO 41
<211> LENGTH: 85
<212> TYPE: DNA
<213> ORGANISM: Artificial Sequence
<220> FEATURE:
<223> OTHER INFORMATION: Synthetic Construct

<400> SEQUENCE: 41
gaucugcgaa ucggucuggg ggcugccgga cgauggugaa gccacagaug caucggucug 60
ggggcugccg gacgaugugc ugauc 85

<210> SEQ ID NO 42
<211> LENGTH: 79
<212> TYPE: DNA
<213> ORGANISM: Artificial Sequence
<220> FEATURE:
<223> OTHER INFORMATION: Synthetic Construct

<400> SEQUENCE: 42
gaucugcgag aaaccacccu ugaguaguuu ccgugaagcc acagauggga aaccacccuu 60
gaguaguuuc cugcugauc 79

<210> SEQ ID NO 43
<211> LENGTH: 79
<212> TYPE: DNA
<213> ORGANISM: Artificial Sequence
<220> FEATURE:
<223> OTHER INFORMATION: Synthetic Construct

<400> SEQUENCE: 43

-continued

```
gaucugcgag aaacuacucu ugaguaguuu ccgugaagcc acagauggga aacuacucuu     60

gaguaguuuc cugcugauc                                                   79


<210> SEQ ID NO 44
<211> LENGTH: 80
<212> TYPE: DNA
<213> ORGANISM: Artificial Sequence
<220> FEATURE:
<223> OTHER INFORMATION: Synthetic Construct

<400> SEQUENCE: 44

gatctgcgct tagatccagg gctcataatg tgaagccaca gatgattatg agccctggat     60

ctaattgctg atcactagta                                                  80


<210> SEQ ID NO 45
<211> LENGTH: 80
<212> TYPE: DNA
<213> ORGANISM: Artificial Sequence
<220> FEATURE:
<223> OTHER INFORMATION: Synthetic Construct

<400> SEQUENCE: 45

acgcgaatct aggtcccgag tattacactt cggtgtctac taatactcgg gacctagatt     60

aacgactagt gatcatgcgc                                                  80


<210> SEQ ID NO 46
<211> LENGTH: 176
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (88)..(88)
<223> OTHER INFORMATION: n is a, c, g, t or u
<220> FEATURE:
<221> NAME/KEY: misc_feature
<222> LOCATION: (89)..(89)
<223> OTHER INFORMATION: n is a, c, g, t or u
<220> FEATURE:
<221> NAME/KEY: misc_feature
<222> LOCATION: (176)..(176)
<223> OTHER INFORMATION: n is a, c, g, t or u

<400> SEQUENCE: 46

ntgatctgcg cttagatcca gggctcataa tgtgaagcca cagatgatta tgagccctgg     60

atctaattgc tgatcactag tacgcgtnna ctagacgcga atctaggtcc cgagtattac    120

acttcggtgt ctactaatac tcgggaccta gattaacgac tagtgatcat gcgcan        176


<210> SEQ ID NO 47
<211> LENGTH: 226
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a, c, g, t or u
<220> FEATURE:
<221> NAME/KEY: misc_feature
<222> LOCATION: (226)..(226)
<223> OTHER INFORMATION: n is a, c, g, t or u
```

<400> SEQUENCE: 47
ntgatctgcg cttagatcca gggctcataa tgtgaagcca cagatgatta tgagccctgg 60
atctaattgc tgatctgcgc ggtagagact tactgaccaa gtgaagccac agatgttggt 120
cagtaagtct ctaccttgct gatctgcgca gaacatagag accaatgcag tgaagccaca 180
gatgtgcatt ggtctctatg ttctttgctg atcactagta cgcgtn 226

<210> SEQ ID NO 48
<211> LENGTH: 142
<212> TYPE: DNA
<213> ORGANISM: Artificial Sequence
<220> FEATURE:
<223> OTHER INFORMATION: Synthetic Construct

<400> SEQUENCE: 48
cctgcaggta agtcactgct gtctatgcct gggaaagggg ggcaggagat ggggcagtgc 60
aggaaaagtg gcactatgaa cccgtgatca ctagtacgcg tgtacaattg tactaacctt 120
cttctctttc ctctcctgca gg 142

<210> SEQ ID NO 49
<211> LENGTH: 19
<212> TYPE: DNA
<213> ORGANISM: Artificial Sequence
<220> FEATURE:
<223> OTHER INFORMATION: Synthetic Construct

<400> SEQUENCE: 49
ataagcttac ccttactga 19

<210> SEQ ID NO 50
<211> LENGTH: 54
<212> TYPE: DNA
<213> ORGANISM: Artificial Sequence
<220> FEATURE:
<223> OTHER INFORMATION: Synthetic Construct

<400> SEQUENCE: 50
tcccaataag cttaccctta ctgattcaag agatcagtaa gggtaagctt attt 54

<210> SEQ ID NO 51
<211> LENGTH: 54
<212> TYPE: DNA
<213> ORGANISM: Artificial Sequence
<220> FEATURE:
<223> OTHER INFORMATION: Synthetic Construct

<400> SEQUENCE: 51
caaaaaataa gcttaccctt actgatctct tgaatcagta agggtaagct tatt 54

<210> SEQ ID NO 52
<211> LENGTH: 19
<212> TYPE: DNA
<213> ORGANISM: Artificial Sequence
<220> FEATURE:
<223> OTHER INFORMATION: Synthetic Construct

<400> SEQUENCE: 52
ataagcttac ccttactga 19

<210> SEQ ID NO 53
<211> LENGTH: 53
<212> TYPE: DNA

<213> ORGANISM: Artificial Sequence
<220> FEATURE:
<223> OTHER INFORMATION: Synthetic Construct

<400> SEQUENCE: 53
tcccaataag cttaccctta ctgattcaag agatcagtaa gggtaagctt att 53

<210> SEQ ID NO 54
<211> LENGTH: 53
<212> TYPE: DNA
<213> ORGANISM: Artificial Sequence
<220> FEATURE:
<223> OTHER INFORMATION: Synthetic Construct

<400> SEQUENCE: 54
caaaaataag cttaccctta ctgatctctt gaatcagtaa gggtaagctt att 53

<210> SEQ ID NO 55
<211> LENGTH: 18
<212> TYPE: DNA
<213> ORGANISM: Artificial Sequence
<220> FEATURE:
<223> OTHER INFORMATION: Synthetic Construct

<400> SEQUENCE: 55
taagcttacc cttactga 18

<210> SEQ ID NO 56
<211> LENGTH: 53
<212> TYPE: DNA
<213> ORGANISM: Artificial Sequence
<220> FEATURE:
<223> OTHER INFORMATION: Synthetic Construct

<400> SEQUENCE: 56
tcccataagc ttacccttac tgattcaaga gatcagtaag ggtaagctta ttt 53

<210> SEQ ID NO 57
<211> LENGTH: 53
<212> TYPE: DNA
<213> ORGANISM: Artificial Sequence
<220> FEATURE:
<223> OTHER INFORMATION: Synthetic Construct

<400> SEQUENCE: 57
caaaaaataa gcttaccctt actgatctct tgaatcagta agggtaagct tat 53

<210> SEQ ID NO 58
<211> LENGTH: 18
<212> TYPE: DNA
<213> ORGANISM: Artificial Sequence
<220> FEATURE:
<223> OTHER INFORMATION: Synthetic Construct

<400> SEQUENCE: 58
taagcttacc cttactga 18

<210> SEQ ID NO 59
<211> LENGTH: 52
<212> TYPE: DNA
<213> ORGANISM: Artificial Sequence
<220> FEATURE:
<223> OTHER INFORMATION: Synthetic Construct

<400> SEQUENCE: 59
tcccataagc ttacccttac tgattcaaga gatcagtaag ggtaagctta tt 52

<210> SEQ ID NO 60
<211> LENGTH: 52
<212> TYPE: DNA
<213> ORGANISM: Artificial Sequence
<220> FEATURE:
<223> OTHER INFORMATION: Synthetic Construct

<400> SEQUENCE: 60
caaaaataag cttaccctta ctgatctctt gaatcagtaa gggtaagctt at 52

<210> SEQ ID NO 61
<211> LENGTH: 19
<212> TYPE: DNA
<213> ORGANISM: Artificial Sequence
<220> FEATURE:
<223> OTHER INFORMATION: Synthetic Construct

<400> SEQUENCE: 61
aagcaatcct tgatgaata 19

<210> SEQ ID NO 62
<211> LENGTH: 54
<212> TYPE: DNA
<213> ORGANISM: Artificial Sequence
<220> FEATURE:
<223> OTHER INFORMATION: Synthetic Construct

<400> SEQUENCE: 62
tcccaaagca atccttgatg aatattcaag agatattcat caaggattgc tttt 54

<210> SEQ ID NO 63
<211> LENGTH: 54
<212> TYPE: DNA
<213> ORGANISM: Artificial Sequence
<220> FEATURE:
<223> OTHER INFORMATION: Synthetic Construct

<400> SEQUENCE: 63
caaaaaaagc aatccttgat gaatatctct tgaatattca tcaaggattg cttt 54

<210> SEQ ID NO 64
<211> LENGTH: 19
<212> TYPE: DNA
<213> ORGANISM: Artificial Sequence
<220> FEATURE:
<223> OTHER INFORMATION: Synthetic Construct

<400> SEQUENCE: 64
aagcaatcct tgatgaata 19

<210> SEQ ID NO 65
<211> LENGTH: 52
<212> TYPE: DNA
<213> ORGANISM: Artificial Sequence
<220> FEATURE:
<223> OTHER INFORMATION: Synthetic Construct

<400> SEQUENCE: 65
tcccaaagca atccttgatg aatattcaag agatattcat caaggattgc tt 52

<210> SEQ ID NO 66
<211> LENGTH: 52
<212> TYPE: DNA
<213> ORGANISM: Artificial Sequence
<220> FEATURE:

<223> OTHER INFORMATION: Synthetic Construct

<400> SEQUENCE: 66
caaaaagcaa tccttgatga atatctcttg aatattcatc aaggattgct tt 52

<210> SEQ ID NO 67
<211> LENGTH: 18
<212> TYPE: DNA
<213> ORGANISM: Artificial Sequence
<220> FEATURE:
<223> OTHER INFORMATION: Synthetic Construct

<400> SEQUENCE: 67
agcaatcctt gatgaata 18

<210> SEQ ID NO 68
<211> LENGTH: 53
<212> TYPE: DNA
<213> ORGANISM: Artificial Sequence
<220> FEATURE:
<223> OTHER INFORMATION: Synthetic Construct

<400> SEQUENCE: 68
tcccaagcaa tccttgatga atattcaaga gatattcatc aaggattgct ttt 53

<210> SEQ ID NO 69
<211> LENGTH: 53
<212> TYPE: DNA
<213> ORGANISM: Artificial Sequence
<220> FEATURE:
<223> OTHER INFORMATION: Synthetic Construct

<400> SEQUENCE: 69
caaaaaaagc aatccttgat gaatatctct tgaatattca tcaaggattg ctt 53

<210> SEQ ID NO 70
<211> LENGTH: 18
<212> TYPE: DNA
<213> ORGANISM: Artificial Sequence
<220> FEATURE:
<223> OTHER INFORMATION: Synthetic Construct

<400> SEQUENCE: 70
agcaatcctt gatgaata 18

<210> SEQ ID NO 71
<211> LENGTH: 51
<212> TYPE: DNA
<213> ORGANISM: Artificial Sequence
<220> FEATURE:
<223> OTHER INFORMATION: Synthetic Construct

<400> SEQUENCE: 71
tcccaagcaa tccttgatga atattcaaga gatattcatc aaggattgct t 51

<210> SEQ ID NO 72
<211> LENGTH: 51
<212> TYPE: DNA
<213> ORGANISM: Artificial Sequence
<220> FEATURE:
<223> OTHER INFORMATION: Synthetic Construct

<400> SEQUENCE: 72
caaaaagcaa tccttgatga atatctcttg aatattcatc aaggattgct t 51

<210> SEQ ID NO 73
<211> LENGTH: 19
<212> TYPE: DNA
<213> ORGANISM: Artificial Sequence
<220> FEATURE:
<223> OTHER INFORMATION: Synthetic Construct

<400> SEQUENCE: 73
tgatgaatat gactacaga 19

<210> SEQ ID NO 74
<211> LENGTH: 54
<212> TYPE: DNA
<213> ORGANISM: Artificial Sequence
<220> FEATURE:
<223> OTHER INFORMATION: Synthetic Construct

<400> SEQUENCE: 74
tcccatgatg aatatgacta cagattcaag agatctgtag tcatattcat catt 54

<210> SEQ ID NO 75
<211> LENGTH: 54
<212> TYPE: DNA
<213> ORGANISM: Artificial Sequence
<220> FEATURE:
<223> OTHER INFORMATION: Synthetic Construct

<400> SEQUENCE: 75
caaaaatgat gaatatgact acagatctct tgaatctgta gtcatattca tcat 54

<210> SEQ ID NO 76
<211> LENGTH: 19
<212> TYPE: DNA
<213> ORGANISM: Artificial Sequence
<220> FEATURE:
<223> OTHER INFORMATION: Synthetic Construct

<400> SEQUENCE: 76
gaaggtgggt tatgtgtag 19

<210> SEQ ID NO 77
<211> LENGTH: 54
<212> TYPE: DNA
<213> ORGANISM: Artificial Sequence
<220> FEATURE:
<223> OTHER INFORMATION: Synthetic Construct

<400> SEQUENCE: 77
tcccagaagg tgggttatgt gtagttcaag agactacaca taacccacct tctt 54

<210> SEQ ID NO 78
<211> LENGTH: 54
<212> TYPE: DNA
<213> ORGANISM: Artificial Sequence
<220> FEATURE:
<223> OTHER INFORMATION: Synthetic Construct

<400> SEQUENCE: 78
caaaaagaag gtgggttatg tgtagtctct tgaactacac ataacccacc ttct 54

<210> SEQ ID NO 79
<211> LENGTH: 19
<212> TYPE: DNA
<213> ORGANISM: Artificial Sequence
<220> FEATURE:
<223> OTHER INFORMATION: Synthetic Construct

<400> SEQUENCE: 79
gaaggaggat tatgtgtag 19

<210> SEQ ID NO 80
<211> LENGTH: 54
<212> TYPE: DNA
<213> ORGANISM: Artificial Sequence
<220> FEATURE:
<223> OTHER INFORMATION: Synthetic Construct

<400> SEQUENCE: 80
tcccagaagg aggattatgt gtagttcaag agactacaca taatcctcct tctt 54

<210> SEQ ID NO 81
<211> LENGTH: 54
<212> TYPE: DNA
<213> ORGANISM: Artificial Sequence
<220> FEATURE:
<223> OTHER INFORMATION: Synthetic Construct

<400> SEQUENCE: 81
caaaaagaag gaggattatg tgtagtctct tgaactacac ataatcctcc ttct 54

<210> SEQ ID NO 82
<211> LENGTH: 19
<212> TYPE: DNA
<213> ORGANISM: Artificial Sequence
<220> FEATURE:
<223> OTHER INFORMATION: Synthetic Construct

<400> SEQUENCE: 82
tccatcgcgt ggttcctta 19

<210> SEQ ID NO 83
<211> LENGTH: 54
<212> TYPE: DNA
<213> ORGANISM: Artificial Sequence
<220> FEATURE:
<223> OTHER INFORMATION: Synthetic Construct

<400> SEQUENCE: 83
tcccatccat cgcgtggttc cttattcaag agataaggaa ccacgcgatg gatt 54

<210> SEQ ID NO 84
<211> LENGTH: 54
<212> TYPE: DNA
<213> ORGANISM: Artificial Sequence
<220> FEATURE:
<223> OTHER INFORMATION: Synthetic Construct

<400> SEQUENCE: 84
caaaaatcca tcgcgtggtt ccttatctct tgaataagga accacgcgat ggat 54

<210> SEQ ID NO 85
<211> LENGTH: 19
<212> TYPE: DNA
<213> ORGANISM: Artificial Sequence
<220> FEATURE:
<223> OTHER INFORMATION: Synthetic Construct

<400> SEQUENCE: 85
gtggttcctt actctgtca 19

<210> SEQ ID NO 86
<211> LENGTH: 54

<212> TYPE: DNA
<213> ORGANISM: Artificial Sequence
<220> FEATURE:
<223> OTHER INFORMATION: Synthetic Construct

<400> SEQUENCE: 86
tcccagtggt tccttactct gtcattcaag agatgacaga gtaaggaacc actt 54

<210> SEQ ID NO 87
<211> LENGTH: 54
<212> TYPE: DNA
<213> ORGANISM: Artificial Sequence
<220> FEATURE:
<223> OTHER INFORMATION: Synthetic Construct

<400> SEQUENCE: 87
caaaaagtgg ttccttactc tgtcatctct tgaatgacag agtaaggaac cact 54

<210> SEQ ID NO 88
<211> LENGTH: 19
<212> TYPE: DNA
<213> ORGANISM: Artificial Sequence
<220> FEATURE:
<223> OTHER INFORMATION: Synthetic Construct

<400> SEQUENCE: 88
ctcctcaagt taatggtaa 19

<210> SEQ ID NO 89
<211> LENGTH: 54
<212> TYPE: DNA
<213> ORGANISM: Artificial Sequence
<220> FEATURE:
<223> OTHER INFORMATION: Synthetic Construct

<400> SEQUENCE: 89
tcccactcct caagttaatg gtaattcaag agattaccat taacttgagg agtt 54

<210> SEQ ID NO 90
<211> LENGTH: 54
<212> TYPE: DNA
<213> ORGANISM: Artificial Sequence
<220> FEATURE:
<223> OTHER INFORMATION: Synthetic Construct

<400> SEQUENCE: 90
caaaaactcc tcaagttaat ggtaatctct tgaattacca ttaacttgag gagt 54

<210> SEQ ID NO 91
<211> LENGTH: 19
<212> TYPE: DNA
<213> ORGANISM: Artificial Sequence
<220> FEATURE:
<223> OTHER INFORMATION: Synthetic Construct

<400> SEQUENCE: 91
ctatagatat aatcggcca 19

<210> SEQ ID NO 92
<211> LENGTH: 54
<212> TYPE: DNA
<213> ORGANISM: Artificial Sequence
<220> FEATURE:
<223> OTHER INFORMATION: Synthetic Construct

<400> SEQUENCE: 92

-continued tcccactata gatataatcg gccattcaag agatggccga ttatatctat agtt 54

<210> SEQ ID NO 93
<211> LENGTH: 54
<212> TYPE: DNA
<213> ORGANISM: Artificial Sequence
<220> FEATURE:
<223> OTHER INFORMATION: Synthetic Construct

<400> SEQUENCE: 93
caaaaactat agatataatc ggccatctct tgaatggccg attatatcta tagt 54

<210> SEQ ID NO 94
<211> LENGTH: 19
<212> TYPE: DNA
<213> ORGANISM: Artificial Sequence
<220> FEATURE:
<223> OTHER INFORMATION: Synthetic Construct

<400> SEQUENCE: 94
agagaggcgt cgaagggaa 19

<210> SEQ ID NO 95
<211> LENGTH: 54
<212> TYPE: DNA
<213> ORGANISM: Artificial Sequence
<220> FEATURE:
<223> OTHER INFORMATION: Synthetic Construct

<400> SEQUENCE: 95
tcccaagaga ggcgtcgaag ggaattcaag agattccctt cgacgcctct cttt 54

<210> SEQ ID NO 96
<211> LENGTH: 54
<212> TYPE: DNA
<213> ORGANISM: Artificial Sequence
<220> FEATURE:
<223> OTHER INFORMATION: Synthetic Construct

<400> SEQUENCE: 96
caaaaaagag aggcgtcgaa gggaatctct tgaattccct tcgacgcctc tctt 54

<210> SEQ ID NO 97
<211> LENGTH: 19
<212> TYPE: DNA
<213> ORGANISM: Artificial Sequence
<220> FEATURE:
<223> OTHER INFORMATION: Synthetic Construct

<400> SEQUENCE: 97
ccaaggcctt ctgagccaa 19

<210> SEQ ID NO 98
<211> LENGTH: 54
<212> TYPE: DNA
<213> ORGANISM: Artificial Sequence
<220> FEATURE:
<223> OTHER INFORMATION: Synthetic Construct

<400> SEQUENCE: 98
tcccaccaag gccttctgag ccaattcaag agattggctc agaaggcctt ggtt 54

<210> SEQ ID NO 99
<211> LENGTH: 54
<212> TYPE: DNA
<213> ORGANISM: Artificial Sequence
<220> FEATURE:
<223> OTHER INFORMATION: Synthetic Construct

<400> SEQUENCE: 99
caaaaaccaa ggccttctga gccaatctct tgaattggct cagaaggcct tggt 54

<210> SEQ ID NO 100
<211> LENGTH: 19
<212> TYPE: DNA
<213> ORGANISM: Artificial Sequence
<220> FEATURE:
<223> OTHER INFORMATION: Synthetic Construct

<400> SEQUENCE: 100
gaacatagag accaatgca 19

<210> SEQ ID NO 101
<211> LENGTH: 54
<212> TYPE: DNA
<213> ORGANISM: Artificial Sequence
<220> FEATURE:
<223> OTHER INFORMATION: Synthetic Construct

<400> SEQUENCE: 101
tcccagaaca tagagaccaa tgcattcaag agatgcattg gtctctatgt tctt 54

<210> SEQ ID NO 102
<211> LENGTH: 54
<212> TYPE: DNA
<213> ORGANISM: Artificial Sequence
<220> FEATURE:
<223> OTHER INFORMATION: Synthetic Construct

<400> SEQUENCE: 102
caaaaagaac atagagacca atgcatctct tgaatgcatt ggtctctatg ttct 54

<210> SEQ ID NO 103
<211> LENGTH: 19
<212> TYPE: DNA
<213> ORGANISM: Artificial Sequence
<220> FEATURE:
<223> OTHER INFORMATION: Synthetic Construct

<400> SEQUENCE: 103
tgacctacat cgaattgta 19

<210> SEQ ID NO 104
<211> LENGTH: 54
<212> TYPE: DNA
<213> ORGANISM: Artificial Sequence
<220> FEATURE:
<223> OTHER INFORMATION: Synthetic Construct

<400> SEQUENCE: 104
tcccatgacc tacatcgaat tgtattcaag agatacaatt cgatgtaggt catt 54

<210> SEQ ID NO 105
<211> LENGTH: 54
<212> TYPE: DNA
<213> ORGANISM: Artificial Sequence
<220> FEATURE:
<223> OTHER INFORMATION: Synthetic Construct

<400> SEQUENCE: 105
caaaaatgac ctacatcgaa ttgtatctct tgaatacaat tcgatgtagg tcat 54

<210> SEQ ID NO 106
<211> LENGTH: 19
<212> TYPE: DNA
<213> ORGANISM: Artificial Sequence
<220> FEATURE:
<223> OTHER INFORMATION: Synthetic Construct

<400> SEQUENCE: 106
tcagtaacct agaggaatc 19

<210> SEQ ID NO 107
<211> LENGTH: 54
<212> TYPE: DNA
<213> ORGANISM: Artificial Sequence
<220> FEATURE:
<223> OTHER INFORMATION: Synthetic Construct

<400> SEQUENCE: 107
tcccatcagt aacctagagg aatcttcaag agagattcct ctaggttact gatt 54

<210> SEQ ID NO 108
<211> LENGTH: 54
<212> TYPE: DNA
<213> ORGANISM: Artificial Sequence
<220> FEATURE:
<223> OTHER INFORMATION: Synthetic Construct

<400> SEQUENCE: 108
caaaaatcag taacctagag gaatctctct tgaagattcc tctaggttac tgat 54

<210> SEQ ID NO 109
<211> LENGTH: 19
<212> TYPE: DNA
<213> ORGANISM: Artificial Sequence
<220> FEATURE:
<223> OTHER INFORMATION: Synthetic Construct

<400> SEQUENCE: 109
taacctacat cgaattgta 19

<210> SEQ ID NO 110
<211> LENGTH: 54
<212> TYPE: DNA
<213> ORGANISM: Artificial Sequence
<220> FEATURE:
<223> OTHER INFORMATION: Synthetic Construct

<400> SEQUENCE: 110
tcccataacc tacatcgaat tgtattcaag agatacaatt cgatgtaggt tatt 54

<210> SEQ ID NO 111
<211> LENGTH: 54
<212> TYPE: DNA
<213> ORGANISM: Artificial Sequence
<220> FEATURE:
<223> OTHER INFORMATION: Synthetic Construct

<400> SEQUENCE: 111
caaaaataac ctacatcgaa ttgtatctct tgaatacaat tcgatgtagg ttat 54

<210> SEQ ID NO 112
<211> LENGTH: 19
<212> TYPE: DNA
<213> ORGANISM: Artificial Sequence
<220> FEATURE:
<223> OTHER INFORMATION: Synthetic Construct

<400> SEQUENCE: 112
acatcgaatt gtaacagaa 19

<210> SEQ ID NO 113
<211> LENGTH: 54
<212> TYPE: DNA
<213> ORGANISM: Artificial Sequence
<220> FEATURE:
<223> OTHER INFORMATION: Synthetic Construct

<400> SEQUENCE: 113
tcccaacatc gaattgtaac agaattcaag agattctgtt acaattcgat gttt 54

<210> SEQ ID NO 114
<211> LENGTH: 54
<212> TYPE: DNA
<213> ORGANISM: Artificial Sequence
<220> FEATURE:
<223> OTHER INFORMATION: Synthetic Construct

<400> SEQUENCE: 114
caaaaaacat cgaattgtaa cagaatctct tgaattctgt tacaattcga tgtt 54

<210> SEQ ID NO 115
<211> LENGTH: 19
<212> TYPE: DNA
<213> ORGANISM: Artificial Sequence
<220> FEATURE:
<223> OTHER INFORMATION: Synthetic Construct

<400> SEQUENCE: 115
acatcgaatt gtaacagaa 19

<210> SEQ ID NO 116
<211> LENGTH: 53
<212> TYPE: DNA
<213> ORGANISM: Artificial Sequence
<220> FEATURE:
<223> OTHER INFORMATION: Synthetic Construct

<400> SEQUENCE: 116
tcccaacatc gaattgtaac agaattcaag agattctgtt acaattcgat gtt 53

<210> SEQ ID NO 117
<211> LENGTH: 53
<212> TYPE: DNA
<213> ORGANISM: Artificial Sequence
<220> FEATURE:
<223> OTHER INFORMATION: Synthetic Construct

<400> SEQUENCE: 117
caaaaacatc gaattgtaac agaatctctt gaattctgtt acaattcgat gtt 53

<210> SEQ ID NO 118
<211> LENGTH: 18
<212> TYPE: DNA
<213> ORGANISM: Artificial Sequence
<220> FEATURE:
<223> OTHER INFORMATION: Synthetic Construct

<400> SEQUENCE: 118
catcgaattg taacagaa 18

<210> SEQ ID NO 119

<211> LENGTH: 53
<212> TYPE: DNA
<213> ORGANISM: Artificial Sequence
<220> FEATURE:
<223> OTHER INFORMATION: Synthetic Construct

<400> SEQUENCE: 119
tcccacatcg aattgtaaca gaattcaaga gattctgtta caattcgatg ttt 53

<210> SEQ ID NO 120
<211> LENGTH: 53
<212> TYPE: DNA
<213> ORGANISM: Artificial Sequence
<220> FEATURE:
<223> OTHER INFORMATION: Synthetic Construct

<400> SEQUENCE: 120
caaaaaacat cgaattgtaa cagaatctct tgaattctgt tacaattcga tgt 53

<210> SEQ ID NO 121
<211> LENGTH: 18
<212> TYPE: DNA
<213> ORGANISM: Artificial Sequence
<220> FEATURE:
<223> OTHER INFORMATION: Synthetic Construct

<400> SEQUENCE: 121
catcgaattg taacagaa 18

<210> SEQ ID NO 122
<211> LENGTH: 52
<212> TYPE: DNA
<213> ORGANISM: Artificial Sequence
<220> FEATURE:
<223> OTHER INFORMATION: Synthetic Construct

<400> SEQUENCE: 122
tcccacatcg aattgtaaca gaattcaaga gattctgtta caattcgatg tt 52

<210> SEQ ID NO 123
<211> LENGTH: 52
<212> TYPE: DNA
<213> ORGANISM: Artificial Sequence
<220> FEATURE:
<223> OTHER INFORMATION: Synthetic Construct

<400> SEQUENCE: 123
caaaaacatc gaattgtaac agaatctctt gaattctgtt acaattcgat gt 52

<210> SEQ ID NO 124
<211> LENGTH: 19
<212> TYPE: DNA
<213> ORGANISM: Artificial Sequence
<220> FEATURE:
<223> OTHER INFORMATION: Synthetic Construct

<400> SEQUENCE: 124
tctctcacct ggttactta 19

<210> SEQ ID NO 125
<211> LENGTH: 54
<212> TYPE: DNA
<213> ORGANISM: Artificial Sequence
<220> FEATURE:
<223> OTHER INFORMATION: Synthetic Construct

<400> SEQUENCE: 125
tcccatctct cacctggtta cttattcaag agataagtaa ccaggtgaga gatt 54

<210> SEQ ID NO 126
<211> LENGTH: 54
<212> TYPE: DNA
<213> ORGANISM: Artificial Sequence
<220> FEATURE:
<223> OTHER INFORMATION: Synthetic Construct

<400> SEQUENCE: 126
caaaaatctc tcacctggtt acttatctct tgaataagta accaggtgag agat 54

<210> SEQ ID NO 127
<211> LENGTH: 19
<212> TYPE: DNA
<213> ORGANISM: Artificial Sequence
<220> FEATURE:
<223> OTHER INFORMATION: Synthetic Construct

<400> SEQUENCE: 127
agaaggagga ttatgtgta 19

<210> SEQ ID NO 128
<211> LENGTH: 54
<212> TYPE: DNA
<213> ORGANISM: Artificial Sequence
<220> FEATURE:
<223> OTHER INFORMATION: Synthetic Construct

<400> SEQUENCE: 128
tcccaagaag gaggattatg tgtattcaag agatacacat aatcctcctt cttt 54

<210> SEQ ID NO 129
<211> LENGTH: 54
<212> TYPE: DNA
<213> ORGANISM: Artificial Sequence
<220> FEATURE:
<223> OTHER INFORMATION: Synthetic Construct

<400> SEQUENCE: 129
caaaaaagaa ggaggattat gtgtatctct tgaatacaca taatcctcct tctt 54

<210> SEQ ID NO 130
<211> LENGTH: 19
<212> TYPE: DNA
<213> ORGANISM: Artificial Sequence
<220> FEATURE:
<223> OTHER INFORMATION: Synthetic Construct

<400> SEQUENCE: 130
agaaggagga ttatgtgta 19

<210> SEQ ID NO 131
<211> LENGTH: 53
<212> TYPE: DNA
<213> ORGANISM: Artificial Sequence
<220> FEATURE:
<223> OTHER INFORMATION: Synthetic Construct

<400> SEQUENCE: 131
tcccaagaag gaggattatg tgtattcaag agatacacat aatcctcctt ctt 53

<210> SEQ ID NO 132
<211> LENGTH: 53
<212> TYPE: DNA

<213> ORGANISM: Artificial Sequence
<220> FEATURE:
<223> OTHER INFORMATION: Synthetic Construct

<400> SEQUENCE: 132
caaaaagaag gaggattatg tgtatctctt gaatacacat aatcctcctt ctt 53

<210> SEQ ID NO 133
<211> LENGTH: 18
<212> TYPE: DNA
<213> ORGANISM: Artificial Sequence
<220> FEATURE:
<223> OTHER INFORMATION: Synthetic Construct

<400> SEQUENCE: 133
gaaggaggat tatgtgta 18

<210> SEQ ID NO 134
<211> LENGTH: 53
<212> TYPE: DNA
<213> ORGANISM: Artificial Sequence
<220> FEATURE:
<223> OTHER INFORMATION: Synthetic Construct

<400> SEQUENCE: 134
tcccagaagg aggattatgt gtattcaaga gatacacata atcctccttc ttt 53

<210> SEQ ID NO 135
<211> LENGTH: 53
<212> TYPE: DNA
<213> ORGANISM: Artificial Sequence
<220> FEATURE:
<223> OTHER INFORMATION: Synthetic Construct

<400> SEQUENCE: 135
caaaaaagaa ggaggattat gtgtatctct tgaatacaca taatcctcct tct 53

<210> SEQ ID NO 136
<211> LENGTH: 18
<212> TYPE: DNA
<213> ORGANISM: Artificial Sequence
<220> FEATURE:
<223> OTHER INFORMATION: Synthetic Construct

<400> SEQUENCE: 136
gaaggaggat tatgtgta 18

<210> SEQ ID NO 137
<211> LENGTH: 52
<212> TYPE: DNA
<213> ORGANISM: Artificial Sequence
<220> FEATURE:
<223> OTHER INFORMATION: Synthetic Construct

<400> SEQUENCE: 137
tcccagaagg aggattatgt gtattcaaga gatacacata atcctccttc tt 52

<210> SEQ ID NO 138
<211> LENGTH: 52
<212> TYPE: DNA
<213> ORGANISM: Artificial Sequence
<220> FEATURE:
<223> OTHER INFORMATION: Synthetic Construct

<400> SEQUENCE: 138
caaaaagaag gaggattatg tgtatctctt gaatacacat aatcctcctt ct 52

<210> SEQ ID NO 139
<211> LENGTH: 19
<212> TYPE: DNA
<213> ORGANISM: Artificial Sequence
<220> FEATURE:
<223> OTHER INFORMATION: Synthetic Construct

<400> SEQUENCE: 139
ccaccttact atgagggaa 19

<210> SEQ ID NO 140
<211> LENGTH: 54
<212> TYPE: DNA
<213> ORGANISM: Artificial Sequence
<220> FEATURE:
<223> OTHER INFORMATION: Synthetic Construct

<400> SEQUENCE: 140
tcccaccacc ttactatgag ggaattcaag agattccctc atagtaaggt ggtt 54

<210> SEQ ID NO 141
<211> LENGTH: 54
<212> TYPE: DNA
<213> ORGANISM: Artificial Sequence
<220> FEATURE:
<223> OTHER INFORMATION: Synthetic Construct

<400> SEQUENCE: 141
caaaaaccac cttactatga gggaatctct tgaattccct catagtaagg tggt 54

<210> SEQ ID NO 142
<211> LENGTH: 19
<212> TYPE: DNA
<213> ORGANISM: Artificial Sequence
<220> FEATURE:
<223> OTHER INFORMATION: Synthetic Construct

<400> SEQUENCE: 142
gtagtcctac agaatagaa 19

<210> SEQ ID NO 143
<211> LENGTH: 54
<212> TYPE: DNA
<213> ORGANISM: Artificial Sequence
<220> FEATURE:
<223> OTHER INFORMATION: Synthetic Construct

<400> SEQUENCE: 143
tcccagtagt cctacagaat agaattcaag agattctatt ctgtaggact actt 54

<210> SEQ ID NO 144
<211> LENGTH: 54
<212> TYPE: DNA
<213> ORGANISM: Artificial Sequence
<220> FEATURE:
<223> OTHER INFORMATION: Synthetic Construct

<400> SEQUENCE: 144
caaaaagtag tcctacagaa tagaatctct tgaattctat tctgtaggac tact 54

<210> SEQ ID NO 145
<211> LENGTH: 19
<212> TYPE: DNA
<213> ORGANISM: Artificial Sequence
<220> FEATURE:

<223> OTHER INFORMATION: Synthetic Construct

<400> SEQUENCE: 145
ggaactgtgt aacctctaa 19

<210> SEQ ID NO 146
<211> LENGTH: 54
<212> TYPE: DNA
<213> ORGANISM: Artificial Sequence
<220> FEATURE:
<223> OTHER INFORMATION: Synthetic Construct

<400> SEQUENCE: 146
tcccaggaac tgtgtaacct ctaattcaag agattagagg ttacacagtt cctt 54

<210> SEQ ID NO 147
<211> LENGTH: 54
<212> TYPE: DNA
<213> ORGANISM: Artificial Sequence
<220> FEATURE:
<223> OTHER INFORMATION: Synthetic Construct

<400> SEQUENCE: 147
caaaaaggaa ctgtgtaacc tctaatctct tgaattagag gttacacagt tcct 54

<210> SEQ ID NO 148
<211> LENGTH: 19
<212> TYPE: DNA
<213> ORGANISM: Artificial Sequence
<220> FEATURE:
<223> OTHER INFORMATION: Synthetic Construct

<400> SEQUENCE: 148
acaaccaggc tccattcta 19

<210> SEQ ID NO 149
<211> LENGTH: 54
<212> TYPE: DNA
<213> ORGANISM: Artificial Sequence
<220> FEATURE:
<223> OTHER INFORMATION: Synthetic Construct

<400> SEQUENCE: 149
tcccaacaac caggctccat tctattcaag agatagaatg gagcctggtt gttt 54

<210> SEQ ID NO 150
<211> LENGTH: 54
<212> TYPE: DNA
<213> ORGANISM: Artificial Sequence
<220> FEATURE:
<223> OTHER INFORMATION: Synthetic Construct

<400> SEQUENCE: 150
caaaaaacaa ccaggctcca ttctatctct tgaatagaat ggagcctggt tgtt 54

<210> SEQ ID NO 151
<211> LENGTH: 19
<212> TYPE: DNA
<213> ORGANISM: Artificial Sequence
<220> FEATURE:
<223> OTHER INFORMATION: Synthetic Construct

<400> SEQUENCE: 151
acaaccaggc tccattcta 19

-continued

<210> SEQ ID NO 152
<211> LENGTH: 53
<212> TYPE: DNA
<213> ORGANISM: Artificial Sequence
<220> FEATURE:
<223> OTHER INFORMATION: Synthetic Construct

<400> SEQUENCE: 152
tcccaacaac caggctccat tctattcaag agatagaatg gagcctggtt gtt 53

<210> SEQ ID NO 153
<211> LENGTH: 53
<212> TYPE: DNA
<213> ORGANISM: Artificial Sequence
<220> FEATURE:
<223> OTHER INFORMATION: Synthetic Construct

<400> SEQUENCE: 153
caaaaacaac caggctccat tctatctctt gaatagaatg gagcctggtt gtt 53

<210> SEQ ID NO 154
<211> LENGTH: 18
<212> TYPE: DNA
<213> ORGANISM: Artificial Sequence
<220> FEATURE:
<223> OTHER INFORMATION: Synthetic Construct

<400> SEQUENCE: 154
caaccaggct ccattcta 18

<210> SEQ ID NO 155
<211> LENGTH: 53
<212> TYPE: DNA
<213> ORGANISM: Artificial Sequence
<220> FEATURE:
<223> OTHER INFORMATION: Synthetic Construct

<400> SEQUENCE: 155
tcccacaacc aggctccatt ctattcaaga gatagaatgg agcctggttg ttt 53

<210> SEQ ID NO 156
<211> LENGTH: 53
<212> TYPE: DNA
<213> ORGANISM: Artificial Sequence
<220> FEATURE:
<223> OTHER INFORMATION: Synthetic Construct

<400> SEQUENCE: 156
caaaaaacaa ccaggctcca ttctatctct tgaatagaat ggagcctggt tgt 53

<210> SEQ ID NO 157
<211> LENGTH: 18
<212> TYPE: DNA
<213> ORGANISM: Artificial Sequence
<220> FEATURE:
<223> OTHER INFORMATION: Synthetic Construct

<400> SEQUENCE: 157
caaccaggct ccattcta 18

<210> SEQ ID NO 158
<211> LENGTH: 52
<212> TYPE: DNA
<213> ORGANISM: Artificial Sequence
<220> FEATURE:
<223> OTHER INFORMATION: Synthetic Construct

<400> SEQUENCE: 158
tcccacaacc aggctccatt ctattcaaga gatagaatgg agcctggttg tt 52

<210> SEQ ID NO 159
<211> LENGTH: 52
<212> TYPE: DNA
<213> ORGANISM: Artificial Sequence
<220> FEATURE:
<223> OTHER INFORMATION: Synthetic Construct

<400> SEQUENCE: 159
caaaaacaac caggctccat tctatctctt gaatagaatg gagcctggtt gt 52

<210> SEQ ID NO 160
<211> LENGTH: 19
<212> TYPE: DNA
<213> ORGANISM: Artificial Sequence
<220> FEATURE:
<223> OTHER INFORMATION: Synthetic Construct

<400> SEQUENCE: 160
caaccaggct ccattctaa 19

<210> SEQ ID NO 161
<211> LENGTH: 54
<212> TYPE: DNA
<213> ORGANISM: Artificial Sequence
<220> FEATURE:
<223> OTHER INFORMATION: Synthetic Construct

<400> SEQUENCE: 161
tcccacaacc aggctccatt ctaattcaag agattagaat ggagcctggt tgtt 54

<210> SEQ ID NO 162
<211> LENGTH: 54
<212> TYPE: DNA
<213> ORGANISM: Artificial Sequence
<220> FEATURE:
<223> OTHER INFORMATION: Synthetic Construct

<400> SEQUENCE: 162
caaaaacaac caggctccat tctaatctct tgaattagaa tggagcctgg ttgt 54

<210> SEQ ID NO 163
<211> LENGTH: 19
<212> TYPE: DNA
<213> ORGANISM: Artificial Sequence
<220> FEATURE:
<223> OTHER INFORMATION: Synthetic Construct

<400> SEQUENCE: 163
ccaggctcca ttctaacta 19

<210> SEQ ID NO 164
<211> LENGTH: 54
<212> TYPE: DNA
<213> ORGANISM: Artificial Sequence
<220> FEATURE:
<223> OTHER INFORMATION: Synthetic Construct

<400> SEQUENCE: 164
tcccaccagg ctccattcta actattcaag agatagttag aatggagcct ggtt 54

<210> SEQ ID NO 165
<211> LENGTH: 54

-continued

<212> TYPE: DNA
<213> ORGANISM: Artificial Sequence
<220> FEATURE:
<223> OTHER INFORMATION: Synthetic Construct

<400> SEQUENCE: 165
caaaaaccag gctccattct aactatctct tgaatagtta gaatggagcc tggt 54

<210> SEQ ID NO 166
<211> LENGTH: 19
<212> TYPE: DNA
<213> ORGANISM: Artificial Sequence
<220> FEATURE:
<223> OTHER INFORMATION: Synthetic Construct

<400> SEQUENCE: 166
ggaccaggac catcctcta 19

<210> SEQ ID NO 167
<211> LENGTH: 54
<212> TYPE: DNA
<213> ORGANISM: Artificial Sequence
<220> FEATURE:
<223> OTHER INFORMATION: Synthetic Construct

<400> SEQUENCE: 167
tcccaggacc aggaccatcc tctattcaag agatagagga tggtcctggt cctt 54

<210> SEQ ID NO 168
<211> LENGTH: 54
<212> TYPE: DNA
<213> ORGANISM: Artificial Sequence
<220> FEATURE:
<223> OTHER INFORMATION: Synthetic Construct

<400> SEQUENCE: 168
caaaaaggac caggaccatc ctctatctct tgaatagagg atggtcctgg tcct 54

<210> SEQ ID NO 169
<211> LENGTH: 19
<212> TYPE: DNA
<213> ORGANISM: Artificial Sequence
<220> FEATURE:
<223> OTHER INFORMATION: Synthetic Construct

<400> SEQUENCE: 169
ggaccatcct ctaacataa 19

<210> SEQ ID NO 170
<211> LENGTH: 54
<212> TYPE: DNA
<213> ORGANISM: Artificial Sequence
<220> FEATURE:
<223> OTHER INFORMATION: Synthetic Construct

<400> SEQUENCE: 170
tcccaggacc atcctctaac ataattcaag agattatgtt agaggatggt cctt 54

<210> SEQ ID NO 171
<211> LENGTH: 54
<212> TYPE: DNA
<213> ORGANISM: Artificial Sequence
<220> FEATURE:
<223> OTHER INFORMATION: Synthetic Construct

<400> SEQUENCE: 171
caaaaaggac catcctctaa cataatctct tgaattatgt tagaggatgg tcct    54

<210> SEQ ID NO 172
<211> LENGTH: 21
<212> TYPE: DNA
<213> ORGANISM: Artificial Sequence
<220> FEATURE:
<223> OTHER INFORMATION: Synthetic Construct

<400> SEQUENCE: 172
gccttcaggc ggttcacccc t    21

<210> SEQ ID NO 173
<211> LENGTH: 58
<212> TYPE: DNA
<213> ORGANISM: Artificial Sequence
<220> FEATURE:
<223> OTHER INFORMATION: Synthetic Construct

<400> SEQUENCE: 173
tcccagcctt caggcggttc acccctttca agagaagggg tgaaccgcct gaaggctt    58

<210> SEQ ID NO 174
<211> LENGTH: 58
<212> TYPE: DNA
<213> ORGANISM: Artificial Sequence
<220> FEATURE:
<223> OTHER INFORMATION: Synthetic Construct

<400> SEQUENCE: 174
caaaaagcct tcaggcggtt caccccttct cttgaaaggg gtgaaccgcc tgaaggct    58

<210> SEQ ID NO 175
<211> LENGTH: 19
<212> TYPE: DNA
<213> ORGANISM: Artificial Sequence
<220> FEATURE:
<223> OTHER INFORMATION: Synthetic Construct

<400> SEQUENCE: 175
gccttcaggc ggttcaccc    19

<210> SEQ ID NO 176
<211> LENGTH: 54
<212> TYPE: DNA
<213> ORGANISM: Artificial Sequence
<220> FEATURE:
<223> OTHER INFORMATION: Synthetic Construct

<400> SEQUENCE: 176
tcccagcctt caggcggttc acccttcaag agagggtgaa ccgcctgaag gctt    54

<210> SEQ ID NO 177
<211> LENGTH: 54
<212> TYPE: DNA
<213> ORGANISM: Artificial Sequence
<220> FEATURE:
<223> OTHER INFORMATION: Synthetic Construct

<400> SEQUENCE: 177
caaaaagcct tcaggcggtt caccctctct tgaagggtga accgcctgaa ggct    54

<210> SEQ ID NO 178
<211> LENGTH: 18
<212> TYPE: DNA
<213> ORGANISM: Artificial Sequence
<220> FEATURE:
<223> OTHER INFORMATION: Synthetic Construct

<400> SEQUENCE: 178
gggttacagg aggctgag 18

<210> SEQ ID NO 179
<211> LENGTH: 53
<212> TYPE: DNA
<213> ORGANISM: Artificial Sequence
<220> FEATURE:
<223> OTHER INFORMATION: Synthetic Construct

<400> SEQUENCE: 179
tcccagggtt acaggaggct gagttcaaga gaactcagcc tcctgtaacc ctt 53

<210> SEQ ID NO 180
<211> LENGTH: 54
<212> TYPE: DNA
<213> ORGANISM: Artificial Sequence
<220> FEATURE:
<223> OTHER INFORMATION: Synthetic Construct

<400> SEQUENCE: 180
caaaaagggt tacaggaggc tgagttctct tgaaactcag cctcctgtaa ccct 54

<210> SEQ ID NO 181
<211> LENGTH: 19
<212> TYPE: DNA
<213> ORGANISM: Artificial Sequence
<220> FEATURE:
<223> OTHER INFORMATION: Synthetic Construct

<400> SEQUENCE: 181
gaggctgagt tacgtgatc 19

<210> SEQ ID NO 182
<211> LENGTH: 54
<212> TYPE: DNA
<213> ORGANISM: Artificial Sequence
<220> FEATURE:
<223> OTHER INFORMATION: Synthetic Construct

<400> SEQUENCE: 182
tcccagaggc tgagttacgt gatcttcaag agagatcacg taactcagcc tctt 54

<210> SEQ ID NO 183
<211> LENGTH: 54
<212> TYPE: DNA
<213> ORGANISM: Artificial Sequence
<220> FEATURE:
<223> OTHER INFORMATION: Synthetic Construct

<400> SEQUENCE: 183
caaaaagagg ctgagttacg tgatctctct tgaagatcac gtaactcagc ctct 54

<210> SEQ ID NO 184
<211> LENGTH: 19
<212> TYPE: DNA
<213> ORGANISM: Artificial Sequence
<220> FEATURE:
<223> OTHER INFORMATION: Synthetic Construct

<400> SEQUENCE: 184
tgagttacgt gatctagtg 19

<210> SEQ ID NO 185
<211> LENGTH: 54
<212> TYPE: DNA
<213> ORGANISM: Artificial Sequence
<220> FEATURE:
<223> OTHER INFORMATION: Synthetic Construct

<400> SEQUENCE: 185
tcccatgagt tacgtgatct agtgttcaag agacactaga tcacgtaact catt 54

<210> SEQ ID NO 186
<211> LENGTH: 55
<212> TYPE: DNA
<213> ORGANISM: Artificial Sequence
<220> FEATURE:
<223> OTHER INFORMATION: Synthetic Construct

<400> SEQUENCE: 186
caaaaatgag ttacgtgatc tagtgtctct tgaacactag atcacgtaac tcatt 55

<210> SEQ ID NO 187
<211> LENGTH: 19
<212> TYPE: DNA
<213> ORGANISM: Artificial Sequence
<220> FEATURE:
<223> OTHER INFORMATION: Synthetic Construct

<400> SEQUENCE: 187
gttacgtgat ctagtgaga 19

<210> SEQ ID NO 188
<211> LENGTH: 54
<212> TYPE: DNA
<213> ORGANISM: Artificial Sequence
<220> FEATURE:
<223> OTHER INFORMATION: Synthetic Construct

<400> SEQUENCE: 188
tcccagttac gtgatctagt gagattcaag agatctcact agatcacgta actt 54

<210> SEQ ID NO 189
<211> LENGTH: 55
<212> TYPE: DNA
<213> ORGANISM: Artificial Sequence
<220> FEATURE:
<223> OTHER INFORMATION: Synthetic Construct

<400> SEQUENCE: 189
caaaaagtta cgtgatctag tgagatctct tgaatctcac tagatcacgt aactt 55

<210> SEQ ID NO 190
<211> LENGTH: 19
<212> TYPE: DNA
<213> ORGANISM: Artificial Sequence
<220> FEATURE:
<223> OTHER INFORMATION: Synthetic Construct

<400> SEQUENCE: 190
gcagagaagg tgtattaca 19

<210> SEQ ID NO 191
<211> LENGTH: 54
<212> TYPE: DNA
<213> ORGANISM: Artificial Sequence
<220> FEATURE:
<223> OTHER INFORMATION: Synthetic Construct

<400> SEQUENCE: 191
tcccagcaga gaaggtgtat tacattcaag agatgtaata caccttctct gctt 54

<210> SEQ ID NO 192
<211> LENGTH: 55
<212> TYPE: DNA
<213> ORGANISM: Artificial Sequence
<220> FEATURE:
<223> OTHER INFORMATION: Synthetic Construct

<400> SEQUENCE: 192
caaaaagcag agaaggtgta ttacatctct tgaatgtaat acaccttctc tgctt 55

<210> SEQ ID NO 193
<211> LENGTH: 19
<212> TYPE: DNA
<213> ORGANISM: Artificial Sequence
<220> FEATURE:
<223> OTHER INFORMATION: Synthetic Construct

<400> SEQUENCE: 193
aaggacactg ggcaaggaa 19

<210> SEQ ID NO 194
<211> LENGTH: 54
<212> TYPE: DNA
<213> ORGANISM: Artificial Sequence
<220> FEATURE:
<223> OTHER INFORMATION: Synthetic Construct

<400> SEQUENCE: 194
tcccaaagga cactgggcaa ggaattcaag agattccttg cccagtgtcc tttt 54

<210> SEQ ID NO 195
<211> LENGTH: 54
<212> TYPE: DNA
<213> ORGANISM: Artificial Sequence
<220> FEATURE:
<223> OTHER INFORMATION: Synthetic Construct

<400> SEQUENCE: 195
caaaaaaagg acactgggca aggaatctct tgaattcctt gcccagtgtc cttt 54

<210> SEQ ID NO 196
<211> LENGTH: 19
<212> TYPE: DNA
<213> ORGANISM: Artificial Sequence
<220> FEATURE:
<223> OTHER INFORMATION: Synthetic Construct

<400> SEQUENCE: 196
ggagccctat atccttacg 19

<210> SEQ ID NO 197
<211> LENGTH: 54
<212> TYPE: DNA
<213> ORGANISM: Artificial Sequence
<220> FEATURE:
<223> OTHER INFORMATION: Synthetic Construct

<400> SEQUENCE: 197
tcccaggagc cctatatcct tacgttcaag agacgtaagg atatagggct cctt 54

<210> SEQ ID NO 198

<211> LENGTH: 54
<212> TYPE: DNA
<213> ORGANISM: Artificial Sequence
<220> FEATURE:
<223> OTHER INFORMATION: Synthetic Construct

<400> SEQUENCE: 198
caaaaaggag ccctatatcc ttacgtctct tgaacgtaag gatatagggc tcct 54

<210> SEQ ID NO 199
<211> LENGTH: 19
<212> TYPE: DNA
<213> ORGANISM: Artificial Sequence
<220> FEATURE:
<223> OTHER INFORMATION: Synthetic Construct

<400> SEQUENCE: 199
gatcctccgc catgggtta 19

<210> SEQ ID NO 200
<211> LENGTH: 54
<212> TYPE: DNA
<213> ORGANISM: Artificial Sequence
<220> FEATURE:
<223> OTHER INFORMATION: Synthetic Construct

<400> SEQUENCE: 200
tcccagatcc tccgccatgg gttattcaag agataaccca tggcggagga tctt 54

<210> SEQ ID NO 201
<211> LENGTH: 54
<212> TYPE: DNA
<213> ORGANISM: Artificial Sequence
<220> FEATURE:
<223> OTHER INFORMATION: Synthetic Construct

<400> SEQUENCE: 201
caaaaagatc ctccgccatg ggttatctct tgaataaccc atggcggagg atct 54

<210> SEQ ID NO 202
<211> LENGTH: 19
<212> TYPE: DNA
<213> ORGANISM: Artificial Sequence
<220> FEATURE:
<223> OTHER INFORMATION: Synthetic Construct

<400> SEQUENCE: 202
tcctggctct tggagagaa 19

<210> SEQ ID NO 203
<211> LENGTH: 54
<212> TYPE: DNA
<213> ORGANISM: Artificial Sequence
<220> FEATURE:
<223> OTHER INFORMATION: Synthetic Construct

<400> SEQUENCE: 203
tcccatcctg gctcttggag agaattcaag agattctctc caagagccag gatt 54

<210> SEQ ID NO 204
<211> LENGTH: 54
<212> TYPE: DNA
<213> ORGANISM: Artificial Sequence
<220> FEATURE:
<223> OTHER INFORMATION: Synthetic Construct

<400> SEQUENCE: 204
caaaaatcct ggctcttgga gagaatctct tgaattctct ccaagagcca ggat 54

<210> SEQ ID NO 205
<211> LENGTH: 19
<212> TYPE: DNA
<213> ORGANISM: Artificial Sequence
<220> FEATURE:
<223> OTHER INFORMATION: Synthetic Construct

<400> SEQUENCE: 205
tcctggctct tggagagaa 19

<210> SEQ ID NO 206
<211> LENGTH: 54
<212> TYPE: DNA
<213> ORGANISM: Artificial Sequence
<220> FEATURE:
<223> OTHER INFORMATION: Synthetic Construct

<400> SEQUENCE: 206
tcccatcctg gctcttggag agaattcaag agattctctc caagagccag gatt 54

<210> SEQ ID NO 207
<211> LENGTH: 54
<212> TYPE: DNA
<213> ORGANISM: Artificial Sequence
<220> FEATURE:
<223> OTHER INFORMATION: Synthetic Construct

<400> SEQUENCE: 207
caaaaatcct ggctcttgga gagaatctct tgaattctct ccaagagcca ggat 54

<210> SEQ ID NO 208
<211> LENGTH: 19
<212> TYPE: DNA
<213> ORGANISM: Artificial Sequence
<220> FEATURE:
<223> OTHER INFORMATION: Synthetic Construct

<400> SEQUENCE: 208
tcctggctct tggagagaa 19

<210> SEQ ID NO 209
<211> LENGTH: 54
<212> TYPE: DNA
<213> ORGANISM: Artificial Sequence
<220> FEATURE:
<223> OTHER INFORMATION: Synthetic Construct

<400> SEQUENCE: 209
tcccatcctg gctcttggag agaattcaag agattctctc caagagccag gatt 54

<210> SEQ ID NO 210
<211> LENGTH: 54
<212> TYPE: DNA
<213> ORGANISM: Artificial Sequence
<220> FEATURE:
<223> OTHER INFORMATION: Synthetic Construct

<400> SEQUENCE: 210
caaaaatcct ggctcttgga gagaatctct tgaattctct ccaagagcca ggat 54

<210> SEQ ID NO 211
<211> LENGTH: 21
<212> TYPE: DNA

<213> ORGANISM: Artificial Sequence
<220> FEATURE:
<223> OTHER INFORMATION: Synthetic Construct

<400> SEQUENCE: 211
gttagatcca gggctcataa t 21

<210> SEQ ID NO 212
<211> LENGTH: 58
<212> TYPE: DNA
<213> ORGANISM: Artificial Sequence
<220> FEATURE:
<223> OTHER INFORMATION: Synthetic Construct

<400> SEQUENCE: 212
tcccagttag atccagggct cataatttca agagaattat gagccctgga tctaactt 58

<210> SEQ ID NO 213
<211> LENGTH: 58
<212> TYPE: DNA
<213> ORGANISM: Artificial Sequence
<220> FEATURE:
<223> OTHER INFORMATION: Synthetic Construct

<400> SEQUENCE: 213
caaaaagtta gatccagggc tcataattct cttgaaatta tgagccctgg atctaact 58

<210> SEQ ID NO 214
<211> LENGTH: 19
<212> TYPE: DNA
<213> ORGANISM: Artificial Sequence
<220> FEATURE:
<223> OTHER INFORMATION: Synthetic Construct

<400> SEQUENCE: 214
agacgagatc gcgatatta 19

<210> SEQ ID NO 215
<211> LENGTH: 54
<212> TYPE: DNA
<213> ORGANISM: Artificial Sequence
<220> FEATURE:
<223> OTHER INFORMATION: Synthetic Construct

<400> SEQUENCE: 215
tcccaagacg agatcgcgat attattcaag agataatatc gcgatctcgt cttt 54

<210> SEQ ID NO 216
<211> LENGTH: 54
<212> TYPE: DNA
<213> ORGANISM: Artificial Sequence
<220> FEATURE:
<223> OTHER INFORMATION: Synthetic Construct

<400> SEQUENCE: 216
caaaaaagac gagatcgcga tattatctct tgaataatat cgcgatctcg tctt 54

<210> SEQ ID NO 217
<211> LENGTH: 19
<212> TYPE: DNA
<213> ORGANISM: Artificial Sequence
<220> FEATURE:
<223> OTHER INFORMATION: Synthetic Construct

<400> SEQUENCE: 217
gcagatctct ataattgga 19

<210> SEQ ID NO 218
<211> LENGTH: 54
<212> TYPE: DNA
<213> ORGANISM: Artificial Sequence
<220> FEATURE:
<223> OTHER INFORMATION: Synthetic Construct

<400> SEQUENCE: 218
tcccagcaga tctctataat tggattcaag agatccaatt atagagatct gctt 54

<210> SEQ ID NO 219
<211> LENGTH: 54
<212> TYPE: DNA
<213> ORGANISM: Artificial Sequence
<220> FEATURE:
<223> OTHER INFORMATION: Synthetic Construct

<400> SEQUENCE: 219
caaaaagcag atctctataa ttggatctct tgaatccaat tatagagatc tgct 54

<210> SEQ ID NO 220
<211> LENGTH: 21
<212> TYPE: DNA
<213> ORGANISM: Artificial Sequence
<220> FEATURE:
<223> OTHER INFORMATION: Synthetic Construct

<400> SEQUENCE: 220
ttggaaaact aaccatcccc c 21

<210> SEQ ID NO 221
<211> LENGTH: 58
<212> TYPE: DNA
<213> ORGANISM: Artificial Sequence
<220> FEATURE:
<223> OTHER INFORMATION: Synthetic Construct

<400> SEQUENCE: 221
tcccattgga aaactaacca tccccttca agagaggggg atggttagtt ttccaatt 58

<210> SEQ ID NO 222
<211> LENGTH: 58
<212> TYPE: DNA
<213> ORGANISM: Artificial Sequence
<220> FEATURE:
<223> OTHER INFORMATION: Synthetic Construct

<400> SEQUENCE: 222
caaaaattgg aaaactaacc atccccctct cttgaagggg gatggttagt tttccaat 58

<210> SEQ ID NO 223
<211> LENGTH: 19
<212> TYPE: DNA
<213> ORGANISM: Artificial Sequence
<220> FEATURE:
<223> OTHER INFORMATION: Synthetic Construct

<400> SEQUENCE: 223
agtcccttat gttctctca 19

<210> SEQ ID NO 224
<211> LENGTH: 54
<212> TYPE: DNA
<213> ORGANISM: Artificial Sequence
<220> FEATURE:

<223> OTHER INFORMATION: Synthetic Construct

<400> SEQUENCE: 224
tcccaagtcc cttatgttct ctcattcaag agatgagaga acataaggga cttt 54

<210> SEQ ID NO 225
<211> LENGTH: 55
<212> TYPE: DNA
<213> ORGANISM: Artificial Sequence
<220> FEATURE:
<223> OTHER INFORMATION: Synthetic Construct

<400> SEQUENCE: 225
caaaaaagtc ccttatgttc tctcatctct tgaatgagag aacataaggg acttt 55

<210> SEQ ID NO 226
<211> LENGTH: 19
<212> TYPE: DNA
<213> ORGANISM: Artificial Sequence
<220> FEATURE:
<223> OTHER INFORMATION: Synthetic Construct

<400> SEQUENCE: 226
ctacttggga tgattgtca 19

<210> SEQ ID NO 227
<211> LENGTH: 54
<212> TYPE: DNA
<213> ORGANISM: Artificial Sequence
<220> FEATURE:
<223> OTHER INFORMATION: Synthetic Construct

<400> SEQUENCE: 227
tcccactact tgggatgatt gtcattcaag agatgacaat catcccaagt agtt 54

<210> SEQ ID NO 228
<211> LENGTH: 54
<212> TYPE: DNA
<213> ORGANISM: Artificial Sequence
<220> FEATURE:
<223> OTHER INFORMATION: Synthetic Construct

<400> SEQUENCE: 228
caaaaactac ttgggatgat tgtcatctct tgaatgacaa tcatcccaag tagt 54

<210> SEQ ID NO 229
<211> LENGTH: 21
<212> TYPE: DNA
<213> ORGANISM: Artificial Sequence
<220> FEATURE:
<223> OTHER INFORMATION: Synthetic Construct

<400> SEQUENCE: 229
ttaagaaggg accttgggag a 21

<210> SEQ ID NO 230
<211> LENGTH: 58
<212> TYPE: DNA
<213> ORGANISM: Artificial Sequence
<220> FEATURE:
<223> OTHER INFORMATION: Synthetic Construct

<400> SEQUENCE: 230
tcccattaag aagggacctt gggagattca agagatctcc caaggtccct tcttaatt 58

<210> SEQ ID NO 231
<211> LENGTH: 58
<212> TYPE: DNA
<213> ORGANISM: Artificial Sequence
<220> FEATURE:
<223> OTHER INFORMATION: Synthetic Construct

<400> SEQUENCE: 231
caaaaattaa gaagggacct tgggagatct cttgaatctc ccaaggtccc ttcttaat 58

<210> SEQ ID NO 232
<211> LENGTH: 19
<212> TYPE: DNA
<213> ORGANISM: Artificial Sequence
<220> FEATURE:
<223> OTHER INFORMATION: Synthetic Construct

<400> SEQUENCE: 232
acacggctga aggtaggga 19

<210> SEQ ID NO 233
<211> LENGTH: 54
<212> TYPE: DNA
<213> ORGANISM: Artificial Sequence
<220> FEATURE:
<223> OTHER INFORMATION: Synthetic Construct

<400> SEQUENCE: 233
tcccaacacg gctgaaggta gggattcaag agatccctac cttcagccgt gttt 54

<210> SEQ ID NO 234
<211> LENGTH: 54
<212> TYPE: DNA
<213> ORGANISM: Artificial Sequence
<220> FEATURE:
<223> OTHER INFORMATION: Synthetic Construct

<400> SEQUENCE: 234
caaaaaacac ggctgaaggt agggatctct tgaatcccta ccttcagccg tgtt 54

<210> SEQ ID NO 235
<211> LENGTH: 19
<212> TYPE: DNA
<213> ORGANISM: Artificial Sequence
<220> FEATURE:
<223> OTHER INFORMATION: Synthetic Construct

<400> SEQUENCE: 235
cacggctgaa ggtagggag 19

<210> SEQ ID NO 236
<211> LENGTH: 54
<212> TYPE: DNA
<213> ORGANISM: Artificial Sequence
<220> FEATURE:
<223> OTHER INFORMATION: Synthetic Construct

<400> SEQUENCE: 236
tcccacacgg ctgaaggtag ggagttcaag agactcccta ccttcagccg tgtt 54

<210> SEQ ID NO 237
<211> LENGTH: 54
<212> TYPE: DNA
<213> ORGANISM: Artificial Sequence
<220> FEATURE:
<223> OTHER INFORMATION: Synthetic Construct

<400> SEQUENCE: 237
caaaaacacg gctgaaggta gggagtctct tgaactccct accttcagcc gtgt 54

<210> SEQ ID NO 238
<211> LENGTH: 17
<212> TYPE: DNA
<213> ORGANISM: Artificial Sequence
<220> FEATURE:
<223> OTHER INFORMATION: Synthetic Construct

<400> SEQUENCE: 238
tctatcgcca ggctctg 17

<210> SEQ ID NO 239
<211> LENGTH: 50
<212> TYPE: DNA
<213> ORGANISM: Artificial Sequence
<220> FEATURE:
<223> OTHER INFORMATION: Synthetic Construct

<400> SEQUENCE: 239
tcccatctat cgccaggctc tgttcaagag acagagcctg gcgatagatt 50

<210> SEQ ID NO 240
<211> LENGTH: 50
<212> TYPE: DNA
<213> ORGANISM: Artificial Sequence
<220> FEATURE:
<223> OTHER INFORMATION: Synthetic Construct

<400> SEQUENCE: 240
caaaaatcta tcgccaggct ctgtctcttg aacagagcct ggcgatagat 50

<210> SEQ ID NO 241
<211> LENGTH: 21
<212> TYPE: DNA
<213> ORGANISM: Artificial Sequence
<220> FEATURE:
<223> OTHER INFORMATION: Synthetic Construct

<400> SEQUENCE: 241
gcaagctgac cctgaagttc a 21

<210> SEQ ID NO 242
<211> LENGTH: 58
<212> TYPE: DNA
<213> ORGANISM: Artificial Sequence
<220> FEATURE:
<223> OTHER INFORMATION: Synthetic Construct

<400> SEQUENCE: 242
tcccagcaag ctgaccctga agttcattca agagatgaac ttcagggtca gcttgctt 58

<210> SEQ ID NO 243
<211> LENGTH: 58
<212> TYPE: DNA
<213> ORGANISM: Artificial Sequence
<220> FEATURE:
<223> OTHER INFORMATION: Synthetic Construct

<400> SEQUENCE: 243
caaaaagcaa gctgaccctg aagttcatct cttgaatgaa cttcagggtc agcttgct 58

<210> SEQ ID NO 244
<211> LENGTH: 19

-continued

<212> TYPE: DNA
<213> ORGANISM: Artificial Sequence
<220> FEATURE:
<223> OTHER INFORMATION: Synthetic Construct

<400> SEQUENCE: 244
gtagagactt actgaccaa 19

<210> SEQ ID NO 245
<211> LENGTH: 54
<212> TYPE: DNA
<213> ORGANISM: Artificial Sequence
<220> FEATURE:
<223> OTHER INFORMATION: Synthetic Construct

<400> SEQUENCE: 245
tcccagtaga gacttactga ccaattcaag agattggtca gtaagtctct actt 54

<210> SEQ ID NO 246
<211> LENGTH: 54
<212> TYPE: DNA
<213> ORGANISM: Artificial Sequence
<220> FEATURE:
<223> OTHER INFORMATION: Synthetic Construct

<400> SEQUENCE: 246
caaaaagtag agacttactg accaatctct tgaattggtc agtaagtctc tact 54

<210> SEQ ID NO 247
<211> LENGTH: 19
<212> TYPE: DNA
<213> ORGANISM: Artificial Sequence
<220> FEATURE:
<223> OTHER INFORMATION: Synthetic Construct

<400> SEQUENCE: 247
acctgttgcc tacctgtca 19

<210> SEQ ID NO 248
<211> LENGTH: 54
<212> TYPE: DNA
<213> ORGANISM: Artificial Sequence
<220> FEATURE:
<223> OTHER INFORMATION: Synthetic Construct

<400> SEQUENCE: 248
tcccaacctg ttgcctacct gtcattcaag agatgacagg taggcaacag gttt 54

<210> SEQ ID NO 249
<211> LENGTH: 54
<212> TYPE: DNA
<213> ORGANISM: Artificial Sequence
<220> FEATURE:
<223> OTHER INFORMATION: Synthetic Construct

<400> SEQUENCE: 249
caaaaaacct gttgcctacc tgtcatctct tgaatgacag gtaggcaaca ggtt 54

<210> SEQ ID NO 250
<211> LENGTH: 19
<212> TYPE: DNA
<213> ORGANISM: Artificial Sequence
<220> FEATURE:
<223> OTHER INFORMATION: Synthetic Construct

<400> SEQUENCE: 250
cctgttgcct acctgtcaa 19

<210> SEQ ID NO 251
<211> LENGTH: 54
<212> TYPE: DNA
<213> ORGANISM: Artificial Sequence
<220> FEATURE:
<223> OTHER INFORMATION: Synthetic Construct

<400> SEQUENCE: 251
tcccacctgt tgcctacctg tcaattcaag agattgacag gtaggcaaca ggtt 54

<210> SEQ ID NO 252
<211> LENGTH: 54
<212> TYPE: DNA
<213> ORGANISM: Artificial Sequence
<220> FEATURE:
<223> OTHER INFORMATION: Synthetic Construct

<400> SEQUENCE: 252
caaaaacctg ttgcctacct gtcaatctct tgaattgaca ggtaggcaac aggt 54

<210> SEQ ID NO 253
<211> LENGTH: 19
<212> TYPE: DNA
<213> ORGANISM: Artificial Sequence
<220> FEATURE:
<223> OTHER INFORMATION: Synthetic Construct

<400> SEQUENCE: 253
gaagctcgat cctgtagcc 19

<210> SEQ ID NO 254
<211> LENGTH: 54
<212> TYPE: DNA
<213> ORGANISM: Artificial Sequence
<220> FEATURE:
<223> OTHER INFORMATION: Synthetic Construct

<400> SEQUENCE: 254
tcccagaagc tcgatcctgt agccttcaag agaggctaca ggatcgagct tctt 54

<210> SEQ ID NO 255
<211> LENGTH: 54
<212> TYPE: DNA
<213> ORGANISM: Artificial Sequence
<220> FEATURE:
<223> OTHER INFORMATION: Synthetic Construct

<400> SEQUENCE: 255
caaaaagaag ctcgatcctg tagcctctct tgaaggctac aggatcgagc ttct 54

<210> SEQ ID NO 256
<211> LENGTH: 19
<212> TYPE: DNA
<213> ORGANISM: Artificial Sequence
<220> FEATURE:
<223> OTHER INFORMATION: Synthetic Construct

<400> SEQUENCE: 256
ccgtggccat actggtcaa 19

<210> SEQ ID NO 257
<211> LENGTH: 54
<212> TYPE: DNA
<213> ORGANISM: Artificial Sequence
<220> FEATURE:
<223> OTHER INFORMATION: Synthetic Construct

<400> SEQUENCE: 257
tcccaccgtg gccatactgg tcaattcaag agattgacca gtatggccac ggtt 54

<210> SEQ ID NO 258
<211> LENGTH: 54
<212> TYPE: DNA
<213> ORGANISM: Artificial Sequence
<220> FEATURE:
<223> OTHER INFORMATION: Synthetic Construct

<400> SEQUENCE: 258
caaaaaccgt ggccatactg gtcaatctct tgaattgacc agtatggcca cggt 54

<210> SEQ ID NO 259
<211> LENGTH: 19
<212> TYPE: DNA
<213> ORGANISM: Artificial Sequence
<220> FEATURE:
<223> OTHER INFORMATION: Synthetic Construct

<400> SEQUENCE: 259
gcctgcttct cacagagag 19

<210> SEQ ID NO 260
<211> LENGTH: 54
<212> TYPE: DNA
<213> ORGANISM: Artificial Sequence
<220> FEATURE:
<223> OTHER INFORMATION: Synthetic Construct

<400> SEQUENCE: 260
tcccagcctg cttctcacag agagttcaag agactctctg tgagaagcag gctt 54

<210> SEQ ID NO 261
<211> LENGTH: 54
<212> TYPE: DNA
<213> ORGANISM: Artificial Sequence
<220> FEATURE:
<223> OTHER INFORMATION: Synthetic Construct

<400> SEQUENCE: 261
caaaaagcct gcttctcaca gagagtctct tgaactctct gtgagaagca ggct 54

<210> SEQ ID NO 262
<211> LENGTH: 19
<212> TYPE: DNA
<213> ORGANISM: Artificial Sequence
<220> FEATURE:
<223> OTHER INFORMATION: Synthetic Construct

<400> SEQUENCE: 262
ccactcttct gcctgaaga 19

<210> SEQ ID NO 263
<211> LENGTH: 54
<212> TYPE: DNA
<213> ORGANISM: Artificial Sequence
<220> FEATURE:
<223> OTHER INFORMATION: Synthetic Construct

<400> SEQUENCE: 263
tcccaccact cttctgcctg aagattcaag agatcttcag gcagaagagt ggtt 54

<210> SEQ ID NO 264
<211> LENGTH: 54
<212> TYPE: DNA
<213> ORGANISM: Artificial Sequence
<220> FEATURE:
<223> OTHER INFORMATION: Synthetic Construct

<400> SEQUENCE: 264
caaaaaccac tcttctgcct gaagatctct tgaatcttca ggcagaagag tggt 54

<210> SEQ ID NO 265
<211> LENGTH: 19
<212> TYPE: DNA
<213> ORGANISM: Artificial Sequence
<220> FEATURE:
<223> OTHER INFORMATION: Synthetic Construct

<400> SEQUENCE: 265
tgaagagact gatgaacca 19

<210> SEQ ID NO 266
<211> LENGTH: 54
<212> TYPE: DNA
<213> ORGANISM: Artificial Sequence
<220> FEATURE:
<223> OTHER INFORMATION: Synthetic Construct

<400> SEQUENCE: 266
tcccatgaag agactgatga accattcaag agatggttca tcagtctctt catt 54

<210> SEQ ID NO 267
<211> LENGTH: 54
<212> TYPE: DNA
<213> ORGANISM: Artificial Sequence
<220> FEATURE:
<223> OTHER INFORMATION: Synthetic Construct

<400> SEQUENCE: 267
caaaaatgaa gagactgatg aaccatctct tgaatggttc atcagtctct tcat 54

<210> SEQ ID NO 268
<211> LENGTH: 19
<212> TYPE: DNA
<213> ORGANISM: Artificial Sequence
<220> FEATURE:
<223> OTHER INFORMATION: Synthetic Construct

<400> SEQUENCE: 268
tcactgtgtt gaccctcca 19

<210> SEQ ID NO 269
<211> LENGTH: 54
<212> TYPE: DNA
<213> ORGANISM: Artificial Sequence
<220> FEATURE:
<223> OTHER INFORMATION: Synthetic Construct

<400> SEQUENCE: 269
tcccatcact gtgttgaccc tccattcaag agatggaggg tcaacacagt gatt 54

<210> SEQ ID NO 270
<211> LENGTH: 54
<212> TYPE: DNA
<213> ORGANISM: Artificial Sequence
<220> FEATURE:
<223> OTHER INFORMATION: Synthetic Construct -continued

```
<400> SEQUENCE: 270

caaaaatcac tgtgttgacc ctccatctct tgaatggagg gtcaacacag tgat          54


<210> SEQ ID NO 271
<211> LENGTH: 19
<212> TYPE: DNA
<213> ORGANISM: Artificial Sequence
<220> FEATURE:
<223> OTHER INFORMATION: Synthetic Construct

<400> SEQUENCE: 271

gtacaggact tgagagagg                                                 19


<210> SEQ ID NO 272
<211> LENGTH: 54
<212> TYPE: DNA
<213> ORGANISM: Artificial Sequence
<220> FEATURE:
<223> OTHER INFORMATION: Synthetic Construct

<400> SEQUENCE: 272

tcccagtaca ggacttgaga gaggttcaag agacctctct caagtcctgt actt          54
```